US009644022B2

(12) United States Patent
Depla et al.

(10) Patent No.: US 9,644,022 B2
(45) Date of Patent: May 9, 2017

(54) AMINO ACID SEQUENCES DIRECTED AGAINST HUMAN RESPIRATORY SYNCYTIAL VIRUS (HRSV) AND POLYPEPTIDES COMPRISING THE SAME FOR THE PREVENTION AND/OR TREATMENT OF RESPIRATORY TRACT INFECTIONS

(75) Inventors: Erik Depla, Destelbergen (BE); Catelijne Stortelers, Ghent (BE)

(73) Assignee: Ablynx N.V., Zwijnaarde (BE)

( * ) Notice: Subject to any disclaimer, the term of this patent is extended or adjusted under 35 U.S.C. 154(b) by 322 days.

(21) Appl. No.: 13/512,100

(22) PCT Filed: Nov. 30, 2010

(86) PCT No.: PCT/EP2010/068503
§ 371 (c)(1),
(2), (4) Date: Aug. 14, 2012

(87) PCT Pub. No.: WO2011/064382
PCT Pub. Date: Jun. 3, 2011

(65) Prior Publication Data
US 2012/0301469 A1  Nov. 29, 2012

Related U.S. Application Data

(60) Provisional application No. 61/264,927, filed on Nov. 30, 2009.

(51) Int. Cl.
| | |
|---|---|
| *A61K 39/395* | (2006.01) |
| *C12P 21/00* | (2006.01) |
| *A61K 39/12* | (2006.01) |
| *C07K 16/00* | (2006.01) |
| *G01N 33/53* | (2006.01) |
| *C07K 16/10* | (2006.01) |

(52) U.S. Cl.
CPC ...... *C07K 16/1027* (2013.01); *C07K 2317/22* (2013.01); *C07K 2317/24* (2013.01); *C07K 2317/56* (2013.01); *C07K 2317/569* (2013.01); *C07K 2317/76* (2013.01); *C07K 2317/92* (2013.01); *C07K 2319/00* (2013.01)

(58) Field of Classification Search
CPC ............ C07K 16/1027; C07K 2317/76; C07K 2317/565; C07K 14/005; A61K 2039/505
USPC ........................................................ 424/135
See application file for complete search history.

(56) References Cited

U.S. PATENT DOCUMENTS

| | | | |
|---|---|---|---|
| 3,302,834 A | 2/1967 | Alsop | |
| 6,818,216 B2 | 11/2004 | Young et al. | |
| 8,945,567 B2 | 2/2015 | Depla et al. | |
| 9,193,780 B2 | 11/2015 | Hultberg et al. | |
| 2006/0013824 A1* | 1/2006 | Scallon ...................... | 424/186.1 |
| 2006/0083683 A1 | 4/2006 | Hsei et al. | |
| 2006/0228367 A1 | 10/2006 | Ulbrandt et al. | |
| 2008/0085277 A1* | 4/2008 | Cho et al. .................. | 424/136.1 |
| 2011/0182897 A1 | 7/2011 | Hultberg et al. | |
| 2012/0128669 A1 | 5/2012 | Depla et al. | |
| 2016/0152693 A1 | 6/2016 | Stortelers et al. | |

FOREIGN PATENT DOCUMENTS

| | | |
|---|---|---|
| EP | 2 096 121 A1 | 9/2009 |
| WO | WO 96/40252 A1 | 12/1996 |
| WO | WO 98/19704 A1 | 5/1998 |
| WO | WO 00/65057 A1 | 11/2000 |
| WO | WO 00/69462 A1 | 11/2000 |
| WO | WO0069462 * | 11/2000 |
| WO | WO 03/051912 A2 | 6/2003 |
| WO | WO 03/080672 A1 | 10/2003 |
| WO | WO 03/105894 A1 | 12/2003 |
| WO | WO 2004/003019 A2 | 1/2004 |
| WO | WO 2005/079479 A2 | 9/2005 |
| WO | WO 2006/034292 A2 | 3/2006 |
| WO | WO 2006/040153 A2 | 4/2006 |
| WO | WO 2006/050166 A2 | 5/2006 |
| WO | WO 2006/050280 A2 | 5/2006 |
| WO | WO 2006/107617 A2 | 10/2006 |
| WO | WO 2008/077945 A2 | 7/2008 |
| WO | WO 2009/147248 A2 | 12/2009 |

(Continued)

OTHER PUBLICATIONS

Delagrave et al., "Effects of humanization by variable domain resurfacing on the antiviral activity of a single-chain antibody against respiratory syncytial virus", 1999, Protein Engineering, 12(4): 357-362.*
Graham, "Biological Challenges and Technological Opportunities for Respiratory Syncytial Virus Vaccine Development", Immunol. Rev., 2011, 239(1):pdf 1-27.*
Ichihashi et al., "Cross-protective peptide vaccine against influenza A viruses developed in HLA-A 2402 Human immunity model", PLoS One, 2011, 6(9): pdf 1-9.*
[No Author Listed] ALEXION Pharmaceuticals™ Antibody Therapy Shown Effective in Model for Severe Allergic Asthma. Last accessed at http://www.alxn.com/news/article.aspx?relid=216307 on Aug. 14, 2012.
Harmsen et al., Properties, production, and applications of camelid single-domain antibody fragments. Appl Microbiol Biotechnol. Nov. 2007;77(1):13-22. Epub Aug. 18, 2007.

(Continued)

*Primary Examiner* — Janet L Andres
*Assistant Examiner* — Barry A Chestnut
(74) *Attorney, Agent, or Firm* — Wolf, Greenfield & Sacks, P.C.

(57) ABSTRACT

Amino acid sequences are provided that are directed against/ and or that can specifically bind protein F of hRSV, as well as to compounds or constructs, and in particular proteins and polypeptides, that comprise or essentially consist of one or more such amino acid sequences. The amino acid sequences, polypeptides and therapeutic compounds and compositions provided by the invention show an improved stability, less immunogenicity and/or improved affinity and/or avidity for protein F of hRSV. The invention also relates to the uses of such amino acid sequences, polypeptides, compounds or constructs for prophylactic and/or therapeutic purposes.

39 Claims, 4 Drawing Sheets

(56) References Cited

FOREIGN PATENT DOCUMENTS

| WO | WO2009147248 | * | 12/2009 |
| WO | WO 2010/081856 A1 | | 7/2010 |
| WO | WO 2010/125187 A2 | | 11/2010 |
| WO | WO 2010/139808 A2 | | 12/2010 |

OTHER PUBLICATIONS

Deschacht et al., A novel promiscuous class of camelid single-domain antibody contributes to theantigen-binding repertoire. J Immunol. May 15, 2010;184(10):5696-704. doi:10.4049/jimmunol.0903722. Epub Apr. 19, 2010.

Greenspan et al., Defining epitopes: It's not as easy as it seems, Nat Biotechnol. Oct. 1999;17(10):936-7.

Harmsen et al. Passive immunization of guinea pigs with llama single-domain antibody fragments against foot-and-mouth disease. Vet Microbiol. Mar. 10, 2007;120(3-4):193-206. Epub Oct. 28, 2006.

Haynes LM., Progress and challenges in RSV prophylaxis and vaccine development. J Infect Dis. Dec. 15, 2013;208 Suppl 3:S177-83. doi: 10.1093/infdis/jit512.

Hudson et al., High avidity scFv multimers; diabodies and triabodies. J Immunol Methods. Dec. 10, 1999;231(1-2):177-89.

Ibanez et al.,Nanobodies with in vitro neutralizing activity protect mice against H5N1 influenza virus infection. J Infect Dis. Apr. 15, 2011;203(8):1063-72.

Johnson et al., A direct comparison of the activities of two humanized respiratory syncytial virus monoclonal antibodies: MEDI-493 and RSHZ19. J Infect Dis. Jul. 1999;180(1):35-40.

Kashmiri et al., SDR grafting—a new approach to antibody humanization. Methods. May 2005;36(1):25-34.

Kim et al., Respiratory syncytial virus disease in infants despite prior administration of antigenic inactivated vaccine. Am J Epidemiol. Apr. 1969;89(4):422-34.

Rudikoff et al., Single amino acid substitution altering antigen-binding specificity. Proc Natl Acad Sci U S A. Mar. 1982;79(6):1979-83.

Schepens et al., Nanobodies® specific for respiratory syncytial virus fusion protein protect against infection by inhibition of fusion. J Infect Dis. Dec. 1, 2011;204(11):1692-701. doi: 10.1093/infdis/jir622. Epub Oct. 12, 2011.

Serruys et al., In vitro inhibition of HbsAg secretion by single-domain intrabodies, 12th International Symposium on Viral Hepatitis and Liver Disease, Jul. 1-5, 2006, Paris (Poster).

Serruys et al., HBsAg-specific single-domain intrabodies reduce the secretion of Hepatitis B virus and HBsAg in vivo, Novel Compounds and Strategies to Combat Pathogenic Microorganisms (Symposium Belgian Society for Microbiology), Nov. 24, 2006, Brussels (Poster).

Serruys et al., Generation, characterization and in vitro study of Hepatitis B surface antigen specific single-domain intrabodies, International Meeting on The Molecular Biology of Hepatitis B Viruses, Sep. 16-20, 2007, Rome (Poster).

Serruys et al., Single-domain intrabodies inhibit Hepatitis B Virus replication in mice, International Meeting on The Molecular Biology of Hepatitis B Viruses, Sep. 16-20, 2007, Rome (Poster).

Serruys, Single domain-intrabodies against the Hepatitis B virus (HBV) New Insights in HBV Diversity, Pathogenesis, Diagnosis and Treatment, Dec. 12-14, 2007, Ghent (Oral Presentation).

Serruys et al., Single-Domain Intrabodies Inhibit Hepatitis B Virus (HBV) Replication in Mice (NBC-12), Mar. 13-14, 2008, Ede (Oral Presentation).

Tamura et al., Structural correlates of an anticarcinoma antibody: identification of specificity-determining residues (SDRs) and development of a minimally immunogenic antibody variant by retention of SDRs only. J Immunol. Feb. 1, 2000;164(3):1432-41.

Vincke et al., General strategy to humanize a camelid single-domain antibody and identification of a universal humanized nanobody scaffold. J Biol Chem. Jan. 30, 2009;284(5):3273-84. doi: 10.1074/jbc.M806889200. Epub Nov. 14, 2008.

Wu et al., Ultra-potent antibodies against respiratory syncytial virus: effects of binding kinetics and binding valence on viral neutralization. J Mol Biol. Jul. 1, 2005;350(1):126-44.

[No Author Listed] Domain antibodies. http://www.domantis.com/domain.htm. Accessed on Oct. 28, 2009.

Gómez-Sebastián et al., Rotavirus A-specific single-domain antibodies produced in baculovirus-infected insect larvae are protective in vivo. BMC Biotechnol. Sep. 7, 2012;12:59.

Houdebine, Production of pharmaceutical proteins by transgenic animals. Comp Immunol Microbiol Infect Dis. Mar. 2009;32(2):107-21. doi: 10.1016/j.cimid.2007.11.005. Epub Feb. 19, 2008.

Ko et al., Production of antibodies in plants: approaches and perspectives. Curr Top Microbiol Immunol. 2009;332:55-78. doi: 10.1007/978-3-540-70868-1_4.

Mikulecký et al., Increasing affinity of interferon-γ receptor 1 to interferon-γ by computer-aided design. Biomed Res Int. 2013;2013:752514. 12 pages. doi: 10.1155/2013/752514. Epub Oct. 2, 2013.

Pakula et al., Genetic analysis of protein stability and function. Annu Rev Genet. 1989;23:305-306.

Sikora et al., SMR proteins SugE and EmrE bind ligand with similar affinity and stoichiometry. Biochem Biophys Res Commun. Sep. 16, 2005;335(1):105-11.

Stech et al., A continuous-exchange cell-free protein synthesis system based on extracts from cultured insect cells. PLoS One. May 7, 2014;9(5):e96635. doi: 10.1371/journal.pone.0096635. eCollection 2014.

Walsh et al., The high—and low-affinity receptor binding sites of growth hormone are allosterically coupled. Proc Natl Acad Sci U S A. Dec. 7, 2004;101(49):17078-83. Epub Nov. 24, 2004.

Wang et al., All human Na(+)-K(+)-ATPase alpha-subunit isoforms have a similar affinity for cardiac glycosides. Am J Physiol Cell Physiol. Oct. 2001;281(4):C1336-43.

Zhao et al., In vivo selection of respiratory syncytial viruses resistant to palivizumab. J Virol. Apr. 2005;79(7):3962-8.

[No Author Listed] Palivizumab, a humanized respiratory syncytial virus monoclonal antibody, reduces hospitalization from respiratory syncytial virus infection in high-risk infants. The IMpact-RSV Study Group. Pediatrics. Sep. 1998;102(3 Pt 1):531-7.

Filpula, Antibody engineering and modification technologies. Biomol Eng. Jun. 2004;24(2):201-15. Epub Mar. 31, 2007.

Huang et al., Respiratory syncytial virus-neutralizing monoclonal antibodies motavizumab and palivizumab inhibit fusion. J Virol. Aug. 2010;84(16):8132-40. doi: 10.1128/JVI.02699-09. Epub Jun. 2, 2010.

Jaehnichen et al., CXCR4 nanobodies (VHH-based single variable domains) potently inhibit chemotaxis and HIV-1 replication and mobilize stem cells. Proc Natl Acad Sci U S A. Nov. 23, 2010;107(47):20565-70. doi:10.1073/pnas.1012865107. Epub Nov. 8, 2010.

Johnson et al., Development of a humanized monoclonal antibody (MEDI-493) with potent in vitro and in vivo activity against respiratory syncytial virus. J Infect Dis. Nov. 1997;176(5):1215-24.

Kaliberov et al., Adenoviral targeting using genetically incorporated camelid single variable domains. Lab Invest. Aug. 2014;94(8):893-905. doi: 10.1038/labinvest.2014.82. Epub Jun. 16, 2014.

Maussang et al., Llama-derived single variable domains (nanobodies) directed against chemokine receptor CXCR7 reduce head and neck cancer cell growth in vivo. J Biol Chem. Oct. 11, 2013;288(41):29562-72. doi: 10.1074/jbc.M113.498436. Epub Aug. 26, 2013.

Mejías et al., Anti-respiratory syncytial virus (RSV) neutralizing antibody decreases lung inflammation, airway obstruction, and airway hyperresponsiveness in a murine RSV model. Antimicrob Agents Chemother. May 2004;48(5):1811-22.

Beaucage et al., Using Inhalation Devices. In: Comprehensive Management of Chronic Obstructive Pulmonary Disease. 2002. Chapter 6. 83-107.

Dolovich et al., Device selection and outcomes of aerosol therapy: Evidence-based guidelines: American College of Chest Physicians/American College of Asthma, Allergy, and Immunology. Chest. Jan. 2005;127(1):335-71.

(56) References Cited

OTHER PUBLICATIONS

Geller, Comparing clinical features of the nebulizer, metered-dose inhaler, and dry powder inhaler. Respir Care. Oct. 2005;50(10):1313-21; discussion 1321-2.
Gilbert et al., MegaRibavirin aerosol for the treatment of influenza A virus infections in mice. Antiviral Res. Jun. 2008;78(3):223-9. doi:10.1016/j.antiviral.2008.01.005. Epub Feb. 4, 2008.
Guirakhoo et al., Cloning, expression and functional activities of a single chain antibody fragment directed to fusion protein of respiratory syncytial virus. Immunotechnology. Sep. 1996;2(3):219-28.
Newman et al., The Omron MicroAir vibrating mesh technology nebuliser, a 21$^{st}$ century approach to inhalation therapy. J Appl Ther Res. 2005;5:29-33.
[No Author Listed], Rabies Antibody Combination. Crucell. http://www.crucell.com/R_and_D-Clinical_Development-Rabies_Antibody_Product. Last accessed on Dec. 16, 2010. 2 pages.
[No Author Listed], Rabies Monoclonal Antibody Cocktail. Crucell. http://www.crucell.com/R_and_D-Clinical_Development-Rabies_Antibody_Product. Last accessed on Oct. 30, 2008. 2 pages.
[No Author Listed], Rabies. WHO Fact Sheet No. 99. World Heath Organization. Sep. 2006. http://www.who.int/mediacentre/factsheets/fs099/en/print.html. Last accessed on Oct. 30, 2008. 3 pages.
[No Author Listed], Rabies. WHO Fact Sheet No. 99. World Heath Organization. Updated Sep. 2010. http://www.who.int/mediacentre/factsheets/fs099/en/index.html. Last accessed on Dec. 16, 2010. 4 pages.
Abarca et al., Safety, Tolerability, Pharmacokinetics, and Immunogenicity of Motavizumab, a Humanized, Enhanced-Potency Monoclonal Antibody for the Prevention of Respiratory Syncytial Virus Infection in At-Risk Children. Pediat Infect Dis J. 2009;28(4):267-72.
Arbiza et al., Characterization of two antigenic sites recognized by neutralizing monoclonal antibodies directed against the fusion glycoprotein of human respiratory syncytial virus. J Gen Virol. 1992;73:2225-34.
Awasthi et al., Imaging findings in rabies encephalitis. AJNR Am J Neuroradiol. Apr. 2001;22(4):677-80.
Baker et al., Structural basis for paramyxovirus-mediated membrane fusion. Mol Cell. Mar. 1999;3(3):309-19.
Barbas et al., Human monoclonal Fab fragments derived from a combinatorial library bind to respiratory syncytial virus F glycoprotein and neutralize infectivity. Proc Natl Acad Sci U S A. Nov. 1, 1992;89(21):10164-8.
Burioni et al., Recombinant human Fab to glycoprotein D neutralizes infectivity and prevents cell-to-cell transmission of herpes simplex viruses 1 and 2 in vitro. Proc Natl Acad Sci U S A.
Cardoso et al., Nanobodies® with in vitro neutralizing activity protect mice against H5N1 influenza virus infection. Antivirals Congress, Amsterdam, The Netherlands. Nov. 7-9, 2010. Meeting Abstract. 2 pages.
Chen et al., N—and C-terminal residues combine in the fusion-pH influenza hemagglutinin HA(2) subunit to form an N cap that terminates the triple-stranded coiled coil. Proc Natl Acad Sci U S A. Aug. 3, 1999;96(16):8967-72.
Corral et al., High level expression of soluble glycoproteins in the allantoic fluid of embryonated chicken eggs using a Sendai virus minigenome system. BMC Biotechnol. Apr. 5, 2007;7:17. 9 pages.
Crowe et al., Recombinant human respiratory syncytial virus (RSV) monoclonal antibody Fab is effective therapeutically when introduced directly into the lungs of RSV-infected mice. Proc Natl Acad Sci U S A. Feb. 15, 1994;91(4):1386-90.
De Haard et al., Llama antibodies against a lactococcal protein located at the tip of the phage tail prevent phage infection. J Bacteriol. Jul. 2005;187(13):4531-41.
Dekker et al., Intracellularly expressed single-domain antibody against p15 matrix protein prevents the production of porcine retroviruses. J Virol. Nov. 2003;77(22):12132-9.
Delagrave et al., Effects of humanization by variable domain resurfacing on the antiviral activity of a single-chain antibody against respiratory syncytial virus. Protein Eng. Apr. 1999;12(4):357-62.
Depla et al., Generation and characterization of ultra-potent RSV neutralising Nanobodies. 7th International Respiratory Syncytial Virus Symposium. Rotterdam, The Netherlands. Dec. 2-5, 2010. Presentation Abstract. 2 pages. Final Programme p. 162.
Depla et al., Prophylactic and therapeutic efficacy of anti-RSV Nanobody in a cotton rat challenge model. 7th International Respiratory Syncytial Virus Symposium. Rotterdam, The Netherlands. Dec. 2-5, 2010. Poster Abstract. 2 pages. Final Programme p. 169.
Detalle et al., Assessment of in vivo and in vitro efficacy of an anti-RSV Nanobody®: superior potency over palivizumab and prophylactic effect after pulmonary administration. 1st Symposium on Single Domain Antibodies. Ghent, Belgium. Oct. 14-15, 2010. Meeting Abstract P12.
Deyev et al., Multivalency: the hallmark of antibodies used for optimization of tumor targeting by design. BioEssays. 2008;30(9):904-18.
Dietzschold et al., Differences in cell-to-cell spread of pathogenic and apathogenic rabies virus in vivo and in vitro. J Virol. Oct. 1985;56(1):12-8.
Dimitrov, Cell biology of virus entry. Cell. Jun. 23, 2000;101(7):697-702.
Earp et al., The many mechanisms of viral membrane fusion proteins. Curr Top Microbiol Immunol. 2005;285:25-66.
Fiers et al., A "universal" human influenza A vaccine. Virus Res. Jul. 2004;103(1-2):173-6.
Forsman et al., EU-WHO Neut workshop. Italy. Mar. 2007. Abstract.
Fujinami et al., Antiviral antibody reacting on the plasma membrane alters measles virus expression inside the cell. Nature. Jun. 7, 1979;279(5713):529-30.
Gerhard, The role of the antibody response in influenza virus infection. Curr Top Microbiol Immunol. 2001;260:171-90.
Goldman et al, Facile generation of heat-stable antiviral and antitoxin single domain antibodies from a semisynthetic llama library. Anal Chem. Dec. 15, 2006;78(24):8245-55.
Hanson et al., Passive immunoprophylaxis and therapy with humanized monoclonal antibody specific for influenza A H5 hemagglutinin in mice. Respir Res. Oct. 14, 2006;7:126.
Harmsen et al., Passive immunization of pigs with bispecific llama single-domain antibody fragments against foot-and-mouth disease and porcine immunoglobulin. Vet Microbiol. 2008. doi:10.1016/j.vetmic.2008.04.30.
Heldwein et al., Crystal structure of glycoprotein B from herpes simplex virus 1. Science. Jul. 14, 2006;313(5784):217-20.
Helenius et al., On the entry of Semliki forest virus into BHK-21 cells. J Cell Biol. Feb. 1980;84(2):404-20.
Holliger et al., Engineered antibody fragments and the rise of single domains. Nat Biotechnol. Sep. 2005;23(9):1126-36.
Hultberg et al., Lactobacillli expressing llama VHH fragments neutralise Lactococcus phages. BMC Biotechnol. Sep. 17, 2007;7:58.
Hultberg et al., Llama-derived immunoglobulin single variable domains to build multivalent superpotent and broadened neutralizing anti-viral molecules. XIV International Conference on Negative Stand Viruses. Brugge, Belgium. Jun. 20-25, 2010. Abstract No. 345.
Hultberg et al., Llama-derived single domain antibodies to build multivalent, superpotent and broadened neutralizing anti-viral molecules. PLoS One. Apr. 1, 2011;6(4):e17665. doi: 10.1371/journal.pone.0017665.
Ibanez et al., Nanobodies® with in vitro neutralizing activity protect mice against H5N1 influenza virus infection. XIV International Conference on Negative Strand Viruses. Brugge, Belgium. Jun. 20-25, 2010. Abstract 307.
Ibanez et al., Single domain antibodies with in vitro and in vivo neutralizing activity protect mice against H5N1influenza virus infection. 1st Symposium on Single Domain Antibodies. Ghent, Belgium. Oct. 14-15, 2010. Meeting Abstract P19.

(56) References Cited

OTHER PUBLICATIONS

Ibanez et al., Single-domain antibodies with in vitro and in vivo neutralizing activity protect mice against H5N1 influenza virus infection. Options for the Control of Influenza VII. Abstract Book. Hong Kong SAR, China. Sep. 3-7, 2010. Abstract P-174.
Jain et al., Engineering antibodies for clinical applications. Trends Biotechnol. Jul. 2007;25(7):307-16.
Kielian et al., Virus membrane-fusion proteins: more than one way to make a hairpin. Nat Rev Microbiol. Jan. 2006;4(1):67-76.
Kielian, Class II virus membrane fusion proteins. Virology. Jan. 5, 2006;344(1):38-47.
Kodama et al., Specific and effective targeting cancer immunotherapy with a combination of three bispecific antibodies. Immunol Lett. Apr. 22, 2002;81(2):99-106.
Lamarre et al., Protection from lethal coronavirus infection by immunoglobulin fragments. J Immunol. Apr. 15, 1995;154(8):3975-84.
Ledeboer et al., Preventing phage lysis of Lactococcus lactis in cheese production using a neutralizing heavy-chain antibody fragment from llama. J Dairy Sci. Jun. 2002;85(6):1376-82.
Lescar et al., The Fusion glycoprotein shell of Semliki Forest virus: an icosahedral assembly primed for fusogenic activation at endosomal pH. Cell. Apr. 6, 2001;105(1):137-48.
Levine et al., Antibody-mediated clearance of alphavirus infection from neurons. Science. Nov. 8, 1991;254(5033):856-60.
Lu et al., Passive immunotherapy for influenza a H5N1 virus infection with equine hyperimmune globulin F(ab')2 in mice. Respir Res. Mar. 23, 2006;7:43.
Mason et al., Cloning and expression of a single-chain antibody fragment specific for foot-and-mouth disease virus. Virology. Oct. 15, 1996;224(2):548-54.
Modis et al., A ligand-binding pocket in the dengue virus envelope glycoprotein. Proc Natl Acad Sci U S A. Jun. 10, 2003;100(12):6986-91. Epub May 20, 2003.
Monegal, et al., Immunological applications of single-domain llama recombinant antibodies isolated from a naïve library. Prot Eng Des Sel. 2009;22(4):273-80.
Montano-Hirose et al., Protective activity of a murine monoclonal antibody against European bat lyssavirus 1 (EBL1) infection in mice. Vaccine. Sep. 1993;11(12):1259-66.
Moore et al., The entry of entry inhibitors: a fusion of science and medicine. Proc Natl Acad Sci U S A. Sep. 16, 2003;100(19):10598-602. Epub Sep. 5, 2003.
Morton et al., Structural characterization of respiratory syncytial virus fusion inhibitor escape mutants: homology model of the F protein and a syncytium formation assay. Virol. 2003;311:275-88.
Murphy et al., Current approaches to the development of vaccines effective against parainfluenza and respiratory syncytial viruses. Virus Res. Aug. 1988;11(1):1-15.
Nguyen et al., Efficient generation of respiratory syncytial virus (RSV)-neutralizing human MoAbs via human peripheral blood lymphocyte (hu-PBL)-SCID mice and scFv phage display libraries. Clin Exp Immunol. Oct. 2000;122(1):85-93.
Ogra, Respiratory syncytial virus: the virus, the disease and the immune response. Paediatr Respir Rev. 2004;5 Suppl A:S119-26. Review.
Okuno et al., A common neutralizing epitope conserved between the hemagglutinins of influenza A virus H1 and H2 strains. J Virol. May 1993;67(5):2552-8.
Palladino et al., Virus-neutralizing antibodies of immunoglobulin G (IgG) but not of IgM or IgA isotypes can cure influenza virus pneumonia in SCID mice. J Virol. Apr. 1995;69(4):2075-81.
Pantaleo et al., Effect of anti-V3 antibodies on cell-free and cell-to-cell human immunodeficiency virus transmission. Eur J Immunol. Jan. 1995;25(1):226-31.
Prince et al., Mechanism of antibody-mediated viral clearance in immunotherapy of respiratory syncytial virus infection of cotton rats. J Virol. Jun. 1990;64(6):3091-2.
Renegar et al., Role of IgA versus IgG in the control of influenza viral infection in the murine respiratory tract. J Immunol. Aug. 1, 2004;173(3):1978-86.
Rey et al., The envelope glycoprotein from tick-borne encephalitis virus at 2 A resolution. Nature. May 25, 1995;375(6529):291-8.
Roche et al., Crystal structure of the low-pH form of the vesicular stomatitis virus glycoprotein G. Science. Jul. 14, 2006;313(5784):187-91. Erratum in: Science. Sep. 8, 2006;313(5792):1389.
Rosseels et al., Prophylactic treatment with anti-rabies Nanobodies® can protect mice from lethal rabies virus challenge. XIV International Conference on Negative Strand Viruses. Brugge, Belgium. Jun. 20-25, 2010. Abstract 301.
Rosseels et al., VHH selected against the viral spike protein can protect mice against lethal rabies virus challenge. Annual Scientific Meeting of the Institute Pasteur International Network. Hong Kong. Nov. 22-23, 2010. Abstract P025.
Rosseels et al., VHH-based Nanobodies® selected against the viral spike protein can protect mice against lethal rabies virus challenge. WIV-ISP Scientific Report. 2008-2009. pp. 92-95.
Sawyer, Antibodies for the prevention and treatment of viral diseases. Antiviral Res. Aug. 2000;47(2):57-77.
Schepens et al., Nanobodies® protect mice against human respiratory syncytial virus infection by inhibiting viral fusion. $1^{st}$ Symposium on Single Domain Antibodies. Ghent, Belgium. Oct. 14-15, 2010. Meeting Abstract.
Schepens et al., Nanobodies® protect mice against human respiratory syncytial virus infection by inhibiting viral fusion. $7^{th}$ International Respiratory Syncytial Virus Symposium. Rotterdam, The Netherlands. Dec. 2-5, 2010. Presentation Abstract. Final Programme p. 178.
Schepens et al., Nanobodies® protect mice against human respiratory syncytial virus infection. XIV International Conference on Negative Strand Viruses. Brugge, Belgium. Jun. 20-25, 2010. Abstract 318.
Schofield et al., Variations in the neutralizing and haemagglutination-inhibiting activities of five influenza A virus-specific IgGs and their antibody fragments. J Gen Virol. Oct. 1997;78 ( Pt 10):2431-9.
Schumacher et al., Inhibition of immune responses against rabies virus by monoclonal antibodies directed against rabies virus antigens. Vaccine. 1992;10(11):754-60.
Serruys, In vitro inhibition of HbsAg secretion by single-domain intrabodies. 12th International Symposium on Viral Hepatitis and Liver Disease. 2006. Abstract P.026. p. S69.
Sherwood et al., Rapid assembly of sensitive antigen-capture assays for Marburg virus, using in vitro selection of llama single-domain antibodies, at biosafety level 4. J Infect Dis. Nov. 15, 2007;196 Suppl 2:S213-9.
Sieczkarski et al., Viral entry. Curr Top Microbiol Immunol. 2005;285:1-23.
Skehel et al., Coiled coils in both intracellular vesicle and viral membrane fusion. Cell. Dec. 23, 1998;95(7):871-4.
Smirnov et al., Prevention and treatment of bronchopneumonia in mice caused by mouse-adapted variant of avian H5N2 influenza A virus using monoclonal antibody against conserved epitope in the HA stem region. Arch Virol. 2000;145(8):1733-41.
Smith et al., How viruses enter animal cells. Science. Apr. 9, 2004;304(5668):237-42.
Souriau et al., Recombinant antibodies for cancer diagnosis and therapy. Expert Opin Biol Ther. Apr. 2003;3(2):305-18.
Spinelli et al., Lactococcal bacteriophage p2 receptor-binding protein structure suggests a common ancestor gene with bacterial and mammalian viruses. Nat Struct Mol Biol. Jan. 2006;13(1):85-9.
Spinelli et al., The crystal structure of a llama heavy chain variable domain. Nat Struct Biol. Sep. 1996;3(9):752-7.
Subbarao et al., Scientific barriers to developing vaccines against avian influenza viruses. Nat Rev Immunol. Apr. 2007;7(4):267-78.
Thullier et al., A recombinant Fab neutralizes dengue virus in vitro. J Biotechnol. Apr. 15, 1999;69(2-3):183-90.
Tremblay et al., Receptor-binding protein of Lactococcus lactis phages: identification and characterization of the saccharide receptor-binding site. J Bacteriol. Apr. 2006;188(7):2400-10.

(56) References Cited

OTHER PUBLICATIONS

Verschueren, Design of experiments in the framework of a cell based potency assay. BEBPA's 3$^{rd}$ Annual biological Assay Conference. Pre-Conference Workshop: Practical Tools for the Bioassay Scientist. Barcelona, Spain. Sep. 29-Oct. 1, 2010. 9:30am-10:15am. Abstract.

Weissenhorn et al., Virus membrane fusion. FEBS Lett. May 22, 2007;581(11):2150-5. Epub 2007 Feb. 16, 2007.

Wilson et al., Structure of the haemagglutinin membrane glycoprotein of influenza virus at 3 A resolution. Nature. Jan. 29, 1981;289(5796):366-73.

Woldehiwet, Rabies: recent developments. Res Vet Sci. Aug. 2002;73(1):17-25.

Wright et al., The efficacy of current rabies vaccines and novel Nanobody®-based antivirals against highly pathogenic phylogroup -1 and -2 members of the Lyssavirus genus. XXI International meeting on Rabies in the Americas (RITA XXI). Guadalajara, Jal. Oct. 17-22, 2010.

Wright et al., The efficacy of current vaccines and novel nanobody-based antivirals against highly pathogenic rabies and lyssaviruses. SGM Spring 2010 Meeting. Edinburgh International Conference Centre. Edinburgh, UK. Mar. 29-Apr. 1, 2010. Abstract. p. 81-82.

Wu et al., Development of Motavizumab, an Ultra-potent Antibody for the Prevention of Respiratory Syuncytial Virus Infection in the Upper and Lower Respiratory Tract. J Mol Biol. 2007;368:652-65.

Wu et al., Immunoprophylaxis of RSV Infection: Advancing from RSV-IGIV to Palivizumab and Motavizumab. Curr Top Microbiol Immunol. 2008;317:103-23.

Yin et al., Structure of the uncleaved ectodomain of the paramyxovirus (hPIV3) fusion protein. Proc Natl Acad Sci U S A. Jun. 28, 2005;102(26):9288-93. Epub Jun. 17, 2005.

\* cited by examiner

SEQUENCE LISTING

```
<160> NUMBER OF SEQ ID NOS: 68

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
cttagcagaa aaccgtga                                                         18

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
tgggttgatt tgggattg                                                         18

<210> SEQ ID NO 3
<211> LENGTH: 19
<212> TYPE: DNA
```

```
<213> ORGANISM: Artificial Sequence
<220> FEATURE:
<223> OTHER INFORMATION: primer

<400> SEQUENCE: 3
ggactgatag aggatggta                                                    19

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
gctgacttca cttggtaa                                                     18

<210> SEQ ID NO 5
<211> LENGTH: 125
<212> TYPE: PRT
<213> ORGANISM: Artificial Sequence
<220> FEATURE:
<223> OTHER INFORMATION: Nanobody

<400> SEQUENCE: 5
```

Glu Val Gln Leu Val Glu Ser Gly Gly Gly Leu Val Gln Pro Gly Gly
1               5                   10                  15

Ser Leu Arg Val Ser Cys Ala Ala Ser Gly Phe Thr Phe Asn Asp Tyr
            20                  25                  30

Ile Met Gly Trp Phe Arg Gln Ala Pro Gly Lys Glu Arg Met Phe Ile
        35                  40                  45

Ala Ala Ile Ser Gly Thr Gly Thr Ile Lys Tyr Tyr Gly Asp Leu Val
    50                  55                  60

Arg Gly Arg Phe Thr Ile Ser Arg Asp Asn Ala Lys Asn Thr Val Tyr
65                  70                  75                  80

Leu Arg Ile Asp Ser Leu Asn Pro Glu Asp Thr Ala Val Tyr Tyr Cys
                85                  90                  95

Ala Ala Arg Gln Asp Tyr Gly Leu Gly Tyr Arg Glu Ser His Glu Tyr
            100                 105                 110

Asp Tyr Trp Gly Gln Gly Thr Gln Val Thr Val Ser Ser
        115                 120                 125

```
<210> SEQ ID NO 6
<211> LENGTH: 127
<212> TYPE: PRT
<213> ORGANISM: Artificial Sequence
<220> FEATURE:
<223> OTHER INFORMATION: Nanobody

<400> SEQUENCE: 6
```

Glu Val Gln Leu Val Glu Ser Gly Gly Gly Leu Val Gln Ala Gly Ala
1               5                   10                  15

Ser Leu Arg Leu Ser Cys Ala Ala Ser Gly Leu Ala Phe Ser Arg Tyr
            20                  25                  30

Ala Met Gly Trp Phe Arg Gln Ala Pro Gly Lys Glu Arg Glu Ser Val
        35                  40                  45

Ala Ala Ile Ser Ser Ser Gly Asp Asn Ile Tyr Tyr Ala Asp Ser Val
    50                  55                  60

Lys Gly Gln Phe Thr Met Ser Arg Asp Asn Ala Lys Ser Val Tyr
65                  70                  75                  80

```
Leu Gln Met Ile Asn Leu Lys Pro Glu Asp Thr Ala Val Tyr Tyr Cys
                85                  90                  95

Ala Ala Thr Ser Pro Leu Phe Val Ala Ser Asp Tyr Phe Glu Ala Ser
            100                 105                 110

Arg Tyr Gly Tyr Trp Gly Gln Gly Thr Gln Val Thr Val Ser Ser
        115                 120                 125

<210> SEQ ID NO 7
<211> LENGTH: 126
<212> TYPE: PRT
<213> ORGANISM: Artificial Sequence
<220> FEATURE:
<223> OTHER INFORMATION: Nanobody

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Leu Asp Tyr Tyr
            20                  25                  30

Ala Leu Gly Trp Phe Arg Gln Ala Pro Gly Lys Glu Arg Glu Gly Val
        35                  40                  45

Ser Cys Ile Ser Ser Ala Asp His Ser Thr Thr Tyr Ala Asp Ser Val
    50                  55                  60

Lys Gly Arg Phe Thr Ile Ser Trp Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Pro Ala Leu Gly Cys Tyr Ser Gly Asn Tyr Tyr Pro Arg
            100                 105                 110

Tyr Asp Tyr Trp Gly Gln Gly Thr Gln Val Thr Val Ser Ser
        115                 120                 125

<210> SEQ ID NO 8
<211> LENGTH: 133
<212> TYPE: PRT
<213> ORGANISM: Artificial Sequence
<220> FEATURE:
<223> OTHER INFORMATION: Nanobody

<400> SEQUENCE: 8

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Ala Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Ser Asp Asn Ala Lys Asn Met Val Tyr
65                  70                  75                  80

Leu Gln Met Asn Ser Leu Lys Pro Glu Asp Thr Ala Val Tyr Tyr Cys
                85                  90                  95

Ala Ala Asp Leu Leu Arg Thr Ala Val Gly Cys Leu Tyr Arg Gly
            100                 105                 110

Thr Tyr Tyr Pro Arg Thr Thr Met Asp Tyr Arg Gly Lys Gly Thr Leu
        115                 120                 125

Val Thr Val Ser Ser
        130
```

<210> SEQ ID NO 9
<211> LENGTH: 125
<212> TYPE: PRT
<213> ORGANISM: Artificial Sequence
<220> FEATURE:
<223> OTHER INFORMATION: Nanobody

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Trp Asp Tyr Tyr
            20                  25                  30

Val Ile Gly Trp Phe Arg Gln Ala Pro Gly Lys Glu Arg Glu Gly Leu
        35                  40                  45

Ser Cys Ile Ser Ser Asp Gly Ser Thr Thr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Glu Pro Glu Asp Thr Ala Val Tyr Tyr Cys Ala
                85                  90                  95

Thr Asp Pro Ala Leu Gly Cys Tyr Ser Gly Ser Tyr Tyr Pro Arg Tyr
            100                 105                 110

Asp Tyr Trp Gly Gln Gly Thr Gln Val Thr Val Ser Ser
        115                 120                 125
```

<210> SEQ ID NO 10
<211> LENGTH: 126
<212> TYPE: PRT
<213> ORGANISM: Artificial Sequence
<220> FEATURE:
<223> OTHER INFORMATION: Nanobody

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Leu Asp Tyr Tyr
            20                  25                  30

Ala Leu Gly Trp Phe Arg Gln Ala Pro Gly Lys Glu Arg Glu Gly Val
        35                  40                  45

Ser Cys Ile Ser Ser Ser Asp His Thr Thr Thr Tyr Thr Asp Ser Val
    50                  55                  60

Lys Gly Arg Phe Thr Ile Ser Trp Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Asp Pro Ala Leu Gly Cys Tyr Ser Gly Ser Tyr Tyr Pro Arg
            100                 105                 110

Tyr Asp Phe Trp Gly Gln Gly Thr Gln Val Thr Val Ser Ser
        115                 120                 125
```

<210> SEQ ID NO 11
<211> LENGTH: 126
<212> TYPE: PRT
<213> ORGANISM: Artificial Sequence
<220> FEATURE:
<223> OTHER INFORMATION: Nanobody

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Glu Asp Tyr Tyr
            20                  25                  30

Val Ile Gly Trp Phe Arg Gln Ala Pro Gly Lys Glu Arg Glu Gly Val
        35                  40                  45

Ser Cys Met Ser Ser Ser Gly Asp Ser Thr Thr Tyr Ala Asp Ser Val
50                  55                  60

Lys Gly Arg Phe Thr Ile Ser Arg Asp Asn Ala Lys Asn Met Val Tyr
65                  70                  75                  80

Leu Gln Met Thr Ser Leu Lys Pro Glu Asp Thr Ala Val Tyr Tyr Cys
            85                  90                  95

Ala Ala Asp Phe Ala Leu Gly Cys Tyr Ser Gly Ser Tyr Tyr Pro Arg
            100                 105                 110

Tyr Asp Tyr Trp Gly Gln Gly Thr Gln Val Thr Val Ser Ser
            115                 120                 125
```

<210> SEQ ID NO 12
<211> LENGTH: 128
<212> TYPE: PRT
<213> ORGANISM: Artificial Sequence
<220> FEATURE:
<223> OTHER INFORMATION: Nanobody

<400> SEQUENCE: 12

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Arg Tyr
            20                  25                  30

Ile Met Gly Trp Phe Arg Gln Ala Pro Gly Lys Glu Arg Glu Phe Val
        35                  40                  45

Gly Ala Ile Ser Arg Ser Gly Asp Ile Thr Ser Phe Ala Asp Phe Val
50                  55                  60

Lys Gly Arg Phe Thr Met Ser Arg Asp Asn Ala Lys Asn Thr Leu Tyr
65                  70                  75                  80

Leu Gln Met Asn Ser Leu Glu Pro Glu Asp Thr Ala Val Tyr Ser Cys
            85                  90                  95

Ala Ala Asn Ser Asp Thr Tyr Tyr Ile Tyr Ser Asp Ile Val Val Pro
            100                 105                 110

Glu Arg Tyr Asp Tyr Trp Gly Gln Gly Thr Gln Val Thr Val Ser Ser
            115                 120                 125
```

<210> SEQ ID NO 13
<211> LENGTH: 123
<212> TYPE: PRT
<213> ORGANISM: Artificial Sequence
<220> FEATURE:
<223> OTHER INFORMATION: Nanobody

<400> SEQUENCE: 13

```
Glu Val Gln Leu Met Glu Ser Gly Gly Gly Leu Val Gln Ala Gly Gly
1               5                   10                  15

Ser Leu Arg Leu Ser Cys Ala Ser Gly Gly Thr Phe Ser Ser Tyr
            20                  25                  30

Ala Met Gly Trp Phe Arg Gln Ala Pro Gly Glu Glu Arg Asp Phe Val
        35                  40                  45

Ala Ala Ile Gly Trp Ser Gly Asn Ser Pro Tyr Tyr Ala Gln Phe Val
50                  55                  60
```

```
Lys Gly Arg Phe Thr Ile Ser Arg Asp Asn Ala Lys Asn Thr Val His
 65                  70                  75                  80

Leu Gln Met Asn Ser Leu Lys Pro Glu Asp Thr Ala Val Tyr Tyr Cys
                 85                  90                  95

Ala Ala Ala His Asn Thr Met Gly Ser Asp Tyr Glu Gly Tyr Asp Tyr
            100                 105                 110

Trp Gly Gln Gly Thr Gln Val Thr Val Ser Ser
        115                 120

<210> SEQ ID NO 14
<211> LENGTH: 127
<212> TYPE: PRT
<213> ORGANISM: Artificial Sequence
<220> FEATURE:
<223> OTHER INFORMATION: Nanobody

<400> SEQUENCE: 14

Glu Val Gln Leu Val Glu Ser Gly Gly Gly Leu Val Gln Ala Gly Gly
 1               5                  10                  15

Ser Leu Arg Leu Ser Cys Ala Ala Ser Gly Pro Thr Phe Ser Ala Asp
                 20                  25                  30

Thr Met Gly Trp Phe Arg Gln Ala Pro Gly Lys Glu Arg Glu Phe Val
             35                  40                  45

Ala Thr Ile Pro Trp Ser Gly Gly Ile Ala Tyr Tyr Ser Asp Ser Val
         50                  55                  60

Lys Gly Arg Phe Thr Met Ser Arg Asp Asn Ala Lys Asn Thr Val Asp
 65                  70                  75                  80

Leu Gln Met Asn Ser Leu Lys Pro Glu Asp Thr Ala Leu Tyr Tyr Cys
                 85                  90                  95

Ala Gly Ser Ser Arg Ile Tyr Ile Tyr Ser Asp Ser Leu Ser Glu Arg
            100                 105                 110

Ser Tyr Asp Tyr Trp Gly Gln Gly Thr Gln Val Thr Val Ser Ser
        115                 120                 125

<210> SEQ ID NO 15
<211> LENGTH: 129
<212> TYPE: PRT
<213> ORGANISM: Artificial Sequence
<220> FEATURE:
<223> OTHER INFORMATION: Nanobody

<400> SEQUENCE: 15

Glu Val Gln Leu Val Glu Ser Gly Gly Gly Leu Val Gln Ala Gly Gly
 1               5                  10                  15

Ser Leu Arg Leu Ser Cys Ala Ala Ser Glu Arg Thr Phe Ser Tyr Tyr
                 20                  25                  30

Ala Met Gly Trp Phe Arg Gln Ala Pro Gly Lys Glu Arg Glu Phe Val
             35                  40                  45

Ala Thr Ile Ser Arg Ser Gly Trp Ile Tyr Tyr Lys Asp Ala Met Lys
         50                  55                  60

Lys Gly Arg Phe Thr Ile Ser Arg Asp Asn Ala Asn Asn Ala Val Tyr
 65                  70                  75                  80

Leu Gln Met Asn Ser Leu Gln Pro Glu Asp Thr Ala Ile Tyr Tyr Cys
                 85                  90                  95

Ala Ala Asp Ser Leu Gly Gly Phe Arg Ser Ala Ser Asp Tyr Tyr Asn
            100                 105                 110

Thr Asn Thr Tyr Ala Tyr Trp Gly Gln Gly Thr Gln Val Thr Val Ser
```

Ser

<210> SEQ ID NO 16
<211> LENGTH: 127
<212> TYPE: PRT
<213> ORGANISM: Artificial Sequence
<220> FEATURE:
<223> OTHER INFORMATION: Nanobody

<400> SEQUENCE: 16

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser
        115                 120                 125

<210> SEQ ID NO 17
<211> LENGTH: 127
<212> TYPE: PRT
<213> ORGANISM: Artificial Sequence
<220> FEATURE:
<223> OTHER INFORMATION: Nanobody

<400> SEQUENCE: 17

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Trp Trp Ser Gly Gly Ser Thr Tyr Tyr Ala Asp Ser Val
    50                  55                  60

Lys Gly Arg Phe Thr Met Ser Arg Asp Asn Ala Lys Asn Thr Val Tyr
65                  70                  75                  80

Leu Glu Met Asn Asn Leu Lys Pro Glu Asp Thr Ala Val Tyr Tyr Cys
                85                  90                  95

Ala Ala Asp Thr Asp Ser Ser Asn Ser Gly Ser Tyr Leu Tyr Thr Trp
            100                 105                 110

Ala Tyr Asp Tyr Trp Gly Gln Gly Thr Gln Val Thr Val Ser Ser
        115                 120                 125

<210> SEQ ID NO 18
<211> LENGTH: 126
<212> TYPE: PRT
<213> ORGANISM: Artificial Sequence
<220> FEATURE:
<223> OTHER INFORMATION: Nanobody

<400> SEQUENCE: 18

Glu Val Gln Leu Val Glu Ser Gly Gly Ser Val Gln Ala Gly Gly
1               5                   10                  15

Ser Leu Arg Leu Ser Cys Ala Ala Ser Gly Gly Ser Phe Asn Arg Phe
            20                  25                  30

Gly Met Gly Trp Phe Arg Ala Pro Gly Lys Glu Arg Asp Phe Val
        35                  40                  45

Ala Ala Ile Asn Leu Ser Gly Asp Thr Thr Tyr Tyr Val Asp Ser Val
50                  55                  60

Gln Gly Arg Phe Thr Ile Ser Arg Asp Asn Ala Asn Asn Ile Met Tyr
65                  70                  75                  80

Leu Gln Met Asn Leu Leu Lys Pro Glu Asp Thr Ala Asp Tyr Tyr Cys
                85                  90                  95

Ala Ala Asp Pro Asp Pro Ile Thr Ala Trp Lys Gln Ser Gly Ala Gly
            100                 105                 110

Met Asp Tyr Trp Gly Lys Gly Thr Gln Val Thr Val Ser Ser
        115                 120                 125

<210> SEQ ID NO 19
<211> LENGTH: 128
<212> TYPE: PRT
<213> ORGANISM: Artificial Sequence
<220> FEATURE:
<223> OTHER INFORMATION: Nanobody

<400> SEQUENCE: 19

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Phe Ser Ser Tyr
            20                  25                  30

Gly Met Gly Trp Phe Arg Gln Ala Pro Gly Lys Glu Arg Glu Phe Val
        35                  40                  45

Ala Ala Val Ser Arg Leu Ser Gly Pro Arg Thr Val Tyr Ala Asp Ser
50                  55                  60

Val Lys Gly Arg Phe Thr Ile Ser Arg Asp Asn Ala Glu Asn Thr Val
65                  70                  75                  80

Tyr Leu Gln Met Asn Ser Leu Lys Pro Glu Asp Thr Ala Val Tyr Thr
                85                  90                  95

Cys Ala Ala Glu Leu Thr Asn Arg Asn Pro Gly Ala Tyr Tyr Tyr Thr
            100                 105                 110

Trp Ala Tyr Asp Tyr Trp Gly Gln Gly Thr Gln Val Thr Val Ser Ser
        115                 120                 125

<210> SEQ ID NO 20
<211> LENGTH: 128
<212> TYPE: PRT
<213> ORGANISM: Artificial Sequence
<220> FEATURE:
<223> OTHER INFORMATION: Nanobody

<400> SEQUENCE: 20

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Tyr Ser Arg Tyr
            20                  25                  30

Gly Met Gly Trp Phe Arg Gln Ala Pro Gly Lys Glu Arg Glu Phe Val
        35                  40                  45

```
Ala Ala Val Ser Arg Leu Ser Gly Pro Arg Thr Val Tyr Ala Asp Ser
        50                  55                  60

Val Lys Gly Arg Phe Thr Ile Ser Arg Asp Asn Ala Glu Asn Thr Val
 65                  70                  75                  80

Tyr Leu Gln Met Asn Ser Leu Lys Pro Glu Asp Thr Ala Val Tyr Thr
                85                  90                  95

Cys Ala Ala Glu Leu Thr Asn Arg Asn Ser Gly Ala Tyr Tyr Tyr Ala
            100                 105                 110

Trp Ala Tyr Asp Tyr Trp Gly Gln Gly Thr Gln Val Thr Val Ser Ser
            115                 120                 125

<210> SEQ ID NO 21
<211> LENGTH: 126
<212> TYPE: PRT
<213> ORGANISM: Artificial Sequence
<220> FEATURE:
<223> OTHER INFORMATION: Nanobody

<400> SEQUENCE: 21

Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Ser Phe Ser Asn Tyr
                20                  25                  30

Val Leu Gly Trp Phe Arg Gln Ala Pro Gly Lys Glu Arg Glu Phe Val
            35                  40                  45

Ala Ala Ile Ser Phe Arg Gly Asp Ser Ala Ile Gly Ala Pro Ser Val
        50                  55                  60

Glu Gly Arg Phe Thr Ile Ser Arg Asp Asn Ala Lys Asn Thr Gly Tyr
 65                  70                  75                  80

Leu Gln Met Asn Ser Leu Val Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser
            115                 120                 125

<210> SEQ ID NO 22
<211> LENGTH: 128
<212> TYPE: PRT
<213> ORGANISM: Artificial Sequence
<220> FEATURE:
<223> OTHER INFORMATION: Nanobody

<400> SEQUENCE: 22

Glu Val Gln Leu Val Glu Ser Gly Gly Gly Leu Val Gln Ala Gly Gly
 1               5                  10                  15

Ser Leu Arg Leu Ser Cys Glu Ala Ser Gly Arg Thr Phe Ser Ser Tyr
                20                  25                  30

Asp Met Gly Trp Phe Arg Gln Ala Pro Gly Lys Glu Arg Glu Phe Val
            35                  40                  45

Ala Ala Val Thr Arg Trp Ser Gly Ala Arg Gly Val Tyr Ala Asp Ser
        50                  55                  60

Val Lys Gly Arg Phe Thr Ile Ser Arg Asp Asn Ala Glu Asn Thr Val
 65                  70                  75                  80

His Leu Gln Met Asn Ser Leu Lys Pro Glu Asp Thr Ala Val Tyr Thr
                85                  90                  95

Cys Ala Ala Asp Ser Thr Asn Arg Asn Ser Gly Ala Val Tyr Tyr Thr
```

```
                    100                 105                 110
Trp Ala Tyr Asp Tyr Trp Gly Gln Gly Thr Gln Val Thr Val Ser Ser
            115                 120                 125

<210> SEQ ID NO 23
<211> LENGTH: 127
<212> TYPE: PRT
<213> ORGANISM: Artificial Sequence
<220> FEATURE:
<223> OTHER INFORMATION: Nanobody

<400> SEQUENCE: 23

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Phe
            20                  25                  30

Ala Met Gly Trp Phe Arg Gln Ala Pro Gly Lys Glu Arg Glu Phe Val
        35                  40                  45

Ala Ala Ile Ser Trp Ser Gly Ser Thr Tyr Tyr Ala Asp Ser Val
    50                  55                  60

Lys Gly Arg Phe Thr Ile Ser Gly Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Asp Ser Glu Ile Leu Asn Ser Gly Ala Tyr Tyr Pro Trp
            100                 105                 110

Ala Tyr Val Tyr Trp Gly Gln Gly Thr Gln Val Thr Val Ser Ser
            115                 120                 125

<210> SEQ ID NO 24
<211> LENGTH: 126
<212> TYPE: PRT
<213> ORGANISM: Artificial Sequence
<220> FEATURE:
<223> OTHER INFORMATION: Nanobody

<400> SEQUENCE: 24

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser
            115                 120                 125

<210> SEQ ID NO 25
<211> LENGTH: 23
<212> TYPE: PRT
<213> ORGANISM: Artificial Sequence
<220> FEATURE:
```

<223> OTHER INFORMATION: tag sequence

<400> SEQUENCE: 25

Ala Ala Ala Glu Gln Lys Leu Ile Ser Glu Glu Asp Leu Asn Gly Ala
1               5                   10                  15

Ala His His His His His His
            20

<210> SEQ ID NO 26
<211> LENGTH: 411
<212> TYPE: PRT
<213> ORGANISM: Artificial Sequence
<220> FEATURE:
<223> OTHER INFORMATION: Nanobody

<400> SEQUENCE: 26

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
        115                 120                 125

Gly Gly Gly Ser Gly Gly Gly Gly Ser Gly Gly Gly Gly Ser Glu Val
    130                 135                 140

Gln Leu Val Glu Ser Gly Gly Gly Leu Val Gln Ala Gly Asp Ser Leu
145                 150                 155                 160

Arg Leu Ser Cys Ala Ala Ser Gly Arg Thr Phe Ser Ser Tyr Ala Met
                165                 170                 175

Gly Trp Phe Arg Gln Ala Pro Gly Lys Glu Arg Glu Phe Val Ala Ala
            180                 185                 190

Ile Ser Trp Ser Asp Gly Ser Thr Tyr Tyr Ala Asp Ser Val Lys Gly
        195                 200                 205

Arg Phe Thr Ile Ser Arg Asp Asn Ala Lys Asn Thr Val Tyr Leu Gln
    210                 215                 220

Met Asn Ser Leu Lys Pro Glu Asp Thr Ala Val Tyr Tyr Cys Ala Ala
225                 230                 235                 240

Asp Leu Thr Ser Thr Asn Pro Gly Ser Tyr Ile Tyr Ile Trp Ala Tyr
                245                 250                 255

Asp Tyr Trp Gly Gln Gly Thr Gln Val Thr Val Ser Ser Gly Gly Gly
            260                 265                 270

Gly Ser Gly Gly Gly Gly Ser Gly Gly Gly Gly Ser Glu Val Gln Leu
        275                 280                 285

Val Glu Ser Gly Gly Gly Leu Val Gln Ala Gly Asp Ser Leu Arg Leu
    290                 295                 300

Ser Cys Ala Ala Ser Gly Arg Thr Phe Ser Ser Tyr Ala Met Gly Trp
305                 310                 315                 320

```
Phe Arg Gln Ala Pro Gly Lys Glu Arg Glu Phe Val Ala Ala Ile Ser
                325                 330                 335

Trp Ser Asp Gly Ser Thr Tyr Tyr Ala Asp Ser Val Lys Gly Arg Phe
            340                 345                 350

Thr Ile Ser Arg Asp Asn Ala Lys Asn Thr Val Tyr Leu Gln Met Asn
        355                 360                 365

Ser Leu Lys Pro Glu Asp Thr Ala Val Tyr Tyr Cys Ala Ala Asp Leu
    370                 375                 380

Thr Ser Thr Asn Pro Gly Ser Tyr Ile Tyr Ile Trp Ala Tyr Asp Tyr
385                 390                 395                 400

Trp Gly Gln Gly Thr Gln Val Thr Val Ser Ser
                405                 410

<210> SEQ ID NO 27
<211> LENGTH: 414
<212> TYPE: PRT
<213> ORGANISM: Artificial Sequence
<220> FEATURE:
<223> OTHER INFORMATION: Nanobody

<400> SEQUENCE: 27

Glu Val Gln Leu Val Glu Ser Gly Gly Gly Leu Val Gln Ala Gly Gly
1               5                   10                  15

Ser Leu Arg Leu Ser Cys Glu Ala Ser Gly Arg Thr Phe Ser Ser Tyr
            20                  25                  30

Gly Met Gly Trp Phe Arg Gln Ala Pro Gly Lys Glu Arg Glu Phe Val
        35                  40                  45

Ala Ala Val Ser Arg Leu Ser Gly Pro Arg Thr Val Tyr Ala Asp Ser
    50                  55                  60

Val Lys Gly Arg Phe Thr Ile Ser Arg Asp Asn Ala Glu Asn Thr Val
65                  70                  75                  80

Tyr Leu Gln Met Asn Ser Leu Lys Pro Glu Asp Thr Ala Val Tyr Thr
                85                  90                  95

Cys Ala Ala Glu Leu Thr Asn Arg Asn Pro Gly Ala Tyr Tyr Tyr Thr
            100                 105                 110

Trp Ala Tyr Asp Tyr Trp Gly Gln Gly Thr Gln Val Thr Val Ser Ser
        115                 120                 125

Gly Gly Gly Gly Ser Gly Gly Gly Ser Gly Gly Gly Gly Ser Glu
        130                 135                 140

Val Gln Leu Val Glu Ser Gly Gly Gly Leu Val Gln Ala Gly Gly Ser
145                 150                 155                 160

Leu Arg Leu Ser Cys Glu Ala Ser Gly Arg Thr Phe Ser Ser Tyr Gly
            165                 170                 175

Met Gly Trp Phe Arg Gln Ala Pro Gly Lys Glu Arg Glu Phe Val Ala
        180                 185                 190

Ala Val Ser Arg Leu Ser Gly Pro Arg Thr Val Tyr Ala Asp Ser Val
    195                 200                 205

Lys Gly Arg Phe Thr Ile Ser Arg Asp Asn Ala Glu Asn Thr Val Tyr
    210                 215                 220

Leu Gln Met Asn Ser Leu Lys Pro Glu Asp Thr Ala Val Tyr Thr Cys
225                 230                 235                 240

Ala Ala Glu Leu Thr Asn Arg Asn Pro Gly Ala Tyr Tyr Tyr Thr Trp
            245                 250                 255

Ala Tyr Asp Tyr Trp Gly Gln Gly Thr Gln Val Thr Val Ser Ser Gly
        260                 265                 270
```

```
Gly Gly Gly Ser Gly Gly Gly Ser Gly Gly Gly Ser Glu Val
            275                 280                 285

Gln Leu Val Glu Ser Gly Gly Gly Leu Val Gln Ala Gly Gly Ser Leu
290                 295                 300

Arg Leu Ser Cys Glu Ala Ser Gly Arg Thr Phe Ser Ser Tyr Gly Met
305                 310                 315                 320

Gly Trp Phe Arg Gln Ala Pro Gly Lys Glu Arg Glu Phe Val Ala Ala
                325                 330                 335

Val Ser Arg Leu Ser Gly Pro Arg Thr Val Tyr Ala Asp Ser Val Lys
                340                 345                 350

Gly Arg Phe Thr Ile Ser Arg Asp Asn Ala Glu Asn Thr Val Tyr Leu
                355                 360                 365

Gln Met Asn Ser Leu Lys Pro Glu Asp Thr Ala Val Tyr Thr Cys Ala
370                 375                 380

Ala Glu Leu Thr Asn Arg Asn Pro Gly Ala Tyr Tyr Tyr Thr Trp Ala
385                 390                 395                 400

Tyr Asp Tyr Trp Gly Gln Gly Thr Gln Val Thr Val Ser Ser
                405                 410

<210> SEQ ID NO 28
<211> LENGTH: 410
<212> TYPE: PRT
<213> ORGANISM: Artificial Sequence
<220> FEATURE:
<223> OTHER INFORMATION: Nanobody

<400> SEQUENCE: 28

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
            35                  40                  45

Ala Ala Ile Ser Trp Ser Asp Gly Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
        115                 120                 125

Gly Gly Gly Ser Gly Gly Gly Ser Gly Gly Gly Ser Glu Val
            130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Leu Thr Leu Asp Tyr Tyr Ala Leu
                165                 170                 175

Gly Trp Phe Arg Gln Ala Pro Gly Lys Glu Arg Glu Val Ser Cys
            180                 185                 190

Ile Ser Ser Ser Asp His Thr Thr Thr Tyr Thr Asp Ser Val Lys Gly
        195                 200                 205

Arg Phe Thr Ile Ser Trp Asp Asn Ala Lys Asn Thr Leu Tyr Leu Gln
    210                 215                 220
```

```
Met Asn Ser Leu Lys Pro Glu Asp Thr Ala Val Tyr Tyr Cys Ala Ala
225                 230                 235                 240

Asp Pro Ala Leu Gly Cys Tyr Ser Gly Ser Tyr Tyr Pro Arg Tyr Asp
            245                 250                 255

Phe Trp Gly Gln Gly Thr Gln Val Thr Val Ser Ser Gly Gly Gly Gly
        260                 265                 270

Ser Gly Gly Gly Gly Ser Gly Gly Gly Ser Glu Val Gln Leu Val
    275                 280                 285

Glu Ser Gly Gly Gly Leu Val Gln Ala Gly Asp Ser Leu Arg Leu Ser
    290                 295                 300

Cys Ala Ala Ser Gly Arg Thr Phe Ser Ser Tyr Ala Met Gly Trp Phe
305                 310                 315                 320

Arg Gln Ala Pro Gly Lys Glu Arg Glu Phe Val Ala Ala Ile Ser Trp
            325                 330                 335

Ser Asp Gly Ser Thr Tyr Tyr Ala Asp Ser Val Lys Gly Arg Phe Thr
        340                 345                 350

Ile Ser Arg Asp Asn Ala Lys Asn Thr Val Tyr Leu Gln Met Asn Ser
    355                 360                 365

Leu Lys Pro Glu Asp Thr Ala Val Tyr Tyr Cys Ala Ala Asp Leu Thr
370                 375                 380

Ser Thr Asn Pro Gly Ser Tyr Ile Tyr Ile Trp Ala Tyr Asp Tyr Trp
385                 390                 395                 400

Gly Gln Gly Thr Gln Val Thr Val Ser Ser
                405                 410

<210> SEQ ID NO 29
<211> LENGTH: 398
<212> TYPE: PRT
<213> ORGANISM: Artificial Sequence
<220> FEATURE:
<223> OTHER INFORMATION: Nanobody

<400> SEQUENCE: 29

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
        115                 120                 125

Gly Gly Gly Ser Gly Gly Ser Glu Val Gln Leu Val Glu Ser Gly
    130                 135                 140

Gly Gly Leu Val Gln Pro Gly Gly Ser Leu Arg Leu Ser Cys Ala Ala
145                 150                 155                 160

Ser Gly Leu Thr Leu Asp Tyr Tyr Ala Leu Gly Trp Phe Arg Gln Ala
                165                 170                 175
```

```
Pro Gly Lys Glu Arg Glu Gly Val Ser Cys Ile Ser Ser Asp His
            180                 185                 190

Thr Thr Thr Tyr Thr Asp Ser Val Lys Gly Arg Phe Thr Ile Ser Trp
        195                 200                 205

Asp Asn Ala Lys Asn Thr Leu Tyr Leu Gln Met Asn Ser Leu Lys Pro
210                 215                 220

Glu Asp Thr Ala Val Tyr Tyr Cys Ala Ala Asp Pro Ala Leu Gly Cys
225                 230                 235                 240

Tyr Ser Gly Ser Tyr Tyr Pro Arg Tyr Asp Phe Trp Gly Gln Gly Thr
                245                 250                 255

Gln Val Thr Val Ser Ser Gly Gly Gly Ser Gly Gly Gly Ser Glu
            260                 265                 270

Val Gln Leu Val Glu Ser Gly Gly Gly Leu Val Gln Ala Gly Asp Ser
        275                 280                 285

Leu Arg Leu Ser Cys Ala Ala Ser Gly Arg Thr Phe Ser Ser Tyr Ala
    290                 295                 300

Met Gly Trp Phe Arg Gln Ala Pro Gly Lys Glu Arg Glu Phe Val Ala
305                 310                 315                 320

Ala Ile Ser Trp Ser Asp Gly Ser Thr Tyr Tyr Ala Asp Ser Val Lys
                325                 330                 335

Gly Arg Phe Thr Ile Ser Arg Asp Asn Ala Lys Asn Thr Val Tyr Leu
            340                 345                 350

Gln Met Asn Ser Leu Lys Pro Glu Asp Thr Ala Val Tyr Tyr Cys Ala
        355                 360                 365

Ala Asp Leu Thr Ser Thr Asn Pro Gly Ser Tyr Ile Tyr Ile Trp Ala
370                 375                 380

Tyr Asp Tyr Trp Gly Gln Gly Thr Gln Val Thr Val Ser Ser
385                 390                 395

<210> SEQ ID NO 30
<211> LENGTH: 409
<212> TYPE: PRT
<213> ORGANISM: Artificial Sequence
<220> FEATURE:
<223> OTHER INFORMATION: Nanobody

<400> SEQUENCE: 30

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
        115                 120                 125

Gly Gly Gly Ser Gly Gly Gly Ser Gly Gly Gly Ser Glu Val
    130                 135                 140
```

Gln Leu Val Glu Ser Gly Gly Leu Val Gln Pro Gly Gly Ser Leu
145                 150                 155                 160

Arg Val Ser Cys Ala Ala Ser Gly Phe Thr Phe Asn Asp Tyr Ile Met
            165                 170                 175

Gly Trp Phe Arg Gln Ala Pro Gly Lys Glu Arg Met Phe Ile Ala Ala
            180                 185                 190

Ile Ser Gly Thr Gly Thr Ile Lys Tyr Tyr Gly Asp Leu Val Arg Gly
            195                 200                 205

Arg Phe Thr Ile Ser Arg Asp Asn Ala Lys Asn Thr Val Tyr Leu Arg
    210                 215                 220

Ile Asp Ser Leu Asn Pro Glu Asp Thr Ala Val Tyr Tyr Cys Ala Ala
225                 230                 235                 240

Arg Gln Asp Tyr Gly Leu Gly Tyr Arg Glu Ser His Glu Tyr Asp Tyr
            245                 250                 255

Trp Gly Gln Gly Thr Gln Val Thr Val Ser Ser Gly Gly Gly Gly Ser
            260                 265                 270

Gly Gly Gly Gly Ser Gly Gly Gly Gly Ser Glu Val Gln Leu Val Glu
        275                 280                 285

Ser Gly Gly Gly Leu Val Gln Ala Gly Asp Ser Leu Arg Leu Ser Cys
    290                 295                 300

Ala Ala Ser Gly Arg Thr Phe Ser Ser Tyr Ala Met Gly Trp Phe Arg
305                 310                 315                 320

Gln Ala Pro Gly Lys Glu Arg Glu Phe Val Ala Ala Ile Ser Trp Ser
            325                 330                 335

Asp Gly Ser Thr Tyr Tyr Ala Asp Ser Val Lys Gly Arg Phe Thr Ile
            340                 345                 350

Ser Arg Asp Asn Ala Lys Asn Thr Val Tyr Leu Gln Met Asn Ser Leu
            355                 360                 365

Lys Pro Glu Asp Thr Ala Val Tyr Tyr Cys Ala Ala Asp Leu Thr Ser
    370                 375                 380

Thr Asn Pro Gly Ser Tyr Ile Tyr Ile Trp Ala Tyr Asp Tyr Trp Gly
385                 390                 395                 400

Gln Gly Thr Gln Val Thr Val Ser Ser
                405

<210> SEQ ID NO 31
<211> LENGTH: 397
<212> TYPE: PRT
<213> ORGANISM: Artificial Sequence
<220> FEATURE:
<223> OTHER INFORMATION: Nanobody

<400> SEQUENCE: 31

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
            115                 120                 125

Gly Gly Gly Ser Gly Gly Gly Ser Glu Val Gln Leu Val Glu Ser Gly
130                 135                 140

Gly Gly Leu Val Gln Pro Gly Gly Ser Leu Arg Val Ser Cys Ala Ala
145                 150                 155                 160

Ser Gly Phe Thr Phe Asn Asp Tyr Ile Met Gly Trp Phe Arg Gln Ala
            165                 170                 175

Pro Gly Lys Glu Arg Met Phe Ile Ala Ala Ile Ser Gly Thr Gly Thr
            180                 185                 190

Ile Lys Tyr Tyr Gly Asp Leu Val Arg Gly Arg Phe Thr Ile Ser Arg
            195                 200                 205

Asp Asn Ala Lys Asn Thr Val Tyr Leu Arg Ile Asp Ser Leu Asn Pro
210                 215                 220

Glu Asp Thr Ala Val Tyr Tyr Cys Ala Ala Arg Gln Asp Tyr Gly Leu
225                 230                 235                 240

Gly Tyr Arg Glu Ser His Glu Tyr Asp Tyr Trp Gly Gln Gly Thr Gln
            245                 250                 255

Val Thr Val Ser Ser Gly Gly Gly Ser Gly Gly Gly Ser Glu Val
            260                 265                 270

Gln Leu Val Glu Ser Gly Gly Leu Val Gln Ala Gly Asp Ser Leu
            275                 280                 285

Arg Leu Ser Cys Ala Ala Ser Gly Arg Thr Phe Ser Ser Tyr Ala Met
            290                 295                 300

Gly Trp Phe Arg Gln Ala Pro Gly Lys Glu Arg Glu Phe Val Ala Ala
305                 310                 315                 320

Ile Ser Trp Ser Asp Gly Ser Thr Tyr Tyr Ala Asp Ser Val Lys Gly
            325                 330                 335

Arg Phe Thr Ile Ser Arg Asp Asn Ala Lys Asn Thr Val Tyr Leu Gln
            340                 345                 350

Met Asn Ser Leu Lys Pro Glu Asp Thr Ala Val Tyr Tyr Cys Ala Ala
            355                 360                 365

Asp Leu Thr Ser Thr Asn Pro Gly Ser Tyr Ile Tyr Ile Trp Ala Tyr
            370                 375                 380

Asp Tyr Trp Gly Gln Gly Thr Gln Val Thr Val Ser Ser
385                 390                 395

<210> SEQ ID NO 32
<211> LENGTH: 408
<212> TYPE: PRT
<213> ORGANISM: Artificial Sequence
<220> FEATURE:
<223> OTHER INFORMATION: Nanobody

<400> SEQUENCE: 32

Glu Val Gln Leu Val Glu Ser Gly Gly Gly Leu Val Gln Ala Gly Gly
1               5                   10                  15

Ser Leu Ser Ile Ser Cys Ala Ala Ser Gly Ser Leu Ser Asn Tyr
            20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
            115                 120                 125

Gly Gly Ser Gly Gly Gly Ser Gly Gly Gly Ser Glu Val Gln
130                 135                 140

Leu Val Glu Ser Gly Gly Gly Leu Val Gln Ala Gly Ser Leu Ser
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
            195                 200                 205

Phe Thr Ile Ser Arg Asp Asn Ala Lys Asn Thr Gly Tyr Leu Gln Met
    210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
            245                 250                 255

Trp Gly Arg Gly Thr Gln Val Thr Val Ser Ser Gly Gly Gly Gly Ser
            260                 265                 270

Gly Gly Gly Gly Ser Gly Gly Gly Ser Glu Val Gln Leu Val Glu
            275                 280                 285

Ser Gly Gly Gly Leu Val Gln Ala Gly Gly Ser Leu Ser Ile Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
            325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
            355                 360                 365

Ala Pro Asp Asp Thr Ala Val Tyr Tyr Cys Gly Ala Gly Thr Pro Leu
            370                 375                 380

Asn Pro Gly Ala Tyr Ile Tyr Asp Trp Ser Tyr Asp Tyr Trp Gly Arg
385                 390                 395                 400

Gly Thr Gln Val Thr Val Ser Ser
                405

<210> SEQ ID NO 33
<211> LENGTH: 127
<212> TYPE: PRT
<213> ORGANISM: Artificial Sequence
<220> FEATURE:
<223> OTHER INFORMATION: Nanobody

<400> SEQUENCE: 33

Glu Val Gln Leu Val Glu Ser Gly Gly Gly Leu Val Gln Pro Gly Asp
1               5                   10                  15

```
Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
            35                  40                  45

Ala Ala Ile Ser Trp Ser Asp Gly Ser Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Arg Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Leu Val Thr Val Ser Ser
            115                 120                 125

<210> SEQ ID NO 34
<211> LENGTH: 127
<212> TYPE: PRT
<213> ORGANISM: Artificial Sequence
<220> FEATURE:
<223> OTHER INFORMATION: Nanobody

<400> SEQUENCE: 34

Asp Val Gln Leu Val Glu Ser Gly Gly Gly Leu Val Gln Pro Gly Asp
 1               5                  10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
            35                  40                  45

Ala Ala Ile Ser Trp Ser Asp Gly Ser Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Arg Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Leu Val Thr Val Ser Ser
            115                 120                 125

<210> SEQ ID NO 35
<211> LENGTH: 127
<212> TYPE: PRT
<213> ORGANISM: Artificial Sequence
<220> FEATURE:
<223> OTHER INFORMATION: Nanobody

<400> SEQUENCE: 35

Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
            35                  40                  45

Ala Ala Ile Ser Trp Ser Asp Gly Ser Thr Tyr Tyr Ala Asp Ser Val
 50                  55                  60

Lys Gly Arg Phe Thr Ile Ser Arg Asp Asn Ala Lys Asn Thr Val Tyr
```

```
                65                  70                  75                  80
Leu Gln Met Asn Ser Leu Arg Pro Glu Asp Thr Ala Val Tyr Tyr Cys
                    85                  90                  95

Ala Ala Asp Leu Thr Ser Thr Asn Pro Gly Ser Tyr Ile Tyr Ile Trp
                100                 105                 110

Ala Tyr Asp Tyr Trp Gly Gln Gly Thr Leu Val Thr Val Ser Ser
                115                 120                 125

<210> SEQ ID NO 36
<211> LENGTH: 127
<212> TYPE: PRT
<213> ORGANISM: Artificial Sequence
<220> FEATURE:
<223> OTHER INFORMATION: Nanobody

<400> SEQUENCE: 36

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
                35                  40                  45

Ala Ala Ile Ser Trp Ser Asp Gly Ser Thr Tyr Tyr Ala Asp Ser Val
                50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                    85                  90                  95

Ala Ala Asp Leu Thr Ser Thr Asn Pro Gly Ser Tyr Ile Tyr Ile Trp
                100                 105                 110

Ala Tyr Asp Tyr Trp Gly Gln Gly Thr Leu Val Thr Val Ser Ser
                115                 120                 125

<210> SEQ ID NO 37
<211> LENGTH: 127
<212> TYPE: PRT
<213> ORGANISM: Artificial Sequence
<220> FEATURE:
<223> OTHER INFORMATION: Nanobody

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
                35                  40                  45

Ala Ala Ile Ser Trp Ser Glu Gly Ser Thr Tyr Tyr Ala Asp Ser Val
                50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                    85                  90                  95

Ala Ala Asp Leu Thr Ser Thr Asn Pro Gly Ser Tyr Ile Tyr Ile Trp
                100                 105                 110

Ala Tyr Asp Tyr Trp Gly Gln Gly Thr Leu Val Thr Val Ser Ser
                115                 120                 125
```

<210> SEQ ID NO 38
<211> LENGTH: 127
<212> TYPE: PRT
<213> ORGANISM: Artificial Sequence
<220> FEATURE:
<223> OTHER INFORMATION: Nanobody

<400> SEQUENCE: 38

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Glu Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Leu Val Thr Val Ser Ser
        115                 120                 125

<210> SEQ ID NO 39
<211> LENGTH: 127
<212> TYPE: PRT
<213> ORGANISM: Artificial Sequence
<220> FEATURE:
<223> OTHER INFORMATION: Nanobody

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Ala Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Leu Val Thr Val Ser Ser
        115                 120                 125

<210> SEQ ID NO 40
<211> LENGTH: 127
<212> TYPE: PRT
<213> ORGANISM: Artificial Sequence
<220> FEATURE:
<223> OTHER INFORMATION: Nanobody

<400> SEQUENCE: 40

Asp Val Gln Leu Val Glu Ser Gly Gly Gly Leu Val Gln Pro Gly Gly

```
            1               5                  10                 15
Ser Leu Arg Leu Ser Cys Ala Ala Ser Gly Arg Thr Phe Ser Ser Tyr
                20                  25                 30

Ala Met Gly Trp Phe Arg Gln Ala Pro Gly Lys Glu Arg Glu Phe Val
        35                  40                 45

Ala Ala Ile Ser Trp Ser Asp Ala Ser Thr Tyr Tyr Ala Asp Ser Val
            50                  55                 60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Thr Ser Thr Asn Pro Gly Ser Tyr Ile Tyr Ile Trp
                100                 105                110

Ala Tyr Asp Tyr Trp Gly Gln Gly Thr Leu Val Thr Val Ser Ser
                115                 120                125
```

<210> SEQ ID NO 41
<211> LENGTH: 411
<212> TYPE: PRT
<213> ORGANISM: Artificial Sequence
<220> FEATURE:
<223> OTHER INFORMATION: Nanobody

<400> SEQUENCE: 41

```
Asp Val Gln Leu Val Glu Ser Gly Gly Gly Leu Val Gln Pro Gly Asp
1               5                   10                  15

Ser Leu Arg Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Thr Ser Thr Asn Pro Gly Ser Tyr Ile Tyr Ile Trp
                100                 105                 110

Ala Tyr Asp Tyr Trp Gly Gln Gly Thr Leu Val Thr Val Ser Ser Gly
                115                 120                 125

Gly Gly Ser Gly Gly Gly Gly Ser Gly Gly Gly Gly Ser Glu Val
        130                 135                 140

Gln Leu Val Glu Ser Gly Gly Gly Leu Val Gln Pro Gly Asp Ser Leu
145                 150                 155                 160

Arg Leu Ser Cys Ala Ala Ser Gly Arg Thr Phe Ser Ser Tyr Ala Met
                165                 170                 175

Gly Trp Phe Arg Gln Ala Pro Gly Lys Glu Arg Glu Phe Val Ala Ala
                180                 185                 190

Ile Ser Trp Ser Asp Gly Ser Thr Tyr Tyr Ala Asp Ser Val Lys Gly
            195                 200                 205

Arg Phe Thr Ile Ser Arg Asp Asn Ala Lys Asn Thr Val Tyr Leu Gln
                210                 215                 220

Met Asn Ser Leu Arg Pro Glu Asp Thr Ala Val Tyr Tyr Cys Ala Ala
225                 230                 235                 240

Asp Leu Thr Ser Thr Asn Pro Gly Ser Tyr Ile Tyr Ile Trp Ala Tyr
```

```
                    245                 250                 255
Asp Tyr Trp Gly Gln Gly Thr Leu Val Thr Val Ser Ser Gly Gly Gly
                260                 265                 270

Gly Ser Gly Gly Gly Ser Gly Gly Gly Ser Glu Val Gln Leu
        275                 280                 285

Val Glu Ser Gly Gly Gly Leu Val Gln Pro Gly Asp Ser Leu Arg Leu
    290                 295                 300

Ser Cys Ala Ala Ser Gly Arg Thr Phe Ser Ser Tyr Ala Met Gly Trp
305                 310                 315                 320

Phe Arg Gln Ala Pro Gly Lys Glu Arg Glu Phe Val Ala Ala Ile Ser
                325                 330                 335

Trp Ser Asp Gly Ser Thr Tyr Tyr Ala Asp Ser Val Lys Gly Arg Phe
                340                 345                 350

Thr Ile Ser Arg Asp Asn Ala Lys Asn Thr Val Tyr Leu Gln Met Asn
                355                 360                 365

Ser Leu Arg Pro Glu Asp Thr Ala Val Tyr Tyr Cys Ala Ala Asp Leu
370                 375                 380

Thr Ser Thr Asn Pro Gly Ser Tyr Ile Tyr Ile Trp Ala Tyr Asp Tyr
385                 390                 395                 400

Trp Gly Gln Gly Thr Leu Val Thr Val Ser Ser
                405                 410

<210> SEQ ID NO 42
<211> LENGTH: 411
<212> TYPE: PRT
<213> ORGANISM: Artificial Sequence
<220> FEATURE:
<223> OTHER INFORMATION: Nanobody

<400> SEQUENCE: 42

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
            35                  40                  45

Ala Ala Ile Ser Trp Ser Asp Gly Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Leu Val Thr Val Ser Ser Gly
        115                 120                 125

Gly Gly Gly Ser Gly Gly Gly Ser Gly Gly Gly Ser Glu Val
    130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Arg Thr Phe Ser Ser Tyr Ala Met
                165                 170                 175

Gly Trp Phe Arg Gln Ala Pro Gly Lys Glu Arg Glu Phe Val Ala Ala
            180                 185                 190

Ile Ser Trp Ser Asp Gly Ser Thr Tyr Tyr Ala Asp Ser Val Lys Gly
```

-continued

```
                195                 200                 205
Arg Phe Thr Ile Ser Arg Asp Asn Ala Lys Asn Thr Val Tyr Leu Gln
210                 215                 220

Met Asn Ser Leu Arg Pro Glu Asp Thr Ala Val Tyr Tyr Cys Ala Ala
225                 230                 235                 240

Asp Leu Thr Ser Thr Asn Pro Gly Ser Tyr Ile Tyr Ile Trp Ala Tyr
                245                 250                 255

Asp Tyr Trp Gly Gln Gly Thr Leu Val Thr Val Ser Ser Gly Gly Gly
                260                 265                 270

Gly Ser Gly Gly Gly Ser Gly Gly Gly Ser Glu Val Gln Leu
            275                 280                 285

Val Glu Ser Gly Gly Gly Leu Val Gln Pro Gly Gly Ser Leu Arg Leu
290                 295                 300

Ser Cys Ala Ala Ser Gly Arg Thr Phe Ser Ser Tyr Ala Met Gly Trp
305                 310                 315                 320

Phe Arg Gln Ala Pro Gly Lys Glu Arg Glu Phe Val Ala Ala Ile Ser
                325                 330                 335

Trp Ser Asp Gly Ser Thr Tyr Tyr Ala Asp Ser Val Lys Gly Arg Phe
                340                 345                 350

Thr Ile Ser Arg Asp Asn Ala Lys Asn Thr Val Tyr Leu Gln Met Asn
                355                 360                 365

Ser Leu Arg Pro Glu Asp Thr Ala Val Tyr Tyr Cys Ala Ala Asp Leu
370                 375                 380

Thr Ser Thr Asn Pro Gly Ser Tyr Ile Tyr Ile Trp Ala Tyr Asp Tyr
385                 390                 395                 400

Trp Gly Gln Gly Thr Leu Val Thr Val Ser Ser
                405                 410

<210> SEQ ID NO 43
<211> LENGTH: 411
<212> TYPE: PRT
<213> ORGANISM: Artificial Sequence
<220> FEATURE:
<223> OTHER INFORMATION: Nanobody

<400> SEQUENCE: 43

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
            35                  40                  45

Ala Ala Ile Ser Trp Ser Glu Gly Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Leu Val Thr Val Ser Ser Gly
            115                 120                 125

Gly Gly Gly Ser Gly Gly Gly Ser Gly Gly Gly Ser Glu Val
        130                 135                 140

Gln Leu Val Glu Ser Gly Gly Gly Leu Val Gln Pro Gly Gly Ser Leu
```

```
                145                 150                 155                 160
        Arg Leu Ser Cys Ala Ala Ser Gly Arg Thr Phe Ser Ser Tyr Ala Met
                        165                 170                 175

Gly Trp Phe Arg Gln Ala Pro Gly Lys Glu Arg Glu Phe Val Ala Ala
                        180                 185                 190

Ile Ser Trp Ser Glu Gly Ser Thr Tyr Tyr Ala Asp Ser Val Lys Gly
                        195                 200                 205

Arg Phe Thr Ile Ser Arg Asp Asn Ala Lys Asn Thr Val Tyr Leu Gln
                        210                 215                 220

Met Asn Ser Leu Arg Pro Glu Asp Thr Ala Val Tyr Tyr Cys Ala Ala
        225                 230                 235                 240

Asp Leu Thr Ser Thr Asn Pro Gly Ser Tyr Ile Tyr Ile Trp Ala Tyr
                        245                 250                 255

Asp Tyr Trp Gly Gln Gly Thr Leu Val Thr Val Ser Ser Gly Gly Gly
                        260                 265                 270

Gly Ser Gly Gly Gly Ser Gly Gly Gly Ser Glu Val Gln Leu
                        275                 280                 285

Val Glu Ser Gly Gly Gly Leu Val Gln Pro Gly Gly Ser Leu Arg Leu
        290                 295                 300

Ser Cys Ala Ala Ser Gly Arg Thr Phe Ser Ser Tyr Ala Met Gly Trp
        305                 310                 315                 320

Phe Arg Gln Ala Pro Gly Lys Glu Arg Glu Phe Val Ala Ala Ile Ser
                        325                 330                 335

Trp Ser Glu Gly Ser Thr Tyr Tyr Ala Asp Ser Val Lys Gly Arg Phe
                        340                 345                 350

Thr Ile Ser Arg Asp Asn Ala Lys Asn Thr Val Tyr Leu Gln Met Asn
                        355                 360                 365

Ser Leu Arg Pro Glu Asp Thr Ala Val Tyr Tyr Cys Ala Ala Asp Leu
                        370                 375                 380

Thr Ser Thr Asn Pro Gly Ser Tyr Ile Tyr Ile Trp Ala Tyr Asp Tyr
        385                 390                 395                 400

Trp Gly Gln Gly Thr Leu Val Thr Val Ser Ser
                        405                 410

<210> SEQ ID NO 44
<211> LENGTH: 411
<212> TYPE: PRT
<213> ORGANISM: Artificial Sequence
<220> FEATURE:
<223> OTHER INFORMATION: Nanobody

<400> SEQUENCE: 44

Asp Val Gln Leu Val Glu Ser Gly Gly Gly Leu Val Gln Pro Gly Gly
        1               5                   10                  15

Ser Leu Arg Leu Ser Cys Ala Ala Ser Gly Arg Thr Phe Ser Ser Tyr
                        20                  25                  30

Ala Met Gly Trp Phe Arg Gln Ala Pro Gly Lys Glu Arg Glu Phe Val
                        35                  40                  45

Ala Ala Ile Ser Trp Ser Asp Ala Ser Thr Tyr Tyr Ala Asp Ser Val
                        50                  55                  60

Lys Gly Arg Phe Thr Ile Ser Arg Asp Asn Ala Lys Asn Thr Val Tyr
        65                  70                  75                  80

Leu Gln Met Asn Ser Leu Arg Pro Glu Asp Thr Ala Val Tyr Tyr Cys
                        85                  90                  95

Ala Ala Asp Leu Thr Ser Thr Asn Pro Gly Ser Tyr Ile Tyr Ile Trp
```

-continued

```
                100                 105                 110
Ala Tyr Asp Tyr Trp Gly Gln Gly Thr Leu Val Thr Val Ser Ser Gly
            115                 120                 125

Gly Gly Ser Gly Gly Gly Ser Gly Gly Gly Ser Glu Val
130                 135                 140

Gln Leu Val Glu Ser Gly Gly Leu Val Gln Pro Gly Gly Ser Leu
145                 150                 155                 160

Arg Leu Ser Cys Ala Ala Ser Gly Arg Thr Phe Ser Ser Tyr Ala Met
                165                 170                 175

Gly Trp Phe Arg Gln Ala Pro Gly Lys Glu Arg Glu Phe Val Ala Ala
                180                 185                 190

Ile Ser Trp Ser Asp Ala Ser Thr Tyr Tyr Ala Asp Ser Val Lys Gly
                195                 200                 205

Arg Phe Thr Ile Ser Arg Asp Asn Ala Lys Asn Thr Val Tyr Leu Gln
                210                 215                 220

Met Asn Ser Leu Arg Pro Glu Asp Thr Ala Val Tyr Tyr Cys Ala Ala
225                 230                 235                 240

Asp Leu Thr Ser Thr Asn Pro Gly Ser Tyr Ile Tyr Ile Trp Ala Tyr
                245                 250                 255

Asp Tyr Trp Gly Gln Gly Thr Leu Val Thr Val Ser Ser Gly Gly Gly
                260                 265                 270

Gly Ser Gly Gly Gly Ser Gly Gly Gly Ser Glu Val Gln Leu
            275                 280                 285

Val Glu Ser Gly Gly Gly Leu Val Gln Pro Gly Gly Ser Leu Arg Leu
            290                 295                 300

Ser Cys Ala Ala Ser Gly Arg Thr Phe Ser Ser Tyr Ala Met Gly Trp
305                 310                 315                 320

Phe Arg Gln Ala Pro Gly Lys Glu Arg Glu Phe Val Ala Ala Ile Ser
                325                 330                 335

Trp Ser Asp Ala Ser Thr Tyr Tyr Ala Asp Ser Val Lys Gly Arg Phe
                340                 345                 350

Thr Ile Ser Arg Asp Asn Ala Lys Asn Thr Val Tyr Leu Gln Met Asn
                355                 360                 365

Ser Leu Arg Pro Glu Asp Thr Ala Val Tyr Tyr Cys Ala Ala Asp Leu
            370                 375                 380

Thr Ser Thr Asn Pro Gly Ser Tyr Ile Tyr Ile Trp Ala Tyr Asp Tyr
385                 390                 395                 400

Trp Gly Gln Gly Thr Leu Val Thr Val Ser Ser
                405                 410
```

<210> SEQ ID NO 45
<211> LENGTH: 411
<212> TYPE: PRT
<213> ORGANISM: Artificial Sequence
<220> FEATURE:
<223> OTHER INFORMATION: Nanobody

<400> SEQUENCE: 45

```
Glu Val Gln Leu Val Glu Ser Gly Gly Gly Leu Val Gln Pro Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
```

```
            50                  55                  60
Lys Gly Arg Phe Thr Ile Ser Arg Asp Asn Ala Lys Asn Thr Val Tyr
 65                  70                  75                  80

Leu Gln Met Asn Ser Leu Arg Pro Glu Asp Thr Ala Val Tyr Tyr Cys
                 85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Leu Val Thr Val Ser Ser Gly
        115                 120                 125

Gly Gly Gly Ser Gly Gly Gly Ser Gly Gly Gly Ser Glu Val
    130                 135                 140

Gln Leu Val Glu Ser Gly Gly Leu Val Gln Pro Gly Asp Ser Leu
145                 150                 155                 160

Arg Leu Ser Cys Ala Ala Ser Gly Arg Thr Phe Ser Tyr Ala Met
                165                 170                 175

Gly Trp Phe Arg Gln Ala Pro Gly Lys Glu Arg Glu Phe Val Ala Ala
            180                 185                 190

Ile Ser Trp Ser Asp Gly Ser Thr Tyr Tyr Ala Asp Ser Val Lys Gly
        195                 200                 205

Arg Phe Thr Ile Ser Arg Asp Asn Ala Lys Asn Thr Val Tyr Leu Gln
    210                 215                 220

Met Asn Ser Leu Arg Pro Glu Asp Thr Ala Val Tyr Tyr Cys Ala Ala
225                 230                 235                 240

Asp Leu Thr Ser Thr Asn Pro Gly Ser Tyr Ile Tyr Ile Trp Ala Tyr
                245                 250                 255

Asp Tyr Trp Gly Gln Gly Thr Leu Val Thr Val Ser Ser Gly Gly Gly
            260                 265                 270

Gly Ser Gly Gly Gly Ser Gly Gly Gly Ser Glu Val Gln Leu
        275                 280                 285

Val Glu Ser Gly Gly Leu Val Gln Pro Gly Asp Ser Leu Arg Leu
    290                 295                 300

Ser Cys Ala Ala Ser Gly Arg Thr Phe Ser Ser Tyr Ala Met Gly Trp
305                 310                 315                 320

Phe Arg Gln Ala Pro Gly Lys Glu Arg Glu Phe Val Ala Ala Ile Ser
                325                 330                 335

Trp Ser Asp Gly Ser Thr Tyr Tyr Ala Asp Ser Val Lys Gly Arg Phe
            340                 345                 350

Thr Ile Ser Arg Asp Asn Ala Lys Asn Thr Val Tyr Leu Gln Met Asn
        355                 360                 365

Ser Leu Arg Pro Glu Asp Thr Ala Val Tyr Tyr Cys Ala Ala Asp Leu
    370                 375                 380

Thr Ser Thr Asn Pro Gly Ser Tyr Ile Tyr Ile Trp Ala Tyr Asp Tyr
385                 390                 395                 400

Trp Gly Gln Gly Thr Leu Val Thr Val Ser Ser
                405                 410

<210> SEQ ID NO 46
<211> LENGTH: 410
<212> TYPE: PRT
<213> ORGANISM: Artificial Sequence
<220> FEATURE:
<223> OTHER INFORMATION: Nanobody

<400> SEQUENCE: 46

Val Gln Leu Val Glu Ser Gly Gly Gly Leu Val Gln Pro Gly Asp Ser
```

```
  1               5                   10                  15
Leu Arg Leu Ser Cys Ala Ala Ser Gly Arg Thr Phe Ser Ser Tyr Ala
                20                  25                  30

Met Gly Trp Phe Arg Gln Ala Pro Gly Lys Glu Arg Glu Phe Val Ala
            35                  40                  45

Ala Ile Ser Trp Ser Asp Gly Ser Thr Tyr Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Ala
                85                  90                  95

Ala Asp Leu Thr Ser Thr Asn Pro Gly Ser Tyr Ile Tyr Ile Trp Ala
            100                 105                 110

Tyr Asp Tyr Trp Gly Gln Gly Thr Leu Val Thr Val Ser Ser Gly Gly
        115                 120                 125

Gly Gly Ser Gly Gly Gly Gly Ser Gly Gly Gly Ser Glu Val Gln
130                 135                 140

Leu Val Glu Ser Gly Gly Gly Leu Val Gln Pro Gly Asp Ser Leu Arg
145                 150                 155                 160

Leu Ser Cys Ala Ala Ser Gly Arg Thr Phe Ser Ser Tyr Ala Met Gly
                165                 170                 175

Trp Phe Arg Gln Ala Pro Gly Lys Glu Arg Glu Phe Val Ala Ala Ile
            180                 185                 190

Ser Trp Ser Asp Gly Ser Thr Tyr Tyr Ala Asp Ser Val Lys Gly Arg
        195                 200                 205

Phe Thr Ile Ser Arg Asp Asn Ala Lys Asn Thr Val Tyr Leu Gln Met
210                 215                 220

Asn Ser Leu Arg Pro Glu Asp Thr Ala Val Tyr Tyr Cys Ala Ala Asp
225                 230                 235                 240

Leu Thr Ser Thr Asn Pro Gly Ser Tyr Ile Tyr Ile Trp Ala Tyr Asp
                245                 250                 255

Tyr Trp Gly Gln Gly Thr Leu Val Thr Val Ser Ser Gly Gly Gly Gly
            260                 265                 270

Ser Gly Gly Gly Gly Ser Gly Gly Gly Ser Glu Val Gln Leu Val
        275                 280                 285

Glu Ser Gly Gly Gly Leu Val Gln Pro Gly Asp Ser Leu Arg Leu Ser
290                 295                 300

Cys Ala Ala Ser Gly Arg Thr Phe Ser Ser Tyr Ala Met Gly Trp Phe
305                 310                 315                 320

Arg Gln Ala Pro Gly Lys Glu Arg Glu Phe Val Ala Ala Ile Ser Trp
                325                 330                 335

Ser Asp Gly Ser Thr Tyr Tyr Ala Asp Ser Val Lys Gly Arg Phe Thr
            340                 345                 350

Ile Ser Arg Asp Asn Ala Lys Asn Thr Val Tyr Leu Gln Met Asn Ser
        355                 360                 365

Leu Arg Pro Glu Asp Thr Ala Val Tyr Tyr Cys Ala Ala Asp Leu Thr
370                 375                 380

Ser Thr Asn Pro Gly Ser Tyr Ile Tyr Ile Trp Ala Tyr Asp Tyr Trp
385                 390                 395                 400

Gly Gln Gly Thr Leu Val Thr Val Ser Ser
                405                 410

<210> SEQ ID NO 47
```

<211> LENGTH: 411
<212> TYPE: PRT
<213> ORGANISM: Artificial Sequence
<220> FEATURE:
<223> OTHER INFORMATION: Nanobody

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Leu Val Thr Val Ser Ser Gly
        115                 120                 125

Gly Gly Gly Ser Gly Gly Gly Ser Gly Gly Gly Gly Ser Glu Val
    130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Arg Thr Phe Ser Ser Tyr Ala Met
                165                 170                 175

Gly Trp Phe Arg Gln Ala Pro Gly Lys Glu Arg Glu Phe Val Ala Ala
            180                 185                 190

Ile Ser Trp Ser Asp Gly Ser Thr Tyr Tyr Ala Asp Ser Val Lys Gly
        195                 200                 205

Arg Phe Thr Ile Ser Arg Asp Asn Ala Lys Asn Thr Val Tyr Leu Gln
    210                 215                 220

Met Asn Ser Leu Arg Pro Glu Asp Thr Ala Val Tyr Tyr Cys Ala Ala
225                 230                 235                 240

Asp Leu Thr Ser Thr Asn Pro Gly Ser Tyr Ile Tyr Ile Trp Ala Tyr
                245                 250                 255

Asp Tyr Trp Gly Gln Gly Thr Leu Val Thr Val Ser Ser Gly Gly Gly
            260                 265                 270

Gly Ser Gly Gly Gly Ser Gly Gly Gly Gly Ser Glu Val Gln Leu
        275                 280                 285

Val Glu Ser Gly Gly Gly Leu Val Gln Pro Gly Gly Ser Leu Arg Leu
    290                 295                 300

Ser Cys Ala Ala Ser Gly Arg Thr Phe Ser Ser Tyr Ala Met Gly Trp
305                 310                 315                 320

Phe Arg Gln Ala Pro Gly Lys Glu Arg Glu Phe Val Ala Ala Ile Ser
                325                 330                 335

Trp Ser Asp Gly Ser Thr Tyr Tyr Ala Asp Ser Val Lys Gly Arg Phe
            340                 345                 350

Thr Ile Ser Arg Asp Asn Ala Lys Asn Thr Val Tyr Leu Gln Met Asn
        355                 360                 365

Ser Leu Arg Pro Glu Asp Thr Ala Val Tyr Tyr Cys Ala Ala Asp Leu
    370                 375                 380
```

```
Thr Ser Thr Asn Pro Gly Ser Tyr Ile Tyr Ile Trp Ala Tyr Asp Tyr
385                 390                 395                 400

Trp Gly Gln Gly Thr Leu Val Thr Val Ser Ser
                405                 410

<210> SEQ ID NO 48
<211> LENGTH: 411
<212> TYPE: PRT
<213> ORGANISM: Artificial Sequence
<220> FEATURE:
<223> OTHER INFORMATION: Nanobody

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Glu Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Leu Val Thr Val Ser Ser Gly
        115                 120                 125

Gly Gly Gly Ser Gly Gly Gly Ser Gly Gly Gly Ser Glu Val
    130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Arg Thr Phe Ser Ser Tyr Ala Met
                165                 170                 175

Gly Trp Phe Arg Gln Ala Pro Gly Lys Glu Arg Glu Phe Val Ala Ala
            180                 185                 190

Ile Ser Trp Ser Glu Gly Ser Thr Tyr Tyr Ala Asp Ser Val Lys Gly
        195                 200                 205

Arg Phe Thr Ile Ser Arg Asp Asn Ala Lys Asn Thr Val Tyr Leu Gln
    210                 215                 220

Met Asn Ser Leu Arg Pro Glu Asp Thr Ala Val Tyr Tyr Cys Ala Ala
225                 230                 235                 240

Asp Leu Thr Ser Thr Asn Pro Gly Ser Tyr Ile Tyr Ile Trp Ala Tyr
                245                 250                 255

Asp Tyr Trp Gly Gln Gly Thr Leu Val Thr Val Ser Ser Gly Gly Gly
            260                 265                 270

Gly Ser Gly Gly Gly Ser Gly Gly Gly Ser Glu Val Gln Leu
    275                 280                 285

Val Glu Ser Gly Gly Gly Leu Val Gln Pro Gly Gly Ser Leu Arg Leu
290                 295                 300

Ser Cys Ala Ala Ser Gly Arg Thr Phe Ser Ser Tyr Ala Met Gly Trp
305                 310                 315                 320

Phe Arg Gln Ala Pro Gly Lys Glu Arg Glu Phe Val Ala Ala Ile Ser
                325                 330                 335
```

```
Trp Ser Glu Gly Ser Thr Tyr Ala Asp Ser Val Lys Gly Arg Phe
            340                 345                 350

Thr Ile Ser Arg Asp Asn Ala Lys Asn Thr Val Tyr Leu Gln Met Asn
            355                 360                 365

Ser Leu Arg Pro Glu Asp Thr Ala Val Tyr Tyr Cys Ala Ala Asp Leu
    370                 375                 380

Thr Ser Thr Asn Pro Gly Ser Tyr Ile Tyr Ile Trp Ala Tyr Asp Tyr
385                 390                 395                 400

Trp Gly Gln Gly Thr Leu Val Thr Val Ser Ser
                405                 410

<210> SEQ ID NO 49
<211> LENGTH: 411
<212> TYPE: PRT
<213> ORGANISM: Artificial Sequence
<220> FEATURE:
<223> OTHER INFORMATION: Nanobody

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Ala Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Leu Val Thr Val Ser Ser Gly
        115                 120                 125

Gly Gly Gly Ser Gly Gly Gly Gly Ser Gly Gly Gly Gly Ser Glu Val
    130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Arg Thr Phe Ser Ser Tyr Ala Met
                165                 170                 175

Gly Trp Phe Arg Gln Ala Pro Gly Lys Glu Arg Glu Phe Val Ala Ala
            180                 185                 190

Ile Ser Trp Ser Asp Ala Ser Thr Tyr Tyr Ala Asp Ser Val Lys Gly
        195                 200                 205

Arg Phe Thr Ile Ser Arg Asp Asn Ala Lys Asn Thr Val Tyr Leu Gln
    210                 215                 220

Met Asn Ser Leu Arg Pro Glu Asp Thr Ala Val Tyr Tyr Cys Ala Ala
225                 230                 235                 240

Asp Leu Thr Ser Thr Asn Pro Gly Ser Tyr Ile Tyr Ile Trp Ala Tyr
                245                 250                 255

Asp Tyr Trp Gly Gln Gly Thr Leu Val Thr Val Ser Ser Gly Gly Gly
            260                 265                 270

Gly Ser Gly Gly Gly Gly Ser Gly Gly Gly Gly Ser Glu Val Gln Leu
        275                 280                 285
```

```
Val Glu Ser Gly Gly Gly Leu Val Gln Pro Gly Gly Ser Leu Arg Leu
        290                 295                 300

Ser Cys Ala Ala Ser Gly Arg Thr Phe Ser Ser Tyr Ala Met Gly Trp
305                 310                 315                 320

Phe Arg Gln Ala Pro Gly Lys Glu Arg Glu Phe Val Ala Ala Ile Ser
                325                 330                 335

Trp Ser Asp Ala Ser Thr Tyr Tyr Ala Asp Ser Val Lys Gly Arg Phe
                340                 345                 350

Thr Ile Ser Arg Asp Asn Ala Lys Asn Thr Val Tyr Leu Gln Met Asn
            355                 360                 365

Ser Leu Arg Pro Glu Asp Thr Ala Val Tyr Tyr Cys Ala Ala Asp Leu
        370                 375                 380

Thr Ser Thr Asn Pro Gly Ser Tyr Ile Tyr Ile Trp Ala Tyr Asp Tyr
385                 390                 395                 400

Trp Gly Gln Gly Thr Leu Val Thr Val Ser Ser
                405                 410

<210> SEQ ID NO 50
<211> LENGTH: 411
<212> TYPE: PRT
<213> ORGANISM: Artificial Sequence
<220> FEATURE:
<223> OTHER INFORMATION: Nanobody

<400> SEQUENCE: 50

Asp Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser Gly
        115                 120                 125

Gly Gly Gly Ser Gly Gly Gly Ser Gly Gly Gly Ser Glu Val
    130                 135                 140

Gln Leu Val Glu Ser Gly Gly Gly Leu Val Gln Ala Gly Asp Ser Leu
145                 150                 155                 160

Arg Leu Ser Cys Ala Ala Ser Gly Arg Thr Phe Ser Ser Tyr Ala Met
                165                 170                 175

Gly Trp Phe Arg Gln Ala Pro Gly Lys Glu Arg Glu Phe Val Ala Ala
            180                 185                 190

Ile Ser Trp Ser Asp Gly Ser Thr Tyr Tyr Ala Asp Ser Val Lys Gly
        195                 200                 205

Arg Phe Thr Ile Ser Arg Asp Asn Ala Lys Asn Thr Val Tyr Leu Gln
    210                 215                 220

Met Asn Ser Leu Lys Pro Glu Asp Thr Ala Val Tyr Tyr Cys Ala Ala
225                 230                 235                 240
```

```
Asp Leu Thr Ser Thr Asn Pro Gly Ser Tyr Ile Tyr Ile Trp Ala Tyr
            245                 250                 255

Asp Tyr Trp Gly Gln Gly Thr Gln Val Thr Val Ser Ser Gly Gly Gly
        260                 265                 270

Gly Ser Gly Gly Gly Gly Ser Gly Gly Gly Ser Glu Val Gln Leu
        275                 280                 285

Val Glu Ser Gly Gly Gly Leu Val Gln Ala Gly Asp Ser Leu Arg Leu
        290                 295                 300

Ser Cys Ala Ala Ser Gly Arg Thr Phe Ser Ser Tyr Ala Met Gly Trp
305                 310                 315                 320

Phe Arg Gln Ala Pro Gly Lys Glu Arg Glu Phe Val Ala Ala Ile Ser
                325                 330                 335

Trp Ser Asp Gly Ser Thr Tyr Tyr Ala Asp Ser Val Lys Gly Arg Phe
                340                 345                 350

Thr Ile Ser Arg Asp Asn Ala Lys Asn Thr Val Tyr Leu Gln Met Asn
            355                 360                 365

Ser Leu Lys Pro Glu Asp Thr Ala Val Tyr Tyr Cys Ala Ala Asp Leu
        370                 375                 380

Thr Ser Thr Asn Pro Gly Ser Tyr Ile Tyr Ile Trp Ala Tyr Asp Tyr
385                 390                 395                 400

Trp Gly Gln Gly Thr Gln Val Thr Val Ser Ser
                405                 410

<210> SEQ ID NO 51
<211> LENGTH: 127
<212> TYPE: PRT
<213> ORGANISM: Artificial Sequence
<220> FEATURE:
<223> OTHER INFORMATION: Nanobody

<400> SEQUENCE: 51

Asp Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Thr Ser Thr Asn Pro Gly Ser Tyr Ile Tyr Ile Trp
            100                 105                 110

Ala Tyr Asp Tyr Trp Gly Gln Gly Thr Gln Val Thr Val Ser Ser
        115                 120                 125

<210> SEQ ID NO 52
<211> LENGTH: 5
<212> TYPE: PRT
<213> ORGANISM: Artificial Sequence
<220> FEATURE:
<223> OTHER INFORMATION: Linker sequence

<400> SEQUENCE: 52

Gly Gly Gly Gly Ser
```

```
1               5

<210> SEQ ID NO 53
<211> LENGTH: 7
<212> TYPE: PRT
<213> ORGANISM: Artificial Sequence
<220> FEATURE:
<223> OTHER INFORMATION: Linker sequence

<400> SEQUENCE: 53

Ser Gly Gly Ser Gly Gly Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Linker sequence

<400> SEQUENCE: 54

Gly Gly Gly Gly Ser Gly Gly Gly Ser
1               5

<210> SEQ ID NO 55
<211> LENGTH: 10
<212> TYPE: PRT
<213> ORGANISM: Artificial Sequence
<220> FEATURE:
<223> OTHER INFORMATION: Linker sequence

<400> SEQUENCE: 55

Gly Gly Gly Gly Ser Gly Gly Gly Gly Ser
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Linker sequence

<400> SEQUENCE: 56

Gly Gly Gly Gly Ser Gly Gly Gly Ser Gly Gly Gly Gly Ser
1               5                   10                  15

<210> SEQ ID NO 57
<211> LENGTH: 18
<212> TYPE: PRT
<213> ORGANISM: Artificial Sequence
<220> FEATURE:
<223> OTHER INFORMATION: Linker sequence

<400> SEQUENCE: 57

Gly Gly Gly Gly Ser Gly Gly Gly Gly Ser Gly Gly Gly Gly Gly
1               5                   10                  15

Gly Ser

<210> SEQ ID NO 58
<211> LENGTH: 20
<212> TYPE: PRT
<213> ORGANISM: Artificial Sequence
<220> FEATURE:
<223> OTHER INFORMATION: Linker sequence

<400> SEQUENCE: 58
```

Gly Gly Gly Gly Ser Gly Gly Gly Gly Ser Gly Gly Gly Ser Gly
1               5                   10                  15

Gly Gly Gly Ser
        20

<210> SEQ ID NO 59
<211> LENGTH: 25
<212> TYPE: PRT
<213> ORGANISM: Artificial Sequence
<220> FEATURE:
<223> OTHER INFORMATION: Linker sequence

<400> SEQUENCE: 59

Gly Gly Gly Gly Ser Gly Gly Gly Gly Ser Gly Gly Gly Ser Gly
1               5                   10                  15

Gly Gly Gly Ser Gly Gly Gly Gly Ser
        20                  25

<210> SEQ ID NO 60
<211> LENGTH: 30
<212> TYPE: PRT
<213> ORGANISM: Artificial Sequence
<220> FEATURE:
<223> OTHER INFORMATION: Linker sequence

<400> SEQUENCE: 60

Gly Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Gly Ser
        20                  25                  30

<210> SEQ ID NO 61
<211> LENGTH: 35
<212> TYPE: PRT
<213> ORGANISM: Artificial Sequence
<220> FEATURE:
<223> OTHER INFORMATION: Linker sequence

<400> SEQUENCE: 61

Gly Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Ser Gly Gly
        20                  25                  30

Gly Gly Ser
        35

<210> SEQ ID NO 62
<211> LENGTH: 15
<212> TYPE: PRT
<213> ORGANISM: Artificial Sequence
<220> FEATURE:
<223> OTHER INFORMATION: Linker sequence

<400> SEQUENCE: 62

Glu Pro Lys Ser Cys Asp Lys Thr His Thr Cys Pro Pro Cys Pro
1               5                   10                  15

<210> SEQ ID NO 63
<211> LENGTH: 24
<212> TYPE: PRT
<213> ORGANISM: Artificial Sequence
<220> FEATURE:
<223> OTHER INFORMATION: Linker sequence

<400> SEQUENCE: 63

Gly Gly Gly Gly Ser Gly Gly Gly Ser Glu Pro Lys Ser Cys Asp Lys
1               5                   10                  15

Thr His Thr Cys Pro Pro Cys Pro
                20

<210> SEQ ID NO 64
<211> LENGTH: 62
<212> TYPE: PRT
<213> ORGANISM: Artificial Sequence
<220> FEATURE:
<223> OTHER INFORMATION: Linker sequence

<400> SEQUENCE: 64

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
                20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro
        50                  55                  60

<210> SEQ ID NO 65
<211> LENGTH: 3
<212> TYPE: PRT
<213> ORGANISM: Artificial Sequence
<220> FEATURE:
<223> OTHER INFORMATION: Linker sequence

<400> SEQUENCE: 65

Ala Ala Ala
1

<210> SEQ ID NO 66
<211> LENGTH: 574
<212> TYPE: PRT
<213> ORGANISM: respiratory syncytial virus

<400> SEQUENCE: 66

Met Glu Leu Pro Ile Leu Lys Ala Asn Ala Ile Thr Thr Ile Leu Ala
1 5 10 15

Ala Val Thr Phe Cys Phe Ala Ser Ser Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Ala Asn Asn Arg Ala Arg Arg Glu Leu Pro
100 105 110

Arg Phe Met Asn Tyr Thr Leu Asn Asn Thr Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Thr Ala Val Ser Lys Val Leu His Leu
145 150 155 160

```
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asp Lys Gln Leu Leu Pro Ile Val Asn
        195                 200                 205
Lys Gln Ser Cys Arg Ile Ser Asn Ile Glu Thr Val Ile Glu Phe Gln
    210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
    290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
    370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Gln Glu Gly
    450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
            500                 505                 510
Leu His His Val Asn Ala Gly Lys Ser Thr Thr Asn Ile Met Ile Thr
        515                 520                 525
Thr Ile Ile Ile Val Ile Ile Val Ile Leu Leu Ser Leu Ile Ala Val
    530                 535                 540
Gly Leu Leu Leu Tyr Cys Lys Ala Arg Ser Thr Pro Val Thr Leu Ser
545                 550                 555                 560
Lys Asp Gln Leu Ser Gly Ile Asn Asn Ile Ala Phe Ser Asn
                565                 570
```

<210> SEQ ID NO 67
<211> LENGTH: 574
<212> TYPE: PRT
<213> ORGANISM: respiratory syncytial virus

<400> SEQUENCE: 67

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

```
Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 68
<211> LENGTH: 574
<212> TYPE: PRT
<213> ORGANISM: respiratory syncytial virus

<400> SEQUENCE: 68

Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
```

-continued

```
                180                 185                 190
Leu Asp Leu Lys Asn Tyr Ile Asn Asn Arg Leu Leu Pro Ile Val Asn
            195                 200                 205

Gln Gln Ser Cys Arg Ile Ser Asn Ile Glu Thr Val Ile Glu Phe Gln
        210                 215                 220

Gln Met Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
        290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
        370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Leu Ile Ala Ile
        530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570
```

AMINO ACID SEQUENCES DIRECTED AGAINST HUMAN RESPIRATORY SYNCYTIAL VIRUS (HRSV) AND POLYPEPTIDES COMPRISING THE SAME FOR THE PREVENTION AND/OR TREATMENT OF RESPIRATORY TRACT INFECTIONS

RELATED APPLICATIONS

This application is a national stage filing under 35 U.S.C. §371 of international application PCT/EP2010/068503, filed Nov. 30, 2010, which claims the benefit under 35 U.S.C. §119(e) of U.S. provisional application Ser. No. 61/264,927, filed Nov. 30, 2009, the disclosure of which is incorporated by reference herein in its entirety.

FIELD OF THE INVENTION

The present invention relates to amino acid sequences that are directed against/and or that can specifically bind (as defined herein) protein F of hRSV, as well as to compounds or constructs, and in particular proteins and polypeptides, that comprise or essentially consist of one or more such amino acid sequences (also referred to herein as "amino acid sequences of the invention", "compounds of the invention", "constructs of the invention" and "polypeptides of the invention", respectively).

The invention also relates to nucleic acids encoding such amino acid sequences and polypeptides (also referred to herein as "nucleic acids of the invention" or "nucleotide sequences of the invention"); to methods for preparing such amino acid sequences and polypeptides; to host cells expressing or capable of expressing such amino acid sequences or polypeptides; to compositions, and in particular to pharmaceutical compositions, that comprise such amino acid sequences, polypeptides, compounds or constructs, nucleic acids and/or host cells; and to uses of such amino acid sequences, polypeptides, compounds or constructs, nucleic acids, host cells and/or compositions, in particular for prophylactic and/or therapeutic purposes, such as the prophylactic and/or therapeutic purposes mentioned herein.

Other aspects, embodiments, advantages and applications of the invention will become clear from the further description herein.

BACKGROUND ART

Human respiratory syncytial virus (hRSV) is a member of the Paramyxoviridae family and is an enveloped virus with two main surface glycoproteins that make the spikes of the virus particle. One of these glycoproteins (protein G) is the attachment protein that mediates binding of the virus to the cell surface. The other glycoprotein (protein F or fusion) mediates fusion of the viral and cell membranes, allowing the entry of the viral nucleocapsid into the cell cytoplasm. Inhibition of the steps mediated by either G or F glycoproteins blocks the initial stages of the infectious cycle and neutralizes virus infectivity. Therefore, antibodies directed against either G or F, and which inhibit their respective activities, may neutralize virus infectivity and may protect against a hRSV infection. The F protein is highly conserved and forms trimeric spikes that undergo conformational changes upon activation.

hRSV is the leading cause of severe lower respiratory tract infections (bronchiolitis and pneumonia) in infants and very young children and causes annual epidemics during the winter months. The virus also causes a substantial disease burden among the elderly and adults with underlying cardiopulmonary disorders and/or immunosuppressive conditions are also at risk of severe hRSV disease. The immune response does not prevent re-infections.

There is no vaccine available to prevent hRSV infections. The only drug product available in the market is a humanized monoclonal antibody (Synagis®) directed against one of the viral glycoproteins (protein F) which is used prophylactically in children that are at a very high risk of suffering a severe hRSV infection. The restricted use of Synagis® is due, at least in part, to the high cost of this product. There is clearly a need for improved and/or cheaper prophylactic and/or therapeutic agents for the prevention and or treatment of infections by hRSV.

SUMMARY OF THE INVENTION

The present invention provides amino acid sequences (also referred to as "amino acid sequence(s) of the invention"), polypeptides (also referred to as "polypeptide(s) of the invention") and therapeutic compounds and compositions that are directed against protein F of hRSV and that have improved prophylactic, therapeutic and/or pharmacological properties, in addition to other advantageous properties (such as, for example, improved ease of preparation and/or reduced costs of goods), compared to the prior art amino acid sequences and antibodies. These improved and advantageous properties will become clear from the further description herein. Without being limiting, the amino acid sequences, polypeptides and therapeutic compounds and compositions provided by the invention may show an improved stability, less immunogenicity, improved binding to protein F of hRSV, improved affinity and/or avidity for protein F of hRSV, improved efficacy and/or potency for neutralizing hRSV (as defined herein), an increased selectivity for protein F of hRSV and/or they may be capable of partially or preferably totally blocking the interaction of protein F of hRSV with the target host cell and/or its membrane. They may be capable of neutralizing hRSV by modulating, inhibiting and/or preventing hRSV infectivity, by modulating, inhibiting and/or preventing hRSV fusion with (the cell membrane of) the target host cell, and/or by modulating, inhibiting and/or prevent hRSV entry in the target host cell (as defined herein). They may be cross reactive with and/or capable of neutralizing different strains of hRSV and/or different hRSV escape mutants.

In an aspect, the present invention provides a number of humanized amino acid sequences that are particularly suited for binding protein F of hRSV. The amino acid sequences of the present invention show reduced immunogenicity upon administration to a human subject compared to prior amino acid sequences (as described in PCT application PCT/EP2009/056975 entitled "Amino acid sequences directed against envelope proteins of a virus and polypeptides comprising the some for the treatment of viral disease" filed by Ablynx N. V. on 5 Jun. 2009). Apart from this and/or in addition, the amino acid sequences of the present invention show increased product stability such as reduced isomerisation of certain amino acids and/or reduced pyroglutamate post-translational modification of the N-terminus compared to the prior amino acid sequences (as described in PCT application PCT/EP2009/056975 entitled "Amino acid sequences directed against envelope proteins of a virus and polypeptides comprising the same for the treatment of viral diseases" filed by Ablynx N. V. on 5 Jun. 2009). In addition, the amino acid sequences of the present invention show other good properties such as e.g. good binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) for protein F of hRSV, good affinity and/or good avidity for protein F of hRSV and/or good efficacy and/or potency for neutralizing hRSV.

Accordingly, in one aspect, the present invention provides amino acid sequences chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:
  i) the amino acid sequence has Praline (Pro, P) at position 14, Arginine (Arg, R) at position 83 and/or Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the amino acid sequence of the invention comprises or essentially consists of SEQ ID NO: 33-40.

In another aspect, the present invention provides a number of sequence optimized amino acid sequences and/or Nanobodies® that show increased stability upon storage during stability studies and that are particularly suited for binding protein F of hRSV. Accordingly, the present invention also provides amino acid sequences chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
  i) the amino acid sequence has Glycine (Gly, G) at position 16, Glutamic acid (Glu, E) at position 54 and/or Alanine (Ala, A) at position 55 (said positions determined according to Kabat numbering); and
  ii) the amino add sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred amino acid sequences of the invention comprise or essentially consist of one of SEQ ID NO's: 35-40.

In another aspect of the present invention, amino acid sequences and/or Nanobodies® are provided chosen from the following:
a) SEQ ID NO's: 34, 36, 38, 40, 51;
b) amino acid sequences that have no more than 3, preferably no more than 2, more preferably no more than 1 amino acid difference with one of SEQ ID NO's: δ 34, 36, 38, 40, 51, provided that:
  i) the amino acid sequence has Aspartic acid (Asp, D) at position 1 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the amino acid sequence and/or Nanobody® of the invention comprises or essentially consists of one of SEQ ID NO's: δ 34, 36, 38, 40, 51.

The amino acid sequences and Nanobodies® provided by the invention are preferably in essentially isolated form (as defined herein), or form part of a protein or polypeptide of the invention (also referred to as "polypeptide of the invention" or "protein of the invention"), which may comprise or essentially consist of one or more amino acid sequences or Nanobodies® of the invention and which may optionally further comprise one or more further amino acid sequences or Nanobodies® (all optionally linked via one or more suitable linkers).

Accordingly, in another aspect, the invention also relates to a protein or polypeptide (also referred to herein as a "polypeptide of the invention", respectively) that comprises or essentially consists of one or more amino acid sequences and/or Nanobodies® of the invention (or suitable fragments thereof).

For example, and without limitation, the one or more amino acid sequences and/or Nanobodies® of the invention may be used as a binding unit in such a protein or polypeptide, so as to provide a monovalent, multivalent or multiparatopic polypeptide of the invention, respectively, all as described herein. The present invention thus also relates to a polypeptide which is a monovalent construct comprising or essentially consisting of an amino acid sequence or a Nanobody® of the invention. The present invention thus also relates to a polypeptide which is a multivalent polypeptide, such as e.g. a bivalent or trivalent polypeptide. The present invention also relates to a polypeptide which is a multiparatopic polypeptide, such as e.g. a biparatopic or triparatopic polypeptide.

In a preferred aspect, the invention provides a multivalent, preferably a bivalent or trivalent polypeptide comprising or essentially consisting of at least two amino acid sequences and/or Nanobodies® of the invention (as described above).

In one aspect, the invention provides a multivalent, preferably a bivalent or trivalent polypeptide comprising or essentially consisting of at least two or at least three amino acid sequences or Nanobodies® chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:
  i) the amino acid sequence has Proline (Pro, P) at position 14, Arginine (Arg, R) at position 83 and/or Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least two (preferably identical) amino acid sequences or Nanobodies® chosen from the group consisting of SEQ ID NO's: 33-40.

In another aspect, the invention provides a multivalent, preferably a bivalent or trivalent polypeptide comprising or essentially consisting of at least two amino acid sequences or Nanobodies® chosen from the following:
- a) SEQ ID NO's: 35-40;
- b) amino acid sequences that have no more than 3, preferably no more than 2, more preferably no more than 1 amino acid difference with one of SEQ ID NO's: 35-40, provided that:
  - i) the amino acid sequence has Glycine (Glu, G) at position 16, Glutamic acid (Glu, E) at position 54 and/or Alanine (Ala, A) at position 55 (said positions determined according to Kabat numbering); and
  - ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least two (preferably identical) amino acid sequences or Nanobodies® chosen from the group consisting of SEQ ID NO's: 35-40.

In another preferred aspect, the invention provides a multivalent, preferably a trivalent polypeptide comprising or essentially consisting of at least three amino acid sequences or Nanobodies® chosen from the following:
- a) SEQ ID NO's: 33-40;
- b) amino acid sequences that have no more than 3, preferably no more than 2, more preferably no more than 1 amino acid difference with one of SEQ ID NO's: 33-40, provided that:
  - i) the amino acid sequence has Proline (Pro, P) at position 14, Arginine (Arg, R) at position 83 and/or Leucine (Leu, L) at position 108 (said positions determined according to Kabat numbering); and
  - ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least three (preferably identical) amino acid sequences or Nanobodies® chosen from the group consisting of SEQ ID NO's: 33-40.

In another preferred aspect, the invention provides a multivalent, preferably a trivalent polypeptide comprising or essentially consisting of at least three amino acid sequences or Nanobodies® chosen from the following:
- a) SEQ ID NO's: 35-40;
- b) amino acid sequences that have no more than 3, preferably no more than 2, more preferably no more than 1 amino acid difference with one of SEQ ID NO's: 35-40, provided that:
  - i) the amino acid sequence has Glycine (Gly, G) at position 16, Glutamic acid (Glu, E) at position 54 and/or Alanine (Ala, A) at position 55 (said positions determined according to Kabat numbering); and
  - ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least three (preferably identical) amino acid sequences or Nanobodies® chosen from the group consisting of SEQ ID NO's: 35-40.

A preferred multivalent polypeptide of the invention comprises or essentially consists of two or three amino acid sequences or Nanobodies® with SEQ ID NO: 33. Another preferred multivalent polypeptide of the invention comprises or essentially consists of two or three amino acid sequences or Nanobodies® with SEQ ID NO: 35. Another preferred multivalent polypeptide of the invention comprises or essentially consists of two or three amino acid sequences or Nanobodies® with SEQ ID NO: 37. Another preferred multivalent polypeptide of the invention comprises or essentially consists of two or three amino acid sequences or Nanobodies® with SEQ ID NO: 39.

In another aspect, the invention provides a multivalent, preferably a bivalent or trivalent polypeptide comprising or essentially consisting of at least one amino acid sequence or Nanobody® chosen from the following:
- a) SEQ ID NO's: 34, 36, 38, 40, 51;
- b) amino acid sequences that have no more than 3, preferably no more than 2, more preferably no more than 1 amino acid difference with one of SEQ ID NO's: 34, 36, 38, 40, 51, provided that:
  - i) the amino acid sequence has a Aspartic acid (Asp, D) at position 1 (said position determined according to Kabat numbering); and
  - ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least one amino acid sequence or Nanobody® chosen from the group consisting of SEQ ID NO's: 34, 36, 38, 40, 51.

In another preferred aspect, the invention provides a multivalent, preferably a trivalent polypeptide comprising or essentially consisting of at least one amino acid sequence or Nanobody® chosen from the following:
- a) SEQ ID NO's: 34, 36, 38, 40, 51;
- b) amino acid sequences that have no more than 3, preferably no more than 2, more preferably no more than 1 amino acid difference with one of SEQ ID NO's: 34, 36, 38, 40, 51, provided that:
  - i) the amino acid sequence has a Aspartic acid (Asp, D) at position 1 (said position determined according to Kabat numbering); and
  - ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least one amino acid sequence or Nanobody chosen from the group consisting of SEQ ID NO's: 34, 36, 38, 40, 51. A preferred multivalent polypeptide of the invention comprises or essentially consists of one amino acid sequence or Nanobody with SEQ ID NO: 34 and two amino acid sequences or Nanobodies® with SEQ ID NO: 33. Another preferred multivalent polypeptide of the invention comprises or essentially consists of one amino acid sequence or Nanobody with SEQ ID NO: 36 and two amino acid sequences or Nanobodies® with SEQ ID NO: 35. Another preferred multivalent polypeptide of the invention comprises or essentially consists of one amino acid sequence or Nanobody with SEQ ID NO: 38 and two amino acid sequences or Nanobodies® with SEQ ID NO: 37. Another preferred multivalent polypeptide of the invention comprises or essentially consists of one amino acid sequence or Nanobody with SEQ ID NO: 40 and two amino acid sequences or Nanobodies® with SEQ ID NO: 39. Another preferred multivalent polypeptide of the invention comprises or essentially consists of one amino acid sequence or Nanobody with SEQ ID NO: 51 and two amino acid sequences or Nanobodies® with SEQ ID NO: 16.

In another preferred aspect, the invention provides a trivalent polypeptide chosen from the following polypeptides:
a) SEQ ID NO's: 41-49;
b) polypeptides that have no more than 3, preferably no more than 2, more preferably no more than 1 amino acid difference with one of SEQ ID NO's: 41-49, provided that:
  i) the amino acid sequence or Nanobody® encompassed in said polypeptide has Proline (Pro, P) at position 14, Arginine (Arg, R) at position 83 and/or Leucine (Leu, L) at position 108 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Preferred trivalent polypeptides of the invention comprise or essentially consist of one of SEQ ID NO's: 41-49.

In another preferred aspect, the invention provides a trivalent polypeptide chosen from the following polypeptides:
a) SEQ ID NO's: 42, 43, 44, 47, 48, 49;
b) polypeptides that have no more than 3, preferably no more than 2, more preferably no more than 1 amino acid difference with one of SEQ ID NO's: 42, 43, 44, 47, 48, 49, provided that:
  i) the amino acid sequence or Nanobody® encompassed in said polypeptide has Glycine (Gly, G) at position 16, Glutamic acid (Glu, E) at position 54 and/or Alanine (Ala, A) at position 55 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Preferred trivalent polypeptides of the invention comprise or essentially consist of one of SEQ ID NO's: 42, 43, 44, 47, 48, 49.

In another preferred aspect, the invention provides a trivalent polypeptide chosen from the following polypeptides:

a) SEQ ID NO's: 41-44, and 50;
b) polypeptides that have no more than 3, preferably no more than 2, more preferably no more than 1 amino acid difference with one of SEQ ID NO's: 41-44, and 50, provided that:
  i) the first amino acid sequence or Nanobody® encompassed in said polypeptide has Aspartic add (Asp, D) at position 1 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the amino acid sequence without the 3, 2 or 1 amino acid difference.

Preferred trivalent polypeptides of the invention comprise or essentially consist of one of SEQ ID NO's: 41-44, and 50.

Polypeptides with these sequences show advantageous properties for use as prophylactic, therapeutic and/or pharmacologically active agents such as e.g. improved stability and less immunogenicity compared to the prior polypeptides (e.g. as described in PCT application PCT/EP2009/056975 entitled "Amino acid sequences directed against envelope proteins of a virus and polypeptides comprising the same for the treatment of viral diseases" filed by Ablynx N. V. on 5 Jun. 2009). In addition, these polypeptides show good binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), good affinity and/or good avidity for protein F of hRSV and/or good efficacy and/or potency for neutralizing hRSV.

The invention further relates to a compounds or constructs, and in particular a proteins or polypeptides (also referred to herein as a "compound(s) of the invention") that comprises or essentially consists of one or more amino acid sequences, Nanobodies® and/or polypeptides of the invention (or suitable fragments thereof), and optionally further comprises one or more other groups, residues, moieties or binding units. As will become clear to the skilled person from the further disclosure herein, such further groups, residues, moieties, binding units or amino acid sequences may or may not provide further functionality to the amino acid sequence, Nanobody® or polypeptide of the invention (and/or to the compound or construct in which it is present) and may or may not modify the properties of the amino acid sequence, Nanobody® and/or polypeptide of the invention.

It is also within the scope of the invention to use parts, fragments, analogs, mutants, variants, alleles and/or derivatives of the amino acid sequences and/or polypeptides of the invention, and/or to use proteins or polypeptides comprising or essentially consisting of one or more of such parts, fragments, analogs, mutants, variants, alleles and/or derivatives, as long as these are suitable for the uses envisaged herein. Such parts, fragments, analogs, mutants, variants, alleles and/or derivatives will usually contain (at least part of) a functional antigen-binding site for binding against antigenic site II on protein F of hRSV; and more preferably will be capable of specific binding to antigenic site II on protein F of hRSV, and even more preferably capable of binding to antigenic site II on protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Such parts, fragments, analogs, mutants, variants, alleles and/or derivatives will usually also have a hRSV neutralization efficacy and/or potency as defined herein. Some non-limiting examples of such parts, fragments, analogs, mutants, variants, alleles, derivatives, proteins and/or polypeptides will become clear from the further description herein. Additional fragments or polypeptides of the invention may also be provided by suitably combining (i.e. by linking or genetic fusion) one or more (smaller) parts or fragments as described herein.

The invention also relates to nucleic acids or nucleotide sequences that encode an amino acid sequence of the invention, a Nanobody® of the invention and/or a polypeptide of the invention (or a suitable fragment thereof). Such a nucleic acid will also be referred to herein as "nucleic acid(s) of the invention" and may for example be in the form of a genetic construct, as further described herein. Accordingly, the present invention also relates to a nucleic acid or nucleotide sequence that is in the form of a genetic construct.

The invention further relates to a host or host cell that expresses (or that under suitable circumstances is capable of expressing) an amino acid sequence of the invention, a Nanobody® of the invention, a polypeptide of the invention and/or a compound or construct of the invention; and/or that contains a nucleic acid of the invention. Some preferred but non-limiting examples of such hosts or host cells will become clear from the further description herein.

The invention further relates to a product or composition containing or comprising at least one amino acid sequence of the invention (or a suitable fragment thereof), at least one Nanobody® of the invention, at least one polypeptide of the invention, at least one compound or construct of the invention, at least one monovalent construct of the invention and/or at least one nucleic acid of the invention, and optionally one or more further components of such compositions known per se, i.e. depending on the intended use of the composition. Such a product or composition may for example be a pharmaceutical composition (as described herein) or a veterinary composition. Some preferred but non-limiting examples of such products or compositions will become clear from the further description herein.

The invention further relates to methods far preparing the amino acid sequences, Nanobodies®, polypeptides, nucleic acids, host cells, products and compositions described herein.

The invention further relates to applications and uses of the amino acid sequences, Nanobodies®, polypeptides, compounds, nucleic acids, host cells, products and compositions described herein, as well as to methods for the prevention and/or treatment of respiratory tract infection caused by hRSV. Some preferred but non-limiting applications and uses will become clear from the further description herein.

The amino acid sequences, Nanobodies®, polypeptides, compounds and compositions of the present invention can generally be used to block the interaction of protein F of hRSV with the target host cell and/or its membrane, to neutralize hRSV (different hRSV strains and/or escape mutants), to modulate, inhibit and/or prevent hRSV infectivity (of different hRSV strains and/or escape mutants), to modulate, inhibit and/or prevent fusion (of different hRSV strains and/or escape mutants) with (the cell membrane of) the target host cell and/or to modulate, inhibit and/or prevent hRSV entry in the target host cell (of different hRSV strains and/or escape mutants).

As such, the amino acid sequences, Nanobodies®, polypeptides, compounds and compositions of the present invention can be used for the prevention and/or treatment of diseases and disorders associated with hRSV infection. Examples of such diseases and disorders associated with hRSV infection will be clear to the skilled person based on the disclosure herein, and for example include the following diseases and disorders: respiratory illness, upper respiratory tract infection, lower respiratory tract infection, bronchiolitis (inflammation of the small airways in the lung), pneumonia, dyspnea, cough, (recurrent) wheezing and asthma.

Accordingly, the present invention also relates to a method for the prevention and/or treatment of respiratory illness, upper respiratory tract infection, lower respiratory tract infection, bronchiolitis (inflammation of the small airways in the lung), pneumonia, dyspnea, cough, (recurrent) wheezing and/or asthma caused by hRSV, said method comprising administering, to a subject in need thereof, a pharmaceutically active amount of at least one amino acid sequence of the invention, Nanobody® of the invention, polypeptide of the invention, compound or construct of the invention or monovalent construct of the invention, or a composition of the invention.

The invention also relates to the use of an amino acid sequence of the invention, a Nanobody® of the invention, a polypeptide of the invention, a compound or construct of the invention or a monovalent construct of the invention in the preparation of a pharmaceutical composition for the prevention and/or treatment of respiratory illness, upper respiratory tract infection, lower respiratory tract infection, bronchiolitis (inflammation of the small airways in the lung), pneumonia, dyspnea, cough, (recurrent) wheezing and/or asthma; and/or for use in one or more of the methods described herein.

The invention also relates to an amino acid sequence of the invention, a Nanobody® of the invention, a polypeptide of the invention, a compound or construct of the invention or monovalent construct of the invention for prevention and/or treatment of respiratory illness, upper respiratory tract infection, lower respiratory tract infection, bronchiolitis (inflammation of the small airways in the lung), pneumonia, dyspnea, cough, (recurrent) wheezing and/or asthma.

Other applications and uses of the amino acid sequences, Nanobodies®, polypeptides and compounds of the invention will become clear to the skilled person from the further disclosure herein.

DETAILED DESCRIPTION OF THE INVENTION

Figure 1A:
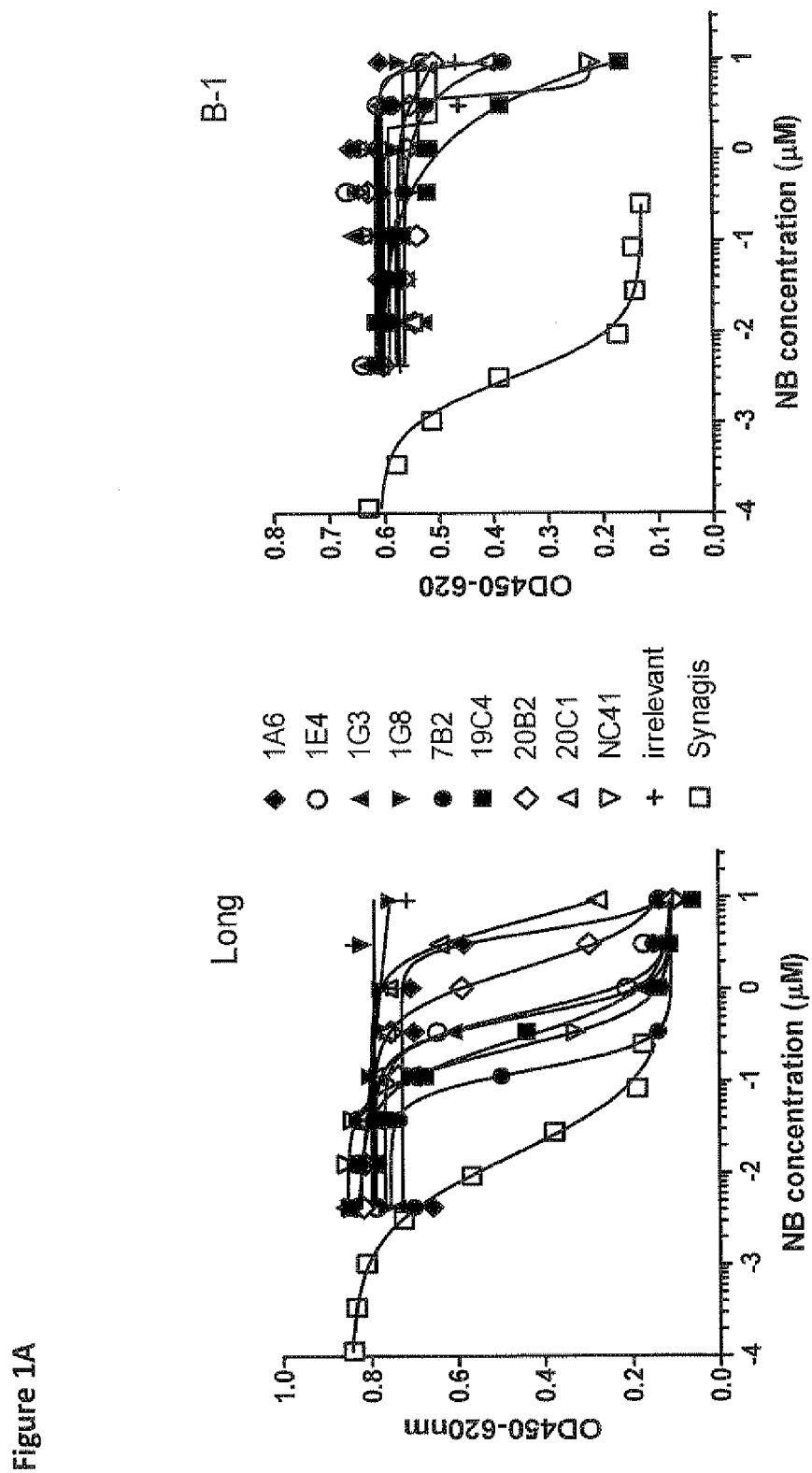
FIG. 1: depicts the neutralization of RSV LM-2 Long and B-1 strains by Nanobodies.

In the present description, examples and claims:
a) Unless indicated or defined otherwise, all terms used have their usual meaning in the art, which will be clear to the skilled person. Reference is for example made to the standard handbooks mentioned in paragraph a) on page 46 of WO 08/020,079.
b) Unless indicated otherwise, the terms "immunoglobulin sequence", "sequence", "nucleotide sequence" and "nucleic acid" are as described in paragraph b) on page 46 of WO 08/020,079.
c) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, 5106-12, Gonzales et al., Tumour Biol., 2005, 26(1), 31-43, which describe techniques for protein engineering, such as affinity maturation and other techniques for improving the specificity and other desired properties of proteins such as immunoglobulins.

d) Amino acid residues will be indicated according to the standard three-letter or one-letter amino acid code. Reference is made to Table A-2 on page 48 of WO 08/020,079.

e) When a nucleotide sequence or amino acid sequence is said to "comprise" another nucleotide sequence or amino acid sequence, respectively, or to "essentially consist of" another nucleotide sequence or amino acid sequence, this has the meaning given in paragraph i) on pages 51-52 of WO 08/020,079.

f) The term "in essentially isolated form" has the meaning given to it in paragraph on pages 52 and 53 of WO 08/020,079.

g) The terms "domain" and "binding domain" have the meanings given to it in paragraph k) on page 53 of WO 08/020,079.

h) The terms "antigenic determinant" and "epitope", which may also be used interchangeably herein, have the meanings given to it in paragraph l) on page 53 of WO 08/020,079.

i) As further described in paragraph m) on page 53 of WO 08/020,079, an amino acid sequence (such as a Nanobody®, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

j) The term "specificity" has the meaning given to it in paragraph n) on pages 53-56 of WO 08/020,079; and as mentioned therein refers to the number of different types of antigens or antigenic determinants to which a particular antigen-binding molecule or antigen-binding protein (such as a Nanobody® or a polypeptide of the invention) molecule can bind. The specificity of an antigen-binding protein can be determined based on affinity and/or avidity, as described on pages 53-56 of WO 08/020,079 (incorporated herein by reference), which also describes some preferred techniques for measuring binding between an antigen-binding molecule (such as a Nanobody® or polypeptide of the invention) and the pertinent antigen. Typically, antigen-binding proteins (such as the amino acid sequences, Nanobodies® and/or polypeptides of the invention) will bind to their antigen with a dissociation constant ($K_D$) of $10^{-5}$ to $10^{12}$ moles/liter or less, and preferably $10^{-7}$ to $10^{12}$ moles/liter or less and more preferably $10^8$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ M$^{-1}$) liters/mol is generally considered to indicate non-specific binding. Preferably, a monovalent immunoglobulin sequence of the invention will bind to the desired antigen with an affinity less than 500 nM, preferably less than 200 nM, more preferably less than 10 nM, such as e.g. between 10 and 5 nM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein. As will be clear to the skilled person, and as described on pages 53-56 of WO 08/020,079, the dissociation constant may be the actual or apparent dissociation constant. Methods for determining the dissociation constant will be clear to the skilled person, and for example include the techniques mentioned on pages 53-56 of WO 08/020,079.

k) The half-life of an amino add sequence, compound or polypeptide of the invention can generally be defined as described in paragraph o) on page 57 of WO 08/020,079 and as mentioned therein refers to the time taken for the serum concentration of the amino acid sequence, compound or polypeptide to be reduced by 50%, in vivo, for example due to degradation of the amino acid sequence, compound or polypeptide and/or clearance or sequestration of the amino acid sequence, compound or polypeptide by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 08/020,079. As also mentioned in paragraph o) on page 57 of WO 08/020,079, the half-life can be expressed using parameters such as the t1/2-alpha, t1/2-beta and the area under the curve (AUC). Reference is for example made to the Experimental Part below, as well as to the standard handbooks, such as Kenneth, A et al: Chemical Stability of Pharmaceuticals: A Handbook for Pharmacists and Peters et al, Pharmacokinetic analysis: A Practical Approach (1996). Reference is also made to "Pharmacokinetics", M Gibaldi & D Perron, published by Marcel Dekker, 2nd Rev. edition (1982). The terms "increase in half-life" or "increased half-life" as also as defined in paragraph o) on page 57 of WO 08/020,079 and in particular refer to an increase in the t1/2-beta, either with or without an increase in the t1/2-alpha and/or the AUC or both.

l) In respect of a target or antigen, the term "interaction site" on the target or antigen means a site, epitope, antigenic determinant, part, domain or stretch of amino acid residues on the target or antigen that is a site for binding to a receptor or other binding partner, a catalytic site, a cleavage site, a site for allosteric interaction, a site involved in multimerization (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signalling, biological mechanism or biological effect in which the target or antigen is involved) is modulated (as defined herein).

m) An amino acid sequence or polypeptide is said to be "specific for" a first target or antigen compared to a second target or antigen when is binds to the first antigen with an affinity (as described above, and suitably expressed as a $K_D$ value, $K_A$ value, $K_{off}$ rate and/or K, rate) that is at least 10 times, such as at least 100 times, and preferably at least 1000 times, and up to 10000 times or more better than the affinity with which said amino acid sequence or polypeptide binds to the second target or antigen. For example, amino acid sequence or polypeptide may bind to the first target or antigen with a $K_D$ value that is at least 10 times less, such as at least 100 times less, and preferably at least 1000 times less, such as 10.000 times less or even less than that, than the $K_D$ with which said amino acid sequence or polypeptide binds to the second target or antigen. Preferably, when an amino acid sequence or polypeptide is "specific for" a first target or antigen compared to a second target or antigen, it is directed against (as defined herein) said first target or antigen, but not directed against said second target or antigen.

n) The terms "(cross)-block", "(cross)-blocked" and "(cross)-blocking" are used interchangeably herein to mean the ability of an amino acid sequence or other binding agent (such as a polypeptide of the invention) to interfere with the binding of other amino acid sequences or binding agents of the invention to a given target. The extent to which an amino acid sequence or other binding agents of the invention is able to interfere with the binding of another to the target, and therefore whether it can be said to cross-block according to the invention, can be determined using competition binding assays. One particularly suitable quantitative cross-blocking assay uses a Biacore machine which can measure the extent of interactions using surface plasmon resonance technology. Another suitable quantitative cross-blocking assay uses an ELISA-based approach to measure competition between amino acid sequences or other binding agents in terms of their binding to the target.

The following generally describes a suitable Biacore assay for determining whether an amino acid sequence or other binding agent cross-blocks or is capable of cross-blocking according to the invention. It will be appreciated that the assay can be used with any of the amino acid sequences or other binding agents described herein. The Biacore machine (for example the Biacore 3000) is operated in line with the manufacturer's recommendations. Thus in one cross-blocking assay, the target protein is coupled to a CM5 Biacore chip using standard amine coupling chemistry to generate a surface that is coated with the target. Typically 200-800 resonance units of the target would be coupled to the chip (an amount that gives easily measurable levels of binding but that is readily saturable by the concentrations of test reagent being used). Two test amino acid sequences (termed A* and B*) to be assessed for their ability to cross-block each other are mixed at a one to one molar ratio of binding sites in a suitable buffer to create the test mixture. When calculating the concentrations on a binding site basis the molecular weight of an amino acid sequence is assumed to be the total molecular weight of the amino acid sequence divided by the number of target binding sites on that amino acid sequence. The concentration of each amino acid sequence in the test mix should be high enough to readily saturate the binding sites for that amino acid sequence on the target molecules captured on the Biacore chip. The amino acid sequences in the mixture are at the same molar concentration (on a binding basis) and that concentration would typically be between 1.00 and 1.5 micromolar (on a binding site basis). Separate solutions containing A* alone and B* alone are also prepared. A* and B* in these solutions should be in the same buffer and at the same concentration as in the test mix. The test mixture is passed over the target-coated Biacore chip and the total amount of binding recorded. The chip is then treated in such a way as to remove the bound amino acid sequences without damaging the chip-bound target. Typically this is done by treating the chip with 30 mM HCl for 60 seconds. The solution of A* alone is then passed over the target-coated surface and the amount of binding recorded. The chip is again treated to remove all of the bound amino acid sequences without damaging the chip-bound target. The solution of B* alone is then passed over the target-coated surface and the amount of binding recorded. The maximum theoretical binding of the mixture of A* and B* is next calculated, and is the sum of the binding of each amino acid sequence when passed over the target surface alone. If the actual recorded binding of the mixture is less than this theoretical maximum then the two amino acid sequences are cross-blocking each other. Thus, in general, a cross-blocking amino acid sequence or other binding agent according to the invention is one which will bind to the target in the above Biacore cross-blocking assay such that during the assay and in the presence of a second amino acid sequence or other binding agent of the invention the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two amino acid sequences or binding agents in combination. The Biacore assay described above is a primary assay used to determine if amino acid sequences or other binding agents cross-block each other according to the invention. On rare occasions particular amino acid sequences or other binding agents may not bind to a target coupled via amine chemistry to a CM5 Biacore chip (this usually occurs when the relevant binding site on the target is masked or destroyed by the coupling to the chip). In such cases cross-blocking can be determined using a tagged version of the target, for example a N-terminal His-tagged version. In this particular format, an anti-His amino acid sequence would be coupled to the Biacore chip and then the His-tagged target would be passed over the surface of the chip and captured by the anti-His amino acid sequence. The cross blocking analysis would be carried out essentially as described above, except that after each chip regeneration cycle, new His-tagged target would be loaded back onto the anti-His amino acid sequence coated surface. In addition to the example given using N-terminal His-tagged target, C-terminal His-tagged target could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

The following generally describes an ELISA assay for determining whether an amino acid sequence or other binding agent directed against a target cross-blocks or is capable of cross-blocking as defined herein. It will be appreciated that the assay can be used with any of the amino acid sequences (or other binding agents such as polypeptides of the invention) described herein. The general principal of the assay is to have an amino acid sequence or binding agent that is directed against the target coated onto the wells of an ELISA plate. An excess amount of a second, potentially cross-blocking, anti-target amino acid sequence is added in solution (i.e. not bound to the ELISA plate). A limited amount of the target is then added to the wells. The coated amino acid sequence and the amino acid sequence in solution compete for binding of the limited number of target molecules. The plate is washed to remove excess target that has not been bound by the coated amino acid sequence and to also remove the second, solution phase amino acid sequence as well as any complexes formed between the second, solution phase amino acid sequence and target. The amount of bound target is then measured using a reagent that is appropriate to detect the target. An amino acid sequence in solution that is able to cross-block the coated amino acid sequence will be able to cause a decrease in the number of target molecules that the coated amino acid sequence can bind relative to the number of target molecules that the coated amino acid sequence can bind in the absence of the second, solution phase, amino acid sequence. In the instance where the first amino acid sequence, e.g. an Ab-X, is chosen to be the immobilized amino acid sequence, it is coated onto the wells of the ELISA plate, after which the plates are blocked with a suitable blocking solution to minimize non-specific binding of reagents that are subsequently added. An excess amount of the second amino acid sequence, i.e. Ab-Y, is then added to the ELISA plate such that the moles of Ab-Y target binding sites per well are at least 10 fold higher than the moles of Ab-X target binding sites that were used, per well, during the coating of the ELISA plate. Target is then added such that the moles of target added per well are at least 25-fold lower than the moles of Ab-X target binding sites that were used for coating each well. Following a suitable incubation period the ELISA plate is washed and a reagent for detecting the target is added to measure the amount of target specifically bound by the coated anti-target amino acid sequence (in this case Ab-X). The background signal for the assay is defined as the signal obtained in wells with the coated amino acid sequence (in this case Ab-X), second solution phase amino acid sequence (in this case Ab-Y), target buffer only (i.e. without target) and target detection reagents. The positive control signal for the assay is defined as the signal obtained in wells with the coated amino acid sequence (in this case Ab-X), second solution phase amino acid sequence buffer only (i.e. without second solution phase amino acid sequence), target and target detection reagents. The ELISA assay may be run in such a manner so as to have the positive control signal be at least 6 times the background signal. To avoid any artefacts (e.g. significantly different affinities between Ab-X and Ab-Y for the target) resulting from the choice of which amino acid sequence to use as the coating amino acid sequence and which to use as the second (competitor) amino acid sequence, the cross-blocking assay may to be run in two formats: 1) format 1 is where Ab-X is the amino acid sequence that is coated onto the ELISA plate and Ab-Y is the competitor amino acid sequence that is in solution and 2) format 2 is where Ab-Y is the amino acid sequence that is coated onto the ELISA plate and Ab-X is the competitor amino acid sequence that is in solution. Ab-X and Ab-Y are defined as cross-blocking if, either in format 1 or in format 2, the solution phase anti-target amino add sequence is able to cause a reduction of between 60% and 100%, specifically between 70% and 100%, and more specifically between 80% and 100%, of the target detection signal {i.e. the amount of target bound by the coated amino acid sequence) as compared to the target detection signal obtained in the absence of the solution phase anti-target amino acid sequence (i.e. the positive control wells).

o) An amino acid sequence is said to be "cross-reactive" for two different antigens or antigenic determinants (such as e.g. serum albumin from two different species of mammal, such as e.g. human serum albumin and cyno serum albumin, such as e.g. protein F of different strains of hRSV, such as e.g. protein F of different escape mutants of hRSV) if it is specific for (as defined herein) both these different antigens or antigenic determinants.

p) As further described herein, the total number of amino acid residues in a Nanobody® can be in the region of 110-120, is preferably 112-115, and is most preferably 113. It should however be noted that parts, fragments, analogs or derivatives (as further described herein) of a Nanobody® are not particularly limited as to their length and/or size, as long as such parts, fragments, analogs or derivatives meet the further requirements outlined herein and are also preferably suitable for the purposes described herein.

q) As further described in paragraph q) on pages 58 and 59 of WO 08/020,079 (incorporated herein by reference), the amino acid residues of a Nanobody® are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, J. Immunol. Methods 2000 Jun. 23; 240 (1-2): 185-195 (see for example FIG. 2 of this publication), and accordingly FR1 of a Nanobody® comprises the amino acid residues at positions 1-30, CDR1 of a Nanobody® comprises the amino acid residues at positions 31-35, FR2 of a Nanobody® comprises the amino acids at positions 36-49, CDR2 of a Nanobody® comprises the amino acid residues at positions 50-65, FR3 of a Nanobody® comprises the amino acid residues at positions 66-94, CDR3 of a Nanobody® comprises the amino acid residues at positions 95-102, and FR4 of a Nanobody® comprises the amino acid residues at positions 103-113.

r) In the context of the present invention "target host cell (of a virus)" generally refers to a particular cell, which is or is derived from a living subject and which is susceptible to infection by said virus.

s) The term "infectivity of a virus", as used herein, refers to the proportion of living subjects that, when exposed to said virus, actually become infected by said virus.

t) The term "neutralization of a virus", as used herein, refers to the modulation and/or reduction and/or prevention and/or inhibition of the infectivity (as defined herein) of a virus by binding of a neutralizing compound to the virion, as measured using a suitable in vitro, cellular or in vivo assay (such as e.g. the microneutralization assay described by Anderson et al. 1985 (J. Clin. Microbial. 22: 1050-1052) and 1988 (J. Virol. 62: 4232-4238), modifications of these assays such as e.g. described in Example 6; a plaque reduction assay as for example described by Johnson et al. 1997 (J. Inf. Dis. 176: 1215-1224), and modifications thereof and those mentioned herein). In particular, "neutralizing (a virus)" or "to neutralize (a virus)" may mean either modulating, reducing, preventing or inhibiting the infectivity (as defined herein) of a virus as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to normal (i.e. naturally occurring) infectivity (as defined herein) of a virus, in the same assay under the same conditions but without the presence of the amino acid sequence, Nanobody® or polypeptide of the invention.

u) The term "potency of an amino acid sequence of the invention", "potency of a Nanobody® of the invention", "potency of a polypeptide of the invention", and/or "potency of compound or construct of the invention", as used herein, refers to the capacity of said amino acid sequence of the invention, Nanobody® of the invention, polypeptide of the invention, and/or compound or construct of the invention to neutralize a particular virus (such as e.g. hRSV), to modulate, inhibit and/or prevent infectivity of a virus, to modulate, inhibit and/or prevent fusion of a virus with (the cell membrane of) the target host cell, and/or to modulate, inhibit and/or prevent entry of a virus into the target host cell (as defined herein). The potency may be measured by any suitable assay known in the art or described herein, such as e.g. the microneutralization assays as described in the Example section and/or the assays mentioned in point t) above.

v) The term "virus attachment", as used herein, is attachment of a virus (e.g. hRSV) to a target host cell directly (for example by interacting with a viral receptor) or indirectly (for example by mediating the interaction of one or more other proteins or molecules to a viral receptor).

w) The term "virus fusion", as used herein, is fusion of a virus (e.g. hRSV) to a target host cell directly (for example by interacting with membrane compounds of the target host cell) or indirectly (for example by mediating the interaction of one or more other proteins or molecules with membrane compounds of the target host cell).

x) The term "viral entry" used herein encompasses any viral-mediated biological pathway that is needed to accomplish virion attachment to a target host cell and/or viral fusion with a target host cell.

y) When comparing two amino acid sequences, the term "amino acid difference" refers to an insertion, deletion or substitution of a single amino acid residue on a position of the first amino acid sequence, compared to the second amino acid sequence; it being understood that two amino acid sequences can contain one, two or maximal three such amino acid differences. The "amino acid difference" can be any one, any two or maximal any three substitutions, deletions or insertions in the amino acid sequence, i.e. in one or more of the framework regions or in one or more of the CDRs, or any combination thereof, that either improve the properties of the amino acid sequence of the invention or that at least do not detract too much from the desired properties or from the balance or combination of desired properties of the amino acid sequence of the invention. In this respect, the resulting amino acid sequence of the invention should at least bind protein F of hRSV with the same, about the same, or a higher affinity compared to the amino acid sequence without the one, two or maximal three substitutions, deletions or insertions, said affinity as measured by surface plasmon resonance; and/or the resulting amino acid sequence of the invention should at least have a potency that is the same, about the same or higher compared to the amino acid sequence without the one, two or maximal three substitutions, deletions and/or insertions. The skilled person will generally be able to determine and select suitable substitutions, deletions or insertions, or suitable combinations thereof, based on the disclosure herein and optionally after a limited degree of routine experimentation, which may for example involve introducing a limited number of possible substitutions, deletions or insertions and determining their influence on the properties of the amino acid sequence thus obtained.

In one aspect of the invention, the "amino acid difference" is an amino acid substitution. The amino acid substitution may be any one, two or maximal three substitutions in one or more of the framework regions or in one or more of the CDRs, or any combination thereof, that either improve the properties of the amino acid sequence of the invention or that at least do not detract too much from the desired properties or from the balance or combination of desired properties of the amino acid sequence of the invention. In this respect, the resulting amino acid sequence of the invention should at least bind protein F of hRSV with the same, about the same, or a higher affinity compared to the amino acid sequence without the one, two or maximal three substitutions, said affinity as measured by surface plasmon resonance; and/or the resulting amino acid sequence of the invention should at least have a potency that is the same, about the same or higher compared to the amino acid sequence without the one, two or maximal three substitutions. The skilled person will generally be able to determine and select suitable substitutions, based on the disclosure herein and optionally after a limited degree of routine experimentation, which may for example involve introducing a limited number of possible substitutions and determining their influence on the properties of the amino acid sequences thus obtained.

As indicated above, the substitutions, insertions or deletions can be in one or more of the framework regions and/or in one or more of the CDR's.

The amino acid substitution in the one or more CL R's may be a conservative amino acid substitution. "Conservative" amino acid substitutions are generally amino acid substitutions in which an amino acid residue is replaced with another amino acid residue of similar chemical structure and which has little or essentially no influence on the function, activity or other biological properties of the resulting amino acid sequence. Such conservative amino acid substitutions are well known in the art, for example from WO 04/037999, GB-A-3 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein. Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. The amino acid substitution in the one or more CDR's may provide the amino acid sequence with increased affinity for binding to protein F of hRSV. This may be done by techniques such as random or site-directed mutagenesis and/or other techniques for affinity maturation known per se, such as e.g. described in WO 09/004,065, WO 05/003345, WO 06/023144, EP527809, EP397834.

Without being limiting, rules (partly or fully followed) for substitutions of amino acid residues in the CDRs may be as follows (i.e. substitution with amino acids with similar side chain chemistries):

K is substituted by R;
R is substituted by K;
A is substituted by S or T;
S is substituted by A or T;
T is substituted by A or S;
I is substituted by L or V;
L is substituted by I or V;
V is substituted by I or L;
F is substituted by Y;
Y is substituted by F;
N is substituted by D;
D is substituted by N;
Q is substituted by E;
E is substituted by Q;
G is substituted by A;
M is substituted by L;
H, C, W and P are kept constant.

Furthermore, and also without being limiting, the rules (partly or fully followed) for substitutions of amino acid residues in the CDRs may be alternatively as follows for substitutions at positions 27 to 35 and positions 50 to 58 (using Kabat numbering system), wherein for positions 27 to 35:

Original amino acid residue in position 27 (Kabat numbering used) is substituted by F; G; R; S; 2 out of F, G, R, S; 3 out of F, G, R, S; or all of them, preferably all of them;

Original amino acid residue in position 28 (Kabat numbering used) is substituted by A; I; S; T; 2 out of A, I, S, T; 3 out of A, I, S, T; or all of them, preferably all of them;

Original amino acid residue in position 29 (Kabat numbering used) is substituted by F; G; L; S; 2 out of F, G, L, S; 3 out of F, G, L, S; or all of them, preferably all of them;

Original amino acid residue in position 30 (Kabat numbering used) is substituted by D; G; S; T; 2 out of D, G, S, T; 3 out of D, G, S, T; or all of them, preferably all of them;

Original amino acid residue in position 31 (Kabat numbering used) is substituted by D; I; N; S; T; 2 out of D, I, N, S, T; 3 out of D, I, N, S, T; or all of them, preferably all of them;

Original amino acid residue in position 32 (Kabat numbering used) is substituted by D; N; Y; 2 out of D, N, Y; or all of them, preferably all of them;

Original amino acid residue in position 33 (Kabat numbering used) is substituted by A; G; T; V; 2 out of A, G, T, V; 3 out of A, G, T, V; or all of them, preferably all of them;

Original amino acid residue in position 34 (Kabat numbering used) is substituted by I; M; or all of them, preferably all of them;

Original amino acid residue in position 35 (Kabat numbering used) is substituted by A; G; S; 2 out of A, G, S; or all of them, preferably all of them;

and positions 50 to 58 if original amino acid sequence has an amino acid sequence in position 52a (Kabat numbering used), Original amino acid residue in position 50 (Kabat numbering used) is substituted by A; C; G; S; T; 2 out of A, C, G, S, T; 3 out of A, C, G, S, T; 4 out of A, C, G, S, T; or all of them, preferably all of them;

Original amino acid residue in position 51 (Kabat numbering used) is substituted by I;

Original amino acid residue in position 52 (Kabat numbering used) is substituted by N; R; S; T; 2 out of N, R, S, T; 3 out of N, R, S, T; or all of them, preferably all of them;

Original amino acid residue in position 52a (Kabat numbering used) is substituted by R; S; T; W; 2 out of R, S, T, W; 3 out of R, S, T, W; or all of them, preferably all of them;

Original amino acid residue in position 53 (Kabat numbering used) is substituted by D; G; N; S; T; 2 out of O, G, N, S, T; 3 out of D, G, N, S, T; 4 out of D, G, N, S, T; or all of them, preferably all of them;

Original amino acid residue in position 54 (Kabat numbering used) is substituted by D; G; or all of them, preferably all of them;

Original amino acid residue in position 55 (Kabat numbering used) is substituted by D; G; S; 2 out of D, G, S; or all of them, preferably all of them;

Original amino acid residue in position 56 (Kabat numbering used) is substituted by I; N; R; S; T; 2 out of I, N, R, S, T; 3 out of I, N, R, S, T; 4 out of I, N, R, S, T; or all of them, preferably all of them;

Original amino acid residue in position 57 (Kabat numbering used) is substituted by T;

Original amino acid residue in position 58 (Kabat numbering used) is substituted by D; H; N; S; Y; 2 out of D, H, N, S, Y; 3 out of D, H, N, S, Y; 4 out of D, H, N, S, Y; or all of them, preferably all of them;

and wherein for positions 50 to 58 if original amino acid sequence has not an amino acid sequence in position 52a (Kabat numbering used), Original amino acid residue in position 50 (Kabat numbering used) is substituted by A; G; R; S; T; 2 out of A, G, R, S, T; 3 out of A, G, R, S, T; 4 out of A, G, R, S, T; or all of them, preferably all of them;

Original amino acid residue in position 51 (Kabat numbering used) is substituted by I;

Original amino acid residue in position 52 (Kabat numbering used) is substituted by N; S; T; 2 out of N, S, T; or all of them, preferably all of them;

Original amino acid residue in position 53 (Kabat numbering used) is substituted by N; R; S; T; Y; 2 out of N, R, S, T, Y; 3 out of N, R, S, T, Y; 4 out of N, R, S, T, Y; or all of them, preferably all of them;

Original amino acid residue in position 54 (Kabat numbering used) is substituted by D; G; R; S; 2 out of D, G, R, S; 3 out of D, G, R, S; or all of them, preferably all of them;

Original amino acid residue in position 55 (Kabat numbering used) is substituted by G;

Original amino acid residue in position 56 (Kabat numbering used) is substituted by G; N; R; S; T; 2 out of D, N, R, S, T; 3 out of O, N, R, S, T; 4 out of D, N, R, S, T; or all of them, preferably all of them;

Original amino acid residue in position 57 (Kabat numbering used) is substituted by T;

Original amino acid residue in position 58 (Kabat numbering used) is substituted by D; N; T; Y; 2 out of D, N, T, Y; 3 out of D, N, T, Y; or all of them, preferably all of them.

after which one or more of the potentially useful substitutions (or combinations thereof) thus determined can be introduced into said CDR sequence (in any manner known per se, as further described herein) and the resulting amino acid sequence(s) can be tested for affinity for protein F of hRSV, and/or for other desired properties such as e.g. improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), improved affinity and/or improved avidity for protein F of hRSV and/or improved efficacy and/or potency for neutralizing hRSV. In this way, by means of a limited degree of trial and error, other suitable substitutions in the CDRs (or suitable combinations thereof) can be determined by the skilled person based on the disclosure herein. The amino acid sequences comprising a CDR region that has one, two or maximal three substitutions, insertions or deletions, and nucleic acid sequences encoding the same, can be provided in any manner known per se, for example using one or more of the techniques mentioned on pages 103 and 104 of WO 08/020,079.

The resulting amino acid sequences of the invention should preferably bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; and/or neutralize hRSV with an efficacy and/or potency that is as defined herein.

When such substitutions, insertions or deletions are made in one or more of the framework regions, they may be made at one or more of the Hallmark residues (as e.g. defined in WO 08/020,079; Tables A-3 to A-8) and/or at one or more of the other positions in the framework residues, although substitutions, insertions or deletions at the Hallmark residues are generally less preferred (unless these are suitable humanizing substitutions as described herein). By means of non-limiting examples, a substitution may for example be a conservative substitution (as described herein) and/or an amino acid residue may be replaced by another amino acid residue that naturally occurs at the same position in another $V_{HH}$ domain (see WO 08/020,079, Tables A-5 to A-8), although the invention is generally not limited thereto.

Substitutions, insertions or deletions made (preferably) in one or more of the framework regions may be humanizing substitution (i.e. replacing one or more amino acid residues in the amino acid sequence of a naturally occurring $V_{HH}$ sequence (and in particular in the framework sequences) by one or more of the amino acid residues that occur at the corresponding position(s) in a $V_H$ domain from a conventional 4-chain antibody from a human being). Some preferred, but non-limiting humanizing substitutions (and suitable combinations thereof) will become clear to the skilled person based on the disclosure herein. Potentially useful humanizing substitutions can be ascertained by comparing the sequence of the framework regions of one of the amino acid sequence of the invention defined in a) with the corresponding framework sequence of one or more closely related human $V_H$ sequences, after which one or more of the potentially useful humanizing substitutions (or combinations thereof) thus determined can be introduced into said amino acid sequence of the invention defined in a) (in any manner known per se, as further described herein) and the resulting humanized amino acid sequence can be tested for affinity for protein F of hRSV, for stability, for ease and level of expression, and/or for other desired properties defined herein. In this way, by means of a limited degree of trial and error, other suitable humanizing substitutions (or suitable combinations thereof) can be determined by the skilled person based on the disclosure herein.

The humanizing substitutions should be chosen such that the resulting humanized amino acid sequence and/or Nanobody® still retains the favorable properties of Nanobodies® as defined herein. A skilled person will generally be able to determine and select suitable humanizing substitutions or suitable combinations of humanizing substitutions, based on the disclosure herein and optionally after a limited degree of routine experimentation, which may for example involve introducing a limited number of possible humanizing substitutions and determining their influence on the properties of the Nanobodies® thus obtained. Generally, as a result of humanization, the amino acid sequence and/or Nanobody® of the invention may become more "human-like", while still retaining the favorable properties of the Nanobodies® of the invention as described herein. As a result, such humanized amino acid sequence and/or Nanobody® may have several advantages, such as a reduced immunogenicity, compared to the corresponding naturally occurring $V_{HH}$ domain. Again, based on the disclosure herein and optionally after a limited degree of routine experimentation, the skilled person will be able to select humanizing substitutions or suitable combinations of humanizing substitutions which optimize or achieve a desired or suitable balance between the favorable properties provided by the humanizing substitutions on the one hand and the favorable properties of naturally occurring $V_{HH}$ domains on the other hand.

The amino acid sequences and/or Nanobodies® of the invention may be suitably humanized at any framework residue(s), such as at one or more Hallmark residues (as defined herein) or at one or more other framework residues (i.e. non-Hallmark residues) or any suitable combination thereof. One preferred humanizing substitution for Nanobodies® of the "P, R, S-103 group" or the "KERE group" (as defined in WO 08/020,079) is Q108 into L108. Depending on the host organism used to express the amino acid sequence, Nanobody® or polypeptide of the invention, such deletions and/or substitutions may also be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation (again as described herein).

As can be seen from the data on the $V_{HH}$ entropy and $V_{HH}$ variability given in Tables A-5-A-8 of WO 08/020,079, some amino acid residues in the framework regions are more conserved than others. Generally, although the invention in its broadest sense is not limited thereto, any substitutions, deletions or insertions are preferably made at positions that are less conserved. Also, generally, amino acid substitutions are preferred over amino acid deletions or insertions. Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J Molec. Biol. 157: 105-132, 1981, and Goldman et al., Ann. Rev. Biophys. Chem. 15: 321-353, 1986, all incorporated herein in their entirety by reference. Information on the primary, secondary and tertiary structure of Nanobodies® is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

The amino acid sequences and/or Nanobodies® with one, two or maximal three substitutions, insertions or deletions, and nucleic acid sequences encoding the same, can be provided in any manner known per se, for example using one or more of the techniques mentioned on pages 103 and 104 of WO 08/020,079.

The resulting amino acid sequences and/or Nanobodies® of the invention should preferably bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; and/or neutralize hRSV with an efficacy and/or potency that is as defined herein.

z) When comparing two polypeptides, the term "amino acid difference" refers to an insertion, deletion or substitution of a single amino acid residue on a position of the first polypeptide, compared to the second polypeptide; it being understood that two polypeptides can contain one, two or maximal three such amino acid differences.

The "amino acid difference" can be any one, any two or maximal three substitutions, deletions or insertions in the polypeptide, i.e. in one or more of the framework regions or in one or more of the CDRs, or any combination thereof, that either improve the properties of the polypeptide of the invention or that at least do not detract too much from the desired properties or from the balance or combination of desired properties of the polypeptide of the invention. In this respect, the resulting polypeptide of the invention should at least bind protein F of hRSV with the same, about the same, or a higher affinity compared to the polypeptide without the one, two or maximal three substitutions, deletions or insertions, said affinity as measured by surface plasmon resonance; and/or the resulting polypeptide of the invention should at least have a potency that is the same, about the same or higher compared to the polypeptide without the one, two or maximal three substitutions, deletions and/or insertions. The resulting polypeptide should preferably bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; and/or neutralize hRSV with an efficacy and/or potency that is as defined herein. The skilled person will generally be able to determine and select suitable substitutions, deletions or insertions, or suitable combinations thereof, based on the disclosure herein and optionally after a limited degree of routine experimentation, which may for example involve introducing a limited number of possible substitutions, deletions or insertions and determining their influence on the properties of the polypeptide thus obtained.

In one aspect of the invention, the "amino acid difference" is an amino acid substitution. The amino acid substitution may be any one, any two or maximal any three substitutions in the framework regions or in one or more of the CDRs, or any combination thereof, that either improve the properties of the polypeptide of the invention or that at least do not detract too much from the desired properties or from the balance or combination of desired properties of the polypeptide of the invention. In this respect, the resulting polypeptide of the invention should at least bind protein F of hRSV with the same, about the same, or a higher affinity compared to the polypeptide without the one, two or maximal three substitutions, deletions or insertions, said affinity as measured by surface plasmon resonance; and/or the resulting polypeptide of the invention should at least have a potency that is the same, about the same or higher compared to the polypeptide without the one, two or maximal three substitutions, deletions and/or insertions. The resulting polypeptide should preferably bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; and/or neutralize hRSV with an efficacy and/or potency that is as defined herein. The skilled person will generally be able to determine and select suitable substitutions, based on the disclosure herein and optionally after a limited degree of routine experimentation, which may for example involve introducing a limited number of possible substitutions and determining their influence on the properties of polypeptides thus obtained.

As indicated above, the substitutions, insertions or deletions can be in one or more of the framework regions and/or in one or more of the CDR's. As discussed above (see point y)), the substitutions, insertions or deletions in the CDR's may be any possible substitutions, insertions or deletions such as "conservative substitution" (as defined herein), it may be driven by certain rules (as defined herein), and/or it may induce improved properties to the resulting polypeptides.

When such substitutions, insertions or deletions are made in one or more of the framework regions, they may be made at one or more of the Hallmark residues (as e.g. defined in WO 08/020,079; Tables A-3 to A-8) and/or at one or more of the other positions in the framework residues, although substitutions, insertions or deletions at the Hallmark residues are generally less preferred (unless these are suitable humanizing substitutions as described herein). By means of non-limiting examples, a substitution may for example be a conservative substitution (as described herein) and/or an amino acid residue may be replaced by another amino acid residue that naturally occurs at the same position in another $V_{HH}$ domain (see WO 08/020,079, Tables A-5 to A-8), although the invention is generally not limited thereto.

Substitutions, insertions or deletions made (preferably) in one or more of the framework regions may be humanizing substitution. Some preferred, but non-limiting humanizing substitutions (and suitable combinations thereof) will become clear to the skilled person based on the disclosure herein. Potentially useful humanizing substitutions can be ascertained by comparing the sequence of the framework regions of one of the amino acid sequences encompassed in the polypeptide of the invention defined in a) with the corresponding framework sequence of one or more closely related human $V_H$ sequences, after which one or more of the potentially useful humanizing substitutions (or combinations thereof) thus determined can be introduced into said polypeptide of the invention defined in a) (in any manner known per se, as further described herein) and the resulting polypeptide sequence can be tested for affinity for protein F of hRSV, for stability, for ease and level of expression, and/or for other desired properties defined herein. In this way, by means of a limited degree of trial and error, other suitable humanizing substitutions (or suitable combinations thereof) can be determined by the skilled person based on the disclosure herein.

The humanizing substitutions should be chosen such that the resulting humanized polypeptide sequences still retain the favorable properties of Nanobodies® encompassed in the polypeptide as defined herein. A skilled person will generally be able to determine and select suitable humanizing substitutions or suitable combinations of humanizing substitutions, based on the disclosure herein and optionally after a limited degree of routine experimentation, which may for example involve introducing a limited number of possible humanizing substitutions and determining their influence on the properties of the Nanobodies® encompassed in the polypeptide thus obtained.

Generally, as a result of humanization, the polypeptide of the invention may become more "human-like", while still retaining the favorable properties of the Nanobodies® of the invention encompassed in the polypeptide as described herein. As a result, such humanized polypeptides may have several advantages, such as a reduced immunogenicity, compared to the polypeptides that encompass corresponding naturally occurring $V_{HH}$ domains. Again, based on the disclosure herein and optionally after a limited degree of routine experimentation, the skilled person will be able to select humanizing substitutions or suitable combinations of humanizing substitutions which optimize or achieve a desired or suitable balance between the favorable properties provided by the humanizing substitutions on the one hand and the favorable properties of naturally occurring $V_{HH}$ domains on the other hand.

Polypeptides of the invention may be suitably humanized at any framework residue(s), such as at one or more Hallmark residues (as defined herein) or at one or more other framework residues (i.e. non-Hallmark residues) or any suitable combination thereof. One preferred humanizing substitution for Nanobodies® of the "P, R, S-103 group" or the "KERE group" is Q108 into L108.

Depending on the host organism used to express the polypeptide of the invention, such deletions and/or substitutions may also be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation (again as described herein). As can be seen from the data on the $V_{HH}$ entropy and $V_{HH}$ variability given in Tables A-5-A-8 of WO 08/020,079, some amino acid residues in the framework regions are more conserved than others. Generally, although the invention in its broadest sense is not limited thereto, any substitutions, deletions or insertions are preferably made at positions that are less conserved. Also, generally, amino acid substitutions are preferred over amino acid deletions or insertions. Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J. Molec. Biol. 157: 105-132, 1981, and Goldman et al., Ann. Rev. Biophys. Chem. 15: 321-353, 1986, all incorporated herein in their entirety by reference. Information on the primary, secondary and tertiary structure of Nanobodies® is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

The polypeptides with one, two or maximal three substitutions, insertions or deletions, and nucleic acid sequences encoding the same, can be provided in any manner known per se, for example using one or more of the techniques mentioned on pages 103 and 104 of WO 08/020,079.

The resulting polypeptides of the invention should preferably bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; and/or neutralize hRSV with an efficacy and/or potency that is as defined herein.

aa) The figures, sequence listing and the experimental part/examples are only given to further illustrate the invention and should not be interpreted or construed as limiting the scope of the invention and/or of the appended claims in any way, unless explicitly indicated otherwise herein.

For a general description of heavy chain antibodies and the variable domains thereof, reference is inter alia made to the prior art cited herein, as well as to the prior art mentioned on page 59 of WO 08/020,079 and to the list of references mentioned on pages 41-43 of the International application WO 06/040153, which prior art and references are incorporated herein by reference.

For a general description of (single) domain antibodies, reference is also made to the prior art cited above, as well as to EP 0 368 684. For the term "dAb's", reference is for example made to Ward et al. (1989, Nature 341: 544-6), to Holt et al., 2003, Trends Biotechnol. 21: 484-490; as well as to for example WO 06/030220, WO 06/003388 and other published patent applications of Domantis Ltd. It should also be noted that, although less preferred in the context of the present invention because they are not of mammalian origin, single domain antibodies or single variable domains can be derived from certain species of shark (for example, the so-called "IgNAR domains", see for example WO 05/18629).

In particular, the amino acid sequence of the invention may essentially consist of or may be a Nanobody® (as defined herein) or a suitable fragment thereof. [Note: Nanobody®, Nanobodies® and Nanoclone® are registered trademarks of Ablynx N. V.]

For a further general description of Nanobodies®, reference is made to the prior art cited herein, such as e.g. described in WO 08/020,079 (page 16).

Such Nanobodies® may be derived in any suitable manner and from any suitable source, and may for example be naturally occurring $V_{HH}$ sequences (i.e. from a suitable species of Camelid) or synthetic or semi-synthetic amino acid sequences, including but not limited to "humanized" (as defined herein) Nanobodies®, "camelized" (as defined herein) immunoglobulin sequences (and in particular camelized heavy chain variable domain sequences), as well as Nanobodies® that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when a Nanobody® comprises a $V_{HH}$ sequence, said Nanobody® may be suitably humanized, as further described herein, so as to provide one or more further (partially or fully) humanized Nanobodies® of the invention. Similarly, when a Nanobody® comprises a synthetic or semi-synthetic sequence (such as a partially humanized sequence), said Nanobody® may optionally be further suitably humanized, again as described herein, again so as to provide one or more further (partially or fully) humanized Nanobodies® of the invention.

In particular, humanized Nanobodies® may be amino acid sequences that are as generally defined for Nanobodies® (such as e.g. described in WO 08/020,079 (page 16)), but in which at least one amino acid residue is present (and in particular, in at least one of the framework residues) that is and/or that corresponds to a humanizing substitution (as defined herein). Some preferred, but non-limiting humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) a Nanobody® may be partially humanized or fully humanized.

In this respect, some preferred Nanobodies® of the invention are Nanobodies® which specifically bind (as further defined herein) protein F of hRSV and which:
i) are a humanized variant of the amino acid sequence with SEQ ID NO: 16 (see Table A-1); and/or
ii) have at least 80% amino acid identity with at least one of the amino acid sequences of SEQ ID NO: 16 (see Table A-1) and/or at least one of the amino acid sequences of SEQ ID NO's: 33-40, (see Table A-4), in which for the purposes of determining the degree of amino acid identity, the amino acid residues that form the CDR sequences are disregarded;
and in which:
iii) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020,079.

The present invention provides a number of humanized and/or sequence optimized amino acid sequences and/or Nanobodies® that show less immunogenicity and that are particularly suited for binding protein F of hRSV. Therefore, in one aspect of the present invention, amino acid sequences and/or Nanobodies® are provided chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:
  i) the amino acid sequence has Proline (Pro, P) at position 14, Arginine (Arg, R) at position 83 and/or Leucine (Leu, L) at position 108 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another aspect, the present invention provides amino acid sequences and/or Nanobodies® chosen from the following:

a) SEQ ID NO's: 33-40;
b) amino acid sequences that have no more than 3, preferably no more than 2, more preferably no more than 1 amino acid difference with one of SEQ ID NO's: 33-40, provided that:
 i) the amino acid sequence has Proline (Pro, P) at position 14, Arginine (Arg, R) at position 83 and Leucine (Leu, L) at position 108 (said positions determined according to Kabat numbering); and
 ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the amino acid sequence and/or Nanobody® of the invention comprises or essentially consists of one of SEQ ID NO's: 33-40.

The amino acid sequences and/or Nanobodies® of the present invention show reduced immunogenicity upon administration to a human subject compared prior amino acid sequences (e.g. as described in PCT application PCT/EP2009/056975 entitled "Amino acid sequences directed against envelope proteins of a virus and polypeptides comprising the same for the treatment of viral diseases" filed by Ablynx N. V. on 5 Jun. 2009). In addition, the amino acid sequences and/or Nanobodies® of the present invention show good binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) for protein F of hRSV The present invention also provides a number of sequence optimized amino acid sequences and/or Nanobodies® that show improved stability upon storage during stability studies and that are particularly suited for binding protein F of hRSV. Therefore, in another aspect of the present invention, amino acid sequences and/or Nanobodies® are provided chosen from the following:

a) SEQ ID NO's: 35-40;
b) amino acid sequences that have no more than 3, preferably no more than 2, more preferably no more than 1 amino acid difference with one of SEQ ID NO's: 35-40, provided that:
 i) the amino acid sequence has Glycine (Gly, G) at position 16, Glutamic acid (Glu, E) at position 54 and/or Alanine (Ala, A) at position 55 (said positions determined according to Kabat numbering); and
 ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the amino acid sequences and/or Nanobodies® are chosen from the following:

a) SEQ ID NO's: 35-40;
b) amino acid sequences that have no more than 3, preferably no more than 2, more preferably no more than 1 amino acid difference with one of SEQ ID NO's: 35-40, provided that:
 i) the amino acid sequence has Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
 ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred amino acid sequences and/or Nanobodies® of the invention comprise or essentially consist of one of SEQ ID NO's: 35-40.

In another preferred aspect, the amino acid sequences and/or Nanobodies® are chosen from the following:

a) SEQ ID NO's: 37-40;
b) amino acid sequences that have no more than 3, preferably no more than 2, more preferably no more than 1 amino acid difference with one of SEQ ID NO's: 37-40, provided that:
 i) the amino acid sequence has Proline (Pro, P) at position 14, Arginine (Arg, R) at position 83, Leucine (Leu, L) at position 108 and Glycine (Gly, G) at position 16; and in addition the amino acid sequence has Glutamic acid (Glu, E) at position 54 or Alanine (Ala, A) at position 55 (said positions determined according to Kabat numbering); and
 ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred amino acid sequences and/or Nanobodies® of the invention comprise or essentially consist of one of SEQ ID NO's: 37-40.

In the present invention, the possibility of pGlu post-translational modification of the N-terminus was eliminated by changing the N-terminal Glutamic acid (E) [HOOC—(CH2)2-protein] into an Aspartic acid (D)[HOOC—CH2-protein] which lead to increased product stability. Accordingly, the present invention also relates to amino acid sequences and Nanobodies as described above wherein the glutamic acid at position 1 (said position determined according to Kabat numbering) is changed into an aspartic acid.

The present invention provides a number of sequence optimized amino acid sequences and/or Nanobodies® that show increased stability upon storage during stability studies. Therefore, in one aspect of the present invention, amino acid sequences and/or Nanobodies® are provided chosen from the following:

a) SEQ ID NO's: 34, 36, 38, 40, 51;

b) amino acid sequences that have no more than 3, preferably no more than 2, more preferably no more than 1 amino acid difference with one of SEQ ID NO's: 34, 36, 38, 40, 51, provided that:

i) the amino acid sequence has Aspartic acid (Asp, D) at position 1 (said position determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred amino acid sequences and/or Nanobodies® of the invention comprise or essentially consist of one of SEQ ID NO's: 34, 36, 38, 40, 51.

In a preferred aspect, the amino acid sequences and/or Nanobodies® are chosen from the following:

a) SEQ ID NO's: 34, 36, 38, 40;

b) amino acid sequences that have no more than 3, preferably no more than 2, more preferably no more than 1 amino acid difference with one of SEQ ID NO's: 34, 36, 38, 40, provided that:

i) the amino acid sequence has Aspartic acid (Asp, D) at position 1, Praline (Pro, P) at position 14, Arginine (Arg, R) at position 83 and Leucine (Leu, L) at position 108 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the amino acid sequences and/or Nanobodies® are chosen from the following:

a) SEQ ID NO's: 36, 38, 40;

b) amino acid sequences that have no more than 3, preferably no more than 2, more preferably no more than 1 amino acid difference with one of SEQ ID NO's: 36, 38, 40, provided that:

i) the amino acid sequence has Aspartic acid (Asp, D) at position 1, Praline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred amino acid sequences and/or Nanobodies® of the invention comprise or essentially consist of one of SEQ ID NO's: 36, 38, 40.

In another preferred aspect, the amino acid sequences and/or Nanobodies® are chosen from the following:

a) SEQ ID NO'S: 38 and 40;

b) amino acid sequences that have no more than 3, preferably no more than 2, more preferably no more than 1 amino acid difference with one of SEQ ID NO's: 38 and 40, provided that:

i) the amino acid sequence has Aspartic acid (Asp, D) at position 1, Proline (Pro, P) at position 14, Arginine (Arg, R) at position 83, Leucine (Leu, L) at position 108 and Glycine (Gly, G) at position 16; and in addition, the amino acid sequence has Glutamic acid (Glu, E) at position 54 or Alanine (Ala, A) at position 55 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Preferred amino acid sequences and/or Nanobodies® of the invention comprise or essentially consist of one of SEQ ID NO's: 38 and 40.

In another aspect, the amino acid sequences and/or Nanobodies® of the invention comprise or essentially consist of SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala.

In another aspect, the amino acid sequences and/or Nanobodies® of the invention comprise or essentially consist of SEQ ID NO: 16, wherein one or more (such as two or three) amino acid residues have been mutated selected from the following: Ala14Pro, Lys83Arg and Gln108Leu.

In another aspect, the amino acid sequences and/or Nanobodies® of the invention comprise or essentially consist of SEQ ID NO: 16, wherein one or more (such as two or three) amino acid residues have been mutated selected from the following: Asp16Gly, Asp54Glu and Gly55Ala.

In another aspect, the amino acid sequences and/or Nanobodies® of the invention comprise or essentially consist of SEQ ID NO: 16, wherein position 1 (Glu) has been changed into Asp.

In another aspect, the amino acid sequences and/or Nanobodies® of the invention comprise or essentially consist of SEQ ID NO: 16, wherein one or more (such as two, three, four, five or six) amino acid residues have been mutated selected from the following: Ala14Pro, Lys83Arg, Gln108Leu, Asp16Gly, Asp54Glu, Gly55Ala, wherein position 1 (Glu) has been changed into Asp.

In another aspect, the amino acid sequences and/or Nanobodies® of the invention comprise or essentially consist of SEQ ID NO: 16, wherein one or more (such as two or three) amino acid residues have been mutated selected from the following: Ala14Pro, Lys83Arg and Gln108Leu, wherein position 1 (Glu) has been changed into Asp.

In another aspect, the amino acid sequences and/or Nanobodies® of the invention comprise or essentially consist of SEQ ID NO: 16, wherein one or more (such as two or three) amino acid residues have been mutated selected from the following: Asp16Gly, Asp54Glu and Gly55Ala, wherein position 1 (Glu) has been changed into Asp.

Preferably, the amino acid sequence and/or Nanobody® of the invention comprises or essentially consists of SEQ ID NO: 16, wherein following amino acid residues have been mutated:

Ala14Pro, Lys83Arg, Gln108Leu;
Ala14Pro, Lys83Arg, Gln108Leu, Asp16Gly;

Ala14Pro, Lys83Arg, Gln108Leu, Asp16Gly, Asp54Glu;
Ala14Pro, Lys83Arg, Gln108Leu, Asp16Gly, Gly55Ala; Glu1Asp;
Glu1Asp, Ala14Pro, Lys83Arg, Gln108Leu;
Glu1Asp, Ala14Pro, Lys83Arg, Gln108Leu, Asp16Gly;
Glu1Asp, Ala14Pro, Lys83Arg, Gln108Leu, Asp16Gly, Asp54Glu; or
Glu1Asp, Ala14Pro, Lys83Arg, Gln108Leu, Asp16Gly, Gly55Ala.

The amino acid sequences and/or Nanobodies® of the present invention show improved properties such as e.g. improved stability and less immunogenicity compared to prior amino acid sequences (e.g. as described in PCT application PCT/EP2009/056975 entitled "Amino acid sequences directed against envelope proteins of a virus and palypeptides comprising the same for the treatment of viral diseases" filed by Ablynx N. V. on 5 Jun. 2009). In addition, the amino acid sequences and/or Nanobodies® of the present invention show good binding characteristics (suitably measured and/or expressed as a $K_D$-value (actual or apparent), a $K_A$-value (actual or apparent), a $k_{on}$-rate and/or a $k_{off}$-rate, or alternatively as an $IC_{52}$ value, as further described herein), good affinity and/or good avidity for protein F of hRSV and/or good efficacy and/or potency for neutralizing hRSV More in particular, the amino acid sequences and/or Nanobodies® of the invention can bind to protein F of hRSV with an affinity (suitably measured and/or expressed as a $K_2$-value (actual or apparent), a $K_A$-value (actual or apparent), a $k_{on}$-rate and/or a $k_{off}$-rate, or alternatively as an $IC_{50}$ value, as further described herein) preferably such that they:

bind to protein F of hRSV with a dissociation constant ($K_D$) of 1000 nM to 1 nM or less, preferably 100 nM to 1 nM or less, more preferably 10 nM to 1 nM or less;

and/or such that they:

bind to protein F of hRSV with a $k_{on}$-rate of between $10^4$ $M^{-1}s^{-1}$ to about $10^7$ $M^{-1}s^{-1}$, preferably between $10^5$ $M^{-1}s^{-1}$ and $10^7$ $M^{-1}s^{-1}$, more preferably about $10^6$ $M^{-1}s^{-1}$ or more;

and/or such that they:

bind to protein F of hRSV with a $k_{off}$-rate between $10^{-2}s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, or lower;

Some preferred IC50 values for binding of the amino acid sequences of the invention to protein F of hRSV will become clear from the further description and examples herein.

Assays to determine the IC50 include competition assays such as competition ELISA (e.g. competition with Synagis® or its Fab fragment) or more preferably neutralization assays such as the microneutralization assay described by Anderson et al. (1985, J. Clin. Microbiol. 22: 1050-1052; 1988, J. Virol. 62: 4232-4238), modifications of this assay such as e.g. described in Example 6, or a plaque reduction assay as for example described by Johnson et al. (1997, J. Inf. Dis. 176: 1215-1224), and modifications thereof.

For example, in a competition assay with the Fab fragment of Synagis®, the amino acid sequences of the invention may have IC50 values between 1 nM and 100 nM, preferably between 10 nM and 50 nM, or less.

For example, in a microneutralization assay on hRSV Long (such as e.g. described in Example 6) the amino acid sequences of the invention may have IC50 values between 100 nM and 1000 nM, preferably between 100 nM and 500 nM, or less.

The amino acid sequences and Nanobodies® provided by the invention are preferably in essentially isolated form (as defined herein), or form part of a polypeptide of the invention (also referred to as "polypeptide of the invention"), which may comprise or essentially consist of one or more amino acid sequences or Nanobodies® of the invention and which may optionally further comprise one or more further amino acid sequences or Nanobodies® (all optionally linked via one or more suitable linkers).

Accordingly, in another aspect, the invention relates to a polypeptide (also referred to herein as a "polypeptide of the invention") that comprises or essentially consists of one or more amino acid sequences or Nanobodies® of the invention (or suitable fragments thereof).

The process of designing/selecting and/or preparing a polypeptide of the invention, starting from an amino acid sequence or Nanobody® of the invention, is also referred to herein as "formatting" said amino acid sequence or Nanobody® of the invention; and an amino acid sequence or Nanobody® of the invention that is made part of a polypeptide of the invention is said to be "formatted" or to be "in the format of" said polypeptide of the invention. Examples of ways in which an amino acid sequence or Nanobody® of the invention can be formatted and examples of such formats will be clear to the skilled person based on the disclosure herein; and such formatted amino acid sequences or Nanobodies® form a further aspect of the invention.

For example, and without limitation, the one or more amino acid sequences or Nanobodies® of the invention may be used as a binding unit in such a polypeptide, which may optionally contain one or more further amino acid sequences that can serve as a binding unit (i.e. against the same or another epitope on protein F of hRSV and/or against one or more other antigens, proteins or targets than protein F of hRSV), so as to provide a monovalent, multivalent, multiparatopic or multispecific polypeptide of the invention, respectively, all as described herein. The present invention thus also relates to a polypeptide which is a monovalent polypeptide or construct comprising or essentially consisting of an amino acid sequence or Nanobody® of the invention. The present invention thus also relates to a polypeptide which is a multivalent polypeptide or construct, such as e.g. a bivalent or trivalent polypeptide or construct. The present invention also relates to a polypeptide which is a multispecific polypeptide or construct, such as e.g. a bispecific or trispecific polypeptide or construct. The present invention also relates to a polypeptide which is a multiparatopic polypeptide or construct, such as e.g. a biparatopic or triparatopic polypeptide or construct.

Accordingly, in a preferred, but non-limiting aspect, the amino acid sequence or Nanobody® of the invention comprises at least one further amino acid sequence or Nanobody®, so as to provide a polypeptide of the invention that comprises at least two, such as two, three, four, five or more amino acid sequences or Nanobodies®, in which said amino acid sequences or Nanobodies® may optionally be linked via one or more linker sequences (as defined herein). Polypeptides of the invention that comprise two or more amino acid sequences or Nanobodies®, of which at least one, and preferably all, is/are an amino acid sequence or Nanobody® of the invention, will also be referred to herein as "multivalent" polypeptides of the invention, and the amino acid sequences or Nanobodies® present in such polypeptides will also be referred to herein as being in a "multivalent format". For example a "bivalent" polypeptide of the invention comprises two amino acid sequences and/or Nanobodies®, optionally linked via a linker sequence, whereas a "trivalent" polypeptide of the invention comprises three amino acid sequences and/or Nanobodies®, optionally linked via two linker sequences; etc.; in which at least one of the amino acid sequences and/or Nanobodies® present in the polypeptide, and up to all of the amino acid sequences and/or Nanobodies® present in the polypeptide, is/are an amino acid sequence and/or Nanobody® of the invention.

In a multivalent polypeptide of the invention, the two or more amino acid sequences or Nanobodies® may be the same or different, and may be directed against the same antigen or antigenic determinant (for example against the same part(s) or epitope(s) or against different parts or epitopes) or may alternatively be directed against different antigens or antigenic determinants; or any suitable combination thereof. For example, a bivalent polypeptide of the invention may comprise (a) two identical amino acid sequences or Nanobodies®; (b) a first amino acid sequence or Nanobody® directed against a first antigenic determinant of a protein or antigen and a second amino acid sequence or Nanobody® directed against the same antigenic determinant of said protein or antigen which is different from the first amino acid sequence or Nanobody®; (c) a first amino acid sequence or Nanobody® directed against a first antigenic determinant of a protein or antigen and a second amino acid sequence or Nanobody® directed against another antigenic determinant of said protein or antigen; or (d) a first amino acid sequence or Nanobody® directed against a first protein or antigen and a second amino acid sequence or Nanobody® directed against a second protein or antigen (i.e. different from said first antigen). Similarly, a trivalent polypeptide of the invention may, for example and without being limited thereto, comprise (a) three identical amino acid sequences or Nanobodies®; (b) two identical amino acid sequences or Nanobody® against a first antigenic determinant of an antigen and a third amino acid sequence or Nanobody® directed against a different antigenic determinant of the same antigen; (c) two identical amino acid sequences or Nanobodies® against a first antigenic determinant of an antigen and a third amino acid sequence or Nanobody® directed against a second antigen different from said first antigen; (d) a first amino acid sequence or Nanobody® directed against a first antigenic determinant of a first antigen, a second amino acid sequence or Nanobody® directed against a second antigenic determinant of said first antigen and a third amino acid sequence or Nanobody® directed against a second antigen different from said first antigen; or (e) a first amino acid sequence or Nanobody® directed against a first antigen, a second amino acid sequence or Nanobody® directed against a second antigen different from said first antigen, and a third amino acid sequence or Nanobody® directed against a third antigen different from said first and second antigen.

In a preferred aspect, the invention provides a multivalent, preferably a bivalent or trivalent polypeptide comprising or essentially consisting of at least two amino acid sequences or Nanobodies® of the invention (as described above).

In one aspect, the invention provides a multivalent, preferably a bivalent or trivalent polypeptide comprising or essentially consisting of at least two amino acid sequences or Nanobodies® chosen from the following:
  a) SEQ ID NO's: 33-40;
  b) amino acid sequences that have no more than 3, preferably no more than 2, more preferably no more than 1 amino acid difference with one of SEQ ID NO's: 33-40, provided that:
    i) the amino acid sequence has Proline (Pro, P) at position 14, Arginine (Arg, R) at position 83 and/or Leucine (Leu, L) at position 108 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the invention provides a multivalent, preferably a bivalent or trivalent polypeptide comprising or essentially consisting of at least two amino acid sequences or Nanobodies® chosen from the following:
  a) SEQ ID NO's: 33-40;
  b) amino acid sequences that have no more than 3, preferably no more than 2, more preferably no more than 1 amino acid difference with one of SEQ ID NO's: 33-40, provided that:
    i) the amino acid sequence has Proline (Pro, P) at position 14, Arginine (Arg, R) at position 83 and Leucine (Leu, L) at position 108 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the polypeptide of the invention comprises or essentially consists of at least two amino acid sequences or Nanobodies® chosen from one of SEQ ID NO's: 33-40.

In another preferred aspect, the invention provides a multivalent, preferably a bivalent or trivalent polypeptide comprising or essentially consisting of at least two amino acid sequences or Nanobodies® chosen from the following:
  a) SEQ ID NO's: 35-40;
  b) amino acid sequences that have no more than 3, preferably no more than 2, more preferably no more than 1 amino acid difference with one of SEQ ID NO's: 35-40, provided that:
    i) the amino acid sequence has Glycine (Gly, G) at position 16, Glutamic acid (Glu, E) at position 54 and/or Alanine (Ala, A) at position 55 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a multivalent, preferably a bivalent or trivalent polypeptide comprising or essentially consisting of at least two amino acid sequences or Nanobodies® chosen from the following:
  a) SEQ ID NO's: 35-40;
  b) amino acid sequences that have no more than 3, preferably no more than 2, more preferably no more than 1 amino acid difference with one of SEQ ID NO's: 35-40, provided that:
    i) the amino acid sequence has Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the polypeptide of the invention comprises or essentially consists of at least two amino acid sequences or Nanobodies® chosen from one of SEQ ID NO's: 35-40.

In another preferred aspect, the invention provides a multivalent, preferably a bivalent or trivalent polypeptide comprising or essentially consisting of at least two amino acid sequences or Nanobodies® chosen from the following:

a) SEQ ID NO's: 37-40;
b) amino acid sequences that have no more than 3, preferably no more than 2, more preferably no more than 1 amino acid difference with one of SEQ ID NO's: 37-40, provided that:
  i) the amino acid sequence has Proline (Pro, P) at position 14, Arginine (Arg, R) at position 83, Leucine (Leu, L) at position 108 and Glycine (Gly, G) at position 16; and in addition the amino acid sequence has Glutamic acid (Glu, E) at position 54 or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least two amino acid sequences or Nanobodies® chosen from SEQ ID NO's: 37-40.

In another preferred aspect, the invention provides a multivalent, preferably a trivalent polypeptide comprising or essentially consisting of at least three (preferably identical) amino acid sequences or Nanobodies® chosen from the following:

a) SEQ ID NO's: 33-40;
b) amino acid sequences that have no more than 3, preferably no more than 2, more preferably no more than 1 amino acid difference with one of SEQ ID NO's: 33-40, provided that:
  i) the amino acid sequence has Praline (Pro, P) at position 14, Arginine (Arg, R) at position 83 and/or Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a multivalent, preferably a trivalent polypeptide comprising or essentially consisting of at least three amino acid sequences or Nanobodies® chosen from the following:

a) SEQ ID NO's: 33-40;
b) amino acid sequences that have no more than 3, preferably no more than 2, more preferably no more than 1 amino acid difference with one of SEQ ID NO's: 33-40, provided that:
  i) the amino acid sequence has Proline (Pro, P) at position 14, Arginine (Arg, R) at position 83 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the polypeptide of the invention comprises or essentially consists of at least three amino acid sequences or Nanobodies® chosen from one of SEQ ID NO's: 33-40.

In another preferred aspect, the invention provides a multivalent, preferably a trivalent polypeptide comprising or essentially consisting of at least three amino acid sequences or Nanobodies® chosen from the following:

a) SEQ ID NO's: 35-40;
b) amino acid sequences that have no more than 3, preferably no more than 2, more preferably no more than 1 amino acid difference with one of SEQ ID NO's: 35-40, provided that:
  i) the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a multivalent, preferably a trivalent polypeptide comprising or essentially consisting of at least three amino acid sequences or Nanobodies® chosen from the following:

a) SEQ ID NO's: 35-40;
b) amino acid sequences that have no more than 3, preferably no more than 2, more preferably no more than 1 amino acid difference with one of SEQ ID NO's: 35-40, provided that:
  i) the amino acid sequence has Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the polypeptide of the invention comprises or essentially consists of at least three identical amino acid sequences or Nanobodies® chosen from one of SEQ ID NO's: 35-40.

In another preferred aspect, the invention provides a multivalent, preferably a trivalent polypeptide comprising or essentially consisting of at least three amino acid sequences or Nanobodies® chosen from the following:
a) SEQ ID NO's: 37-40;
b) amino acid sequences that have no more than 3, preferably no more than 2, more preferably no more than 1 amino acid difference with one of SEQ ID NO's: 37-40, provided that:
  i) the amino acid sequence has Proline (Pro, P) at position 14, Arginine (Arg, R) at position 83, Leucine (Leu, L) at position 108 and Glycine (Gly, G) at position 16; and in addition the amino acid sequence has Glutamic acid (Glu, E) at position 54 or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least three amino acid sequences or Nanobodies® chosen from one of SEQ ID NO's: 37-40.

The invention also provides a multivalent, preferably a bivalent or trivalent polypeptide as described above in which the Glutamic acid at position 1 has been changed into an Aspartic acid.

Accordingly, the invention also provides a multivalent, preferably a bivalent or trivalent polypeptide comprising or essentially consisting of at least one amino acid sequence or Nanobody® chosen from the following:
a) SEQ ID NO's: 34, 36, 38, 40, 51;
b) amino acid sequences that have no more than 3, preferably no more than 2, more preferably no more than 1 amino acid difference with one of SEQ ID NO's: 34, 36, 38, 40, 51, provided that:
  i) the amino acid sequence has Aspartic acid (Asp, D) at position 1 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the polypeptide of the invention comprises or essentially consists of at least one amino acid sequence or Nanobody chosen from one of SEQ ID NO's: 34, 36, 38, 40, 51.

The invention also provides a multivalent, preferably a bivalent or trivalent polypeptide comprising or essentially consisting of at least one amino acid sequence or Nanobody® chosen from the following:
a) SEQ ID NO's: 34, 36, 38, 40;
b) amino acid sequences that have no more than 3, preferably no more than 2, more preferably no more than 1 amino acid difference with one of SEQ ID NO's: 34, 36, 38, 40, provided that:
  i) the amino acid sequence has Aspartic acid (Asp, D) at position 1, Praline (Pro, P) at position 14, Arginine (Arg, R) at position 83 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

The invention also provides a multivalent, preferably a bivalent or trivalent polypeptide comprising or essentially consisting of at least one amino acid sequence or Nanobody® chosen from the following:
a) SEQ ID NO's: 36, 38, 40;
b) amino acid sequences that have no more than 3, preferably no more than 2, more preferably no more than 1 amino acid difference with one of SEQ ID NO's: 36, 38, 40, provided that:
  i) the amino acid sequence has Aspartic acid (Asp, D) at position 1, Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the polypeptide of the invention comprises or essentially consists of at least one amino acid sequence or Nanobody chosen from one of SEQ ID NO's: 36, 38, 40.

The invention also provides a multivalent, preferably a bivalent or trivalent polypeptide comprising or essentially consisting of at least one amino acid sequence or Nanobody® chosen from the following:
a) SEQ ID NO's: 38 and 40;
b) amino acid sequences that have no more than 3, preferably no more than 2, more preferably no more than 1 amino acid difference with one of SEQ ID NO's: 38 and 40, provided that:
  i) the amino acid sequence has Aspartic acid (Asp, D) at position 1, Proline (Pro, P) at position 14, Arginine (Arg, R) at position 83, Leucine (Leu, L) at position 108 and Glycine (Gly, G) at position 16; and in addition, the amino acid sequence has Glutamic acid (Glu, E) at position 54 or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the polypeptide of the invention comprises or essentially consists of at least one amino acid sequence or Nanobody chosen from one of SEQ ID NO's: 38 and 40.

In another preferred aspect, the invention provides a multivalent, preferably a bivalent or trivalent polypeptide comprising or essentially consisting of at least one amino acid sequence or Nanobody that comprises or essentially consists of SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala.

In another preferred aspect, the invention provides a multivalent, preferably a bivalent or trivalent polypeptide comprising or essentially consisting of at least one amino acid sequence or Nanobody that comprises or essentially consists of SEQ ID NO: 16, wherein one or more (such as two or three) amino acid residues have been mutated selected from the following: Ala14Pro, Lys83Arg and Gln108Leu.

In another preferred aspect, the invention provides a multivalent, preferably a bivalent or trivalent polypeptide comprising or essentially consisting of at least one amino acid sequence or Nanobody that comprises or essentially consists of SEQ ID NO: 16, wherein one or more (such as two or three) amino acid residues have been mutated selected from the following: Asp16Gly, Asp54Glu and Gly55Ala.

In another preferred aspect, the invention provides a multivalent, preferably a bivalent or trivalent polypeptide comprising or essentially consisting of at least one amino acid sequence or Nanobody that comprises or essentially consists of SEQ ID NO: 16, wherein position 1 (Glu) has been changed into Asp.

In another preferred aspect, the invention provides a multivalent, preferably a bivalent or trivalent polypeptide comprising or essentially consisting of at least one amino acid sequence or Nanobody that comprises or essentially consists of SEQ ID NO: 16, wherein one or more (such as two, three, four, five or six) amino acid residues have been mutated selected from the following: Ala14Pro, Lys83Arg, Gln108Leu, Asp16Gly, Asp54Glu, Gly55Ala, and wherein position 1 (Glu) has been changed into Asp.

In another preferred aspect, the invention provides a multivalent, preferably a bivalent or trivalent polypeptide comprising or essentially consisting of at least one amino acid sequence or Nanobody that comprises or essentially consists of SEQ ID NO: 16, wherein one or more (such as two or three) amino acid residues have been mutated selected from the following: Ala14Pro, Lys83Arg and Gln108Leu, and wherein position 1 (Glu) has been changed into Asp.

In another preferred aspect, the invention provides a multivalent, preferably a bivalent or trivalent polypeptide comprising or essentially consisting of at least one amino acid sequence or Nanobody that comprises or essentially consists of SEQ ID NO: 16, wherein one or more (such as two or three) amino acid residues have been mutated selected from the following: Asp16Gly, Asp54Glu and Gly55Ala, and wherein position 1 (Glu) has been changed into Asp.

In another preferred aspect, the invention provides a multivalent, preferably a bivalent or trivalent polypeptide comprising or essentially consisting of at least one amino acid sequence or Nanobody® that comprises or essentially consists of SEQ ID NO: 16, in which following amino acid residues have been mutated:
Ala14Pro, Lys83Arg, Gln108Leu;
Ala14Pro, Lys83Arg, Gln108Leu, Asp16Gly;
Ala14Pro, Lys83Arg, Gln108Leu, Asp16Gly, Asp54Glu;
Ala14Pro, Lys83Arg, Gln108Leu, Asp16Gly, Gly55Ala;
Glu1Asp;
Glu1Asp, Ala14Pro, Lys83Arg, Gln108Leu;
Glu1Asp, Ala14Pro, Lys83Arg, Gln108Leu, Asp16Gly;
Glu1Asp, Ala14Pro, Lys83Arg, Gln108Leu, Asp16Gly, Asp54Glu; or
Glu1Asp, Ala14Pro, Lys83Arg, Gln108Leu, Asp16Gly, Gly55Ala.

In another preferred aspect, the invention provides a bivalent polypeptide comprising or essentially consisting of two amino acid sequences or Nanobodies® chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:
i) the amino acid sequence has Proline (Pro, P) at position 14, Arginine (Arg, R) at position 83 and/or Leucine (Leu, L) at position 108 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a bivalent polypeptide comprising or essentially consisting of two amino acid sequences or Nanobodies® chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:
i) the amino acid sequence has Proline (Pro, P) at position 14, Arginine (Arg, R) at position 83 and Leucine (Leu, L) at position 108 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention is a bivalent polypeptide and comprises or essentially consists of two identical amino acid sequences or Nanobodies® chosen from one of SEQ ID NO's: 33-40.

In another preferred aspect, the invention provides a bivalent polypeptide comprising or essentially consisting of two amino acid sequences or Nanobodies® chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
i) the amino acid sequence has Glycine (Gly, G) at position 16, Glutamic add (Glu, E) at position 54 and/or Alanine (Ala, A) at position 55 (said positions determined according to Kabat numbering); and
ii) the amino add sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a bivalent polypeptide comprising or essentially consisting of two amino acid sequences or Nanobodies® chosen from the following:
  a) SEQ ID NO's: 35-40;
  b) amino acid sequences that have no more than 3, preferably no more than 2, more preferably no more than 1 amino acid difference with one of SEQ ID NO's: 35-40, provided that:
    i) the amino acid sequence has Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention is a bivalent polypeptide and comprises or essentially consists of two identical amino acid sequences or Nanobodies® chosen from one of SEQ ID NO's: 35-40.

In another preferred aspect, the invention provides a bivalent polypeptide comprising or essentially consisting of two amino acid sequences or Nanobodies® chosen from the following:
  a) SEQ ID NO's: 37-40;
  b) amino acid sequences that have no more than 3, preferably no more than 2, more preferably no more than 1 amino acid difference with one of SEQ ID NO's: 37-40, provided that:
    i) the amino acid sequence has Praline (Pro, P) at position 14, Arginine (Arg, R) at position 83, Leucine (Leu, L) at position 108 and Glycine (Gly, G) at position 16; and in addition the amino acid sequence has Glutamic acid (Glu, E) at position 54 or Alanine (Ala, A) at position 55 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention is a bivalent polypeptide and comprises or essentially consists of two amino acid sequences or Nanobodies® chosen from SEQ ID NO's: 37-40.

The invention also provides a bivalent polypeptide as described above in which the Glutamic acid at position 1 has been changed into an Aspartic acid.

Accordingly, the invention also provides a bivalent polypeptide comprising or essentially consisting of at least one amino add sequence or Nanobody® chosen from the following:
  a) SEQ ID NO's: 34, 36, 38, 40, 51;
  b) amino add sequences that have no more than 3, preferably no more than 2, more preferably no more than 1 amino acid difference with one of SEQ ID NO's: 34, 36, 38, 40, provided that:
    i) the amino acid sequence has Aspartic acid (Asp, D) at position 1 (said position determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the polypeptide of the invention comprises or essentially consists of at least one amino acid sequence or Nanobody chosen from one of SEQ ID NO's: 34, 36, 38, 40, 51.

The invention also provides a bivalent polypeptide comprising or essentially consisting of at least one amino acid sequence or Nanobody® chosen from the following:
  a) SEQ ID NO's: 34, 36, 38, 40;
  b) amino acid sequences that have no more than 3, preferably no more than 2, more preferably no more than 1 amino acid difference with one of SEQ ID NO's: 34, 36, 38, 40, provided that:
    i) the amino acid sequence has Aspartic acid (Asp, D) at position 1, Praline (Pro, P) at position 14, Arginine (Arg, R) at position 83 and Leucine (Leu, L) at position 108 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

The invention also provides a bivalent polypeptide comprising or essentially consisting of at least one amino acid sequence or Nanobody® chosen from the following:
  a) SEQ ID NO's: 36, 38, 40;
  b) amino acid sequences that have no more than 3, preferably no more than 2, more preferably no more than 1 amino acid difference with one of SEQ ID NO's: 36, 38, 40, provided that:
    i) the amino acid sequence has Aspartic acid (Asp, D) at position 1, Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least one amino acid sequence or Nanobody chosen from one of SEQ ID NO's: 36, 38, 40.

The invention also provides a bivalent polypeptide comprising or essentially consisting of at least one amino acid sequence or Nanobody® chosen from the following:
  a) SEQ ID NO's: 38 and 40;
  b) amino acid sequences that have no more than 3, preferably no more than 2, more preferably no more than 1 amino acid difference with one of SEQ ID NO's: 38 and 40, provided that:
    i) the amino acid sequence has Aspartic acid (Asp, D) at position 1, Praline (Pro, P) at position 14, Arginine (Arg, R) at position 83, Leucine (Leu, 14 at position 108 and Glycine (Gly, G) at position 16; and in addition, Glutamic acid (Glu, E) at position 54 or Alanine (Ala, A) at position 55 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least one amino acid sequence or Nanobody chosen from one of SEQ ID NO's: 38 and 40.

In another preferred aspect, the invention provides a bivalent polypeptide comprising or essentially consisting of at least one amino acid sequence or Nanobody that comprises or essentially consists of SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala.

In another preferred aspect, the invention provides a bivalent polypeptide comprising or essentially consisting of at least one amino acid sequence or Nanobody that comprises or essentially consists of SEQ ID NO: 16, wherein one or more (such as two or three) amino acid residues have been mutated selected from the following: Ala14Pro, Lys83Arg and Gln108Leu.

In another preferred aspect, the invention provides a bivalent polypeptide comprising or essentially consisting of at least one amino acid sequence or Nanobody that comprises or essentially consists of SEQ ID NO: 16, wherein one or more (such as two or three) amino acid residues have been mutated selected from the following: Asp16Gly, Asp54Glu and Gly55Ala.

In another preferred aspect, the invention provides a bivalent polypeptide comprising or essentially consisting of at least one amino acid sequence or Nanobody that comprises or essentially consists of SEQ ID NO: 16, wherein position 1 (Glu) has been changed into Asp.

In another preferred aspect, the invention provides a bivalent polypeptide comprising or essentially consisting of at least one amino acid sequence or Nanobody that comprises or essentially consists of SEQ ID NO: 16, wherein one or more (such as two, three, four, five or six) amino acid residues have been mutated selected from the following: Ala14Pro, Lys83Arg, Gln108Leu, Asp16Gly, Asp54Glu, Gly55Ala, and wherein position 1 (Glu) has been changed into Asp.

In another preferred aspect, the invention provides a bivalent polypeptide comprising or essentially consisting of at least one amino acid sequence or Nanobody that comprises or essentially consists of SEQ ID NO: 16, wherein one or more (such as two or three) amino acid residues have been mutated selected from the following: Ala14Pro, Lys83Arg and Gln108Leu, and wherein position 1 (Glu) has been changed into Asp.

In another preferred aspect, the invention provides a bivalent polypeptide comprising or essentially consisting of at least one amino acid sequence or Nanobody that comprises or essentially consists of SEQ ID NO: 16, wherein one or more (such as two or three) amino acid residues have been mutated selected from the following: Asp16Gly, Asp54Glu and Gly55Ala, and wherein position 1 (Glu) has been changed into Asp.

In another preferred aspect, the invention provides a bivalent polypeptide comprising or essentially consisting of at least one amino acid sequence or Nanobody® that comprises or essentially consists of SEQ ID NO: 15, in which following amino acid residues have been mutated:
  Ala14Pro, Lys83Arg, Gln108Leu;
  Ala14Pro, Lys83Arg, Gln108Leu, Asp16Gly;
  Ala14Pro, Lys83Arg, Gln108Leu, Asp16Gly, Asp54Glu;
  Ala14Pro, Lys83Arg, Gln108Leu, Asp16Gly, Gly55Ala;
  Glu1Asp;
  Glu1Asp, Ala14Pro, Lys83Arg, Gln108Leu;
  Glu1Asp, Ala14Pro, Lys83Arg, Gln108Leu, Asp16Gly;
  Glu1Asp, Ala14Pro, Lys83Arg, Gln108Leu, Asp16Gly, Asp54Glu; or
  Glu1Asp, Ala14Pro, Lys83Arg, Gln108Leu, Asp16Gly, Gly55Ala.

In another preferred aspect, the invention provides a trivalent polypeptide comprising or essentially consisting of three amino acid sequences or Nanobodies® chosen from the following:
  a) SEQ ID NO's: 33-40;
  b) amino acid sequences that have no more than 3, preferably no more than 2, more preferably no more than 1 amino acid difference with one of SEQ ID NO's: 33-40, provided that:
    i) the amino acid sequence has Praline (Pro, P) at position 14, Arginine (Arg, R) at position 83 and/or Leucine (Leu, L) at position 108 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a trivalent polypeptide comprising or essentially consisting of three amino acid sequences or Nanobodies® chosen from the following:
  a) SEQ ID NO's: 33-40;
  b) amino acid sequences that have no more than 3, preferably no more than 2, more preferably no more than 1 amino acid difference with one of SEQ ID NO's: 33-40, provided that:
    i) the amino acid sequence has Proline (Pro, P) at position 14, Arginine (Arg, R) at position 83 and Leucine (Leu, L) at position 108 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the polypeptide of the invention is a trivalent polypeptide and comprises or essentially consists of three amino acid sequences or Nanobodies® chosen from one of SEQ ID NO's: 33-40.

In another preferred aspect, the invention provides a trivalent polypeptide comprising or essentially consisting of three amino acid sequences or Nanobodies® chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
  i) the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the invention provides a trivalent polypeptide comprising or essentially consisting of three amino acid sequences or Nanobodies® chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
  i) the amino acid sequence has Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the polypeptide of the invention is a trivalent polypeptide and comprises or essentially consists of three amino acid sequences or Nanobodies® chosen from one of SEQ ID NO's: 35-40.

In another preferred aspect, the invention provides a trivalent polypeptide comprising or essentially consisting of three amino acid sequences or Nanobodies® chosen from the following:
a) SEQ ID NO's: 37-40;
b) amino acid sequences that have no more than 3, preferably no more than 2, more preferably no more than 1 amino acid difference with one of SEQ ID NO's: 37-40, provided that:
  i) the amino acid sequence has Proline (Pro, P) at position 14, Arginine (Arg, R) at position 83, Leucine (Leu, L) at position 108 and Glycine (Gly, G) at position 16; and in addition the amino acid sequence has Glutamic acid (Glu, E) at position 54 or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In a preferred aspect, the polypeptide of the invention is a trivalent polypeptide and comprises or essentially consists of three amino acid sequences or Nanobodies© chosen from one of SEQ ID NO's: 37-40.

A preferred multivalent polypeptide of the invention comprises or essentially consists of three amino acid sequences or Nanobodies® with SEQ ID NO: 33. Another preferred multivalent polypeptide of the invention comprises or essentially consists of three amino acid sequences or Nanobodies® with SEQ ID NO: 35. Another preferred multivalent polypeptide of the invention comprises or essentially consists of three amino acid sequences or Nanobodies® with SEQ ID NO: 37. Another preferred multivalent polypeptide of the invention comprises or essentially consists of three amino acid sequences or Nanobodies® with SEQ ID NO: 39.

The invention also provides a trivalent polypeptide as described above in which the Glutamic acid at position 1 has been changed into an Aspartic acid.

The invention provides a trivalent polypeptide comprising or essentially consisting of at least one amino acid sequence or Nanobody® chosen from the following:
a) SEQ ID NO's: 34, 36, 38, 40, 51;
b) amino acid sequences that have no more than 3, preferably no more than 2, more preferably no more than 1 amino acid difference with one of SEQ ID NO's: 34, 36, 38, 40, 51, provided that:
  i) the amino acid sequence has Aspartic acid (Asp, D) at position 1 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least one amino acid sequence or Nanobody chosen from one of SEQ ID NO's: 34, 36, 38, 40, 51.

The invention also provides a trivalent polypeptide comprising or essentially consisting of at least one amino acid sequence or Nanobody® chosen from the following:
a) SEQ ID NO's: 34, 36, 38, 40;
b) amino acid sequences that have no more than 3, preferably no more than 2, more preferably no more than 1 amino acid difference with one of SEQ ID NO's: 34, 36, 38, 40, provided that:
  i) the amino acid sequence has Aspartic acid (Asp, D) at position 1, Praline (Pro, P) at position 14, Arginine (Arg, R) at position 83 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

The invention also provides a trivalent polypeptide comprising or essentially consisting of at least one amino acid sequence or Nanobody® chosen from the following:
a) SEQ ID NO's: 36, 38, 40;
b) amino acid sequences that have no more than 3, preferably no more than 2, more preferably no more than 1 amino acid difference with one of SEQ ID NO's: 36, 38, 40, provided that:
  i) the amino acid sequence has Aspartic acid (Asp, D) at position 1, Praline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least one amino acid sequence or Nanobody chosen from one of SEQ ID NO's: 36, 38, 40.

The invention also provides a trivalent polypeptide comprising or essentially consisting of at least one amino acid sequence or Nanobody® chosen from the following:
a) SEQ ID NO's: 38 and 40;
b) amino acid sequences that have no more than 3, preferably no more than 2, more preferably no more than 1 amino acid difference with one of SEQ ID NO's: 38 and 40, provided that:
  i) the amino acid sequence has Aspartic acid (Asp, D) at position 1, Proline (Pro, P) at position 14, Arginine (Arg, R) at position 83, Leucine (Leu, L) at position 108 and Glycine (Gly, G) at position 16; and in addition, the amino acid sequence has Glutamic acid (Glu, E) at position 54 or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

In another preferred aspect, the polypeptide of the invention comprises or essentially consists of at least one amino acid sequence or Nanobody chosen from one of SEQ ID NO's: 38 and 40.

In another preferred aspect, the invention provides a trivalent polypeptide comprising or essentially consisting of at least one amino acid sequence or Nanobody that comprises or essentially consists of SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala.

In another preferred aspect, the invention provides a trivalent polypeptide comprising or essentially consisting of at least one amino acid sequence or Nanobody that comprises or essentially consists of SEQ ID NO: 16, wherein one or more (such as two or three) amino acid residues have been mutated selected from the following: Ala14Pro, Lys83Arg and Gln108Leu.

In another preferred aspect, the invention provides a trivalent polypeptide comprising or essentially consisting of at least one amino acid sequence or Nanobody that comprises or essentially consists of SEQ ID NO: 16, wherein one or more (such as two or three) amino acid residues have been mutated selected from the following: Asp16Gly, Asp54Glu and Gly55Ala.

In another preferred aspect, the invention provides a trivalent polypeptide comprising or essentially consisting of at least one amino acid sequence or Nanobody that comprises or essentially consists of SEQ ID NO: 16, wherein position 1 (Glu) has been changed into Asp.

In another preferred aspect, the invention provides a trivalent polypeptide comprising or essentially consisting of at least one amino acid sequence or Nanobody that comprises or essentially consists of SEQ ID NO: 16, wherein one or more (such as two, three, four, five or six) amino acid residues have been mutated selected from the following: Ala14Pro, Lys83Arg, Gln108Leu, Asp16Gly, Asp54Glu, Gly55Ala, and wherein position 1 (Glu) has been changed into Asp.

In another preferred aspect, the invention provides a trivalent polypeptide comprising or essentially consisting of at least one amino acid sequence or Nanobody that comprises or essentially consists of SEQ ID NO: 16, wherein one or more (such as two or three) amino acid residues have been mutated selected from the following: Ala14Pro, Lys83Arg and Gln108Leu, and wherein position 1 (Glu) has been changed into Asp.

In another preferred aspect, the invention provides a trivalent polypeptide comprising or essentially consisting of at least one amino acid sequence or Nanobody that comprises or essentially consists of SEQ ID NO: 16, wherein one or more (such as two or three) amino acid residues have been mutated selected from the following: Asp16Gly, Asp54Glu and Gly55Ala, and wherein position 1 (Glu) has been changed into Asp.

In another preferred aspect, the invention provides a trivalent polypeptide comprising or essentially consisting of at least one amino acid sequence or Nanobody® that comprises or essentially consists of SEQ ID NO: 16, in which following amino acid residues have been mutated:
  Ala14Pro, Lys83Arg, Gln108Leu;
  Ala14Pro, Lys83Arg, Gln108Leu, Asp16Gly;
  Ala14Pro, Lys83Arg, Gln108Leu, Asp16Gly, Asp54Glu;
  Ala14Pro, Lys83Arg, Gln108Leu, Asp16Gly, Gly55Ala;
  Glu1Asp;
  Glu1Asp, Ala14Pro, Lys83Arg, Gln108Leu;
  Glu1Asp, Ala14Pro, Lys83Arg, Gln108Leu, Asp16Gly;
  Glu1Asp, Ala14Pro, Lys83Arg, Gln108Leu, Asp16Gly, Asp54Glu; or
  Glu1Asp, Ala14Pro, Lys83Arg, Gln108Leu, Asp16Gly, Gly55Ala.

A preferred multivalent polypeptide of the invention comprises or essentially consists of one amino acid sequence or Nanobody with SEQ ID NO: 34 and two amino acid sequences or Nanobodies® with SEQ ID NO: 33. Another preferred multivalent polypeptide of the invention comprises or essentially consists of one amino acid sequence or Nanobody with SEQ ID NO: 36 and two amino acid sequences or Nanobodies® with SEQ ID NO: 35. Another preferred multivalent polypeptide of the invention comprises or essentially consists of one amino acid sequence or Nanobody with SEQ ID NO: 38 and two amino acid sequences or Nanobodies® with SEQ ID NO: 37. Another preferred multivalent polypeptide of the invention comprises or essentially consists of one amino acid sequence or Nanobody with SEQ ID NO: 40 and two amino acid sequences or Nanobodies® with SEQ ID NO: 39. Another preferred multivalent polypeptide of the invention comprises or essentially consists of one amino acid sequence or Nanobody with SEQ ID NO: 51 and two amino acid sequences or Nanobodies® with SEQ ID NO: 16.

In another aspect, the invention provides a trivalent polypeptide chosen from the following polypeptides:
a) SEQ ID NO's: 41-49;
b) polypeptides that have no more than 3, preferably no more than 2, more preferably no more than 1 amino acid difference with one of SEQ ID NO's: 41-49, provided that:
  i) the amino acid sequence or Nanobody® encompassed in said polypeptide has Proline (Pro, P) at position 14, Arginine (Arg, R) at position 83 and/or Leucine (Leu, L) at position 108 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

In another aspect, the invention provides a trivalent polypeptide chosen from the following polypeptides:
a) SEQ ID NO's: 41-49;
b) polypeptides that have no more than 3, preferably no more than 2, more preferably no more than 1 amino acid difference with one of SEQ ID NO's: 41-49, provided that:
  i) the amino acid sequence or Nanobody® encompassed in said polypeptide has Praline (Pro, P) at position 14, Arginine (Arg, R) at position 83 and Leucine (Leu, L) at position 108 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Preferred trivalent polypeptides of the invention comprise or essentially consist of one of SEQ ID NO's: 41-49.

In another preferred aspect, the invention provides a trivalent polypeptide chosen from the following polypeptides:
a) SEQ ID NO's: 42, 43, 44, 47, 48, 49;
b) polypeptides that have no more than 3, preferably no more than 2, more preferably no more than 1 amino acid difference with one of SEQ ID NO's: 42, 43, 44, 47, 48, 49, provided that:
  i) the amino acid sequence or Nanobody® encompassed in said polypeptide has Glycine (Gly, G) at position 16, Glutamic acid (Glu, E) at position 54 and/or Alanine (Ala, A) at position 55 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

In a preferred aspect, the invention provides a trivalent polypeptide chosen from the following polypeptides:
a) SEQ ID NO's: 42, 43, 44, 47, 48, 49;
b) polypeptides that have no more than 3, preferably no more than 2, more preferably no more than 1 amino acid difference with one of SEQ ID NO's: 42, 43, 44, 47, 48, 49, provided that:
  i) the amino acid sequence or Nanobody® encompassed in said polypeptide has Proline (Pro, P) at position 14, Arginine (Arg, R) at position 83 and Leucine (Leu, L) at position 108; and in addition the amino acid sequence or Nanobody® encompassed in said polypeptide has Glycine (Gly, G) at position 16, Glutamic acid (Glu, E) at position 54 and/or Alanine (Ala, A) at position 55 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Preferred trivalent polypeptides of the invention comprise or essentially consist of one of SEQ ID NO's: 42, 43, 44, 47, 48, 49.

In another preferred aspect, the invention provides a trivalent polypeptide chosen from the following polypeptides:
a) SEQ ID NO's: 43-44;
b) polypeptides that have no more than 3, preferably no more than 2, more preferably no more than 1 amino acid difference with one of SEQ ID NO's: 43-44, provided that:
  i) the amino acid sequence or Nanobody® encompassed in said polypeptide has Proline (Pro, P) at position 14, Arginine (Arg, R) at position 83, Leucine (Leu, L) at position 108 and Glycine (Gly, G) at position 16; and in addition, the amino acid sequence or Nanobody® encompassed in said polypeptide has Glutamic acid (Glu, E) at position 54 or Alanine (Ala, A) at position 55 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Preferred trivalent polypeptides of the invention comprise or essentially consist of one of SEQ ID NO's: 43-44.

In another preferred aspect, the invention provides a trivalent polypeptide chosen from the following polypeptides:
a) SEQ ID NO's: 41-44 and 50;
b) polypeptides that have no more than 3, preferably no more than 2, more preferably no more than 1 amino acid difference with one of SEQ ID NO's: 41-44 and 50, provided that:
  i) the first amino acid sequence or Nanobody® encompassed in said polypeptide has Aspartic acid (Asp, D) at position 1 (said positions determined according to Kabat numbering); and ii) the polypeptide binds protein F of hRSV with the same, about the same, or a higher affinity (said affinity as measured by surface plasmon resonance) and/or the polypeptide has the same, about the same, or a higher potency (as defined herein) compared to the amino acid sequence without the 3, 2 or 1 amino acid difference.

The invention also provides a trivalent polypeptide as described above in which the Glutamic acid at position 1 has been changed into an Aspartic acid. Accordingly, in another preferred aspect, the invention provides a trivalent polypeptide chosen from the following polypeptides:

a) SEQ ID NO's: 41-44;
b) polypeptides that have no more than 3, preferably no more than 2, more preferably no more than 1 amino acid difference with one of SEQ ID NO's: 41-44, provided that:
  i) the amino acid sequence or Nanobody® encompassed in said polypeptide has Proline (Pro, P) at position 14, Arginine (Arg, R) at position 83 and Leucine (Leu, L) at position 108; and the first amino acid sequence or Nanobody® encompassed in said polypeptide has Aspartic acid (Asp, D) at position 1 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the amino acid sequence without the 3, 2 or 1 amino acid difference.

In another preferred aspect, the invention provides a trivalent polypeptide chosen from the following polypeptides:

a) SEQ ID NO's: 42-44;
b) polypeptides that have no more than 3, preferably no more than 2, more preferably no more than 1 amino acid difference with one of SEQ ID NO's: 42-44, provided that:
  i) the amino acid sequence or Nanobody® encompassed in said polypeptide has Proline (Pro, P) at position 14, Arginine (Arg, R) at position 83 and Leucine (Leu, L) at position 108; and in addition, the amino acid sequence or Nanobody® encompassed in said polypeptide has Glycine (Gly, G) at position 16, Glutamic acid (Glu, E) at position 54 and/or Alanine (Ala, A) at position 55; and the first amino acid sequence or Nanobody® encompassed in said polypeptide has Aspartic acid (Asp, D) at position 1 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the amino acid sequence without the 3, 2 or 1 amino acid difference.

Preferred trivalent polypeptides of the invention comprise or essentially consist of SEQ ID NO: 42-44.

In another preferred aspect, the invention provides a trivalent polypeptide chosen from the following polypeptides:

a) SEQ ID NO's: 43 and 44;
b) polypeptides that have no more than 3, preferably no more than 2, more preferably no more than 1 amino acid difference with one of SEQ ID NO's: 43 and 44, provided that:
  i) the amino acid sequence or Nanobody® encompassed in said polypeptide has Proline (Pro, P) at position 14, Arginine (Arg, R) at position 83, Leucine (Leu, L) at position 108 and Glycine (Gly, G) at position 16; and in addition, the amino acid sequence or Nanobody® encompassed in said polypeptide has Glutamic acid (Glu, E) at position 54 or Alanine (Ala, A) at position 55; and the first amino acid sequence or Nanobody® encompassed in said polypeptide has Aspartic acid (Asp, D) at position 1 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the amino acid sequence without the 3, 2 or 1 amino acid difference.

Preferred trivalent polypeptides of the invention comprise or essentially consist of SEQ ID NO: 43 and 44.

In another preferred aspect, the invention provides a trivalent polypeptide comprising or essentially consisting of SEQ ID NO: 26, in which in at least one (preferably in two, more preferably in all three) Nanobody®/Nanobodies® that form(s) part of SEQ ID NO: 26, one or more (such as two, three, four, five or six) amino acid residues have been mutated selected from the following: Ala14Pro, Lys83Arg, Gln108Leu, Asp16Gly, Asp54Glu and Gly55Ala.

In another preferred aspect, the invention provides a trivalent polypeptide comprising or essentially consisting of SEQ ID NO: 26, in which in at least one (preferably in two, more preferably in all three) Nanobody®/Nanobodies® that form(s) part of SEQ ID NO: 26, one or more (such as two or three) amino acid residues have been mutated selected from the following: Ala14Pro, Lys83Arg and Gln108Leu.

In another preferred aspect, the invention provides a trivalent polypeptide comprising or essentially consisting of SEQ ID NO: 26, in which in at least one (preferably in two, more preferably in all three) Nanobody®/Nanobodies® that form(s) part of SEQ ID NO: 26, one or more (such as two or three) amino acid residues have been mutated selected from the following: Asp16Gly, Asp54Glu and Gly55Ala.

In another preferred aspect, the invention provides a trivalent polypeptide comprising or essentially consisting of SEQ ID NO: 26, in which position 1 (Glu) has been changed into Asp.

In another preferred aspect, the invention provides a trivalent polypeptide comprising or essentially consisting of SEQ ID NO: 26, in which in at least one (preferably in two, more preferably in all three) Nanobody®/Nanobodies® that form(s) part of SEQ ID NO: 26, one or more (such as two or three) amino acid residues have been mutated selected from the following: Ala14Pro, Lys83Arg and Gln108Leu; and in which position 1 (Glu) has been changed into Asp.

In another preferred aspect, the invention provides a trivalent polypeptide comprising or essentially consisting of SEQ ID NO: 26, in which in at least one (preferably in two, more preferably in all three) Nanobody®/Nanobodies® that form(s) part of SEQ ID NO: 26, one or more (such as two or three) amino acid residues have been mutated selected from the following: Ala14Pro, Lys83Arg and Gln108Leu; and in which position 1 (Glu) has been changed into Asp.

In another preferred aspect, the invention provides a trivalent polypeptide comprising or essentially consisting of SEQ ID NO: 26, in which in at least one (preferably in two, more preferably in all three) Nanobody®/Nanobodies' that form(s) part of SEQ ID NO: 26, one or more (such as two or three) amino acid residues have been mutated selected from the following: Asp16Gly, Asp54Glu and Gly55Ala; and in which position 1 (Glu) has been changed into Asp.

In another preferred aspect, the invention provides a trivalent polypeptide comprising or essentially consisting of SEQ ID NO: 26, in which in at least one (preferably in two, more preferably in all three) Nanobody®/Nanobodies® that form(s) part of SEQ ID NO: 26, following amino acid residues have been mutated:

Ala14Pro, Lys83Arg, Gln108Leu;
Ala14Pro, Lys83Arg, Gln108Leu, Asp16Gly;
Ala14Pro, Lys83Arg, Gln108Leu, Asp16Gly, Asp54Glu;
Ala14Pro, Lys83Arg, Gln108Leu, Asp16Gly, Gly55Ala;
Glu1Asp;
Glu1Asp, Ala14Pro, Lys83Arg, Gln108Leu;
Glu1Asp, Ala14Pro, Lys83Arg, Gln108Leu, Asp16Gly;
Glu1Asp, Ala14Pro, Lys83Arg, Gln108Leu, Asp16Gly, Asp54Glu; or
Glu1Asp, Ala14Pro, Lys83Arg, Gln108Leu, Asp16Gly, Gly55Ala.

In another preferred aspect, the polypeptide of the invention essentially consists of the amino acid sequence of SEQ ID NO: 41. In another preferred aspect, the polypeptide of the invention essentially consists of the amino acid sequence of SEQ ID NO: 42. In another preferred aspect, the polypeptide of the invention essentially consists of the amino acid sequence of SEQ ID NO: 43. In another preferred aspect, the polypeptide of the invention essentially consists of the amino acid sequence of SEQ ID NO: 44.

Polypeptides with the amino acid sequences and polypeptide sequences as described above have shown advantageous properties for use as prophylactic, therapeutic and/or pharmacologically active agents such as e.g. improved stability and less immunogenicity compared to prior amino acid sequences (as described in PCT application PCT/EP2009/056975 entitled "Amino acid sequences directed against envelope proteins of a virus and polypeptides comprising the same for the treatment of viral diseases" filed by Ablynx N. V. on 5 Jun. 2009). In addition, the amino acid sequences and polypeptide sequences as described above show good binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), good affinity and/or good avidity for protein F of hRSV and/or good efficacy and/or potency for neutralizing hRSV.

More in particular, these polypeptides and compounds of the invention can bind to protein F of hRSV with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) preferably such that they:

bind to protein F of hRSV with a dissociation constant ($K_D$) of 100 nM to 0.1 nM or less, preferably 10 nM to 0.1 nM or less, more preferably 1 nM to 0.1 nM or less; and/or such that they:

bind to protein F of hRSV with a $k_{on}$-rate of between $10^4$ $M^{-1}s^{-1}$ to about $10^7$ $M^{-1}s^{-1}$, preferably between $10^5$ $M^{-1}s^{-1}$ and $10^7$ $M^{-1}s^{-1}$, more preferably about $10^6$ $M^{-1}s^{-1}$ or more;

and/or such that they:
bind to protein F of hRSV with a $k_{off}$-rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, more preferably between $5\times10^{-3}s^{-1}$ and $10^{-4}$ $s^{-1}$, or lower;

Some preferred IC50 values for binding of the polypeptides of the invention to protein F of hRSV will become clear from the further description and examples herein.

Assays to determine the IC50 include competition assays such as competition ELISA (e.g. competition with Synagis® or its Fab fragment) or more preferably neutralization assays such as the microneutralization assay described by Anderson et al. (1985, J. Clin. Microbiol. 22: 1050-1052), modification of this assay as described in example 6, or a plaque reduction assay as described by Johnson et al. (1997, J. Inf. Dis. 176: 1215-1224), and modifications thereof.

For example, in a competition assay with Synagis®, the polypeptides of the invention may have IC50 values between 1 nM and 100 nM, preferably between 10 nM and 50 nM, or less.

For example, in a microneutralization assay of RSV strain Long (such as e.g. described in Example 6) the polypeptides of the invention may have IC50 values between 10 pM and 1000 pM, preferably between 10 pM and 250 pM, more preferably between 50 pM and 200 pM or less. In a microneutralization assay, the polypeptides of the invention may have IC50 values that are at least the same and preferably better, at least ten times better, preferably twenty times better, more preferably fifty times better, even more preferably sixty, seventy, eighty or more times better compared to the IC50 value obtained with Synagis®.

The invention also relates to a monovalent polypeptide or construct (also referred to as "monovalent polypeptide of the invention" or "monovalent construct of the invention"), comprising or essentially consisting of one amino acid sequence or Nanobody® of the invention. Preferred monovalent constructs of the invention comprise or essentially consist of one of SEQ ID NO's: 33-40 and 51. Such a monovalent constructs, as well as the amino acid sequences and Nanobodies® of the invention can be used for the preparation of a polypeptide of the invention, such as e.g. the multivalent polypeptides of the invention described above.

The polypeptides of the invention can generally be prepared by a method which comprises at least the step of suitably linking the amino acid sequence, Nanobody® or monovalent construct of the invention to one or more further amino acid sequences, Nanobodies® or monovalent constructs of the invention, optionally via the one or more suitable linkers, so as to provide the polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

A method for preparing multivalent, multiparatopic and/or multispecific amino acids or polypeptides of the invention may comprise at least the steps of linking two or more monovalent amino acid sequences or monovalent constructs of the invention and for example one or more linkers together in a suitable manner. The monovalent constructs (and linkers) can be coupled by any method known in the art and as further described herein. Preferred techniques include the linking of the nucleic acid sequences that encode the monovalent constructs (and linkers) to prepare a genetic construct that expresses the multivalent, multiparatopic and/or multispecific amino acid sequence or polypeptide. Techniques for linking amino acid sequences or nucleic acid sequences will be clear to the skilled person, and reference is again made to the standard handbooks, such as Sambrook et al. and Ausubel et al., mentioned above, as well as the Examples below.

Accordingly, the present invention also relates to the use of an amino acid sequence, a Nanobody® or a monovalent construct of the invention in preparing a multivalent polypeptide of the invention. The method for the preparation of a multivalent polypeptide will comprise the linking of an amino acid sequence, a Nanobody® or a monovalent construct of the invention to at least one further amino acid sequence, Nanobody® or monovalent construct of the invention, optionally via one or more linkers. The amino acid sequence, Nanobody® or monovalent construct is then used as a binding domain or binding unit in providing and/or preparing the multivalent polypeptide comprising two (e.g. in a bivalent polypeptide), three (e.g. in a trivalent polypeptide) or more (e.g. in a multivalent polypeptide) binding units. In this respect, the amino acid sequence, Nanobody® and monovalent construct may be used as a binding domain or binding unit in providing and/or preparing a multivalent and preferably bivalent or trivalent polypeptide of the invention comprising two, three or more binding units. Preferably, the binding domains or binding units are linked via a linker such that the multivalent polypeptide preferably exhibits intramolecular binding compared to intermolecular binding. Also preferably the multivalent polypeptide can simultaneously bind both or all three binding sites on the F protein of RSV.

Accordingly, the present invention also relates to the use of an amino acid sequence or a Nanobody® of the invention (as described above) in preparing a multivalent polypeptide. The method for the preparation of the multivalent polypeptide will comprise the linking of the amino acid sequence or Nanobody® of the invention to at least one further amino acid sequences or Nanobody® of the invention, optionally via one or more linkers.

In a preferred aspect, the present invention relates to the use of an amino acid sequence chosen from the following:
  a) SEQ ID NO's: 33-40;
  b) amino acid sequences that have no more than 3, preferably no more than 2, more preferably no more than 1 amino acid difference with one of SEQ ID NO's: 33-40, provided that:
    i) the amino acid sequence has Praline (Pro, P) at position 14, Arginine (Arg, R) at position 83 and/or Leucine (Leu, L) at position 108 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a multivalent polypeptide. The method for the preparation of the multivalent polypeptide will comprise the linking of said amino acid sequence to at least one further amino acid sequences, optionally via one or more linkers.

In another preferred aspect, the present invention relates to the use of an amino acid sequence chosen from the following:
  a) SEQ ID NO's: 33-40;
  b) amino acid sequences that have no more than 3, preferably no more than 2, more preferably no more than 1 amino acid difference with one of SEQ ID NO's: 33-40, provided that:
    i) the amino acid sequence has Proline (Pro, P) at position 14, Arginine (Arg, R) at position 83 and Leucine (Leu, L) at position 108 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a multivalent polypeptide. The method for the preparation of the multivalent polypeptide will comprise the linking of said amino acid sequence to at least one further amino acid sequences, optionally via one or more linkers.

In a preferred aspect, the amino acid sequence used in preparing a multivalent polypeptide comprises or essentially consists of one of SEQ ID NO's: 33-40.

In another preferred aspect, the present invention relates to the use of an amino acid sequence chosen from the following:
  a) SEQ ID NO's: 35-40;
  b) amino acid sequences that have no more than 3, preferably no more than 2, more preferably no more than 1 amino acid difference with one of SEQ ID NO's: 35-40, provided that:
    i) the amino acid sequence has Glycine (Gly, G) at position 16, Glutamic acid (Glu, E) at position 54 and/or Alanine (Ala, A) at position 55 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a multivalent polypeptide. The method for the preparation of the multivalent polypeptide will comprise the linking of said amino acid sequence to at least one further amino acid sequences, optionally via one or more linkers.

In another preferred aspect, the present invention relates to the use of an amino acid sequence chosen from the following:
  a) SEQ ID NO's: 35-40;
  b) amino acid sequences that have no more than 3, preferably no more than 2, more preferably no more than 1 amino acid difference with one of SEQ ID NO's: 35-40, provided that:
    i) the amino acid sequence has Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a multivalent polypeptide. The method for the preparation of the multivalent polypeptide will comprise the linking of said amino acid sequence to at least one further amino acid sequences, optionally via one or more linkers.

In a preferred aspect, the amino acid sequence used in preparing a multivalent polypeptide comprises or essentially consists of one of SEQ ID NO: 35-40.

In another preferred aspect, the present invention relates to the use of an amino acid sequence chosen from the following:
a) SEQ ID NO's: 37-40;
b) amino acid sequences that have no more than 3, preferably no more than 2, more preferably no more than 1 amino acid difference with one of SEQ ID NO's: 37-40, provided that:
  i) the amino acid sequence has Praline (Pro, P) at position 14, Arginine (Arg, R) at position 83, Leucine (Leu, L) at position 108 and Glycine (Gly, G) at position 16; and in addition the amino acid sequence has Glutamic acid (Glu, E) at position 54 or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a multivalent polypeptide. The method for the preparation of the multivalent polypeptide will comprise the linking of said amino acid sequence to at least one further amino acid sequences, optionally via one or more linkers.

In a preferred aspect, the amino acid sequence used in preparing a multivalent polypeptide comprises or essentially consists of one of SEQ ID NO's: 37-40.

In another preferred aspect, the present invention relates to the use of an amino acid sequence chosen from the above wherein the amino acid (Glutamic acid) at position 1 has been changed into Aspartic acid, in preparing a multivalent polypeptide.

In another preferred aspect, the present invention relates to the use of an amino acid sequence chosen from the following:
a) SEQ ID NO's: 34, 36, 38, 40, 51;
b) amino acid sequences that have no more than 3, preferably no more than 2, more preferably no more than 1 amino acid difference with one of SEQ ID NO's: 34, 36, 38, 40, 51, provided that:
  i) the amino acid sequence has Aspartic acid (Asp, D) at position 1 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a multivalent polypeptide. The method for the preparation of the multivalent polypeptide will comprise the linking of said amino acid sequence to at least one further amino acid sequences, optionally via one or more linkers.

In a preferred aspect, the amino acid sequence used in preparing a multivalent polypeptide comprises or essentially consists of one of SEQ ID NO: 34, 36, 38, 40, 51.

In another preferred aspect, the present invention relates to the use of an amino acid sequence chosen from the following:
a) SEQ ID NO's: 34, 36, 38, 40;
b) amino acid sequences that have no more than 3, preferably no more than 2, more preferably no more than 1 amino acid difference with one of SEQ ID NO's: 34, 36, 38, 40, provided that:
  i) the amino acid sequence has Aspartic acid (Asp, D) at position 1, Proline (Pro, P) at position 14, Arginine (Arg, R) at position 83 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a multivalent polypeptide. The method for the preparation of the multivalent polypeptide will comprise the linking of said amino acid sequence to at least one further amino acid sequences, optionally via one or more linkers.

In another preferred aspect, the present invention relates to the use of an amino acid sequence chosen from the following:
a) SEQ ID NO's: 36, 38, 40;
b) amino acid sequences that have no more than 3, preferably no more than 2, more preferably no more than 1 amino acid difference with one of SEQ ID NO's: 36, 38, 40, provided that:
  i) the amino acid sequence has Aspartic acid (Asp, D) at position 1, Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a multivalent polypeptide. The method for the preparation of the multivalent polypeptide will comprise the linking of said amino acid sequence to at least one further amino acid sequences, optionally via one or more linkers.

In a preferred aspect, the amino acid sequence used in preparing a multivalent polypeptide comprises or essentially consists of one of SEQ ID NO: 36, 38, 40.

In another preferred aspect, the present invention relates to the use of an amino acid sequence chosen from the following:
a) SEQ ID NO's: 38 and 40;
b) amino acid sequences that have no more than 3, preferably no more than 2, more preferably no more than 1 amino acid difference with one of SEQ ID NO's: 38 and 40, provided that:
  i) the amino acid sequence has Aspartic acid (Asp, D) at position 1, Proline (Pro, P) at position 14, Arginine (Arg, R) at position 83, Leucine (Leu, L) at position 108 and Glycine (Gly, G) at position 16; and in addition, the amino acid sequence has Glutamic acid (Glu, E) at position 54 or Alanine (Ala, A) at position 55 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a multivalent polypeptide. The method for the preparation of the multivalent polypeptide will comprise the linking of said amino acid sequence to at least one further amino acid sequences, optionally via one or more linkers.

In a preferred aspect, the amino acid sequence used in preparing a multivalent polypeptide comprises or essentially consists of SEQ ID NO: 38. In another preferred aspect, the amino acid sequence used in preparing a multivalent polypeptide comprises or essentially consists of SEQ ID NO: 40.

In another preferred aspect, the present invention relates to the use of an amino acid sequence that comprises or essentially consists of SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala, in preparing a multivalent polypeptide.

In another preferred aspect, the present invention relates to the use of an amino acid sequence that comprises or essentially consists of SEQ ID NO: 16, wherein one or more (such as two or three) amino acid residues have been mutated selected from the following: Ala14Pro, Lys83Arg and Gln108Leu, in preparing a multivalent polypeptide.

In another preferred aspect, the present invention relates to the use of an amino acid sequence that comprises or essentially consists of SEQ ID NO: 16, wherein one or more (such as two or three) amino acid residues have been mutated selected from the following: Asp16Gly, Asp54Glu and Gly55Ala, in preparing a multivalent polypeptide.

In another preferred aspect, the present invention relates to the use of an amino acid sequence that comprises or essentially consists of SEQ ID NO: 16, wherein position 1 (Glu) has been changed into Asp, in preparing a multivalent polypeptide.

In another preferred aspect, the present invention relates to the use of an amino acid sequence that comprises or essentially consists of SEQ ID NO: 16, wherein one or more (such as two, three, four, five or six) amino acid residues have been mutated selected from the following: Ala14Pro, Lys83Arg, Gln108Leu, Asp16Gly, Asp54Glu, Gly55Ala, and wherein position 1 (Glu) has been changed into Asp, in preparing a multivalent polypeptide.

In another preferred aspect, the present invention relates to the use of an amino acid sequence that comprises or essentially consists of SEQ ID NO: 15, wherein one or more (such as two or three) amino acid residues have been mutated selected from the following: Ala14Pro, Lys83Arg and Gln108Leu, and wherein position 1 (Glu) has been changed into Asp, in preparing a multivalent polypeptide.

In another preferred aspect, the present invention relates to the use of an amino acid sequence that comprises or essentially consists of SEQ ID NO: 16, wherein one or more (such as two or three) amino acid residues have been mutated selected from the following: Asp16Gly, Asp54Glu and Gly55Ala, and wherein position 1 (Glu) has been changed into Asp, in preparing a multivalent polypeptide.

In another preferred aspect, the present invention relates to the use of an amino acid sequence that comprises or essentially consists of SEQ ID NO: 16, in which following amino acid residues have been mutated:

Ala14Pro, Lys83Arg, Gln108Leu;
Ala14Pro, Lys83Arg, Gln108Leu, Asp16Gly;
Ala14Pro, Lys83Arg, Gln108Leu, Asp16Gly, Asp54Glu;
Ala14Pro, Lys83Arg, Gln108Leu, Asp16Gly, Gly55Ala;
Glu1Asp;
Glu1Asp, Ala14Pro, Lys83Arg, Gln108Leu;
Glu1Asp, Ala14Pro, Lys83Arg, Gln108Leu, Asp16Gly;
Glu1Asp, Ala14Pro, Lys83Arg, Gln108Leu, Asp16Gly, Asp54Glu; or
Glu1Asp, Ala14Pro, Lys83Arg, Gln108Leu, Asp16Gly, Gly55Ala, in preparing a multivalent polypeptide.

The present invention also relates to the use of two amino acid sequences and/or Nanobodies® of the invention (as described above) in preparing a bivalent polypeptide. The method for the preparation of the bivalent polypeptide will comprise the linking of the amino acid sequences and/or Nanobodies® of the invention, optionally via a linker.

Accordingly, in a preferred aspect, the present invention relates to the use of two amino acid sequences chosen from the following:

a) SEQ ID NO's: 33-40;
b) amino acid sequences that have no more than 3, preferably no more than 2, more preferably no more than 1 amino acid difference with one of SEQ ID NO's: 33-40, provided that:
  i) the amino acid sequence has Proline (Pro, P) at position 14, Arginine (Arg, R) at position 83 and/or Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a bivalent polypeptide. The method for the preparation of the bivalent polypeptide will comprise the linking of said amino acid sequences to each other, optionally via a linker.

In another preferred aspect, the present invention relates to the use of two amino acid sequences chosen from the following:

a) SEQ ID NO's: 33-40;
b) amino acid sequences that have no more than 3, preferably no more than 2, more preferably no more than 1 amino acid difference with one of SEQ ID NO's: 33-40, provided that:
  i) the amino acid sequence has Praline (Pro, P) at position 14, Arginine (Arg, R) at position 83 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a bivalent polypeptide. The method for the preparation of the bivalent polypeptide will comprise the linking of said amino acid sequences to each other, optionally via a linker.

In a preferred aspect, the two amino acid sequences used in preparing the bivalent polypeptide comprise or essentially consist of one of SEQ ID NO's: 33-40.

In another preferred aspect, the present invention relates to the use of two amino acid sequences chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
 i) the amino acid sequence has Glycine (Gly, G) at position 16, Glutamic acid (Glu, E) at position 54 and/or Alanine (Ala, A) at position 55 (said positions determined according to Kabat numbering); and
 ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a bivalent polypeptide. The method for the preparation of the bivalent polypeptide will comprise the linking of said amino acid sequences to each other, optionally via a linker.

In another preferred aspect, the present invention relates to the use of two amino acid sequences chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
 i) the amino acid sequence has Praline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
 ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a bivalent polypeptide. The method for the preparation of the bivalent polypeptide will comprise the linking of said amino acid sequences to each other, optionally via a linker.

In a preferred aspect, the two amino acid sequences used in preparing the bivalent polypeptide comprise or essentially consist of one of SEQ ID NO's: 35-40.

In another preferred aspect, the present invention relates to the use of two amino acid sequences chosen from the following:
a) SEQ ID NO's: 37-40;
b) amino acid sequences that have no more than 3, preferably no more than 2, more preferably no more than 1 amino acid difference with one of SEQ ID NO's: 37-40, provided that:
 i) the amino acid sequence has Proline (Pro, P) at position 14, Arginine (Arg, R) at position 83, Leucine (Leu, L) at position 108 and Glycine (Gly, G) at position 16; and in addition the amino acid sequence has Glutamic acid (Glu, E) at position 54 or Alanine (Ala, A) at position 55 (said positions determined according to Kabat numbering); and
 ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid, difference, in preparing a bivalent polypeptide. The method for the preparation of the bivalent polypeptide will comprise the linking of said amino acid sequences to each other, optionally via a linker.

In another preferred aspect, the present invention relates to the use of an amino acid sequence chosen from the above wherein the amino acid (Glutamic acid) at position 1 has been changed into Aspartic acid, in preparing a bivalent polypeptide.

In specific aspect, the present invention relates to the use of an amino acid sequence chosen from the following:
a) SEQ ID NO's: 34, 36, 38, 40, 51;
b) amino acid sequences that have no more than 3, preferably no more than 2, more preferably no more than 1 amino acid difference with one of SEQ ID NO's: 34, 36, 38, 40, 51, provided that:
 i) the amino acid sequence has Aspartic acid (Asp, D) at position 1 (said position determined according to Kabat numbering); and
 ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a bivalent polypeptide. The method for the preparation of the bivalent polypeptide will comprise the linking of said amino acid sequence to at least one further amino acid sequences, optionally via one or more linkers.

A preferred amino acid sequence used for preparing a bivalent polypeptide comprises or essentially consist of one of SEQ ID NO's: 34, 36, 38, 40, 51.

In specific aspect, the present invention relates to the use of an amino acid sequence chosen from the following:
a) SEQ ID NO's: 34, 36, 38, 40;
b) amino acid sequences that have no more than 3, preferably no more than 2, more preferably no more than 1 amino acid difference with one of SEQ ID NO's: 34, 36, 38, 40, provided that:
 i) the amino acid sequence has Aspartic acid (Asp, D) at position 1, Proline (Pro, P) at position 14, Arginine (Arg, R) at position 83 and Leucine (Leu, L) at position 108 (said positions determined according to Kabat numbering); and
 ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a bivalent polypeptide. The method for the preparation of the bivalent polypeptide will comprise the linking of said amino acid sequence to at least one further amino acid sequences, optionally via one or more linkers.

In specific aspect, the present invention relates to the use of an amino acid sequence chosen from the following:
a) SEQ ID NO's: 36, 38, 40;
b) amino acid sequences that have no more than 3, preferably no more than 2, more preferably no more than 1 amino acid difference with one of SEQ ID NO's: 36, 38, 40, provided that:
  i) the amino acid sequence has Aspartic acid (Asp, D) at position 1, Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide. The method for the preparation of the bivalent polypeptide will comprise the linking of said amino acid sequence to at least one further amino acid sequences, optionally via one or more linkers.

A preferred amino acid sequence used for preparing a bivalent polypeptide comprises or essentially consist of one of SEQ ID NO's: 36, 38, 40.

In specific aspect, the present invention relates to the use of an amino acid sequence chosen from the following:
a) SEQ ID NO's: 38 and 40;
b) amino acid sequences that have no more than 3, preferably no more than 2, more preferably no more than 1 amino acid difference with one of SEQ ID NO's: 38 and 40, provided that:
  i) the amino acid sequence has Aspartic acid (Asp, D) at position 1, Proline (Pro, P) at position 14, Arginine (Arg, R) at position 83, Leucine (Leu, L) at position 108 and Glycine (Gly, G) at position 16; and in addition, the amino acid sequence has Glutamic acid (Glu, E) at position 54 or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a bivalent polypeptide. The method for the preparation of the bivalent polypeptide will comprise the linking of said amino acid sequence to at least one further amino acid sequences, optionally via one or more linkers.

A preferred amino acid sequence used for preparing a bivalent polypeptide comprises or essentially consist of one of SEQ ID NO's: 36, 38, 40.

In a preferred aspect, the amino acid sequences used in preparing a bivalent polypeptide comprise or essentially consist of SEQ ID NO's: 33 and 34. In another preferred aspect, the amino acid sequences used in preparing a bivalent polypeptide comprise or essentially consist of SEQ ID NO's: 35 and 36. In another preferred aspect, the amino add sequences used in preparing a bivalent polypeptide comprise or essentially consist of SEQ ID NO's: 37 and 38. In another preferred aspect, the amino acid sequences used in preparing a bivalent polypeptide comprise or essentially consist of SEQ ID NO's: 39 and 40. In another preferred aspect, the amino acid sequences used in preparing a bivalent polypeptide comprise or essentially consist of SEQ ID NO's: 51 and 16.

In another preferred aspect, the present invention relates to the use of an amino acid sequence that comprises or essentially consists of SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala, in preparing a bivalent polypeptide.

In another preferred aspect, the present invention relates to the use of an amino acid sequence that comprises or essentially consists of SEQ ID NO: 16, wherein one or more (such as two or three) amino acid residues have been mutated selected from the following: Ala14Pro, Lys83Arg and Gln108Leu, in preparing a bivalent polypeptide.

In another preferred aspect, the present invention relates to the use of an amino acid sequence that comprises or essentially consists of SEQ ID NO: 16, wherein one or more (such as two or three) amino acid residues have been mutated selected from the following: Asp16Gly, Asp54Glu and Gly55Ala, in preparing a bivalent polypeptide.

In another preferred aspect, the present invention relates to the use of an amino acid sequence that comprises or essentially consists of SEQ ID NO: 16, wherein position 1 (Glu) has been changed into Asp, in preparing a bivalent polypeptide.

In another preferred aspect, the present invention relates to the use of an amino acid sequence that comprises or essentially consists of SEQ ID NO: 16, wherein one or more (such as two, three, four, five or six) amino acid residues have been mutated selected from the following: Ala14Pro, Lys83Arg, Gln108Leu, Asp16Gly, Asp54Glu, Gly55Ala, wherein position 1 (Glu) has been changed into Asp, in preparing a bivalent polypeptide.

In another preferred aspect, the present invention relates to the use of an amino acid sequence that comprises or essentially consists of SEQ ID NO: 16, wherein one or more (such as two or three) amino acid residues have been mutated selected from the following: Ala14Pro, Lys83Arg and Gln108Leu, wherein position 1 (Glu) has been changed into Asp, in preparing a bivalent polypeptide.

In another preferred aspect, the present invention relates to the use of an amino acid sequence that comprises or essentially consists of SEQ ID NO: 16, wherein one or more (such as two or three) amino acid residues have been mutated selected from the following: Asp16Gly, Asp54Glu and Gly55Ala, wherein position 1 (Glu) has been changed into Asp, in preparing a bivalent polypeptide.

In another preferred aspect, the present invention relates to the use of an amino acid sequence that comprises or essentially consists of SEQ ID NO: 16, in which following amino acid residues have been mutated:
  Ala14Pro, Lys83Arg, Gln108Leu;
  Ala14Pro, Lys83Arg, Gln108Leu, Asp16Gly;
  Ala14Pro, Lys83Arg, Gln108Leu, Asp16Gly, Asp54Glu;
  Ala14Pro, Lys83Arg, Gln108Leu, Asp16Gly, Gly55Ala;
  Glu1Asp;
  Glu1Asp, Ala14Pro, Lys83Arg, Gln108Leu;
  Glu1Asp, Ala14Pro, Lys83Arg, Gln108Leu, Asp16Gly;
  Glu1Asp, Ala14Pro, Lys83Arg, Gln108Leu, Asp16Gly, Asp54Glu; or
  Glu1Asp, Ala14Pro, Lys83Arg, Gln108Leu, Asp16Gly, Gly55Ala,
in preparing a bivalent polypeptide.

The present invention also relates to the use of three amino acid sequences and/or Nanobodies® of the invention (as described above) in preparing a trivalent polypeptide. The method for the preparation of the trivalent polypeptide will comprise the linking of the amino acid sequences and/or Nanobodies® of the invention, optionally via one or more linkers.

In a preferred aspect, the present invention relates to the use of three (preferably identical) amino acid sequences chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:
   i) the amino acid sequence has Proline (Pro, P) at position 14, Arginine (Arg, R) at position 83 and/or Leucine (Leu, L) at position 108 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide. The method for the preparation of the trivalent polypeptide will comprise the linking of said amino acid sequences to each other, optionally via one or more linkers.

In another preferred aspect, the present invention relates to the use of three (preferably identical) amino acid sequences chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:
   i) the amino acid sequence has Praline (Pro, P) at position 14, Arginine (Arg, R) at position 83 and Leucine (Leu, L) at position 108 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide. The method for the preparation of the trivalent polypeptide will comprise the linking of said amino acid sequences to each other, optionally via one or more linkers.

In a preferred aspect, the three amino acid sequences used in preparing the trivalent polypeptide comprise or essentially consist of one of SEQ ID NO's: 33-40.

In another preferred aspect, the present invention relates to the use of three (preferably identical) amino acid sequences chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
   i) the amino acid sequence has Glycine (Gly, G) at position 16, Glutamic acid (Glu, E) at position 54 and/or Alanine (Ala, A) at position 55 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide. The method for the preparation of the trivalent polypeptide will comprise the linking of said amino acid sequence to each other, optionally via one or more linkers.

In another preferred aspect, the present invention relates to the use of three (preferably identical) amino acid sequences chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
   i) the amino acid sequence has Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference,
in preparing a trivalent polypeptide. The method for the preparation of the trivalent polypeptide will comprise the linking of said amino acid sequences to each other, optionally via one or more linkers.

In a preferred aspect, the three amino acid sequences used in preparing a trivalent polypeptide comprise or essentially consist of one of SEQ ID NO's: 35-40.

In another preferred aspect, the present invention relates to the use of three (preferably identical) amino acid sequences chosen from the following:
a) SEQ ID NO's: 37-40;
b) amino acid sequences that have no more than 3, preferably no more than 2, more preferably no more than 1 amino acid difference with one of SEQ ID NO's: 37-40, provided that:
   i) the amino acid sequence has Proline (Pro, P) at position 14, Arginine (Arg, R) at position 83, Leucine (Leu, 1) at position 108 and Glycine (Gly, G) at position 16; and in addition the amino acid sequence has Glutamic acid (Glu, E) at position 54 or Alanine (Ala, A) at position 55 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a trivalent polypeptide. The method for the preparation of the trivalent polypeptide will comprise the linking of said amino acid sequences to each other, optionally via a linker.

In a preferred aspect, the three amino acid sequences used in preparing the trivalent polypeptide comprise or essentially consist of one of SEQ ID NO's: 37-40.

In another preferred aspect, the present invention relates to the use of an amino acid sequence chosen from the above wherein the amino acid (Glutamic acid) at position 1 has been changed into Aspartic acid, in preparing a bivalent polypeptide.

In another preferred aspect, the present invention relates to the use of an amino acid sequence chosen from the following:

a) SEQ ID NO's: 34, 36, 38, 40, 51;
b) amino acid sequences that have no more than 3, preferably no more than 2, more preferably no more than 1 amino acid difference with one of SEQ ID NO's: 34, 36, 38, 40, 51, provided that:
  i) the amino acid sequence has Aspartic acid (Asp, D) at position 1 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a trivalent polypeptide. The method for the preparation of the trivalent polypeptide will comprise the linking of said amino acid sequence to at least two further amino acid sequences, optionally via one or more linkers.

In a preferred aspect, the three amino acid sequences used in preparing the trivalent polypeptide comprise or essentially consist of one of SEQ ID NO's: 34, 36, 38, 40, 51.

In another preferred aspect, the present invention relates to the use of an amino acid sequence chosen from the following:

a) SEQ ID NO's: 34, 36, 38, 40;
b) amino acid sequences that have no more than 3, preferably no more than 2, more preferably no more than 1 amino acid difference with one of SEQ ID NO's: 34, 36, 38, 40, provided that:
  i) the amino acid sequence has Aspartic acid (Asp, D) at position 1, Proline (Pro, P) at position 14, Arginine (Arg, R) at position 83 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a trivalent polypeptide. The method for the preparation of the trivalent polypeptide will comprise the linking of said amino acid sequence to at least two further amino acid sequences, optionally via one or more linkers.

In another preferred aspect, the present invention relates to the use of an amino acid sequence chosen from the following:

a) SEQ ID NO's: 36, 38, 40;
b) amino acid sequences that have no more than 3, preferably no more than 2, more preferably no more than 1 amino acid difference with one of SEQ ID NO's: 36, 38, 40, provided that:
  i) the amino acid sequence has Aspartic acid (Asp, D) at position 1, Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a trivalent polypeptide. The method for the preparation of the trivalent polypeptide will comprise the linking of said amino acid sequence to at least two further amino acid sequences, optionally via one or more linkers.

In a preferred aspect, the three amino acid sequences used in preparing the trivalent polypeptide comprise or essentially consist of one of SEQ ID NO's: 36, 38, 40.

In another preferred aspect, the present invention relates to the use of an amino acid sequence chosen from the following:

a) SEQ ID NO's: 38 and 40;
b) amino acid sequences that have no more than 3, preferably no more than 2, more preferably no more than 1 amino acid difference with one of SEQ ID NO's: 38 and 40, provided that:
  i) the amino acid sequence has Aspartic acid (Asp, D) at position 1, Proline (Pro, P) at position 14, Arginine (Arg, R) at position 83, Leucine (Leu, L) at position 108 and Glycine (Gly, G) at position 16; and in addition, the amino acid sequence has Glutamic acid (Glu, E) at position 54 or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference, in preparing a trivalent polypeptide. The method for the preparation of the trivalent polypeptide will comprise the linking of said amino acid sequence to at least two further amino acid sequences, optionally via one or more linkers.

In a preferred aspect, the three amino acid sequences used in preparing the trivalent polypeptide comprise or essentially consist of one of SEQ ID NO's: 38 and 40.

In another preferred aspect, the present invention relates to the use of an amino acid sequence that comprises or essentially consists of SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala, in preparing a trivalent polypeptide.

In another preferred aspect, the present invention relates to the use of an amino acid sequence that comprises or essentially consists of SEQ ID NO: 16, wherein one or more (such as two or three) amino acid residues have been mutated selected from the following: Ala14Pro, Lys83Arg and Gln108Leu, in preparing a trivalent polypeptide.

In another preferred aspect, the present invention relates to the use of an amino acid sequence that comprises or essentially consists of SEQ ID NO: 16, wherein one or more (such as two or three) amino acid residues have been mutated selected from the following: Asp16Gly, Asp54Glu and Gly55Ala, in preparing a trivalent polypeptide.

In another preferred aspect, the present invention relates to the use of an amino acid sequence that comprises or essentially consists of SEQ ID NO: 16, wherein position 1 (Glu) has been changed into Asp, in preparing a trivalent polypeptide.

In another preferred aspect, the present invention relates to the use of an amino acid sequence that comprises or essentially consists of SEQ ID NO: 16, wherein one or more (such as two, three, four, five or six) amino acid residues have been mutated selected from the following: Ala14Pro, Lys83Arg, Gln108Leu, Asp16Gly, Asp54Glu, Gly55Ala, wherein position 1 (Glu) has been changed into Asp, in preparing a trivalent polypeptide.

In another preferred aspect, the present invention relates to the use of an amino acid sequence that comprises or essentially consists of SEQ ID NO: 16, wherein one or more (such as two or three) amino acid residues have been mutated selected from the following: Ala14Pro, Lys83Arg and Gln108Leu, wherein position 1 (Glu) has been changed into Asp, in preparing a trivalent polypeptide.

In another preferred aspect, the present invention relates to the use of an amino acid sequence that comprises or essentially consists of SEQ ID NO: 16, wherein one or more (such as two or three) amino acid residues have been mutated selected from the following: Asp16Gly, Asp54Glu and Gly55Ala, wherein position 1 (Glu) has been changed into Asp, in preparing a trivalent polypeptide.

In another preferred aspect, the present invention relates to the use of an amino acid sequence that comprises or essentially consists of SEQ ID NO: 16, in which following amino acid residues have been mutated:
  Ala14Pro, Lys83Arg, Gln108Leu;
  Ala14Pro, Lys83Arg, Gln108Leu, Asp16Gly;
  Ala14Pro, Lys83Arg, Gln108Leu, Asp16Gly, Asp54Glu;
  Ala14Pro, Lys83Arg, Gln108Leu, Asp16Gly, Gly55Ala;
  Glu1Asp;
  Glu1Asp, Ala14Pro, Lys83Arg, Gln108Leu;
  Glu1Asp, Ala14Pro, Lys83Arg, Gln108Leu, Asp16Gly;
  Glu1Asp, Ala14Pro, Lys83Arg, Gln108Leu, Asp16Gly, Asp54Glu; or
  Glu1Asp, Ala14Pro, Lys83Arg, Gln108Leu, Asp16Gly, Gly55Ala,
in preparing a trivalent polypeptide.

In a preferred aspect, the amino acid sequence used in preparing a trivalent polypeptide comprises or essentially consists of SEQ ID NO: 33. In another preferred aspect, the amino acid sequence used in preparing a trivalent polypeptide comprises or essentially consists of SEQ ID NO: 35. In another preferred aspect, the amino acid sequence used in preparing a trivalent polypeptide comprises or essentially consists of SEQ ID NO: 37. In another preferred aspect, the amino acid sequence used in preparing a trivalent polypeptide comprises or essentially consists of SEQ ID NO: 39. In a preferred aspect, the amino acid sequence used in preparing a trivalent polypeptide comprises or essentially consists of SEQ ID NO: 34. In another preferred aspect, the amino acid sequence used in preparing a trivalent polypeptide comprises or essentially consists of SEQ ID NO: 36. In another preferred aspect, the amino acid sequence used in preparing a trivalent polypeptide comprises or essentially consists of SEQ ID NO: 38. In another preferred aspect, the amino acid sequence used in preparing a trivalent polypeptide comprises or essentially consists of SEQ ID NO: 40. In another preferred aspect, the present invention relates to the use of SEQ ID NO's: 33 and 34 in preparing SEQ ID NO: 41. The method for the preparation of the multivalent polypeptide will comprise the linking of an amino acid sequence with SEQ ID NO: 34 to at least two further amino acid sequences with SEQ ID NO: 33, via a 15GS (SEQ ID NO: 56) linker.

In another preferred aspect, the present invention relates to the use of SEQ ID NO's: 35 and 36 in preparing SEQ ID NO: 42. The method for the preparation of the multivalent polypeptide will comprise the linking of an amino acid sequence with SEQ ID NO: 36 to at least two further amino acid sequences with SEQ ID NO: 35, via a 15GS (SEQ ID NO: 56) linker.

In another preferred aspect, the present invention relates to the use of SEQ ID NO's: 37 and 38 in preparing SEQ ID NO: 43. The method for the preparation of the multivalent polypeptide will comprise the linking of an amino acid sequence with SEQ ID NO: 38 to at least two further amino acid sequences with SEQ ID NO: 37, via a 15GS (SEQ ID NO: 56) linker.

In another preferred aspect, the present invention relates to the use of SEQ ID NO's: 39 and 40 in preparing SEQ ID NO: 44. The method for the preparation of the multivalent polypeptide will comprise the linking of an amino acid sequence with SEQ ID NO: 40 to at least two further amino acid sequences with SEQ ID NO: 39, via a 15GS (SEQ ID NO: 56) linker.

In another preferred aspect, the present invention relates to the use of SEQ ID NO's: 16 and 51 in preparing SEQ ID NO: 50. The method for the preparation of the multivalent polypeptide will comprise the linking of an amino acid sequence with SEQ ID NO: 51 to at least two further amino acid sequences with SEQ ID NO: 16, via a 15GS (SEQ ID NO: 56) linker.

Polypeptides of the invention that contain at least two amino acid sequences and/or Nanobodies®, in which at least one amino acid sequence or Nanobody® is directed against a first antigen (i.e. against protein F of hRSV) and at least one amino acid sequence or Nanobody® is directed against a second antigen (i.e. different from protein F of hRSV), will also be referred to as "multispecific" polypeptides of the invention, and the amino acid sequences or Nanobodies® present in such polypeptides will also be referred to herein as being in a "multispecific format". Thus, for example, a "bispecific" polypeptide of the invention is a polypeptide that comprises at least one amino acid sequence or Nanobody® of the invention directed against a first antigen (i.e. protein F of hRSV) and at least one further amino acid sequence or Nanobody® directed against a second antigen (i.e. different from protein F of hRSV), whereas a "trispecific" polypeptide of the invention is a polypeptide that comprises at least one amino acid sequence or Nanobody® of the invention directed against a first antigen (i.e. protein F of hRSV), at least one further amino acid sequence or Nanobody® directed against a second antigen (i.e. different from protein F of hRSV) and at least one further amino acid sequence or Nanobody® directed against a third antigen (i.e. different from both protein F of hRSV, and the second antigen); etc.

Accordingly, in its simplest form, a bispecific polypeptide of the invention is a bivalent polypeptide of the invention (as defined herein), comprising a first amino acid sequence or Nanobody® of the invention directed against protein F of hRSV, and a second amino acid sequence or Nanobody® directed against a second antigen, in which said first and second amino acid sequence or Nanobody® may optionally be linked via a linker sequence (as defined herein); whereas a trispecific polypeptide of the invention in its simplest form is a trivalent polypeptide of the invention (as defined herein), comprising a first amino acid sequence or Nanobody® of the invention directed against protein F of hRSV, a second amino acid sequence or Nanobody® directed against a second antigen and a third amino acid sequence or Nanobody® directed against a third antigen, in which said first, second and third amino acid sequence or Nanobody® may optionally be linked via one or more, and in particular two, linker sequences.

In a specific aspect, the polypeptide of the invention is a trivalent, bispecific polypeptide. A trivalent, bispecific polypeptide of the invention in its simplest form may be a trivalent polypeptide of the invention (as defined herein), comprising two identical amino acid sequences or Nanobodies® against protein F of hRSV and a third amino acid sequence or Nanobody® directed against another antigen, in which said first, second and third amino acid sequence or Nanobody® may optionally be linked via one or more, and in particular two, linker sequences.

A preferred, but non-limiting example of a multispecific polypeptide of the invention comprises at least one amino acid sequence or Nanobody® of the invention and at least one Nanobody® that provides for an increased half-life. Some preferred, but non-limiting examples of such Nanobodies® include Nanobodies® directed against serum proteins, such as human serum albumin, thyroxine-binding protein, (human) transferrin, fibrinogen, an immunoglobulin such as IgG, IgE or IgM, or one of the other serum proteins listed in WO 04/003019.

For example, for experiments in mice, Nanobodies® against mouse serum albumin (MSA) can be used, whereas for pharmaceutical use, Nanobodies® against human serum albumin can be used.

Another embodiment of the present invention is a polypeptide construct as described above wherein said at least one (human) serum protein is any of (human) serum albumin, (human) serum immunoglobulins, (human) thyroxine-binding protein, (human) transferrin, (human) fibrinogen, etc.

Accordingly, in a specific aspect, the polypeptide of the invention is a bispecific polypeptide comprising a first amino acid sequence or Nanobody® of the invention against protein F of hRSV and a second amino acid sequence or Nanobody® directed against (human) serum albumin, in which said first and second amino acid sequence or Nanobody® may optionally be linked via a linker sequence.

In another specific aspect, the polypeptide of the invention is a trivalent, bispecific polypeptide, comprising two identical amino acid sequences or Nanobodies® of the invention against protein F of hRSV and a third amino acid sequence or Nanobody® directed against (human) serum albumin, in which said first, second and third amino acid sequence or Nanobody® may optionally be linked via one or more, and in particular two, linker sequences.

In another specific aspect, the polypeptide of the invention is a tetravalent, bispecific polypeptide, comprising three amino acid sequences or Nanobodies® of the invention against protein F of hRSV and a fourth amino acid sequence or Nanobody® directed against (human) serum albumin, in which said first, second, third and fourth amino acid sequence or Nanobody® may optionally be linked via one or more, and in particular two or three, linker sequences.

According to a specific, but non-limiting aspect of the invention, the polypeptides of the invention contain, besides the one or more amino acid sequences or Nanobodies® of the invention, at least one Nanobody® against human serum albumin. These Nanobodies® against human serum albumin may be as generally described in the applications by Ablynx N. V. cited above (see for example WO 04/062551). Some particularly preferred Nanobodies® that provide for increased half-life and that can be used in the polypeptides of the invention include the Nanobodies® ALB-1 to ALB-10 disclosed in WO 06/122787 (see Tables II and Ill) of which ALB-8 (SEQ ID NO: 62 in WO 06/122787) is particularly preferred.

In another aspect, the invention relates to a compound or construct, and in particular a protein or polypeptide (also referred to herein as a "compound of the invention") that comprises or essentially consists of one or more amino acid sequences, Nanobodies® and/or polypeptides of the invention (or suitable fragments thereof), and optionally further comprises one or more other groups, residues, moieties or binding units. As will become clear to the skilled person from the further disclosure herein, such further groups, residues, moieties, binding units or amino acid sequences may or may not provide further functionality to the amino acid sequence, Nanobody® or polypeptide of the invention (and/or to the compound. construct or polypeptide in which it is present) and may or may not modify the properties of the amino acid sequence, Nanobody® and/or polypeptide of the invention.

Such groups, residues, moieties or binding units may for example be chemical groups, residues, moieties, which may or may not by themselves be biologically and/or pharmacologically active. For example, and without limitation, such groups may be linked to the one or more amino acid sequences, Nanobodies® and/or polypeptides of the invention so as to provide a "derivative" of an amino acid sequence, Nanobody® and/or polypeptide of the invention, as further described herein.

Also within the scope of the present invention are compounds or constructs that comprise or essentially consist of one or more derivates as described herein, and optionally further comprise one or more other groups, residues, moieties or binding units, optionally linked via one or more linkers. Preferably, said one or more other groups, residues, moieties or binding units are amino acid sequences.

In the compounds, constructs or polypeptides described above, the one or more amino acid sequences, Nanobodies® and/or polypeptides of the invention and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting compound, construct or polypeptide is a fusion (protein) or fusion (polypeptide).

A compound or construct of the invention may comprises an amino acid sequence, Nanobody® or polypeptide of the invention, which is fused at its amino terminal end, at its carboxy terminal end, or both at its amino terminal end and at its carboxy terminal end to at least one further amino acid sequence, i.e. so as to provide a fusion protein comprising said amino acid sequence, Nanobody® or polypeptide of the invention and the one or more further amino acid sequences.

The one or more further amino acid sequence may be any suitable and/or desired amino acid sequences. The further amino acid sequences may or may not change, alter or otherwise influence the (biological) properties of the amino acid sequence, Nanobody® or polypeptide of the invention, and may or may not add further functionality to the amino acid sequence, Nanobody® or the polypeptide of the invention. Preferably, the further amino acid sequence is such that it confers one or more desired properties or functionalities to the amino acid sequence, Nanobody® or the polypeptide of the invention.

Example of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson, Nature Biotechnology, 23, 9, 1126-1136 (2005).

For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the compounds of the invention, compared to the amino acid sequence, Nanobody® or polypeptide of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

The further amino acid sequence may also provide a second binding site, which binding site may be directed against any desired protein, polypeptide, antigen, antigenic determinant or epitope (including but not limited to the same protein, polypeptide, antigen, antigenic determinant or epitope against which the amino acid sequence or Nanobody® of the invention is directed, or a different protein, polypeptide, antigen, antigenic determinant or epitope). For example, the further amino acid sequence may provide a second binding site that is directed against a serum protein (such as, for example, human serum albumin or another serum protein such as IgG), so as to provide increased half-life in serum. Such amino acid sequences for example include Nanobodies®, as well as the small peptides and binding proteins described in WO 91/01743, WO 01/45746 and WO 02/076489 and the dAb's described in WO 03/002609 and WO 04/003019. Reference is also made to Harmsen et al., Vaccine, 23 (41); 4926-42, 2005, as well as to EP 0 368 684, as well as to WO 08/028,977, WO 08/043,821, WO 08/043,822 by Ablynx N. V. and WO 08/068,280.

Such amino acid sequences may in particular be directed against serum albumin (and more in particular human serum albumin) and/or against IgG (and more in particular human IgG). For example, such amino acid sequences may be amino acid sequences that are directed against (human) serum albumin and amino acid sequences that can bind to amino acid residues on (human) serum albumin that are not involved in binding of serum albumin to FcRn (see for example WO 06/0122787) and/or amino acid sequences that are capable of binding to amino acid residues on serum albumin that do not form part of domain III of serum albumin (see again for example WO 06/0122787); amino acid sequences that have or can provide an increased half-life (see for example WO 08/028,977); amino acid sequences against human serum albumin that are cross-reactive with serum albumin from at least one species of mammal, and in particular with at least one species of primate (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*), reference is again made to WO 08/028,977); amino acid sequences that can bind to serum albumin in a pH independent manner (see for example WO 08/043,821) and/or amino acid sequences that are conditional binders (see for example WO 08/043,822).

According to another embodiment, the one or more further amino acid sequences may comprise one or more parts, fragments or domains of conventional 4-chain antibodies (and in particular human antibodies) and/or of heavy chain antibodies. For example, although usually less preferred, an amino acid sequence, Nanobody® or polypeptide of the invention may be linked to a conventional (preferably human) $V_H$ or $V_L$ domain or to a natural or synthetic analog of a $V_H$ or $V_L$ domain, again optionally via a linker sequence (including but not limited to other (single) domain antibodies, such as the dAb's described by Ward et al.).

Accordingly, in the compound or construct of the invention, said one or more other groups, residues, moieties or binding units may be chosen from the group consisting of domain antibodies, amino acid sequences that are suitable for use as a domain antibody, single domain antibodies, amino acid sequences that are suitable for use as a single domain antibody, "dAb", amino acid sequences that are suitable for use as a dAb, or Nanobodies®.

In one specific aspect of the invention, the compound, construct or polypeptide of the invention comprising at least one amino add sequence, Nanobody® or polypeptide of the invention may have an increased half-life, compared to the corresponding amino acid sequence, Nanobody® or polypeptide of the invention. Some preferred, but non-limiting examples of such compounds, constructs and polypeptides will become clear to the skilled person based on the further disclosure herein, and for example comprise amino add sequences, Nanobodies® or polypeptides of the invention that have been chemically modified to increase the half-life thereof (for example, by means of pegylation); or compounds of the invention that comprise at least one amino acid sequence, Nanobody® or polypeptide of the invention that is linked to at least one moiety (and in particular at least one amino acid sequence) that increases the half-life of the amino acid sequence, Nanobody® or polypeptide of the invention. Examples of compounds of the invention that comprise such half-life extending moieties will become clear to the skilled person based on the further disclosure herein; and for example include, without limitation, compounds in which the one or more amino acid sequences, Nanobodies® or polypeptides of the invention are suitable linked to one or more serum proteins or fragments thereof (such as serum albumin or suitable fragments thereof) or to one or more binding units that can bind to serum proteins (such as, for example, Nanobodies® or (single) domain antibodies that can bind to serum proteins such as serum albumin, serum immunoglobulins such as IgG, or transferrine); compounds in which an amino acid sequence, Nanobody® or polypeptide of the invention is linked to an Fc portion (such as a human Fc) or a suitable part or fragment thereof; or compounds in which the one or more amino acid sequences, Nanobodies® or polypeptides of the invention are suitable linked to one or more small proteins or peptides that can bind to serum proteins (such as, without limitation, the proteins and peptides described in WO 91/01743, WO 01/45746, WO 02/076489).

The at least one amino acid sequence, Nanobody® or polypeptide may also be linked to one or more (preferably human) $C_H1$, $C_H2$ and/or $C_H3$ domains, optionally via a linker sequence. For instance, an amino acid sequence, Nanobody® or polypeptide linked to a suitable $C_H1$ domain could for example be used—together with suitable light chains—to generate antibody fragments/structures analogous to conventional Fab fragments or F(ab')$_2$ fragments, but in which one or (in case of an F(ab')$_2$ fragment) one or both of the conventional $V_H$ domains have been replaced by an amino acid sequence, Nanobody® or polypeptide of the invention. Also, two amino acid sequences or Nanobodies® could be linked to a $C_H3$ domain (optionally via a linker) to provide a construct with increased half-life in vivo.

According to one specific aspect, one or more amino acid sequences, Nanobodies® or polypeptides of the invention may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the amino acid sequence, Nanobody® or polypeptide of the invention and/or may confer the ability to bind to one or more Fc receptors. For example, for this purpose, and without being limited thereto, the one or more further amino acid sequences may comprise one or more $C_H2$ and/or $C_H3$ domains of an antibody, such as from a heavy chain antibody (as described herein) and more preferably from a conventional human 4-chain antibody; and/or may form (part of) and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid $V_{HH}$ domain or a humanized derivative thereof (i.e. a Nanobody®), in which the Camelidae $C_H2$ and/or $C_H3$ domain have been replaced by human $C_H2$ and $C_H3$ domains, so as to provide an immunoglobulin that consists of 2 heavy chains each comprising a Nanobody® and human $C_H2$ and $C_H3$ domains (but no $C_H1$ domain), which immunoglobulin has the effector function provided by the $C_H2$ and $C_H3$ domains and which immunoglobulin can function without the presence of any light chains. Other amino acid sequences that can be suitably linked to the amino acid sequences, Nanobodies® or polypeptides of the invention so as to provide an effector function will be clear to the skilled person, and may be chosen on the basis of the desired effector function(s). Reference is for example made to WO 04/058820, WO 99/42077, WO 02/056910 and WO 05/017148, as well as the review by Holliger and Hudson, supra; and to WO 09/068,628. Coupling of an amino acid sequence, Nanobody® or polypeptide of the invention to an Fc portion may also lead to an increased half-life, compared to the corresponding amino acid sequence, Nanobody® or polypeptide of the invention. For some applications, the use of an Fc portion and/or of constant domains (i.e. $C_H2$ and/or $C_H3$ domains) that confer increased half-life without any biologically significant effector function may also be suitable or even preferred. Other suitable constructs comprising one or more amino acid sequences, Nanobodies® or polypeptides and one or more constant domains with increased half-life in vivo will be clear to the skilled person, and may for example comprise amino acid sequences, Nanobodies® or polypeptides linked to a $C_H3$ domain, optionally via a linker sequence. Generally, any fusion protein or derivatives with increased half-life will preferably have a molecular weight of more than 50 kD, the cut-off value for renal absorption.

In another specific, but non-limiting, aspect, in order to form a compound of the invention, one or more amino acid sequences, Nanobodies® or polypeptides of the invention may be linked (optionally via a suitable linker or hinge region) to naturally occurring, synthetic or semisynthetic constant domains (or analogs, variants, mutants, parts or fragments thereof) that have a reduced (or essentially no) tendency to self-associate into dimers (i.e. compared to constant domains that naturally occur in conventional 4-chain antibodies). Such monomeric (i.e. not self-associating) Fc chain variants, or fragments thereof, will be clear to the skilled person. For example, Helm et al., J Biol Chem 1996 271 7494, describe monomeric Fc chain variants that can be used in the polypeptide chains of the invention.

Also, such monomeric Fc chain variants are preferably such that they are still capable of binding to the complement or the relevant Fc receptor(s) (depending on the Fc portion from which they are derived), and/or such that they still have some or all of the effector functions of the Fc portion from which they are derived (or at a reduced level still suitable for the intended use). Alternatively, in such a polypeptide chain of the invention, the monomeric Fc chain may be used to confer increased half-life upon the polypeptide chain, in which case the monomeric Ft chain may also have no or essentially no effector functions.

Generally, the amino acid sequences, Nanobodies® or polypeptides of the invention (or compounds, constructs or comprising the same) with increased half-life preferably have a half-life that is at least 1.5 times, preferably at least 2 times, such as at least 5 times, for example at least 10 times or more than 20 times, greater than the half-life of the corresponding amino acid sequence, Nanobody® or polypeptide of the invention per se. For example, the amino acid sequences, Nanobodies®, compounds, constructs or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence, Nanobody® or polypeptide of the invention per se.

In a preferred, but non-limiting aspect of the invention, such amino acid sequences, Nanobodies®, compound, constructs or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), at preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

The further amino acid sequences may also form a signal sequence or leader sequence that directs secretion of the amino acid sequence, Nanobody® or the polypeptide of the invention from a host cell upon synthesis (for example to provide a pre-, pro- or prepro-form of the polypeptide of the invention, depending on the host cell used to express the polypeptide of the invention).

The further amino acid sequence may also form a sequence or signal that allows the amino acid sequence, Nanobody® or polypeptide of the invention to be directed towards and/or to penetrate or enter into specific organs, tissues, cells, or parts or compartments of cells, and/or that allows the amino acid sequence, Nanobody® or polypeptide of the invention to penetrate or cross a biological barrier such as a cell membrane, a cell layer such as a layer of epithelial cells. Suitable examples of such amino acid sequences will be clear to the skilled person, and for example include, but are not limited to, the "Peptrans" vectors mentioned above, the sequences described by Cardinale et al. and the amino acid sequences and antibody fragments known per se that can be used to express or produce the Nanobodies® and polypeptides of the invention as so-called "intrabodies", for example as described in WO 94/02610, WO 95/22618, U.S. Pat. No. 7,004,940, WO 03/014960, WO 99/07414; WO 05/01690; EP 1 512 696; and in Cattaneo, A. & Biocca, S. (1997) Intracellular Antibodies: Development and Applications. Landes and Springer-Verlag; and in Kontermann, Methods 34, (2004), 163-170, and the further references described therein.

Such a protein, polypeptide, compound or construct may also be in essentially isolated form (as defined herein).

The compounds or polypeptides of the invention can generally be prepared by a method which comprises at least the step of suitably linking the one or more amino acid sequences, Nanobodies®, monovalent constructs and/or polypeptides of the invention to the one or more further groups, residues, moieties or binding units, optionally via the one or more suitable linkers, so as to provide the compound or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

Suitable spacers or linkers for use in multivalent and/or multispecific polypeptides or constructs will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each amino acid sequence or Nanobody® by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_z$, such as (for example $(gly_4 ser)_3$ or $(gly_3 ser_2)_3$, as described in WO 99/42077, hinge-like regions such as the hinge regions of naturally occurring heavy chain antibodies or similar sequences (such as described in WO 94/04678).

Some other particularly preferred linkers are poly-alanine (such as AAA), as well as the linkers mentioned in Table A-6, of which GS15 is particularly preferred.

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for protein F of hRSV, or for one or more of the other antigens. Based on the disclosure herein, the skilled person will be able to determine the optimal linker(s) for use in a specific polypeptide of the invention, optionally after some limited routine experiments.

It is also within the scope of the invention that the linker(s) used confer one or more other favorable properties or functionality to the polypeptides of the invention, and/or provide one or more sites for the formation of derivatives and/or for the attachment of functional groups (e.g. as described herein for the derivatives of the amino acid sequences, Nanobodies®, compounds and polypeptides of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for ease of expression and production, a polypeptide of the invention will be a linear polypeptide. However, the invention in its broadest sense is not limited thereto. For example, when a polypeptide of the invention comprises three of more amino acid sequences or Nanobodies®, it is possible to link them by use of a linker with three or more "arms", which each "arm" being linked to an amino acid sequence or Nanobody®, so as to provide a "star-shaped" construct. It is also possible, although usually less preferred, to use circular constructs.

As will also be clear from the disclosure herein, it is also within the scope of the invention to use parts or fragments, or combinations of two or more parts or fragments, of the amino acid sequences, Nanobodies® or polypeptides of the invention as defined herein, and in particular parts or fragments of the amino acid sequences of SEQ ID NO's: 33-40. Thus, according to one embodiment of the invention, the term "amino acid sequence of the invention", "Nanobody® of the invention" and "polypeptide of the invention" in its broadest sense also covers such parts or fragments.

Generally, such parts or fragments of the amino acid sequences, Nanobodies® or polypeptides of the invention (including variants thereof as defined herein) have amino acid sequences in which, compared to the amino acid sequence of the corresponding full length amino acid sequence or Nanobody® of the invention, one or more of the amino acid residues at the N-terminal end, one or more amino acid residues at the C-terminal end, one or more contiguous internal amino acid residues, or any combination thereof, have been deleted and/or removed.

The parts or fragments are preferably such that they can bind to antigenic site II on protein F of hRSV, with an affinity (suitably measured and/or expressed as a $K_D$-value (actual or apparent), a $K_A$-value (actual or apparent), a $k_{in}$-rate and/or a $k_{off}$-rate, or alternatively as an $IC_{50}$ value, as further described herein) that is as defined herein.

In particular, amino acid sequences, Nanobodies®, polypeptides and parts or fragments are preferably such that they:

bind to protein F of hRSV with a dissociation constant ($K_D$) of 1000 nM to 1 nM or less, preferably 100 nM to 1 nM or less, more preferably 10 nM to 1 nM or less;

and/or such that they:

bind to protein F of hRSV with a $k_{on}$-rate of between $10^4$ $M^{-1}s^{-1}$ to about $10^7$ $M^{-1}s^{-1}$, preferably between $10^5$ $M^{-1}s^{-1}$ and $10^7$ $M^{-1}s^{-1}$, more preferably about $10^6$ $M^{-1}s^{-1}$ or more;

and/or such that they:

bind to protein F of hRSV with a $k_{off}$-rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, or lower.

The affinity of the parts or fragments against protein F of hRSV, can be determined in a manner known per se, for example using the assay described herein.

Such parts or fragments will usually also have a hRSV neutralization efficacy and/or potency as defined herein.

Any part or fragment is preferably such that it comprises at least 10 contiguous amino acid residues, preferably at least 20 contiguous amino acid residues, more preferably at least 30 contiguous amino acid residues, such as at least 40 contiguous amino acid residues, of the amino acid sequence of the corresponding full length amino acid sequence, Nanobody® or polypeptide of the invention.

Also, any part or fragment is such preferably that it comprises at least one of the CDR's (and preferably at least CDR3 or part thereof) and at least one other CDR (i.e. CDR1 or CDR2) or at least part thereof, preferably connected by suitable framework sequence(s) or at least part thereof. More preferably, any part or fragment is such that it comprises at least one of the CDR's (and preferably at least CDR3 or part thereof) and at least part of the two remaining CDR's, again preferably connected by suitable framework sequence(s) or at least part thereof.

According to another particularly preferred, but non-limiting embodiment, such a part or fragment comprises at least CDR3, such as FR3, CDR3 and FR4 of the corresponding full length Nanobody® of the invention, i.e. as for example described in the International application WO 03/050531 (tasters et al.).

As already mentioned above, it is also possible to combine two or more of such parts or fragments (i.e. from the same or different amino acid sequences or Nanobodies® of the invention), i.e. to provide further parts or fragments (as defined herein) of an amino acid sequence, a Nanobody® or a polypeptide of the invention. It is for example also possible to combine one or more parts or fragments of an amino acid sequence, a Nanobody® or a polypeptide of the invention with one or more parts or fragments of a human $V_H$ domain.

According to one preferred embodiment, the parts or fragments have a degree of sequence identity of at least 50%, preferably at least 60%, more preferably at least 70%, even more preferably at least 80%, such as at least 90%, 95% or 99% or more with one of the amino acid sequences or Nanobodies® of SEQ ID NO's: 33-40 and 51.

The parts and fragments, and nucleic acid sequences encoding the same, can be provided and optionally combined in any manner known per se. For example, such parts or fragments can be obtained by inserting a stop codon in a nucleic acid that encodes a full-sized amino acid sequence, Nanobody® or polypeptide of the invention, and then expressing the nucleic acid thus obtained in a manner known per se (e.g. as described herein). Alternatively, nucleic acids encoding such parts or fragments can be obtained by suitably restricting a nucleic acid that encodes a full-sized amino acid sequence, Nanobody® or polypeptide of the invention or by synthesizing such a nucleic acid in a manner known per se. Parts or fragments may also be provided using techniques for peptide synthesis known per se.

The invention in its broadest sense also comprises derivatives of the amino acid sequences, Nanobodies®, compounds or polypeptides of the invention. Such derivatives can generally be obtained by modification, and in particular by chemical and/or biological (e.g. enzymatical) modification, of the amino acid sequences, Nanobodies®, compounds or polypeptides of the invention and/or of one or more of the amino acid residues that form the amino acid sequences, Nanobodies®, compounds or polypeptides of the invention.

Examples of such modifications, as well as examples of amino acid residues within the amino acid sequence, Nanobody® sequence, compound or polypeptide sequences that can be modified in such a manner (i.e. either on the protein backbone but preferably on a side chain), methods and techniques that can be used to introduce such modifications and the potential uses and advantages of such modifications will be clear to the skilled person.

For example, such a modification may involve the introduction (e.g. by covalent linking or in another suitable manner) of one or more functional groups, residues or moieties into or onto the amino acid sequence, Nanobody®, compound or polypeptide of the invention, and in particular of one or more functional groups, residues or moieties that confer one or more desired properties or functionalities to the amino acid sequence, Nanobody®, compound or polypeptide of the invention. Example of such functional groups will be clear to the skilled person.

For example, such modification may comprise the introduction (e.g. by covalent binding or in any other suitable manner) of one or more functional groups that that increase the half-life, the solubility and/or the absorption of the amino acid sequence, Nanobody®, compound or polypeptide of the invention, that reduce the immunogenicity and/or the toxicity of the amino acid sequence, Nanobody®, compound or polypeptide of the invention, that eliminate or attenuate any undesirable side effects of the amino acid sequence, Nanobody®, compound or polypeptide of the invention, and/or that confer other advantageous properties to and/or reduce the undesired properties of the amino acid sequence, Nanobody®, compound or polypeptide of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington's Pharmaceutical Sciences, 16th ed., Mack Publishing Co., Easton, Pa. (1980). Such functional groups may for example be linked directly (for example covalently) to an amino acid sequence, Nanobody®, compound or polypeptide of the invention, or optionally via a suitable linker or spacer, as will again be clear to the skilled person.

One of the most widely used techniques for increasing the half-life and/or reducing the immunogenicity of pharmaceutical proteins comprises attachment of a suitable pharmacologically acceptable polymer, such as polyethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04/060965. Various reagents for pegylation of proteins are also commercially available, for example from Nektar Therapeutics, USA.

Preferably, site-directed pegylation is used, in particular via a cysteine-residue (see for example Yang et al., Protein Engineering, 16, 10, 761-770 (2003). For example, for this purpose, PEG may be attached to a cysteine residue that naturally occurs in an amino acid sequence, Nanobody®, compound or polypeptide of the invention, an amino acid sequence, Nanobody®, compound or polypeptide of the invention may be modified so as to suitably introduce one or more cysteine residues for attachment of PEG, or an amino acid sequence comprising one or more cysteine residues for attachment of PEG may be fused to the N- and/or C-terminus of an amino acid sequence, Nanobody®, compound or polypeptide of the invention, all using techniques of protein engineering known per se to the skilled person.

Preferably, for the amino acid sequences, Nanobodies®, compounds or polypeptides of the invention of the invention, a PEG is used with a molecular weight of more than 5000, such as more than 10,000 and less than 200,000, such as less than 100,000; for example in the range of 20,000-50,000.

Another, usually less preferred modification comprises N-linked or O-linked glycosylation, usually as part of co-translational and/or post-translational modification, depending on the host cell used for expressing the amino acid sequence, Nanobody®, compound or polypeptide of the invention.

Yet another modification may comprise the introduction of one or more detectable labels or other signal-generating groups or moieties, depending on the intended use of the labelled amino acid sequence, Nanobody®, compound or polypeptide of the invention. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals such as $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes (such as $^3$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metals chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled amino acid sequences, Nanobodies®, compounds or polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the amino acid sequence, Nanobody®, compound or polypeptide of the invention to another protein, polypeptide or chemical compound that is bound to the other half of the binding pair, i.e. through formation of the binding pair. For example, an amino acid sequence, Nanobody®, compound or polypeptide of the invention may be conjugated to biotin, and linked to another protein, polypeptide, compound or carrier conjugated to avidin or streptavidin. For example, such a conjugated amino acid sequence, Nanobody®, compound or polypeptide of the invention may be used as a reporter, for example in a diagnostic system where a detectable signal-producing agent is conjugated to avidin or streptavidin. Such binding pairs may for example also be used to bind the amino acid sequence, Nanobody®, compound or polypeptide of the invention to a carrier, including carriers suitable for pharmaceutical purposes. One non-limiting example are the liposomal formulations described by Cao and Suresh, Journal of Drug Targeting, 8, 4, 257 (2000). Such binding pairs may also be used to link a therapeutically active agent to the amino acid sequence, Nanobody®, compound or polypeptide of the invention.

Other potential chemical and enzymatical modifications will be clear to the skilled person. Such modifications may also be introduced for research purposes (e.g. to study function-activity relationships). Reference is for example made to Lundblad and Bradshaw, Biotechnol. Appl. Biochem., 26, 143-451 (1997).

Preferably, the derivatives are such that they bind to protein F of hRSV, with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein (i.e. as defined for the amino acid sequences, Nanobodies®, polypeptides or compounds per se). Such derivatives will usually also have a hRSV neutralization efficacy and/or potency as defined herein.

As mentioned above, the invention also relates to proteins or polypeptides that essentially consist of or comprise at least one amino acid sequence, Nanobody®, compound or polypeptide of the invention. By "essentially consist of" is meant that the amino acid sequence of the protein or polypeptide of the invention either is exactly the same as the amino acid sequence, Nanobody®, compound or polypeptide of the invention or corresponds to the amino acid sequence, Nanobody®, compound or polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the amino acid sequence, Nanobody®, compound or polypeptide.

Said amino acid residues may or may not change, alter or otherwise influence the (biological) properties of the amino acid sequence, Nanobody®, compound or polypeptide of the invention and may or may not add further functionality to the amino acid sequence, Nanobody®, compound or polypeptide. For example, such amino acid residues:

a) can comprise an N-terminal Met residue, for example as result of expression in a heterologous host cell or host organism.
b) may form a signal sequence or leader sequence that directs secretion of the amino acid sequence, Nanobody®, compound or polypeptide from a host cell upon synthesis. Suitable secretory leader peptides will be clear to the skilled person, and may be as further described herein. Usually, such a leader sequence will be linked to the N-terminus of the amino acid sequence, Nanobody®, compound or polypeptide, although the invention in its broadest sense is not limited thereto;
c) may form a sequence or signal that allows the amino acid sequence, Nanobody®, compound or polypeptide to be directed towards and/or to penetrate or enter into specific organs, tissues, cells, or parts or compartments of cells, and/or that allows the amino acid sequence, Nanobody®, compound or polypeptide to penetrate or cross a biological barrier such as a cell membrane, a cell layer such as a layer of epithelial cells, a tumor including solid tumors, or the blood-brain-barrier. Examples of such amino acid sequences will be clear to the skilled person. Some non-limiting examples are the small peptide vectors ("Pep-trans vectors") described in WO 03/026700 and in Temsamani et al., Expert Opin. Biol. Ther., 1, 773 (2001); Temsamani and Vidal, Drug Discov. Today, 9, 1012 (004) and Rousselle, J. Pharmacal. Exp. Ther., 296, 124-131 (2001), and the membrane translocator sequence described by Zhao et al., Apoptosis, 8, 631-637 (2003). C-terminal and N-terminal amino acid sequences for intracellular targeting of antibody fragments are for example described by Cardinale et al., Methods, 34, 171 (2004). Other suitable techniques for intracellular targeting involve the expression and/or use of so-called "intrabodies" comprising a amino acid sequence, Nanobody®, compound or polypeptide of the invention, as mentioned below;
d) may form a "tag", for example an amino acid sequence or residue that allows or facilitates the purification of the amino acid sequence, Nanobody®, compound or polypeptide, for example using affinity techniques directed against said sequence or residue. Thereafter, said sequence or residue may be removed (e.g. by chemical or enzymatical cleavage) to provide the amino acid sequence, Nanobody®, compound or polypeptide (for this purpose, the tag may optionally be linked to the amino acid sequence, Nanobody®, compound or polypeptide sequence via a cleavable linker sequence or contain a cleavable motif). Some preferred, but non-limiting examples of such residues are multiple histidine residues, glutatione residues and a myc-tag such as AAAEQKLISEEDLNGAA (SEQ ID NO: 111);
e) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the amino acid sequences, Nanobodies®, compounds or polypeptides of the invention.

The invention further relates to methods for preparing the amino acid sequences, Nanobodies®, polypeptides, compounds, nucleic acids, host cells, products and compositions described herein.

The amino acid sequences, Nanobodies®, polypeptides, compounds and nucleic acids of the invention can be prepared in a manner known per se, as will be clear to the skilled person from the further description herein. For example, the amino acid sequences, Nanobodies® and polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the amino acid sequences, Nanobodies®, polypeptides and nucleic acids include the methods and techniques described herein.

The method for producing an amino acid sequence of the invention, a Nanobody® of the invention, a polypeptide of the invention, or a monovalent construct of the invention may comprise the following steps:

the expression, in a suitable host cell or host organism (also referred to herein as a "host of the invention") or in another suitable expression system of a nucleic acid that encodes said amino acid sequence, Nanobody® or polypeptide of the invention (also referred to herein as a "nucleic acid of the invention"), optionally followed by:

isolating and/or purifying the amino acid sequence, Nanobody® or polypeptide of the invention thus obtained.

In particular, such a method may comprise the steps of:

cultivating and/or maintaining a host of the invention under conditions that are such that said host of the invention expresses and/or produces at least one amino acid sequence, Nanobody® and/or polypeptide of the invention;

optionally followed by:

isolating and/or purifying the amino acid sequence, Nanobody® or polypeptide of the invention thus obtained.

Accordingly, the present invention also relates to a nucleic acid or nucleotide sequence that encodes an amino acid sequence, a Nanobody®, a polypeptide or a monovalent construct of the invention (also referred to as "nucleic acid of the invention" or "nucleotide sequence of the invention"). A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one embodiment of the invention, the nucleic acid of the invention is in essentially isolated from, as defined herein. The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the amino acid sequences, Nanobodies® and/or polypeptides of the invention given herein, and/or can be isolated from a suitable natural source. Also, as will be clear to the skilled person, to prepare a nucleic acid of the invention, also several nucleotide sequences, such as at least one nucleotide sequence encoding an amino acid sequence or Nanobody® and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting embodiment, a genetic construct of the invention comprises
a) at least one nucleic acid of the invention; operably connected to
b) one or more regulatory elements, such as a promoter and optionally a suitable terminator; and optionally also
c) one or more further elements of genetic constructs known per se;
in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used; the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g. a coding sequence—to which it is operably linked (as defined herein).

Some particularly preferred promoters include, but are not limited to, promoters known per se for the expression in the host cells mentioned herein; and in particular promoters for the expression in the bacterial cells, such as those mentioned herein and/or those used in the Examples.

A selection marker should be such that it allows—i.e. under appropriate selection conditions—host cells and/or host organisms that have been (successfully) transformed with the nucleotide sequence of the invention to be distinguished from host cells/organisms that have not been (successfully) transformed. Some preferred, but non-limiting examples of such markers are genes that provide resistance against antibiotics (such as kanamycin or ampicillin), genes that provide for temperature resistance, or genes that allow the host cell or host organism to be maintained in the absence of certain factors, compounds and/or (food) components in the medium that are essential for survival of the non-transformed cells or organisms.

A leader sequence should be such that—in the intended host cell or host organism—it allows for the desired post-translational modifications and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism. Leader sequences may not be required for expression in a bacterial cell. For example, leader sequences known per se for the expression and production of antibodies and antibody fragments (including but not limited to single domain antibodies and ScFv fragments) may be used in an essentially analogous manner.

An expression marker or reporter gene should be such that—in the host cell or host organism—it allows for detection of the expression of (a gene or nucleotide sequence present on) the genetic construct. An expression marker may optionally also allow for the localisation of the expressed product, e.g. in a specific part or organelle of a cell and/or in (a) specific cell(s), tissue(s), organ(s) or part(s) of a multicellular organism. Such reporter genes may also be expressed as a protein fusion with the amino acid sequence, Nanobody® or polypeptide of the invention. Some preferred, but non-limiting examples include fluorescent proteins such as GFP.

Some preferred, but non-limiting examples of suitable promoters, terminator and further elements include those that can be used for the expression in the host cells mentioned herein; and in particular those that are suitable for expression in bacterial cells, such as those mentioned herein and/or those used in the Examples below. For some (further) non-limiting examples of the promoters, selection markers, leader sequences, expression markers and further elements that may be present/used in the genetic constructs of the invention—such as terminators, transcriptional and/or translational enhancers and/or integration factors—reference is made to the general handbooks such as Sambrook et al. and Ausubel et al. mentioned above, as well as to the examples that are given in WO 95/07463, WO 96/23810, WO 95/07463, WO 95/21191, WO 97/11094, WO 97/42320, WO 98/06737, WO 98/21355, U.S. Pat. No. 7,207,410, U.S. Pat. No. 5,693,492 and EP 1 085 089. Other examples will be clear to the skilled person. Reference is also made to the general background art cited above and the further references cited herein.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned herein.

The nucleic acids of the invention and/or the genetic constructs of the invention may be used to transform a host cell or host organism, i.e. for expression and/or production of the amino acid sequence, Nanobody® or polypeptide of the invention. Suitable hosts or host cells will be clear to the skilled person, and may for example be any suitable fungal, prokaryotic or eukaryotic cell or cell line or any suitable fungal, prokaryotic or eukaryotic organism, for example:

- a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus* lactis;
- a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojae*; or from other filamentous fungi;
- a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; of *Yarrowia*, for example of *Yarrowia lipolytica*;
- an amphibian cell or cell line, such as *Xenopus* oocytes;
- an insect-derived cell or cell line, such as cells/cell lines derived from lepidoptera, including but not limited to *Spodoptera* SF9 and Sf21 cells or cells/cell lines derived from *Drosophila*, such as Schneider and Kc cells;
- a plant or plant cell, for example in tobacco plants; and/or
- a mammalian cell or cell line, for example a cell or cell line derived from a human, a cell or a cell line from mammals including but not limited to CHO-cells, BHK-cells (for example BHK-21 cells) and human cells or cell lines such as HeLa, COS (for example COS-7) and PER.C6 cells;

as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al., (1998), supra; Riechmann and Muyldermans, (1999), supra; van der Linden, (2000), supra; Thomassen et al., (2002), supra; Joosten et al., (2003), supra; Joosten et al., (2005), supra; and the further references cited herein.

The amino acid sequences, Nanobodies® and polypeptides of the invention can also be introduced and expressed in one or more cells, tissues or organs of a multicellular organism, for example for prophylactic and/or therapeutic purposes (e.g. as a gene therapy). For this purpose, the nucleotide sequences of the invention may be introduced into the cells or tissues in any suitable way, for example as such (e.g. using liposomes) or after they have been inserted into a suitable gene therapy vector (for example derived from retroviruses such as adenovirus, or parvoviruses such as adeno-associated virus). As will also be clear to the skilled person, such gene therapy may be performed in vivo and/or in situ in the body of a patient by administering a nucleic acid of the invention or a suitable gene therapy vector encoding the same to the patient or to specific cells or a specific tissue or organ of the patient; or suitable cells (often taken from the body of the patient to be treated, such as explanted lymphocytes, bone marrow aspirates or tissue biopsies) may be treated in vitro with a nucleotide sequence of the invention and then be suitably (re-)introduced into the body of the patient. All this can be performed using gene therapy vectors, techniques and delivery systems which are well known to the skilled person, and for example described in Culver, K. W., "Gene Therapy", 1994, p. xii, Mary Ann Liebert, Inc., Publishers, New York, N.Y.); Giordano, Nature F Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77 (1995), 1077-1086;

Onodera, Blood 91; (1998), 30-36; Verma, Gene Ther. 5 (1998), 692-699; Nabel, Ann. N.Y. Acad. Sci.: 811 (1997), 289-292; Verzeletti, Hum. Gene Ther. 9 (1998), 2243-51; Wang, Nature Medicine 2 (1996), 714-716; WO 94/29469; WO 97/00957, U.S. Pat. No. 5,580,859; U.S. Pat. No. 5,895,466; or Schaper, Current Opinion in Biotechnology 7 (1996), 635-640. For example, in situ expression of ScFv fragments (Afanasieva et al., Gene Ther., 10, 1850-1859 (2003)) and of diabodies (Blanco et al., J. Immunol, 171, 1070-1077 (2003)) has been described in the art.

For expression of the amino acid sequences, Nanobodies® or polypeptides in a cell, they may also be expressed as so-called "intrabodies", as for example described in WO 94/02610, WO 95/22618 and U.S. Pat. No. 7,004,940; WO 03/014960; in Cattaneo, A. & Biocca, S. (1997) Intracellular Antibodies: Development and Applications. Landes and Springer-Verlag; and in Kontermann, Methods 34, (2004), 163-170.

The amino acid sequences, Nanobodies® and polypeptides of the invention can for example also be produced in the milk of transgenic mammals, for example in the milk of rabbits, cows, goats or sheep (see for example U.S. Pat. No. 6,741,957, U.S. Pat. No. 6,304,489 and U.S. Pat. No. 6,849,992 for general techniques for introducing transgenes into mammals), in plants or parts of plants including but not limited to their leaves, flowers, fruits, seed, roots or tubers (for example in tobacco, maize, soybean or alfalfa) or in for example pupae of the silkworm *Bombix mori*.

Furthermore, the amino acid sequences, Nanobodies® and polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

As mentioned above, one of the advantages of the use of Nanobodies® is that the polypeptides based thereon can be prepared through expression in a suitable bacterial system, and suitable bacterial expression systems, vectors, host cells, regulatory elements, etc., will be clear to the skilled person, for example from the references cited above. It should however be noted that the invention in its broadest sense is not limited to expression in bacterial systems.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, polypeptides of the invention suitable for pharmaceutical use can be prepared using techniques for peptide synthesis.

For production on industrial scale, preferred heterologous hosts for the (industrial) production of Nanobodies® or Nanobody®-containing protein therapeutics include strains of *E. coli, Pichia pastoris, S. cerevisiae* that are suitable for large scale expression/production/fermentation, and in particular for large scale pharmaceutical expression/production/ fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of a Nanobody®-containing recombinant protein for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression. Preferably, either a human cell or cell line is used (i.e. leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired amino acid sequence, Nanobody® or polypeptide to be obtained.

Thus, according to one non-limiting embodiment of the invention, the amino acid sequence, Nanobody® or polypeptide of the invention is glycosylated. According to another non-limiting embodiment of the invention, the amino acid sequence, Nanobody® or polypeptide of the invention is non-glycosylated.

According to one preferred, but non-limiting embodiment of the invention, the amino acid sequence, Nanobody® or polypeptide of the invention is produced in a bacterial cell, in particular a bacterial cell suitable for large scale pharmaceutical production, such as cells of the strains mentioned above.

According to another preferred, but non-limiting embodiment of the invention, the amino acid sequence, Nanobody® or polypeptide of the invention is produced in a yeast cell, in particular a yeast cell suitable for large scale pharmaceutical production, such as cells of the species mentioned above.

According to yet another preferred, but non-limiting embodiment of the invention, the amino acid sequence, Nanobody® or polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

When expression in a host cell is used to produce the amino acid sequences, Nanobodies® and the polypeptides of the invention, the amino acid sequences, Nanobodies® and polypeptides of the invention can be produced either intracellularly (e.g. in the cytosol, in the periplasma or in inclusion bodies) and then isolated from the host cells and optionally further purified; or can be produced extracellularly (e.g. in the medium in which the host cells are cultured) and then isolated from the culture medium and optionally further purified. When eukaryotic host cells are used, extracellular production is usually preferred since this considerably facilitates the further isolation and downstream processing of the amino acid sequences, Nanobodies®, polypeptides and proteins obtained. Bacterial cells such as the strains of *E. coli* mentioned above normally do not secrete proteins extracellularly, except for a few classes of proteins such as toxins and hemolysin, and secretory production in *E. coli* refers to the translocation of proteins across the inner membrane to the periplasmic space. Periplasmic production provides several advantages over cytosolic production. For example, the N-terminal amino acid sequence of the secreted product can be identical to the natural gene product after cleavage of the secretion signal sequence by a specific signal peptidase. Also, there appears to be much less protease activity in the periplasm than in the cytoplasm. In addition, protein purification is simpler due to fewer contaminating proteins in the periplasm. Another advantage is that correct disulfide bonds may form because the periplasm provides a more oxidative environment than the cytoplasm. Proteins overexpressed in *E. coli* are often found in insoluble aggregates, so-called inclusion bodies. These inclusion bodies may be located in the cytosol or in the periplasm; the recovery of biologically active proteins from these inclusion bodies requires a denaturation/refolding process. Many recombinant proteins, including therapeutic proteins, are recovered from inclusion bodies. Alternatively, as will be clear to the skilled person, recombinant strains of bacteria that have been genetically modified so as to secrete a desired protein, and in particular an amino acid sequence, Nanobody® or a polypeptide of the invention, can be used.

Thus, according to one non-limiting embodiment of the invention, the amino acid sequence, Nanobody® or polypeptide of the invention is an amino acid sequence, Nanobody® or polypeptide that has been produced intracellularly and that has been isolated from the host cell, and in particular from a bacterial cell or from an inclusion body in a bacterial cell. According to another non-limiting embodiment of the invention, the amino acid sequence, Nanobody® or polypeptide of the invention is an amino acid sequence, Nanobody® or polypeptide that has been produced extracellularly, and that has been isolated from the medium in which the host cell is cultivated.

Some preferred, but non-limiting promoters for use with these host cells include,
- for expression in *E. coli*: lac promoter (and derivatives thereof such as the lacUV5 promoter); arabinose promoter; left-(PL) and rightward (PR) promoter of phage lambda; promoter of the trp operon; hybrid lac/trp promoters (tac and trc); 17-promoter (more specifically that of T7-phage gene 10) and other T-phage promoters; promoter of the Tn10 tetracycline resistance gene; engineered variants of the above promoters that include one or more copies of an extraneous regulatory operator sequence;
- for expression in *S. cerevisiae*: constitutive: ADH1 (alcohol dehydrogenase 1), ENO (enolase), CYC1 (cytochrome c iso-1), GAPDH (glyceraldehydes-3-phosphate dehydrogenase), PGK1 (phosphoglycerate kinase), PYK1 (pyruvate kinase); regulated: GAL1, 10,7 (galactose metabolic enzymes), ADH2 (alcohol dehydrogenase 2), PHO5 (acid phosphatase), CUP1 (copper metallothionein); heterologous: CaMV (cauliflower mosaic virus 355 promoter);
- for expression in *Pichia pastoris*: the AOX1 promoter (alcohol oxidase I);
- for expression in mammalian cells: human cytomegalovirus (hCMV) immediate early enhancer/promoter; human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1α (hEF-1α) promoter from human, chimpanzee, mouse or rat; the SV40 early promoter; HIV-1 long terminal repeat promoter; β-actin promoter;

Some preferred, but non-limiting vectors for use with these host cells include:
- vectors for expression in mammalian cells: pMAMneo (Clontech), pcDNA3 (Invitrogen), pMC1neo (Stratagene), pSG5 (Stratagene), EBO-pSV2-neo (ATCC 37593), pBPV-1 (8-2) (ATCC 37110), pdBPV-MMT-neo (342-12) (ATCC 37224), pRSVgpt (ATCC37199), pRSVneo (ATCC37198), pSV2-dhfr (ATCC 37146), pUCTag (ATCC 37460) and 1ZD35 (ATCC 37565), as well as viral-based expression systems, such as those based on adenovirus;
- vectors for expression in bacterial cells: pET vectors (Novagen) and pQE vectors (Qiagen);
- vectors for expression in yeast or other fungal cells: pYES2 (Invitrogen) and *Pichia* expression vectors (Invitrogen);
- vectors for expression in insect cells: pBlueBacII (Invitrogen) and other baculovirus vectors
- vectors for expression in plants or plant cells: for example vectors based on cauliflower mosaic virus or tobacco mosaic virus, suitable strains of *Agrobacterium*, or Ti-plasmid based vectors.

Some preferred, but non-limiting secretory sequences for use with these host cells include: for use in bacterial cells such as *E. coli*: PelB, Bla, OmpA, OmpC, OmpF, OmpT, StII, PhoA, PhoE, MalE, Lpp, LamB, and the like; TAT signal peptide, hemolysin C-terminal secretion signal;
- for use in yeast: α-mating factor prepro-sequence, phosphatase (pho1), invertase (Suc), etc.;
- for use in mammalian cells: indigenous signal in case the target protein is of eukaryotic origin; murine 1 g κ-chain V-J2-C signal peptide; etc.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the amino acid sequence of the invention, e.g. using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g. under suitable conditions), an amino acid sequence, Nanobody® or polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the amino acid sequences, Nanobodies® or polypeptides of the invention, the transformed host cell or transformed host organism may generally be kept, maintained and/or cultured under conditions such that the (desired) amino acid sequence, Nanobody® or polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

It will also be clear to the skilled person that the amino acid sequence, Nanobody® or polypeptide of the invention may (first) be generated in an immature form (as mentioned above), which may then be subjected to post-translational modification, depending on the host cell/host organism used. Also, the amino acid sequence, Nanobody® or polypeptide of the invention may be glycosylated, again depending on the host cell/host organism used.

The amino acid sequence, Nanobody® or polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence, Nanobody® or polypeptide of the invention) and/or preparative immunological techniques (i.e. using antibodies against the amino acid sequence to be isolated).

The invention further relates to a product or composition containing or comprising at least one amino acid sequence of the invention (or a suitable fragment thereof), at least one Nanobody® of the invention, at least one polypeptide of the invention, at least one compound or construct of the invention, at least one monovalent construct of the invention and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

Generally, for pharmaceutical use, the amino acid sequences, Nanobodies® and polypeptides of the invention may be formulated as a pharmaceutical preparation or compositions comprising at least one amino acid sequence, Nanobody® or polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers for use in the preparation thereof, will be clear to the skilled person, and are further described herein.

Thus, in a further aspect, the invention relates to a pharmaceutical composition that contains at least one amino acid of the invention, at least one Nanobody® of the invention, at least one compound or construct of the invention or at least one polypeptide of the invention and at least one suitable carrier, diluent or excipient (i.e. suitable for pharmaceutical use), and optionally one or more further active substances.

Generally, the amino acid sequences, Nanobodies®, compounds, constructs and polypeptides of the invention can be formulated and administered in any suitable manner known per se, for which reference is for example made to the general background art cited above (and in particular to WO 04/041862, WO 04/041863, WO 04/041865, WO 04/041867 and WO 08/020,079) as well as to the standard handbooks, such as Remington's Pharmaceutical Sciences, 18$^{th}$ Ed., Mack Publishing Company, USA (1990), Remington, the Science and Practice of Pharmacy, 21st Edition, Lippincott Williams and Wilkins (2005); or the Handbook of Therapeutic Antibodies (S. Dubel, Ed.), Wiley, Weinheim, 2007 (see for example pages 252-255).

For example, the amino acid sequences, Nanobodies®, compounds, constructs and polypeptides of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (for example intravenous, intraperitoneal, subcutaneous, intramuscular, intraluminal, intra-arterial or intrathecal administration) or for topical (i.e. transdermal or intradermal) administration.

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020,079. Usually, aqueous solutions or suspensions will be preferred.

The amino acid sequences, Nanobodies®, compounds, constructs and polypeptides of the invention can also be administered using gene therapy methods of delivery. See, e.g., U.S. Pat. No. 5,399,346, which is incorporated by reference in its entirety. Using a gene therapy method of delivery, primary cells transfected with the gene encoding an amino acid sequence, Nanobody® or polypeptide of the invention can additionally be transfected with tissue specific promoters to target specific organs, tissue, grafts, tumors, or cells and can additionally be transfected with signal and stabilization sequences for subcellularly localized expression.

Thus, the amino acid sequences, Nanobodies®, compounds, constructs and polypeptides of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the amino acid sequences, Nanobodies®, compounds, constructs and polypeptides of the invention may be combined with one or more excipients and used in the form of ingestible tablets, buccal tablets, troches, capsules, elixirs, suspensions, syrups, wafers, and the like. Such compositions and preparations should contain at least 0.1% of the amino acid sequence, Nanobody®, compound, construct or polypeptide of the invention. Their percentage in the compositions and preparations may, of course, be varied and may conveniently be between about 2 to about 60% of the weight of a given unit dosage form. The amount of the amino acid sequence, Nanobody®, compound, construct or polypeptide of the invention in such therapeutically useful compositions is such that an effective dosage level will be obtained.

The tablets, troches, pills, capsules, and the like may also contain binders, excipients, disintegrating agents, lubricants and sweetening or flavouring agents, for example those mentioned on pages 143-144 of WO 08/020,079. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the amino acid sequences, Nanobodies®, compounds, constructs and polypeptides of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the amino add sequences, Nanobodies®, compounds, constructs and polypeptides of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The amino acid sequences, Nanobodies®, compounds, constructs and polypeptides of the invention may also be administered intravenously or intraperitoneally by infusion or injection, as further described on pages 144 and 145 of WO 08/020,079.

For topical administration, the amino acid sequences, Nanobodies®, compounds, constructs and polypeptides of the invention may be applied in pure form, i.e., when they are liquids. However, it will generally be desirable to administer them to the skin as compositions or formulations, in combination with a dermatologically acceptable carrier, which may be a solid or a liquid, as further described on page 145 of WO 08/020,079.

Generally, the concentration of the amino acid sequences, Nanobodies®, compounds, constructs and polypeptides of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

In a preferred aspect, the amino acid sequences, Nanobodies®, compounds, constructs and/or polypeptides of the invention and/or compositions comprising the same may be administered to the pulmonary tissue. In the context of the present invention, "pulmonary tissue" is for the purposes of this invention equivalent with lung tissue or lung. The lung comprises 2 distinct zones: a conducting and a respiratory zone, within which the airway and vascular compartments lie (see e.g. "Pulmonary Drug Delivery", Edited by Karoline Bechtold-Peters and Henrik Luessen, 2007, ISBN 978-3-87193-322-6 pages 16-28).

For pulmonary delivery, the amino acid sequences, Nanobodies®, compounds, constructs and polypeptides of the invention may be applied in pure form, i.e., when they are liquids or a dry powder. However, it will be preferred to administer them to the pulmonary tissue as composition or formulation comprising an amino acid sequence, Nanobody®, compound, construct and/or polypeptide of the invention and a carrier suitable for pulmonary delivery. Accordingly the present invention also relates to a pharmaceutical composition comprising the amino acid sequence, Nanobody®, compound, construct and/or polypeptide of the invention and a carrier suitable for pulmonary delivery. Carriers suitable for pulmonary delivery are known in the art.

The amino acid sequences, Nanobodies®, compounds, constructs and/or polypeptides of the invention may also be administered as micro- or nanoparticles of pure drugs with particle sizes and distributions favorable for pulmonary delivery.

Accordingly the present invention also relates to a pharmaceutical device suitable for the pulmonary delivery of the amino acid sequences, Nanobodies®, compounds, constructs and/or polypeptides of the invention and suitable in the use of a composition comprising the same. This device may be an inhaler for liquids (e.g. a suspension of fine solid particles or droplets) comprising the amino acid sequence, Nanobody®, compound, constructs and/or polypeptide of the invention. The device may also be a dry powder inhaler comprising the amino acid sequence, Nanobody®, compound, construct and/or polypeptide of the invention in the form of a dry powder.

In a preferred method, the administration to the pulmonary tissue is performed by inhaling the amino acid sequences, Nanobodies®, compounds, constructs and/or polypeptides of the invention and/or the composition comprising the same in an aerosol cloud. According to the invention, inhaling of the aerosol cloud can be performed by an inhaler device. The device should generate from a formulation comprising the amino acid sequences, Nanobodies®, compounds, constructs and/or polypeptides of the invention and/or composition comprising the same an aerosol cloud of the desired particle size (distribution) at the appropriate moment of the mammal's inhalation cycle, containing the right dose of the amino acid sequences, Nanobodies®, compounds, constructs and/or polypeptides of the invention ("Pulmonary drug delivery", Bechtold-Peters and Luessen, eds., ISBN 978-3-87193-322-6, page 125).

In the context of the present invention, "aerosol" denotes a suspension of fine solid particles or liquid droplets (or combination thereof) in a gas wherein for the purposes of this invention the particles and/or droplets comprise the amino acid sequences, Nanobodies®, compounds, constructs and/or polypeptides of the invention.

The device should generate from the formulation an aerosol cloud of the desired particle size (distribution) at the appropriate moment of the mammal's inhalation cycle, containing the right dose of amino acid sequences, Nanobodies®, compounds, constructs and/or polypeptides of the invention. The following 4 requirements (formulation, particle size, time and dose) should be considered ("Pulmonary Drug Delivery", Bechtold-Peters and Luessen, eds., supra, pages 125 and 126):

- The formulations that are used in the devices may vary from aqueous solutions or suspensions used in nebulizers to the propellant-based solutions or suspensions used in metered dose inhaler or even specially engineered powder mixtures for the dry powder inhalers. All these different formulations require different principles for aerosol generation, which emphasizes the mutual dependency of device and formulation;
- Since the site of deposition of aerosol particles depends on their (aerodynamic) size and velocity, the desired particle size of the aerosol cloud varies depending on the desired site of deposition in the lung, which is related to the therapeutic goal of the administration;
- As the aerosol cloud can be tuned to be released at different moments during the inhalation cycle generated by the mammal, it is preferred that for the agents of the invention (to be deposited in the peripheral parts of the lung) the aerosol is released at the start of the inhalation cycle;
- Doses may vary considerably and may e.g. vary e.g. for a human from a few microgram to several hundreds of microgram or even milligrams, e.g. about up to about 10 to 100 milligrams.

Various inhalation systems are e.g. described on pages 129 to 148 in the review ("Pulmonary Drug Delivery", Bechtold-Peters and Luessen, eds., supra) and include, but are not limited to, nebulizers, metered dose inhalers, metered dose liquid inhalers, and dry powder inhalers. Devices taking into account optimized and individualized breathing pattern for controlled inhalation manoeuvres may also be used (see AKITA® technology on page 157 of "Pulmonary Drug Delivery", Bechtold-Peters and Luessen, eds., supra).

However, not only the device is important to pulmonary delivery of the amino acid sequences, Nanobodies®, compounds, constructs and/or polypeptides of the invention but also the right formulation is critical to achieve an effective delivery. This can be in principle achieved by using one of the following approaches:

- Administration of aqueous solutions or suspensions comprising the amino acid sequences, Nanobodies®, compounds, constructs and/or polypeptides of the invention (e.g. nasal drops) into the nasal cavities;
- Nebulisation of aqueous solutions or suspensions comprising the amino acid sequences, Nanobodies®, compounds, constructs and/or polypeptides of the invention;
- Atomization by means of liquefied propellants; and
- Dispersion of dry powders.

Hence formulations of the amino acid sequences, Nanobodies®, compounds, constructs and/or polypeptides of the invention have to be adopted and adjusted to the chosen inhalation device. Appropriate formulations, i.e. the excipients in addition to the amino acid sequences, Nanobodies®, compounds, constructs and/or polypeptides of the invention, are e.g. described in chapter IV of "Pulmonary Drug Delivery", Bechtold-Peters and Luessen, eds., supra.

The amount of the amino acid sequences, Nanobodies®, compounds, constructs and polypeptides of the invention required for use in treatment will vary not only with the particular amino acid sequence, Nanobody®, compounds, constructs or polypeptide selected but also with the route of administration, the nature of the condition being treated and the age and condition of the patient and will be ultimately at the discretion of the attendant physician or clinician. Also the dosage of the amino acid sequences, Nanobodies®, compounds, constructs and polypeptides of the invention varies depending on the target host cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

The invention further relates to applications and uses of the amino acid sequences, Nanobodies®, polypeptides, compounds, nucleic acids, host cells, products and compositions described herein, as well as to methods for the prevention and/or treatment respiratory tract infection caused by hRSV. Some preferred but non-limiting applications and uses will become clear from the further description herein.

The amino acid sequences, Nanobodies®, polypeptides, compounds and compositions of the present invention can generally be used to block the interaction of protein F of hRSV with the target host cell and/or its membrane, to neutralize hRSV (different hRSV strains and/or escape mutants), to modulate, inhibit and/or prevent hRSV infectivity (of different hRSV strains and/or escape mutants), to modulate, inhibit and/or prevent fusion (of different hRSV strains and/or escape mutants) with (the cell membrane of) the target host cell and/or to modulate, inhibit and/or prevent hRSV entry in the target host cell (of different hRSV strains and/or escape mutants).

In one aspect, the amino acid sequences, Nanobodies®, polypeptides, compounds and compositions of the present invention can block the interaction of protein F of hRSV with the target host cell and/or its membrane by at least 1%, preferably at least 5%, such as at least 10% or at least 25%, for example by at least 50%, at least 60%, at least 70%, at least 80%, or 90% or more, compared to the interaction of protein F of hRSV with the target host cell and/or its membrane under the same conditions but without the presence of the amino acid sequence, Nanobody® or polypeptide of the invention, measured in any suitable manner known per se, for example using one of the assays described herein.

In another aspect, the amino acid sequences, Nanobodies®, polypeptides, compounds and compositions of the present invention neutralize hRSV infectivity by at least 1%, preferably at least 5%, such as at least 10% or at least 25%, for example by at least 50%, at least 60%, at least 70%, at least 80%, or 90% or more, compared to, the neutralization of hRSV under the same conditions but without the presence of the amino acid sequence, Nanobody® or polypeptide of the invention, measured in any suitable manner known per se, for example using one of the assays described herein.

In the context of the present invention, "modulating" or "to modulate" generally means either reducing, preventing or inhibiting viral infectivity, fusion and/or viral entry and/or reducing, preventing or inhibiting the biological pathways that are mediated by protein F of hRSV, as measured using a suitable in vitro, cellular or in vivo assay (such as those mentioned herein). In particular, "modulating" or "to modulate" may mean either reducing, preventing or inhibiting viral infectivity, fusion and/or viral entry and/or reducing, preventing or inhibiting the biological pathways that are mediated by protein F of hRSV as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to normal (i.e. naturally occurring) viral infectivity, fusion and/or viral entry and/or normal (i.e. naturally occurring) the biological pathways that are mediated by protein F of hRSV in the same assay under the same conditions but without the presence of the amino acid sequence, Nanobody® or polypeptide of the invention.

In one aspect, the amino acid sequences, Nanobodies®, polypeptides, compounds and compositions of the present invention may modulate, inhibit and/or prevent hRSV infectivity by at least 1%, preferably at least 5%, such as at least 10% or at least 25%, for example by at least 50%, at least 60%, at least 70%, at least 80%, or 90% or more, compared to the infectivity under the same conditions but without the presence of the amino acid sequence, Nanobody® or polypeptide of the invention, measured in any suitable manner known per se, for example using one of the assays described herein.

The term "viral entry" used herein encompasses any viral-mediated biological pathway that is needed to accomplish virion attachment to a target host cell and/or viral fusion with a target host cell. It is encompassed in the present invention that viral entry, which may be any viral-mediated biological pathway that is needed to accomplish virion attachment to a target host cell and/or viral fusion with a target host cell, can be modulated and/or reduced and/or prevented and/or inhibited by specific binding of the amino acid sequences, Nanobodies®, polypeptides and/or compounds of the invention, as measured using a suitable in vitro, cellular or in vivo assay (such as those mentioned herein). In particular, viral entry, which can be mediated by protein F of hRSV, can be modulated, reduced, prevented or inhibited by specific binding of the amino acid sequences, Nanobodies®, polypeptides and/or compounds of the invention to protein F of hRSV, as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to normal (i.e. naturally occurring) viral entry (as defined herein), which can be mediated by protein F of hRSV, in the same assay under the same conditions but without the presence of the amino acid sequence, Nanobody®, polypeptide and/or compound of the invention. Thus, it is also encompassed that that viral attachment and/or viral fusion can be modulated and/or reduced and/or prevented and/or inhibited by specific binding of the amino acid sequences, Nanobodies®, polypeptides and/or compounds of the invention to protein F of hRSV, as measured using a suitable in vitro, cellular or in vivo assay (such as those mentioned herein). In particular, viral attachment and/or viral fusion, which can be mediated by protein F of hRSV, can be modulated, reduced, prevented or inhibited by specific binding of the amino acid sequences, Nanobodies®, polypeptides and/or compounds of the invention to protein F of hRSV, as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to normal (i.e. naturally occurring) viral attachment and/or viral fusion, which can be mediated by protein F of hRSV in the same assay under the same conditions but without the presence of the amino acid sequence, Nanobody®, polypeptide and/or compound of the invention.

In this respect, the amino acid sequences, Nanobodies®, polypeptides, compounds and compositions of the present invention may modulate, inhibit and/or prevent hRSV entry in the target host cell by at least 1%, preferably at least 5%, such as at least 10% or at least 25%, for example by at least 50%, at least 60%, at least 70%, at least 80%, or 90% or more, compared to the entry in the target host cell under the same conditions but without the presence of the amino acid sequence, Nanobody® or polypeptide of the invention, for example using one of the assays described herein.

The amino acid sequences, Nanobodies®, polypeptides, compounds and compositions of the present invention may also modulate, inhibit and/or prevent fusion of hRSV with (the cell membrane of) the target host cell by at least 1%, preferably at least 5%, such as at least 10% or at least 25%, for example by at least 50%, at least 60%, at least 70%, at least 80%, or 90% or more, compared to fusion of hRSV with (the cell membrane of) the target host cell under the same conditions but without the presence of the amino acid sequence, Nanobody® or polypeptide of the invention, measured in any suitable manner known per se, for example using one of the assays described herein.

The multivalent (such as bivalent or trivalent) polypeptides of the invention have shown improved affinity and/or improved cross-reactivity for different genotypes, subtypes, viral escape mutants and/or strains of hRSV compared to the monovalent amino acid sequence or Nanobody®. In one aspect, the multivalent (such as bivalent or trivalent) polypeptides of the invention may bind different strains of RSV (such as e.g. Long, A-2 and/or B-1). In yet another aspect, the multivalent (such as bivalent or trivalent) polypeptides of the invention may bind different escape mutants of hRSV (such as e.g. described in Lopez et al. 1998, J. Viral. 72: 6922-6928) and/or escape mutants specific for antigen site II, antigen site IV-VI or the combination of both antigenic sites.

Accordingly, the invention also relates to the use of a multivalent (e.g. trivalent, bivalent) polypeptide of the invention, and/or of a pharmaceutical composition comprising the same for binding and/or neutralization of different strains of a hRSV. In a preferred aspect, a bivalent humanized and/or sequence optimized 7B2 Nanobody® (such as e.g. a bivalent polypeptide comprising two Nanobodies® selected from SEQ ID NO's: 33-40 and 51) is used. In another preferred aspect, a trivalent humanized and/or sequence optimized 7B2 Nanobody® (such as e.g. a trivalent polypeptide comprising three Nanobodies® selected from SEQ ID NO's: 33-40 and 51) is used. In another preferred aspect, one of SEQ ID NO's: 41-50 is used.

The invention also relates to the use of a multivalent (e.g. trivalent, bivalent) polypeptide of the invention, and/or of a pharmaceutical composition comprising the same for binding and/or neutralization of one or more escape mutants of a hRSV. In a preferred aspect, a bivalent humanized and/or sequence optimized 7B2 Nanobody® (such as e.g. a bivalent polypeptide comprising two Nanobodies® selected from SEQ ID NO's: 33-40 and 51) is used. In another preferred aspect, a trivalent humanized and/or sequence optimized 7B2 Nanobody® (such as e.g. a trivalent polypeptide comprising three Nanobodies® selected from SEQ ID NO's: 33-40 and 51) is used. In another preferred aspect, one of SEQ ID NO's: 41-50 is used.

The invention also relates to a method for the prevention and/or treatment of at least one viral disease, said method comprising administering, to a subject in need thereof, a pharmaceutically active amount of an amino acid sequence of the invention, of a Nanobody® of the invention, of a polypeptide of the invention, of a compound or construct of the invention and/or of a pharmaceutical composition comprising the same.

As such, the amino acid sequences, Nanobodies®, polypeptides, compounds and compositions of the present invention can be used for the prevention and/or treatment of diseases and disorders associated with hRSV infection. Examples of such diseases and disorders associated with hRSV infection will be clear to the skilled person based on the disclosure herein, and for example include the following diseases and disorders: respiratory illness, upper respiratory tract infection, lower respiratory tract infection, bronchiolitis (inflammation of the small airways in the lung), pneumonia, dyspnea, cough, (recurrent) wheezing and asthma.

Accordingly, the present invention also relates to a method for the prevention and/or treatment of respiratory illness, upper respiratory tract infection, lower respiratory tract infection, bronchiolitis (inflammation of the small airways in the lung), pneumonia, dyspnea, cough, (recurrent) wheezing and/or asthma caused by hRSV, said method comprising administering, to a subject in need thereof, a pharmaceutically active amount of at least one amino acid sequence of the invention, Nanobody® of the invention, polypeptide of the invention, compound or construct of the invention or monovalent construct of the invention, or a composition of the invention.

The invention also relates to the use of an amino acid sequence of the invention, a Nanobody® of the invention, a polypeptide of the invention, a compound or construct of the invention or monovalent construct of the invention in the preparation of a pharmaceutical composition for prevention and/or treatment of respiratory illness, upper respiratory tract infection, lower respiratory tract infection, bronchiolitis (inflammation of the small airways in the lung), pneumonia, dyspnea, cough, (recurrent) wheezing and/or asthma; and/or for use in one or more of the methods described herein.

The invention also relates to an amino acid sequence of the invention, a Nanobody® of the invention, a polypeptide of the invention, a compound or construct of the invention or monovalent construct of the invention for prevention and/or treatment of respiratory illness, upper respiratory tract infection, lower respiratory tract infection, bronchiolitis (inflammation of the small airways in the lung), pneumonia, dyspnea, cough, (recurrent) wheezing and/or asthma.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

More in particular, the present invention may relate to a method for the prevention and/or treatment of infection by hRSV, said method comprising administering, to a subject in need thereof, a pharmaceutically active amount of a multivalent (e.g. trivalent or bivalent) polypeptide or compound of the invention, and/or of a pharmaceutical composition comprising the same. More in particular, the present invention may relate to a method for the prevention and/or treatment of infection by hRSV, said method comprising administering, to a subject in need thereof, a pharmaceutically active amount of a bivalent compound or polypeptide of the invention. More in particular, the present invention may relate to a method for the prevention and/or treatment of infection by hRSV, said method comprising administering, to a subject in need thereof, a pharmaceutically active amount of a bivalent humanized and/or sequence optimized 7B2 Nanobody® (such as e.g. a bivalent polypeptide comprising two Nanobodies® selected from SEQ ID NO's: 33-40). More in particular, the present invention may relate to a method for the prevention and/or treatment of infection by hRSV, said method comprising administering, to a subject in need thereof, a pharmaceutically active amount of a trivalent compound or polypeptide of the invention. More in particular, the present invention may relate to a method for the prevention and/or treatment of infection by hRSV, said method comprising administering, to a subject in need thereof, a pharmaceutically active amount of a trivalent humanized 7B2 Nanobody® (such as e.g. a trivalent polypeptide comprising three Nanobodies® selected from SEQ ID NO's: 33-40). More in particular, the present invention may relate to a method for the prevention and/or treatment of infection by hRSV, said method comprising administering, to a subject in need thereof, a pharmaceutically active amount of one of SEQ ID NO's: 41-50.

More in particular, the present invention may relate to a method for the prevention and/or treatment of infection by hRSV said method comprising administering to the pulmonary tissue of a subject in need thereof, a pharmaceutically active amount of an amino acid sequence of the invention, of a Nanobody® of the invention, of a polypeptide of the invention, and/or of a pharmaceutical composition comprising the same.

In another aspect, the invention relates to a method for immunotherapy, and in particular for passive immunotherapy, which method comprises administering, to a subject suffering from or at risk of the diseases and disorders mentioned herein, a pharmaceutically active amount of an amino acid sequence of the invention, of a Nanobody® of the invention, of a polypeptide of the invention, of a compound or construct of the invention and/or of a pharmaceutical composition comprising the same.

In the above methods, the amino acid sequences, Nanobodies®, compounds or constructs and/or polypeptides of the invention and/or the compositions comprising the same can be administered in any suitable manner, depending on the specific pharmaceutical formulation or composition to be used. Thus, the amino acid sequences, Nanobodies® and/or polypeptides of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

Thus, in general, the amino acid sequences, Nanobodies®, compounds or constructs and polypeptides according to the invention and/or the compositions comprising the same can be administered in any suitable manner; for example but not limited thereto, the amino acid sequences, Nanobodies®, compounds or constructs and polypeptides according to the invention and compositions comprising the same can be administered intranasally and/or by inhalation and/or by any other suitable form of pulmonary delivery; methods for pulmonary delivery and/or intranasal delivery and/or delivery by inhalation of a Nanobody®, amino acid sequence, compound or construct and/or polypeptide of the invention will be known to the skilled person and are e.g. described in the handbook "Drug Delivery: Principles and Applications" (2005) by Binghe Wang, Teruna Siahaan and Richard Soltero (Eds. Wiley Interscience (John Wiley & Sons)); in the International application WO 08/049,897 of Ablynx N. V. entitled "Intranasal delivery of polypeptides and proteins"; in "Pharmacology PreTest™ Self-Assessment and Review" ($11^{th}$ Edition) by Rosenfeld G. C., Loose-Mitchell D. S.; and in "Pharmacology" ($3^{rd}$ Edition) by Lippincott Williams & Wilkins, New York; Shlafer M. McGraw-Hill Medical Publishing Division, New York; Yang K. Y., Graff L. R., Caughey A. B. Blueprints Pharmacology, Blackwell Publishing.

Accordingly, the present invention also relates to a method for administering an effective amount of a amino acid sequence, Nanobody®, compound or construct and/or polypeptide of the invention and/or a composition comprising the same, wherein said method comprises the step of administering the amino acid sequence, Nanobody®, compound or construct and/or polypeptide and/or composition comprising the same to the pulmonary tissue. In such method, the amino acid sequence, Nanobody®, compound or construct and/or polypeptide and/or a composition comprising the same can be administered by any method know in the art for pulmonary delivery such as e.g. by use of an inhaler, an intranasal delivery device or a device capable of generating an aerosol cloud.

In a preferred aspect of the invention, the amino acid sequence, Nanobody®, compound or construct and/or polypeptide will bind and/or neutralize virus present in the pulmonary tissue. Preferably in such method for pulmonary delivery at least 5%, preferably at least 10%, 20%, 30%, 40%, more preferably at least 50%, 60%, 70%, and even more preferably at least 80% or more of the amino acid sequence, Nanobody®, compound or construct and/or polypeptide of the invention is stable in the pulmonary tissue for at least 24 hours, preferably at least 48 hours more preferably at least 72 hours.

It has been surprisingly found that the amino acid sequences, Nanobodies®, compounds or constructs and/or polypeptides of the invention have a long lasting stability in the pulmonary tissue. E.g. it has been found that a Nanobody® directed against hRSV remains functional in the lung for at least 48 hours (see WO2010/081856 and WO09/147, 248). Thus, embodiments of the invention with treatment intervals such as once a day, once every $2^{nd}$, $3^{rd}$, $4^{th}$, $5^{th}$, $6^{th}$ or once every week are thought to be possible taken the estimated long lasting stability of the amino acid sequences, Nanobodies®, compounds or constructs and/or polypeptides of the invention.

Accordingly, the invention relates to a method for delivering an amino acid sequence, Nanobody®, compound or construct and/or polypeptide of the invention to the pulmonary tissue of a subject without being inactivated, said method comprising the step of pulmonary administering said amino acid sequence, Nanobody®, compound or construct and/or polypeptide of the invention to said subject.

The invention also relates to a method for the prevention and/or treatment of hRSV infection, said method comprising administering to the pulmonary tissue of a subject in need thereof, a pharmaceutically active amount of an amino acid sequence of the invention, of a Nanobody® of the invention, of a polypeptide of the invention, of a compound or construct of the invention and/or of a pharmaceutical composition comprising the same.

More in particular, the invention relates to a method for the prevention and/or treatment of respiratory illness, upper respiratory tract infection, lower respiratory tract infection, bronchiolitis (inflammation of the small airways in the lung), pneumonia, dyspnea, cough, (recurrent) wheezing and/or asthma, said method comprising administering, to the pulmonary tissue of a subject in need thereof, a pharmaceutically active amount of an amino acid sequence of the invention, of a Nanobody® of the invention, of a polypeptide of the invention, of a compound or construct of the invention and/or of a pharmaceutical composition comprising the same.

More in particular, the present invention may relate to a method for the prevention and/or treatment of infection by hRSV, said method comprising administering, to the pulmonary tissue of a subject in need thereof, a pharmaceutically active amount of a multivalent (e.g. trivalent, bivalent) polypeptide or compound of the invention, and/or of a pharmaceutical composition comprising the same. More in particular, the present invention may relate to a method for the prevention and/or treatment of infection by hRSV, said method comprising administering, to the pulmonary tissue of a subject in need thereof, a pharmaceutically active amount of a bivalent compound or polypeptide of the invention. More in particular, the present invention may relate to a method for the prevention and/or treatment of infection by hRSV, said method comprising administering, to the pulmonary tissue of a subject in need thereof, a pharmaceutically active amount of a bivalent humanized and/or sequence optimized 7B2 Nanobody® (such as e.g. a bivalent polypeptide comprising two Nanobodies® selected from SEQ ID NO's: 33-40). More in particular, the present invention may relate to a method for the prevention and/or treatment of infection by hRSV, said method comprising administering, to the pulmonary tissue of a subject in need thereof, a pharmaceutically active amount of a trivalent compound or polypeptide of the invention. More in particular, the present invention may relate to a method for the prevention and/or treatment of infection by hRSV, said method comprising administering, to the pulmonary tissue of a subject in need thereof, a pharmaceutically active amount of a trivalent humanized and/or sequence optimized 7B2 Nanobody® (such as e.g. a trivalent polypeptide comprising three Nanobodies® selected from SEQ ID NO's: 33-40 and 51). More in particular, the present invention may relate to a method for the prevention and/or treatment of infection by hRSV, said method comprising administering, to the pulmonary tissue of a subject in need thereof, a pharmaceutically active amount of one of SEQ ID NO's: 41-50.

Also for example but not limited thereto, the amino acid sequences, Nanobodies®, compounds or constructs, and polypeptides according to the invention and compositions comprising the same, can be administered intramuscularly and/or by any suitable form of delivery to the brain, such as any suitable form of delivery which allows said amino acid sequences, Nanobodies®, polypeptides, compounds or constructs and compositions comprising the same to be transported across the blood-brain-barrier. Such methods for intramuscular delivery and/or any suitable form of delivery to the brain of a Nanobody®, amino acid sequence and/or polypeptide of the invention will be known to the skilled person and are e.g. described in the handbook "Drug Delivery: Principles and Applications" (2005) by Binghe Wang, Teruna Siahaan and Richard Soltero (Eds. Wiley Interscience (John Wiley & Sons)); in "Pharmacology PreTest™ Self-Assessment and Review" ($11^{th}$ Edition) by Rosenfeld G. C., Loose-Mitchell D. S.; and in "Pharmacology" ($3^{rd}$ Edition) by Lippincott Williams & Wilkins, New York; Shlafer M. McGraw-Hill Medical Publishing Division, New York; Yang K. Y., Graff L. R., Caughey A. B. Blueprints Pharmacology, Blackwell Publishing.

The amino acid sequences, Nanobodies®, compounds or constructs and/or polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific amino acid sequence, Nanobody®, compound or construct or polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more amino acid sequences, Nanobodies®, compounds or constructs and/or polypeptides of the invention, or of one or more compositions comprising the same, in one or more pharmaceutically effective amounts or doses. The specific amount(s) or doses to administered can be determined by the clinician, again based on the factors cited above.

Generally, for the prevention and/or treatment of the diseases and disorders mentioned herein and depending on the specific disease or disorder to be treated, the potency of the specific amino acid sequence, Nanobody®, compound or construct and polypeptide of the invention to be used, the specific route of administration and the specific pharmaceutical formulation or composition used, the amino acid sequences, Nanobodies®, compounds or constructs and polypeptides of the invention will generally be administered in an amount between 1 gram and 1 microgram per kg body weight per day, preferably between 0.1 gram and 10 microgram per kg body weight per day, most preferably between 0.01 gram and 100 microgram per kg body weight per day such as about 0.1, 0.5, 1, 2, 5 or 10 milligram per kg body weight per day, either continuously (e.g. by infusion), as a single daily dose or as multiple divided doses during the day. Amino acid sequences, Nanobodies®, compounds or constructs and polypeptides of the invention that contain a half-life extending moiety may be administered in an amount between 1 milligram and 100 milligram per kg body weight, preferably between 1 milligram and 50 milligram per kg body weight, such as about 10, 15, 20 or 30 milligram per kg body weight once or twice a month. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

When the amino acid sequence, Nanobody®, compound or construct and/or polypeptide and/or a composition comprising the same is administered to the pulmonary tissue the treatment regime may be once or twice daily, preferably once daily, or once every 2, 3, 4, 5, 6, or 7 days.

Usually, in the above method, a single amino acid sequence, Nanobody®, compound or construct, or polypeptide of the invention will be used. It is however within the scope of the invention to use two or more amino acid sequences, Nanobodies®, compounds or constructs and/or polypeptides of the invention in combination.

The Nanobodies®, amino acid sequences, compounds or constructs and polypeptides of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgment.

In particular, the amino acid sequences, Nanobodies®, compounds or constructs, and polypeptides of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of an amino acid sequence, Nanobody®, compound or construct, or polypeptide of the invention in the preparation of a pharmaceutical composition for prevention and/or treatment of at least one viral disease; and/or for use in one or more of the methods of treatment mentioned herein.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention also relates to the use of an amino acid sequence, Nanobody®, compound or construct or polypeptide of the invention in the preparation of a pharmaceutical composition for the prevention and/or treatment of at least one disease or disorder that can be prevented and/or treated by administering an amino acid sequence, Nanobody®, compound or construct or polypeptide of the invention to a patient.

More in particular, the invention relates to the use of an amino acid sequence, Nanobody®, compound or construct or polypeptide of the invention in the preparation of a pharmaceutical composition for the prevention and/or treatment of viral diseases, and in particular for the prevention and treatment of one or more of the diseases and disorders listed herein.

Again, in such a pharmaceutical composition, the one or more amino acid sequences, Nanobodies®, compounds or constructs or polypeptides of the invention may also be suitably combined with one or more other active principles, such as those mentioned herein.

Further uses of the amino acid sequences, Nanobodies®, polypeptides, nucleic acids, genetic constructs and hosts and host cells of the invention will be clear to the skilled person based on the disclosure herein. For example, and without limitation, the amino acid sequences of the invention can be linked to a suitable carrier or solid support so as to provide a medium than can be used in a manner known per se to purify an envelope protein of a virus from compositions and preparations comprising the same. Derivatives of the amino acid sequences of the invention that comprise a suitable detectable label can also be used as markers to determine (qualitatively or quantitatively) the presence of an envelope protein of a virus in a composition or preparation or as a marker to selectively detect the presence of an envelope protein of a virus on the surface of a cell or tissue (for example, in combination with suitable cell sorting techniques).

The invention will now be further described by means of the following non-limiting preferred aspects, examples and figures:

The entire contents of all of the references (including literature references, issued patents, published patent applications, and co-pending patent applications) cited throughout this application are hereby expressly incorporated by reference, in particular for the teaching that is referenced hereinabove.

Aspects

Aspect A-1. Amino acid sequence and/or Nanobody® that is directed against and/or specifically binds protein F of hRSV chosen from the following:
  a) SEQ ID NO's: 33-40;
  b) amino acid sequences that have no more than 3, preferably no more than 2, more preferably no more than 1 amino acid difference with one of SEQ ID NO's: 33-40, provided that:
    i) the amino acid sequence has Proline (Pro, P) at position 14, Arginine (Arg, R) at position 83 and/or Leucine (Leu, L) at position 108 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect A-2. Amino acid sequence and/or Nanobody® according to aspect A-1, that is directed against and/or specifically binds protein F of hRSV chosen from the following:
  a) SEQ ID NO's: 33-40;
  b) amino acid sequences that have no more than 3, preferably no more than 2, more preferably no more than 1 amino acid difference with one of SEQ ID NO's: 33-40, provided that:
    i) the amino acid sequence has Praline (Pro, P) at position 14, Arginine (Arg, R) at position 83 and Leucine (Leu, L) at position 108 (said positions determined according to Kabat numbering); and
    ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect A-3. Amino acid sequence and/or Nanobody® according to any of aspects A-1 or A-2, that comprises or essentially consists of one of SEQ ID NO's: 33-40.

Aspect A-4. Amino acid sequence and/or Nanobody® that is directed against and/or specifically binds protein F of hRSV that is chosen from the following:
  a) SEQ ID NO's: 35-40;
  b) amino acid sequences that have no more than 3, preferably no more than 2, more preferably no more than 1 amino acid difference with one of SEQ ID NO's: 35-40, provided that:
    i) the amino acid sequence has Glycine (Gly, G) at position 16, Glutamic acid (Glu, E) at position 54 and/or Alanine (Ala, A) at position 55 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect A-5. Amino acid sequence and/or Nanobody® according to aspects A-4, that is directed against and/or specifically binds protein F of hRSV chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
  i) the amino acid sequence has Praline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect A-6. Amino acid sequence and/or Nanobody® according to any of aspects A-4 or A-5, that comprises or essentially consists of one of SEQ ID NO's: 35-40.

Aspect A-7. Amino acid sequence and/or Nanobody® according to any of aspects A-4 to A-6, that is chosen from the following:
a) SEQ ID NO's: 37-40;
b) amino acid sequences that have no more than 3, preferably no more than 2, more preferably no more than 1 amino acid difference with one of SEQ ID NO's: 37-40, provided that:
  i) the amino acid sequence has Proline (Pro, P) at position 14, Arginine (Arg, R) at position 83, Leucine (Leu, L) at position 108 and Glycine (Gly, G) at position 16; and in addition the amino acid sequence has Glutamic acid (Glu, E) at position 54 or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect A-8. Amino acid sequence and/or Nanobody® according to any of aspects A-4 to A-7, that comprises or essentially consists of one of SEQ ID NO's: 37-40.

Aspect A-9. Amino acid sequence and/or Nanobody® comprising or essentially consisting of SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala.

Aspect A-10. Amino acid sequence and/or Nanobody® according to aspect A-9, comprising or essentially consisting of SEQ ID NO: 16, wherein one or more (such as two or three) amino acid residues have been mutated selected from the following: Ala14Pro, Lys83Arg and Gln108Leu.

Aspect A-11. Amino acid sequence and/or Nanobody® according to aspect A-10, comprising or essentially consisting of SEQ ID NO: 16, wherein following amino acid residues have been mutated: Ala14Pro, Lys83Arg and Gln108Leu.

Aspect A-12. Amino add sequence and/or Nanobody® according to aspect A-9, comprising or essentially consisting of SEQ ID NO: 16, wherein one or more (such as two or three) amino acid residues have been mutated selected from the following: Asp16Gly, Asp54Glu and Gly55Ala.

Aspect A-13. Amino acid sequence and/or Nanobody® according to aspect A-12, comprising or essentially consisting of SEQ ID NO: 16, wherein two amino acid residues have been mutated selected from the following:
Asp16Gly and Asp54Glu; or
Asp16Gly and Gly55Ala.

Aspect A-14. Amino acid sequence and/or Nanobody® according to aspect A-9, comprising or essentially consisting of SEQ ID NO: 16, wherein following amino acid residues have been mutated:
Ala14Pro, Lys83Arg, Gln108Leu;
Ala14Pro, Lys83Arg, Gln108Leu, Asp16Gly;
Ala14Pro, Lys83Arg, Gln108Leu, Asp16Gly, Asp54Glu; or
Ala14Pro, Lys83Arg, Gln108Leu, Asp16Gly, Gly55Ala.

Aspect A-15. Amino acid sequence and/or Nanobody® according to any of aspects A-1 to A-14, that can specifically bind to protein F of hRSV with a dissociation constant ($K_D$) of 1000 nM to 1 nM or less, preferably 100 nM to 1 nM or less, more preferably 10 nM to 1 nM or less.

Aspect A-16. Amino acid sequence and/or Nanobody® according to any of aspects A-1 to A-15, that can specifically bind to protein F of hRSV with a $k_{on}$-rate of between $10^4$ $M^{-1}s^{-1}$ to about $10^7$ $M^{-1}s^{-1}$, preferably between $10^5$ $M^{-1}s^{-1}$ and $10^7$ $M^{-1}s^{-1}$, more preferably about $10^6$ $M^{-1}s^{-1}$ or more.

Aspect A-17. Amino acid sequence and/or Nanobody® according to any of aspects A-1 to A-16, that can specifically bind to protein F of hRSV with a $k_{off}$ rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, or lower.

Aspect A-18. Amino acid sequence and/or Nanobody® according to any of aspects A-1 to A-17, that can neutralize hRSV (for example, as measured in a microneutralization assay on hRSV Long (such as e.g. described in Example 6) with an IC50 value between 100 nM and 1000 nM, preferably between 100 nM and 500 nM, or less.

Aspect A-19. Amino acid sequence and/or Nanobody® according to any of aspects A-1 to A-18, that specifically binds antigenic site II on protein F of hRSV and/or that competes with Synagis® for binding protein F of hRSV.

Aspect B-1. Amino acid sequence and/or Nanobody® according to any of aspects A-1 to A-19, that is directed against and/or specifically binds protein F of hRSV wherein the amino acid sequence has aspartic acid (Asp, D) at position 1 (said position determined according to Kabat numbering).

Aspect B-2. Amino acid sequence and/or Nanobody® that is directed against and/or specifically binds protein F of hRSV chosen from the following:
a) SEQ ID NO's: 34, 36, 38, 40, 51;
b) amino acid sequences that have no more than 3, preferably no more than 2, more preferably no more than 1 amino acid difference with one of SEQ ID NO's: 34, 36, 38, 40, 51, provided that:
  i) the amino acid sequence has Aspartic acid (Asp, D) at position 1 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect B-3. Amino acid sequence and/or Nanobody® according to aspect B-2, that is directed against and/or specifically binds protein F of hRSV chosen from the following:
a) SEQ ID NO's: 34, 36, 38, 40;
b) amino acid sequences that have no more than 3, preferably no more than 2, more preferably no more than 1 amino acid difference with one of SEQ ID NO's: 34, 36, 38, 40, provided that:
  i) the amino acid sequence has Aspartic acid (Asp, D) at position 1, Proline (Pro, P) at position 14, Arginine (Arg, R) at position 83 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect B-4. Amino acid sequence and/or Nanobody® according to any of aspects B-2 or 8-3, that comprises or essentially consists of one of SEQ ID NO's: 34, 36, 38, 40, 51.

Aspect B-5. Amino add sequence and/or Nanobody® according to any of aspects B-2 to 13-4, that is directed against and/or specifically binds protein F of hRSV chosen from the following:
a) SEQ ID NO's: 36, 38, 40;
b) amino acid sequences that have no more than 3, preferably no more than 2, more preferably no more than 1 amino acid difference with one of SEQ ID NO's: 36, 38, 40, provided that:
  i) the amino acid sequence has Aspartic acid (Asp, D) at position 1, Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect B-6. Amino acid sequence and/or Nanobody® according to any of aspects B-2 to B-5, that comprises or essentially consists of one of SEQ ID NO's: 36, 38, 40.

Aspect B-7. Amino acid sequence and/or Nanobody® according to any of aspects B-2 to B-6, that is directed against and/or specifically binds protein F of hRSV chosen from the following:
a) SEQ ID NO's: 38 and 40;
b) amino acid sequences that have no more than 3, preferably no more than 2, more preferably no more than 1 amino acid difference with one of SEQ ID NO's: 38 and 40, provided that:
  i) the amino acid sequence has Aspartic acid (Asp, D) at position 1, Proline (Pro, P) at position 14, Arginine (Arg, R) at position 83, Leucine (Leu, L) at position 108 and Glycine (Gly, G) at position 16; and in addition, the amino acid sequence has Glutamic acid (Glu, E) at position 54 or Alanine (Ala, A) at position 55 (said positions determined according to Kabat numbering);
  ii) and the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect B-8. Amino acid sequence and/or Nanobody® according to any of aspects B-2 to B-7, that comprises or essentially consists of one of SEQ ID NO's: 38 and 40.

Aspect B-9. Amino acid sequence and/or Nanobody® comprising or essentially consisting of SEQ ID NO: 16, wherein position 1 (Glu) has been changed into Asp.

Aspect B-10. Amino acid sequence and/or Nanobody® according to aspect B-9, comprising or essentially consisting of SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala.

Aspect B-11. Amino acid sequence and/or Nanobody® according to aspect B-10, comprising or essentially consisting of SEQ ID NO: 16, wherein one or more (such as two or three) amino acid residues have been mutated selected from the following: Ala14Pro, Lys83Arg and Gln108Leu.

Aspect B-12. Amino acid sequence and/or Nanobody® according to aspect B-11, comprising or essentially consisting of SEQ ID NO: 16, wherein following amino acid residues have been mutated: Ala14Pro, Lys83Arg and Gln108Leu.

Aspect B-13. Amino acid sequence and/or Nanobody® according to aspect B-10, comprising or essentially consisting of SEQ ID NO: 16, wherein one or more (such as two or three) amino acid residues have been mutated selected from the following: Asp16Gly, Asp54Glu and Gly55Ala.

Aspect B-14. Amino acid sequence and/or Nanobody® according to aspect B-13, comprising or essentially consisting of SEQ ID NO: 16, wherein two amino acid residues have been mutated selected from the following: Asp16Gly and Asp54Glu; or
Asp16Gly and Gly55Ala.

Aspect B-15. Amino acid sequence and/or Nanobody® according to aspect B-9, comprising or essentially consisting of SEQ ID NO: 16, wherein following amino acid residues have been mutated:

Glu1Asp;
Glu1Asp, Ala14Pro, Lys83Arg, Gln108Leu;
Glu1Asp, Ala14Pro, Lys83Arg, Gln108Leu, Asp16Gly;
Glu1Asp, Ala14Pro, Lys83Arg, Gln108Leu, Asp16Gly, Asp54Glu; or
Glu1Asp, Ala14Pro, Lys83Arg, Gln108Leu, Asp16Gly, Gly55Ala.

Aspect B-16. Amino acid sequence and/or Nanobody® according to any of aspects B-1 to B-15, that can specifically bind to protein F of hRSV with a dissociation constant ($K_D$) of 1000 nM to 1 nM or less, preferably 100 nM to 1 nM or less, more preferably 10 nM to 1 nM or less.

Aspect B-17. Amino acid sequence and/or Nanobody® according to any of aspects B-1 to B-16, that can specifically bind to protein F of hRSV with a $k_{on}$-rate of between $10^4$ $M^{-1}s^{-1}$ to about $10^7$ $M^{-1}s^{-1}$, preferably between $10^5$ $M^{-1}s^{-1}$ and $10^7$ $M^{-1}s^{-1}$, more preferably about $10^6$ $M^{-1}s^{-1}$ or more.

Aspect B-18. Amino acid sequence and/or Nanobody® according to any of aspects B-1 to B-17, that can specifically bind to protein F of hRSV with a $k_{off}$-rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-4}$ and $10^{-4}$ $s^{-1}$, or lower.

Aspect B-19. Amino acid sequence and/or Nanobody® according to any of aspects B-1 to B-18, that can neutralize hRSV (for example, as measured in a microneutralization assay on hRSV Long (such as e.g. described in Example 6) with an IC50 value between 100 nM and 1000 nM, preferably between 100 nM and 500 nM, or less.

Aspect B-20. Amino acid sequence and/or Nanobody® according to any of aspects B-1 to B-19, that specifically binds antigenic site II on protein F of hRSV and/or that competes with Synagis® for binding protein F of hRSV.

Aspect E-1: Polypeptide that comprises or essentially consists of one or more amino acid sequences and/or Nanobodies® according to any of aspects A-1 to A-19 and B-1 to B-20, and optionally further comprises one or more other amino acid binding units, optionally linked via one or more peptidic linkers.

Aspect E-2: Polypeptide according to aspect E-1, in which said one or more other binding units are immunoglobulin sequences.

Aspect E-3: Polypeptide according to any of aspects E-1 or E-2, in which said one or more other binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies®.

Aspect E-4: Polypeptide according to any of aspects E-1 to E-3, in which said one or more amino acid sequences are immunoglobulin sequences.

Aspect E-5: Polypeptide according to any of aspects E-1 to E-4, in which said one or more amino acid sequences are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies®.

Aspect E-6: Polypeptide according to any of aspects E-1 to E-5, that comprises or essentially consists of one or more Nanobodies® according to any of aspects A-1 to A-19 and B-1 to B-20 and in which said one or more other binding units are Nanobodies®.

Aspect E-7: Polypeptide according to any of aspects E-1 to E-6, which is a multivalent construct.

Aspect E-8: Multivalent polypeptide according to aspect E-7, that comprises or essentially consists of at least two amino acid sequences and/or Nanobodies® according to any of aspects A-1 to A-19 and B-1 to B-20.

Aspect E-9: Multivalent polypeptide according to aspect E-8, wherein said at least two amino acid sequences and/or Nanobodies® are identical.

Aspect E-10: Multivalent polypeptide according to any of aspects E-7 to E-9, comprising or essentially consisting of at least two amino acid sequences and/or Nanobodies® chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:
  i) the amino acid sequence has Praline (Pro, P) at position 14, Arginine (Arg, R) at position 83 and/or Leucine (Leu, L.) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-11: Multivalent polypeptide according to aspect E-10, comprising or essentially consisting of at least two amino acid sequences and/or Nanobodies® chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:
  i) the amino acid sequence has Proline (Pro, P) at position 14, Arginine (Arg, R) at position 83 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-12: Multivalent polypeptide according to any of aspects E-10 or E-11, wherein said at least two amino acid sequences and/or Nanobodies® are identical.

Aspect E-13: Multivalent polypeptide according to any of aspects E-10 to E-12, that comprises or essentially consists of at least two amino acid sequences and/or Nanobodies® chosen from one of SEQ ID NO's: 33-40.

Aspect E-14: Multivalent polypeptide according to any of aspects E-7 to E-9, comprising or essentially consisting of at least two amino acid sequences and/or Nanobodies® chosen from the following:

a) SEQ ID NO's: 35-40;
b) amino acid sequences that have no more than 3, preferably no more than 2, more preferably no more than 1 amino acid difference with one of SEQ ID NO's: 35-40, provided that:
  i) the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-15: Multivalent polypeptide according to aspect E-14, comprising or essentially consisting of at least two amino acid sequences and/or Nanobodies® chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
  i) the amino acid sequence has Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-16: Multivalent polypeptide according to any of aspects E-14 or E-15, wherein said at least two amino acid sequences and/or Nanobodies® are identical.

Aspect E-17: Multivalent polypeptide according to any of aspects E-14 to E-16, that comprises or essentially consists of at least two amino acid sequences and/or Nanobodies® chosen from one of SEQ ID NO's: 35-40.

Aspect E-18: Multivalent polypeptide according to any of aspects E-10 to E-17, comprising or essentially consisting of at least two amino acid sequences and/or Nanobodies® chosen from the following:
a) SEQ ID NO's: 37-40;
b) amino acid sequences that have no more than 3, preferably no more than 2, more preferably no more than 1 amino acid difference with one of SEQ ID NO's: 37-40, provided that:
  i) the amino acid sequence has Proline (Pro, P) at position 14, Arginine (Arg, R) at position 83, Leucine (Leu, L) at position 108 and Glycine (Gly, G) at position 16; and in addition the amino acid sequence has Glutamic acid (Glu, E) at position 54 or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-19: Multivalent polypeptide according to aspects E-18, wherein said at least two amino acid sequences and/or Nanobodies® are identical.

Aspect E-20: Multivalent polypeptide according to any of aspects E-18 or E-19, that comprises or essentially consists of at least two amino acid sequences and/or Nanobodies® chosen from SEQ ID NO's: 37-40.

Aspect E-21: Multivalent polypeptide comprising or essentially consisting of at least two amino acid sequences and/or Nanobodies® with SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala.

Aspect E-22: Multivalent polypeptide according to aspect E-21, comprising or essentially consisting of at least two amino acid sequences and/or Nanobodies® with SEQ ID NO: 16, wherein one or more (such as two or three) amino acid residues have been mutated selected from the following: Ala14Pro, Lys83Arg and Gln108Leu.

Aspect E-23: Multivalent polypeptide according to aspect E-22, comprising or essentially consisting of at least two amino acid sequences and/or Nanobodies® with SEQ ID NO: 16, wherein following amino acid residues have been mutated: Ala14Pro, Lys83Arg and Gln108Leu.

Aspect E-24: Multivalent polypeptide according to aspect E-21, comprising or essentially consisting of at least two amino acid sequences and/or Nanobodies® with SEQ ID NO: 16, wherein one or more (such as two or three) amino acid residues have been mutated selected from the following: Asp16Gly, Asp54Glu and Gly55Ala.

Aspect A-20. Multivalent polypeptide according to aspect E-24, comprising or essentially consisting of at least two amino acid sequences and/or Nanobodies® with SEQ ID NO: 16, wherein two amino acid residues have been mutated selected from the following:
Asp16Gly and Asp54Glu; or
Asp16Gly and Gly55Ala.

Aspect E-25: Multivalent polypeptide according to aspect E-21, comprising or essentially consisting of at least two amino acid sequences and/or Nanobodies® with SEQ ID NO: 16, in which following amino acid residues have been mutated:
Ala14Pro, Lys83Arg, Gln108Leu;
Ala14Pro, Lys83Arg, Gln108Leu, Asp16Gly;
Ala14Pro, Lys83Arg, Gln108Leu, Asp16Gly, Asp54Glu; or
Ala14Pro, Lys83Arg, Gln108Leu, Asp16Gly, Gly55Ala.

Aspect E-26: Multivalent polypeptide according to aspect E-7, that comprises or essentially consists of at least three amino acid sequences and/or Nanobodies® according to any of aspects A-1 to A-19 and B-1 to B-20.

Aspect E-27: Multivalent polypeptide according to aspect E-26, wherein said at least three amino acid sequences and/or Nanobodies® are identical.

Aspect E-28: Multivalent polypeptide according to any of aspects E-7 and E-26 to E-27, comprising or essentially consisting of at least three amino acid sequences and/or Nanobodies® chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:

i) the amino acid sequence has Proline (Pro, P) at position 14, Arginine (Arg, R) at position 83 and/or Leucine (Leu, L) at position 108 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-29: Multivalent polypeptide according to aspect E-28, comprising or essentially consisting of at least three amino acid sequences and/or Nanobodies® chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:
i) the amino acid sequence has Proline (Pro, P) at position 14, Arginine (Arg, R) at position 83 and Leucine (Leu, L) at position 108 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-30: Multivalent polypeptide according to any of aspects E-28 or E-29, wherein said at least three amino acid sequences and/or Nanobodies® are identical.

Aspect E-31: Multivalent polypeptide according to any of aspects E-28 to E-30, that comprises or essentially consists of at least three amino acid sequences and/or Nanobodies® chosen from one of SEQ ID NO's: 33-40.

Aspect E-32: Multivalent polypeptide according to any of aspects E-7 and E-26 to E-27, comprising or essentially consisting of at least three amino acid sequences and/or Nanobodies® chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
i) the amino acid sequence has Glycine (Gly, G) at position 16, Glutamic acid (Glu, E) at position 54 and/or Alanine (Ala, A) at position 55 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-33: Multivalent polypeptide according to aspect E-32, comprising or essentially consisting of at least three amino acid sequences and/or Nanobodies® chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
i) the amino acid sequence has Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-34: Multivalent polypeptide according to any of aspects E-32 or E-33, wherein said at least three amino acid sequences and/or Nanobodies® are identical.

Aspect E-35: Multivalent polypeptide according to any of aspects E-32 to E-34, that comprises or essentially consists of at least two amino acid sequences and/or Nanobodies® chosen from one of SEQ ID NO's: 35-40.

Aspect E-36: Multivalent polypeptide according to any of aspects E-28 to E-35, comprising or essentially consisting of at least three amino acid sequences and/or Nanobodies® chosen from the following:
a) SEQ ID NO's: 37-40;
b) amino acid sequences that have no more than 3, preferably no more than 2, more preferably no more than 1 amino acid difference with one of SEQ ID NO's: 37-40, provided that:
i) the amino acid sequence has Proline (Pro, P) at position 14, Arginine (Arg, R) at position 83, Leucine (Leu, L) at position 108 and Glycine (Gly, G) at position 16; and in addition the amino acid sequence has Glutamic acid (Glu, E) at position 54 or Alanine (Ala, A) at position 55 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-37: Multivalent polypeptide according to aspects E-36, wherein said at least three amino acid sequences and/or Nanobodies® are identical.

Aspect E-38: Multivalent polypeptide according to any of aspects E-36 or E-37, that comprises or essentially consists of at least three amino acid sequences and/or Nanobodies® chosen from SEQ ID NO's: 37-40.

Aspect E-39: Multivalent polypeptide comprising or essentially consisting of at least three amino add sequences and/or Nanobodies® with SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala.

Aspect E-40: Multivalent polypeptide according to aspect E-39, comprising or essentially consisting of at least three amino acid sequences and/or Nanobodies® with SEQ ID NO: 16, wherein one or more (such as two or three) amino acid residues have been mutated selected from the following: Ala14Pro, Lys83Arg and Gln108Leu.

Aspect E-41: Multivalent polypeptide according to aspect E-40, comprising or essentially consisting of at least three amino acid sequences and/or Nanobodies® with SEQ ID NO: 16, wherein following amino acid residues have been mutated: Ala14Pro, Lys83Arg and Gln108Leu.

Aspect E-42: Multivalent polypeptide according to aspect E-39, comprising or essentially consisting of at least three amino acid sequences and/or Nanobodies® with SEQ ID NO: 16, wherein one or more (such as two or three) amino acid residues have been mutated selected from the following: Asp16Gly, Asp54Glu and Gly55Ala.

Aspect E-43: Multivalent polypeptide according to aspect E-42, comprising or essentially consisting of at least three amino acid sequences and/or Nanobodies® with SEQ ID NO: 16, wherein two amino acid residues have been mutated selected from the following:
Asp16Gly and Asp54Glu; or
Asp16Gly and Gly55Ala.

Aspect E-44: Multivalent polypeptide according to aspect E-39, comprising or essentially consisting of at least three amino acid sequences and/or Nanobodies® with SEQ ID NO: 16, in which following amino acid residues have been mutated:
Ala14Pro, Lys83Arg, Gln108Leu;
Ala14Pro, Lys83Arg, Gln108Leu, Asp16Gly;
Ala14Pro, Lys83Arg, Gln108Leu, Asp16Gly, Asp54Glu; or
Ala14Pro, Lys83Arg, Gln108Leu, Asp16Gly, Gly55Ala.

Aspect E-45: Multivalent polypeptide according to any of aspects E-7 to E-44, that has aspartic acid (Asp, D) at position 1.

Aspect E-46: Multivalent polypeptide according to any of aspects E-7 to E-9, comprising or essentially consisting of at least one amino acid sequence and/or Nanobody chosen from the following:
a) SEQ ID NO's: 34, 36, 38, 40, 51;
b) amino acid sequences that have no more than 3, preferably no more than 2, more preferably no more than 1 amino acid difference with one of SEQ ID NO's: 34, 36, 38, 40, 51, provided that:
i) the amino acid sequence has Aspartic acid (Asp, D) at position 1 (said position determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-47: Multivalent polypeptide according to aspects E-46, comprising or essentially consisting of at least one amino acid sequence and/or Nanobody chosen from the following:
a) SEQ ID NO's: 34, 36, 38, 40;
b) amino acid sequences that have no more than 3, preferably no more than 2, more preferably no more than 1 amino acid difference with one of SEQ ID NO's: 34, 36, 38, 40, provided that:
i) the amino acid sequence has Aspartic acid (Asp, D) at position 1, Proline (Pro, P) at position 14, Arginine (Arg, R) at position 83 and Leucine (Leu, L) at position 108 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-48: Multivalent polypeptide according to any of aspects E-46 or E-47, that comprises or essentially consists of at least one amino acid sequence and/or Nanobody chosen from one of SEQ ID NO's: 34, 36, 38, 40, 51.

Aspect E-49: Multivalent polypeptide according to any of aspects E-46 to E-48, comprising or essentially consisting of at least one amino acid sequence and/or Nanobody chosen from the following:
a) SEQ ID NO's: 36, 38, 40;
b) amino acid sequences that have no more than 3, preferably no more than 2, more preferably no more than 1 amino acid difference with one of SEQ ID NO's: 36, 38, 40, provided that:
i) the amino acid sequence has Aspartic acid (Asp, D) at position 1, Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-50: Multivalent polypeptide according to aspect E-49, that comprises or essentially consists of at least one amino acid sequence and/or Nanobody chosen from one of SEQ ID NO's: 36, 38, 40.

Aspect E-51: Multivalent polypeptide according to any of aspects E-46 to E-50, comprising or essentially consisting of at least one amino acid sequence and/or Nanobody chosen from the following:
a) SEQ ID NO's: 38 and 40;
b) amino acid sequences that have no more than 3, preferably no more than 2, more preferably no more than 1 amino acid difference with one of SEQ ID NO's: 38 and 40, provided that:
i) the amino acid sequence has Aspartic acid (Asp, D) at position 1, Proline (Pro, P) at position 14, Arginine (Arg, R) at position 83, Leucine (Leu, L) at position 108 and Glycine (Gly, G) at position 16; and in addition, the amino acid sequence has Glutamic acid (Glu, E) at position 54 or Alanine (Ala, A) at position 55 (said positions determined according to Kabat numbering);
ii) and the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-52: Multivalent polypeptide according to aspect E-51, that comprises or essentially consists of at least one amino acid sequence and/or Nanobody chosen from one of SEQ ID NO's: 38 and 40.

Aspect E-53: Multivalent polypeptide comprising or essentially consisting of at least one amino acid sequence and/or Nanobody with SEQ ID NO: 16, in which the Glutamic acid at position 1 has been changed into Aspartic acid.

Aspect E-54: Multivalent polypeptide according to aspect E-53, comprising or essentially consisting of at least one amino acid sequence and/or Nanobody with SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala, and wherein position 1 has been changed into Asp.

Aspect E-55: Multivalent polypeptide according to aspect E-54, comprising or essentially consisting of at least one amino acid sequence and/or Nanobody with SEQ ID NO: 16, wherein one or more (such as two or three) amino acid residues have been mutated selected from the following: Ala14Pro, Lys83Arg and Gln108Leu, and wherein position 1 has been changed into Asp.

Aspect E-56: Multivalent polypeptide according to aspect E-55, comprising or essentially consisting of at least one amino acid sequence and/or Nanobody with SEQ ID NO: 16, wherein following amino acid residues have been mutated: Ala14Pro, Lys83Arg and Gln108Leu, and wherein position 1 has been changed into Asp.

Aspect E-57: Multivalent polypeptide according to aspect E-54, comprising or essentially consisting of at least one amino acid sequence and/or Nanobody with SEQ ID NO: 16, wherein one or more (such as two or three) amino acid residues have been mutated selected from the following: Asp16Gly, Asp54Glu and Gly55Ala, and wherein position 1 has been changed into Asp.

Aspect E-58: Multivalent polypeptide according to aspect E-57, comprising or essentially consisting of at least one amino acid sequence and/or Nanobody with SEQ ID NO: 16, wherein two amino acid residues have been mutated selected from the following:
Asp16Gly and Asp54Glu; or
Asp16Gly and Gly55Ala,
and wherein position 1 has been changed into Asp.

Aspect E-59: Multivalent polypeptide according to aspect E-53, comprising or essentially consisting of at least one amino acid sequence and/or Nanobody® with SEQ ID NO: 16, in which following amino acid residues have been mutated:
Glu1Asp;
Glu1Asp, Ala14Pro, Lys83Arg, Gln108Leu;
Glu1Asp, Ala14Pro, Lys83Arg, Gln108Leu, Asp16Gly;
Glu1Asp, Ala14Pro, Lys83Arg, Gln108Leu, Asp16Gly, Asp54Glu; or
Glu1Asp, Ala14Pro, Lys83Arg, Gln108Leu, Asp16Gly, Gly55Ala.

Aspect E-60: Bivalent polypeptide according to aspect E-7, that comprises or essentially consists of two amino acid sequences according to any of aspects A-1 to A-19 and B-1 to B-20.

Aspect E-61: Bivalent polypeptide according to aspect E-60, wherein said two amino acid sequences and/or Nanobodies® are identical.

Aspect E-62: Bivalent polypeptide according to any of aspects E-60 or E-61, comprising or essentially consisting of two amino acid sequences and/or Nanobodies® chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:
  i) the amino acid sequence has Proline (Pro, P) at position 14, Arginine (Arg, R) at position 83 and/or Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-63: Bivalent polypeptide according to aspect E-62, comprising or essentially consisting of two amino acid sequences and/or Nanobodies® chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:
  i) the amino acid sequence has Proline (Pro, P) at position 14, Arginine (Arg, R) at position 83 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-64: Bivalent polypeptide according to any of aspects E-62 or E-63, wherein said two amino acid sequences and/or Nanobodies® are identical.

Aspect E-65: Bivalent polypeptide according to any of aspects E-62 to E-64, that comprises or essentially consists of two amino acid sequences and/or Nanobodies® chosen from one of SEQ ID N0's: 33-40.

Aspect E-66: Bivalent polypeptide according to any of aspects E-60 or E-61, comprising or essentially consisting of two amino acid sequences and/or Nanobodies® chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
  i) the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-67: Bivalent polypeptide according to aspect E-66, comprising or essentially consisting of two amino acid sequences and/or Nanobodies® chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
  i) the amino acid sequence has Praline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-68: Bivalent polypeptide according to any of aspects E-66 or E-67, wherein said two amino acid sequences and/or Nanobodies® are identical.

Aspect E-69: Bivalent polypeptide according to any of aspects E-66 to E-68, that comprises or essentially consists of two amino acid sequences and/or Nanobodies® chosen from one of SEQ ID NO's: 35-40.

Aspect E-70: Bivalent polypeptide according to any of aspects E-62 to E-69, comprising or essentially consisting of two amino acid sequences and/or Nanobodies® chosen from the following:
a) SEQ ID NO's: 37-40;
b) amino acid sequences that have no more than 3, preferably no more than 2, more preferably no more than 1 amino acid difference with one of SEQ ID NO's: 37-40, provided that:
  i) the amino acid sequence has Proline (Pro, P) at position 14, Arginine (Arg, R) at position 83, Leucine (Leu, L) at position 108 and Glycine (Gly, G) at position 16; and in addition the amino acid sequence has Glutamic acid (Glu, E) at position 54 or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-71: Bivalent polypeptide according to aspects E-70, wherein said two amino acid sequences and/or Nanobodies® are identical.

Aspect E-72: Bivalent polypeptide according to any of aspects E-70 or E-71, that comprises or essentially consists of two amino acid sequences and/or Nanobodies® chosen from SEQ ID NO's: 37-40.

Aspect E-73: Bivalent polypeptide comprising or essentially consisting of two amino acid sequences and/or Nanobodies® with SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala.

Aspect E-74: Bivalent polypeptide according to aspects E-73, comprising or essentially consisting of two amino acid sequences and/or Nanobodies® with SEQ ID NO: 16, wherein one or more (such as two or three) amino acid residues have been mutated selected from the following: Ala14Pro, Lys83Arg and Gln108Leu.

Aspect E-75: Bivalent polypeptide according to aspects E-74, comprising or essentially consisting of two amino acid sequences and/or Nanobodies® with SEQ ID NO: 16, wherein following amino acid residues have been mutated: Ala14Pro, Lys83Arg and Gln108Leu.

Aspect E-76: Bivalent polypeptide according to aspects E-73, comprising or essentially consisting of two amino acid sequences and/or Nanobodies® with SEQ ID NO: 16, wherein one or more (such as two or three) amino acid residues have been mutated selected from the following: Asp16Gly, Asp54Glu and Gly55Ala.

Aspect A-21. Bivalent polypeptide according to aspects E-74, comprising or essentially consisting of two amino acid sequences and/or Nanobodies® with SEQ ID NO: 16, wherein two amino acid residues have been mutated selected from the following:
Asp16Gly and Asp54Glu; or
Asp16Gly and Gly55Ala.

Aspect E-77: Bivalent polypeptide according to aspect E-73, comprising or essentially consisting of two amino acid sequences and/or Nanobodies® with SEQ ID NO: 16, in which following amino add residues have been mutated:
Ala14Pro, Lys83Arg, Gln108Leu;
Ala14Pro, Lys83Arg, Gln108Leu, Asp16Gly;
Ala14Pro, Lys83Arg, Gln108Leu, Asp16Gly, Asp54Glu; or
Ala14Pro, Lys83Arg, Gln108Leu, Asp16Gly, Gly55Ala.

Aspect E-78: Bivalent polypeptide according to any of aspects E-60 to E 77, that has aspartic acid (Asp, D) at position 1.

Aspect E-79: Bivalent polypeptide according to any of aspects E-60 to E-61, comprising or essentially consisting of at least one amino acid sequence and/or Nanobody® chosen from the following:
a) SEQ ID NO's: 34, 36, 38, 40, 51;
b) amino acid sequences that have no more than 3, preferably no more than 2, more preferably no more than 1 amino acid difference with one of SEQ ID NO's: 34, 36, 38, 40, 51, provided that:
  i) the amino acid sequence has Aspartic acid (Asp, D) at position 1 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-80: Bivalent polypeptide according to aspects E-79, comprising or essentially consisting of at least one amino acid sequence and/or Nanobody® chosen from the following:
a) SEQ ID NO's: 34, 36, 38, 40;
b) amino acid sequences that have no more than 3, preferably no more than 2, more preferably no more than 1 amino acid difference with one of SEQ ID NO's: 34, 36, 38, 40, provided that:
  i) the amino acid sequence has Aspartic acid (Asp, D) at position 1, Proline (Pro, P) at position 14, Arginine (Arg, R) at position 83 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-81: Bivalent polypeptide according to any of aspects E-79 or E-80, that comprises or essentially consists of at least one amino acid sequence and/or Nanobody® chosen from one of SEQ ID NO's: 34, 36, 38, 40, 51.

Aspect E-82: Bivalent polypeptide according to any of aspects E-79 to E-81, comprising or essentially consisting of at least one amino acid sequence and/or Nanobody® chosen from the following:
a) SEQ ID NO's: 36, 38, 40;
b) amino acid sequences that have no more than 3, preferably no more than 2, more preferably no more than 1 amino acid difference with one of SEQ ID NO's: 36, 38, 40, provided that:
   i) the amino acid sequence has Aspartic acid (Asp, D) at position 1, Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-83: Bivalent polypeptide according to any of aspects E-79 to E-82, that comprises or essentially consists of at least one amino acid sequence and/or Nanobody® chosen from one of SEQ ID NO's: 36, 38, 40.

Aspect E-84: Bivalent polypeptide according to any of aspects E-79 to E-83, comprising or essentially consisting of at least one amino acid sequence and/or Nanobody® chosen from the following:
a) SEQ ID NO's: 38 and 40;
b) amino acid sequences that have no more than 3, preferably no more than 2, more preferably no more than 1 amino acid difference with one of SEQ ID NO's: 38 and 40, provided that:
   i) the amino acid sequence has Aspartic acid (Asp, D) at position 1, Proline (Pro, P) at position 14, Arginine (Arg, R) at position 83, Leucine (Leu, L) at position 108 and Glycine (Gly, G) at position 16; and in addition, the amino acid sequence has Glutamic acid (Glu, E) at position 54 or Alanine (Ala, A) at position 55 (said positions determined according to Kabat numbering);
   ii) and the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-85: Bivalent polypeptide according to any of aspects E-79 to E-84, that comprises or essentially consists of at least one amino acid sequence and/or Nanobody® chosen from one of SEQ ID NO's: 38 and 40.

Aspect E-86: Bivalent polypeptide comprising or essentially consisting of at least one amino acid sequence and/or Nanobody® with SEQ ID NO: 16, wherein position 1 (Glu) has been changed into Asp.

Aspect E-87: Bivalent polypeptide according to aspect E-86, comprising or essentially consisting of at least one amino acid sequence and/or Nanobody® with SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala, and wherein position 1 has been changed into Asp.

Aspect E-88: Bivalent polypeptide according to aspect E-87, comprising or essentially consisting of at least one amino acid sequence and/or Nanobody® with SEQ ID NO: 16, wherein one or more (such as two or three) amino acid residues have been mutated selected from the following: Ala14Pro, Lys83Arg and Gln108Leu, and wherein position 1 has been changed into Asp.

Aspect E-89: Bivalent polypeptide according to aspect E-88, comprising or essentially consisting of at least one amino acid sequence and/or Nanobody® with SEQ ID NO: 16, wherein following amino acid residues have been mutated: Ala14Pro, Lys83Arg and Gln108Leu, and wherein position 1 has been changed into Asp.

Aspect B-21. Bivalent polypeptide according to aspect E-87, comprising or essentially consisting of at least one amino acid sequence and/or Nanobody® with SEQ ID NO: 16, wherein one or more (such as two or three) amino acid residues have been mutated selected from the following: Asp16Gly, Asp54Glu and Gly55Ala, and wherein position 1 has been changed into Asp.

Aspect B-22. Bivalent polypeptide according to aspect E-88, comprising or essentially consisting of at least one amino acid sequence and/or Nanobody® with SEQ ID NO: 16, wherein two amino acid residues have been mutated selected from the following:
Asp16Gly and Asp54Glu; or
Asp16Gly and Gly55Ala,
and wherein position 1 has been changed into Asp.

Aspect E-90: Bivalent polypeptide according to aspect E-86, comprising or essentially consisting of at least one amino acid sequence and/or Nanobody® with SEQ ID NO: 16, in which following amino acid residues have been mutated:
Glu1Asp;
Glu1Asp, Ala14Pro, Lys83Arg, Gln108Leu;
Glu1Asp, Ala14Pro, Lys83Arg, Gln108Leu, Asp16Gly;
Glu1Asp, Ala14Pro, Lys83Arg, Gln108Leu, Asp16Gly, Asp54Glu; or
Glu1Asp, Ala14Pro, Lys83Arg, Gln108Leu, Asp16Gly, Gly55Ala.

Aspect E-91: Trivalent polypeptide according to aspect E-7, that comprises or essentially consists of three amino acid sequences according to any of aspects A-1 to A-19 and B-1 to B-20.

Aspect E-92: Trivalent polypeptide according to aspect E-91, wherein said three amino acid sequences and/or Nanobodies® are identical.

Aspect E-93: Trivalent polypeptide according to any of aspects E-91 or E-92, comprising or essentially consisting of three amino acid sequences and/or Nanobodies® chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:
   i) the amino acid sequence has Proline (Pro, P) at position 14, Arginine (Arg, R) at position 83 and/or Leucine (Leu, L) at position 108 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-94: Trivalent polypeptide according to aspect E-93, comprising or essentially consisting of three amino acid sequences and/or Nanobodies® chosen from the following:
a) SEQ ID NO's: 33-40;
b) amino acid sequences that have no more than 3, preferably no more than 2, more preferably no more than 1 amino acid difference with one of SEQ ID NO's: 33-40, provided that:
   i) the amino acid sequence has Proline (Pro, P) at position 14, Arginine (Arg, R) at position 83 and Leucine (Leu, L) at position 108 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-95: Trivalent polypeptide according to any of aspects E-93 or E-94, wherein said three amino acid sequences and/or Nanobodies® are identical.

Aspect E-96: Trivalent polypeptide according to any of aspects E-93 to E-95, that comprises or essentially consists of three amino acid sequences and/or Nanobodies® chosen from one of SEQ ID NO's: 33-40.

Aspect E-97: Trivalent polypeptide according to any of aspects E-91 or E-92, comprising or essentially consisting of three amino acid sequences and/or Nanobodies® chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
   i) the amino acid sequence has Glycine (Gly, G) at position 16, Glutamic acid (Glu, E) at position 54 and/or Alanine (Ala, A) at position 55 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-98: Trivalent polypeptide according to aspect E-97, comprising or essentially consisting of three amino acid sequences and/or Nanobodies® chosen from the following:
a) SEQ ID NO's: 35-40;
b) amino acid sequences that have no more than 3, preferably no more than 2, more preferably no more than 1 amino acid difference with one of SEQ ID NO's: 35-40, provided that:
   i) the amino acid sequence has Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-99: Trivalent polypeptide according to any of aspects E-97 or E-98, wherein said three amino acid sequences and/or Nanobodies® are identical.

Aspect E-100: Trivalent polypeptide according to any of aspects E-97 to E-99, that comprises or essentially consists of three amino acid sequences and/or Nanobodies® chosen from one of SEQ ID NO's: 35-40.

Aspect E-101: Trivalent polypeptide according to any of aspects E-93 to E-100, comprising or essentially consisting of three amino acid sequences and/or Nanobodies® chosen from the following:
a) SEQ ID NO's: 37-40;
b) amino acid sequences that have no more than 3, preferably no more than 2, more preferably no more than 1 amino acid difference with one of SEQ ID NO's: 37-40, provided that:
   i) the amino acid sequence has Praline (Pro, P) at position 14, Arginine (Arg, R) at position 83, Leucine (Leu, L) at position 108 and Glycine (Gly, G) at position 16; and in addition the amino acid sequence has Glutamic acid (Glu, E) at position 54 or Alanine (Ala, A) at position 55 (said positions determined according to Kabat numbering); and
   ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-102: Trivalent polypeptide according to aspects E-101, wherein said three amino acid sequences and/or Nanobodies® are identical.

Aspect E-103: Trivalent polypeptide according to any of aspects E-101 or E-102, that comprises or essentially consists of three amino acid sequences and/or Nanobodies® chosen from SEQ ID NO's: 37-40.

Aspect E-104: Trivalent polypeptide comprising or essentially consisting of three amino acid sequences and/or Nanobodies® with SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala.

Aspect E-105: Trivalent polypeptide according to aspects E-104, comprising or essentially consisting of three amino acid sequences and/or Nanobodies® with SEQ ID NO: 16, wherein one or more (such as two or three) amino acid residues have been mutated selected from the following: Ala14Pro, Lys83Arg and Gln108Leu.

Aspect E-106: Trivalent polypeptide according to aspects E-105, comprising or essentially consisting of three amino acid sequences and/or Nanobodies® with SEQ ID NO: 16, wherein following amino acid residues have been mutated: Ala14Pro, Lys83Arg and Gln108Leu.

Aspect E-107: Trivalent polypeptide according to aspects E-104, comprising or essentially consisting of three amino acid sequences and/or Nanobodies® with SEQ ID NO: 16, wherein one or more (such as two or three) amino acid residues have been mutated selected from the following: Asp16Gly, Asp54Glu and Gly55Ala.

Aspect E-108: Trivalent polypeptide according to aspects E-107, comprising or essentially consisting of three amino acid sequences and/or Nanobodies® with SEQ ID NO: 16, wherein two amino acid residues have been mutated selected from the following:
Asp16Gly and Asp54Glu; or
Asp16Gly and Gly55Ala.

Aspect E-109: Trivalent polypeptide according to aspect E-104, comprising or essentially consisting of three amino acid sequences and/or Nanobodies® with SEQ ID NO: 16, in which following amino acid residues have been mutated:
Ala14Pro, Lys83Arg, Gln108Leu;
Ala14Pro, Lys83Arg, Gln108Leu, Asp16Gly;
Ala14Pro, Lys83Arg, Gln108Leu, Asp16Gly, Asp54Glu; or
Ala14Pro, Lys83Arg, Gln108Leu, Asp16Gly, Gly55Ala.

Aspect E-110: Trivalent polypeptide according to any of aspects E-91 to E 109, that has aspartic acid (Asp, D) at position 1.

Aspect E-111: Trivalent polypeptide according to any of aspects E-91 or e-92, comprising or essentially consisting of at least one amino acid sequence and/or Nanobody® chosen from the following:
a) SEQ ID NO's: 34, 36, 38, 40, 51;
b) amino acid sequences that have no more than 3, preferably no more than 2, more preferably no more than 1 amino acid difference with one of SEQ ID NO's: 34, 36, 38, 40, 51, provided that:
  i) the amino acid sequence has Aspartic acid (Asp, D) at position 1 (said position determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-112: Trivalent polypeptide according to aspect E-111, comprising or essentially consisting of at least one amino acid sequence and/or Nanobody® chosen from the following:
a) SEQ ID NO's: 34, 36, 38, 40;
b) amino acid sequences that have no more than 3, preferably no more than 2, more preferably no more than 1 amino acid difference with one of SEQ ID NO's: 34, 36, 38, 40, provided that:
  i) the amino acid sequence has Aspartic acid (Asp, D) at position 1, Proline (Pro, P) at position 14, Arginine (Arg, R) at position 83 and Leucine (Leu, L) at position 108 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-113: Trivalent polypeptide according to any of aspects E-111 or E-112, that comprises or essentially consists of at least one amino acid sequence and/or Nanobody® chosen from one of SEQ ID NO's: 34, 36, 38, 40.

Aspect E-114: Trivalent polypeptide according to any of aspects E-111 to E-113, comprising or essentially consisting of at least one amino acid sequence and/or Nanobody® chosen from the following:
a) SEQ ID NO's: 36, 38, 40;
b) amino acid sequences that have no more than 3, preferably no more than 2, more preferably no more than 1 amino acid difference with one of SEQ ID NO's: 36, 38, 40, provided that:
  i) the amino acid sequence has Aspartic acid (Asp, D) at position 1, Proline (Pro, P) at position 14, Arginine (Arg, R) at position 83 and Leucine (Leu, L) at position 108; and in addition, the amino acid sequence has Glycine (Gly, G) at position 16, Glutamic acid (Glu, E) at position 54 and/or Alanine (Ala, A) at position 55 (said positions determined according to Kabat numbering); and
  ii) the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-115: Trivalent polypeptide according to any of aspects E-111 to E-114, that comprises or essentially consists of at least one amino acid sequence and/or Nanobody® chosen from one of SEQ ID NO's: 36, 38, 40.

Aspect E-116: Trivalent polypeptide according to any of aspects E-111 to E-115, comprising or essentially consisting of at least one amino acid sequence and/or Nanobody® chosen from the following:
a) SEQ ID NO's: 38 and 40;
b) amino acid sequences that have no more than 3, preferably no more than 2, more preferably no more than 1 amino acid difference with one of SEQ ID NO's: 38 and 40, provided that:
  i) the amino acid sequence has Aspartic acid (Asp, D) at position 1, Proline (Pro, P) at position 14, Arginine (Arg, R) at position 83, Leucine (Leu, L) at position 108 and Glycine (Gly, G) at position 16; and in addition, the amino acid sequence has Glutamic acid (Glu, E) at position 54 or Alanine (Ala, A) at position 55 (said positions determined according to Kabat numbering);
  ii) and the amino acid sequence binds protein F of hRSV with the same, about the same, or a higher affinity (said affinity as measured by surface plasmon resonance) and/or the amino acid sequence has the same, about the same, or a higher potency (as defined herein) compared to the amino acid sequence without the 3, 2 or 1 amino acid difference.

Aspect E-117: Trivalent polypeptide according to any of aspects E-111 to E-116, that comprises or essentially consists of at least one amino acid sequence and/or Nanobody® chosen from one of SEQ ID NO's: 38 and 40.

Aspect E-118: Trivalent polypeptide comprising or essentially consisting of at least one amino acid sequence and/or Nanobody® with SEQ ID NO: 16, wherein position 1 (Glu) has been changed into Asp.

Aspect E-119: Trivalent polypeptide according to aspect E-118, comprising or essentially consisting of at least one amino acid sequence and/or Nanobody® with SEQ ID NO: 16, wherein one or more (such as two, three, four, five or six) amino acid residues have been mutated selected from the following: Ala14Pro, Lys83Arg, Gln108Leu, Asp16Gly, Asp54Glu and Gly55Ala, and wherein position 1 has been changed into Asp.

Aspect E-120: Trivalent polypeptide according to aspect E-119, comprising or essentially consisting of at least one amino acid sequence and/or Nanobody® with SEQ ID NO: 16, wherein one or more (such as two or three) amino acid residues have been mutated selected from the following: Ala14Pro, Lys83Arg and Gln108Leu, and wherein position 1 has been changed into Asp.

Aspect E-121: Trivalent polypeptide according to aspect E-120, comprising or essentially consisting of at least one amino acid sequence and/or Nanobody® with SEQ ID NO: 16, wherein following amino acid residues have been mutated: Ala14Pro, Lys83Arg and Gln108Leu, and wherein position 1 has been changed into Asp.

Aspect E-122: Trivalent polypeptide according to aspect E-119, comprising or essentially consisting of at least one amino acid sequence and/or Nanobody® with SEQ ID NO: 16, wherein one or more (such as two or three) amino acid residues have been mutated selected from the following: Asp16Gly, Asp54Glu and Gly55Ala, and wherein position 1 has been changed into Asp.

Aspect E-123: Trivalent polypeptide according to aspect E-122, comprising or essentially consisting of at least one amino acid sequence and/or Nanobody® with SEQ ID NO: 16, wherein two amino acid residues have been mutated selected from the following:
Asp16Gly and Asp54Glu; or
Asp16Gly and Gly55Ala,
and wherein position 1 has been changed into Asp.

Aspect E-124: Trivalent polypeptide according to aspect E-118, comprising or essentially consisting of at least one amino acid sequence and/or Nanobody® with SEQ ID NO: 16, in which following amino acid residues have been mutated:
Glu1Asp;
Glu1Asp, Ala14Pro, Lys83Arg, Gln108Leu;
Glu1Asp, Ala14Pro, Lys83Arg, Gln108Leu, Asp16Gly;
Glu1Asp, Ala14Pro, Lys83Arg, Gln108Leu, Asp16Gly, Asp54Glu; or
Glu1Asp, Ala14Pro, Lys83Arg, Gln108Leu, Asp16Gly, Gly55Ala.

Aspect E-125: Trivalent polypeptide, comprising or essentially consisting of at least one amino acid sequence and/or Nanobody® with SEQ ID NO: 34 and two amino acid sequences and/or Nanobodies® with SEQ ID NO: 33.

Aspect E-126: Trivalent polypeptide, comprising or essentially consisting of at least one amino acid sequence and/or Nanobody with SEQ ID NO: 36 and two amino acid sequences and/or Nanobodies® with SEQ ID NO: 35.

Aspect E-127: Trivalent polypeptide, comprising or essentially consisting of at least one amino acid sequence and/or Nanobody with SEQ ID NO: 38 and two amino acid sequences and/or Nanobodies® with SEQ ID NO: 37.

Aspect E-128: Trivalent polypeptide comprising or essentially consisting of at least one amino acid sequence and/or Nanobody with SEQ ID NO: 40 and two amino acid sequences and/or Nanobodies® with SEQ ID NO: 39.

Aspect E-129: Trivalent polypeptide comprising or essentially consisting of at least one amino acid sequence and/or Nanobody with SEQ ID NO: 51 and two amino acid sequences and/or Nanobodies® with SEQ ID NO: 16.

Aspect E-130: Trivalent polypeptide according to any of aspects E-91 or E-92, that is directed against and/or specifically binds protein F of hRSV, chosen from the following polypeptides:
a) SEQ ID NO's: 41-49;
b) polypeptides that have no more than 3, preferably no more than 2, more preferably no more than 1 amino acid difference with one of SEQ ID NO's: 41-49, provided that:
  i) the amino acid sequence or Nanobody® encompassed in said polypeptide has Proline (Pro, P) at position 14, Arginine (Arg, R) at position 83 and/or Leucine (Leu, L) at position 108 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Aspect E-131: Trivalent polypeptide according to aspect E-130, chosen from the following polypeptides:
a) SEQ ID NO's: 41-49;
b) polypeptides that have no more than 3, preferably no more than 2, more preferably no more than 1 amino acid difference with one of SEQ ID NO's: 41-49, provided that:
  i) the amino acid sequence or Nanobody® encompassed in said polypeptide has Proline (Pro, P) at position 14, Arginine (Arg, R) at position 83 and Leucine (Leu, L) at position 108 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino add difference.

Aspect E-132: Trivalent polypeptide according to any of aspects E-130 or E-131, that is directed against and/or specifically binds protein F of hRSV, chosen from one of SEQ ID NO's: 41-49.

Aspect E-133: Trivalent polypeptide according to any of aspects E-91 or E-92, that is directed against and/or specifically binds protein F of hRSV, chosen from the following polypeptides:
a) SEQ ID NO's: 42, 43, 44, 47, 48, 49;
b) polypeptides that have no more than 3, preferably no more than 2, more preferably no more than 1 amino acid difference with one of SEQ ID NO's: 42, 43, 44, 47, 48, 49, provided that:
  i) the amino acid sequence or Nanobody® encompassed in said polypeptide has Glycine (Gly, G) at position 16, Glutamic acid (Glu, E) at position 54 and/or Alanine (Ala, A) at position 55 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Aspect E-134: Trivalent polypeptide according to aspect E-133, chosen from the following polypeptides:

a) SEQ ID NO's: 42, 43, 44, 47, 48, 49;
b) polypeptides that have no more than 3, preferably no more than 2, more preferably no more than 1 amino acid difference with one of SEQ ID NO's: 42, 43, 44, 47, 48, 49, provided that:
   i) the amino acid sequence or Nanobody® encompassed in said polypeptide has Praline (Pro, P) at position 14, Arginine (Arg, R) at position 83 and Leucine (Leu, L) at position 108; and in addition the amino acid sequence or Nanobody® encompassed in said polypeptide has Glycine (Gly, G) at position 16, Glutamic acid (Glu, E) at position 54 and/or Alanine (Ala, A) at position 55 (said positions determined according to Kabat numbering); and
   ii) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Aspect E-135: Trivalent polypeptide according to any of aspects E-133 or E-134, that is directed against and/or specifically binds protein F of hRSV, chosen from one of SEQ ID NO's: 42, 43, 44, 47, 48, 49.

Aspect E-136: Trivalent polypeptide according to any of aspects E-130 to E-135, that is directed against and/or specifically binds protein F of hRSV, chosen from the following polypeptides:
a) SEQ ID NO's: 43-44, 48-49;
b) polypeptides that have no more than 3, preferably no more than 2, more preferably no more than 1 amino acid difference with one of SEQ ID NO's: 43-44, provided that:
   i) the amino acid sequence or Nanobody® encompassed in said polypeptide has Proline (Pro, P) at position 14, Arginine (Arg, R) at position 83, Leucine (Leu, L) at position 108 and Glycine (Gly, G) at position 16; and in addition, the amino acid sequence or Nanobody® encompassed in said polypeptide has Glutamic acid (Glu, E) at position 54 or Alanine (Ala, A) at position 55 (said positions determined according to Kabat numbering); and
   i) the polypeptide binds protein F of hRSV with the same, about the same, or a higher affinity (said affinity as measured by surface plasmon resonance) and/or the polypeptide has the same, about the same, or a higher potency (as defined herein) compared to the polypeptide without the 3, 2 or 1 amino acid difference.

Aspect E-137: Trivalent polypeptide according to aspect E-136, that is directed against and/or specifically binds protein F of hRSV, chosen from one of SEQ ID NO's: 43-44, 48-49.

Aspect E-138: Trivalent polypeptide according to any of aspects E-91, E-92, or E-130 to E 137, that has aspartic acid (Asp, D) at position 1.

Aspect E-139: Trivalent polypeptide according to any of aspects E-91 or E-92, chosen from the following polypeptides:
a) SEQ ID NO's: 41-44 and 50;
b) polypeptides that have no more than 3, preferably no more than 2, more preferably no more than 1 amino acid difference with one of SEQ ID NO's: 41-44 and 50, provided that:
   i) the first amino acid sequence or Nanobody® encompassed in said polypeptide has Aspartic acid (Asp, D) at position 1 (said positions determined according to Kabat numbering); and
   ii) the polypeptide binds protein F of hRSV with the same, about the same, or a higher affinity (said affinity as measured by surface plasmon resonance) and/or the polypeptide has the same, about the same, or a higher potency (as defined herein) compared to the amino acid sequence without the 3, 2 or 1 amino acid difference.

Aspect E-140: Trivalent polypeptide according to aspect E-139, chosen from the following polypeptides:
a) SEQ ID NO's: 41-44;
b) polypeptides that have no more than 3, preferably no more than 2, more preferably no more than 1 amino acid difference with one of SEQ ID NO's: 41-44, provided that:
   i) the amino acid sequence or Nanobody® encompassed in said polypeptide has Proline (Pro, P) at position 14, Arginine (Arg, R) at position 83 and Leucine (Leu, L) at position 108; and the first amino acid sequence or Nanobody® encompassed in said polypeptide has Aspartic acid (Asp, D) at position 1 (said positions determined according to Kabat numbering); and
   ii) the polypeptide binds protein F of hRSV with the same, about the same, or a higher affinity (said affinity as measured by surface plasmon resonance) and/or the polypeptide has the same, about the same, or a higher potency (as defined herein) compared to the amino acid sequence without the 3, 2 or 1 amino acid difference.

Aspect E-141: Trivalent polypeptide according to any of aspect E-139 or E-140, chosen from the following polypeptides:
a) SEQ ID NO's: 42-44;
b) polypeptides that have no more than 3, preferably no more than 2, more preferably no more than 1 amino acid difference with one of SEQ ID NO's: 42-44, provided that:
   i) the amino acid sequence or Nanobody® encompassed in said polypeptide has Proline (Pro, P) at position 14, Arginine (Arg, R) at position 83 and Leucine (Leu, L) at position 108; and in addition, the amino acid sequence or Nanobody® encompassed in said polypeptide has Glycine (Gly, G) at position 16, Glutamic acid (Glu, E) at position 54 and/or Alanine (Ala, A) at position 55; and the first amino acid sequence or Nanobody® encompassed in said polypeptide has Aspartic acid (Asp, D) at position 1 (said positions determined according to Kabat numbering); and
   ii) the polypeptide binds protein F of hRSV with the same, about the same, or a higher affinity (said affinity as measured by surface plasmon resonance) and/or the polypeptide has the same, about the same, or a higher potency (as defined herein) compared to the amino acid sequence without the 3, 2 or 1 amino acid difference.

Aspect E-142: Trivalent polypeptide according to any of aspects E-139 to E-141, chosen from the following polypeptides:

a) SEQ ID NO's: 43 and 44;
b) polypeptides that have no more than 3, preferably no more than 2, more preferably no more than 1 amino acid difference with one of SEQ ID NO's: 43 and 44, provided that:
  i) the amino acid sequence or Nanobody® encompassed in said polypeptide has Praline (Pro, P) at position 14, Arginine (Arg, R) at position 83, Leucine (Leu, L) at position 108 and Glycine (Gly, G) at position 16; and in addition, the amino acid sequence or Nanobody® encompassed in said polypeptide has Glutamic acid (Glu, E) at position 54 or Alanine (Ala, A) at position 55; and the first amino acid sequence or Nanobody® encompassed in said polypeptide has Aspartic acid (Asp, D) at position 1 (said positions determined according to Kabat numbering); and
  ii) the polypeptide binds protein F of hRSV with the same, about the same, or a higher affinity (said affinity as measured by surface plasmon resonance) and/or the polypeptide has the same, about the same, or a higher potency (as defined herein) compared to the amino acid sequence without the 3, 2 or 1 amino acid difference.

Aspect E-143: Trivalent polypeptide comprising or essentially consisting of SEQ ID NO: 26, in which in at least one (preferably in two, more preferably in all three) Nanobody®/Nanobodies® that form(s) part of SEQ ID NO: 26, one or more (such as two, three, four, five or six) amino acid residues have been mutated selected from the following: Ala14Pro, Lys83Arg, Gln108Leu, Asp16Gly, Asp54Glu and Gly55Ala.

Aspect E-144: Trivalent polypeptide according to aspect E-143, comprising or essentially consisting of SEQ ID NO: 26, in which in at least one (preferably in two, more preferably in all three) Nanobody®/Nanobodies® that form(s) part of SEQ ID NO: 26, one or more (such as two or three) amino acid residues have been mutated selected from the following: Ala14Pro, Lys83Arg and Gln108Leu.

Aspect E-145: Trivalent polypeptide according to aspect E-144, comprising or essentially consisting of SEQ ID NO: 26, in which in at least one (preferably in two, more preferably in all three) Nanobody®/Nanobodies® that form(s) part of SEQ ID NO: 26, following amino acid residues have been mutated: Ala14Pro, Lys83Arg and Gln108Leu.

Aspect E-146: Trivalent polypeptide according to aspect E-143, comprising or essentially consisting of SEQ ID NO: 26, in which in at least one (preferably in two, more preferably in all three) Nanobody®/Nanobodies® that form(s) part of SEQ ID NO: 26, one or more (such as two or three) amino acid residues have been mutated selected from the following: Asp16Gly, Asp54Glu and Gly55Ala.

Aspect E-147: Trivalent polypeptide according to aspect E-146, comprising or essentially consisting of SEQ ID NO: 26, in which in at least one (preferably in two, more preferably in all three) Nanobody®/Nanobodies® that form(s) part of SEQ ID NO: 26, two amino acid residues have been mutated selected from the following:
Asp16Gly and Asp54Glu; or
Asp16Gly and Gly55Ala.

Aspect E-148: Trivalent polypeptide comprising or essentially consisting of SEQ ID NO: 26, in which in at least one (preferably in two, more preferably in all three) Nanobody®/Nanobodies® that form(s) part of SEQ ID NO: 26, one or more (such as two, three, four, five or six) amino acid residues have been mutated selected from the following: Ala14Pro, Lys83Arg, Gln108Leu, Asp16Gly, Asp54Glu and Gly55Ala, and in which position 1 (Glu) has been changed into Asp.

Aspect E-149: Trivalent polypeptide according to aspect E-148, comprising or essentially consisting of SEQ ID NO: 26, in which in at least one (preferably in two, more preferably in all three) Nanobody/Nanobodies® that form(s) part of SEQ ID NO: 26, one or more (such as two or three) amino acid residues have been mutated selected from the following: Ala14Pro, Lys83Arg and Gln108Leu, and in which position 1 (Glu) has been changed into Asp.

Aspect E-150: Trivalent polypeptide according to aspect E-149, comprising or essentially consisting of SEQ ID NO: 26, in which in at least one (preferably in two, more preferably in all three) Nanobody®/Nanobodies® that form(s) part of SEQ ID NO: 26, following amino acid residues have been mutated: Ala14Pro, Lys83Arg and Gln108Leu, and in which position 1 (Glu) has been changed into Asp.

Aspect E-151: Trivalent polypeptide according to aspect E-148, comprising or essentially consisting of SEQ ID NO: 26, in which in at least one (preferably in two, more preferably in all three) Nanobody®/Nanobodies® that form(s) part of SEQ ID NO: 26, one or more (such as two or three) amino acid residues have been mutated selected from the following: Asp16Gly, Asp54Glu and Gly55Ala, and in which position 1 (Glu) has been changed into Asp.

Aspect E-152: Trivalent polypeptide according to aspect E-151, comprising or essentially consisting of SEQ ID NO: 26, in which in at least one (preferably in two, more preferably in all three) Nanobody®/Nanobodies® that form(s) part of SEQ ID NO: 26, two amino acid residues have been mutated selected from the following:
Asp16Gly and Asp54Glu; or
Asp16Gly and Gly55Ala,
and in which position 1 (Glu) has been changed into Asp.

Aspect E-153: Trivalent polypeptide comprising or essentially consisting of SEQ ID NO: 26, in which in at least one (preferably in two, more preferably in all three) Nanobody®/Nanobodies® that form(s) part of SEQ ID NO: 26, following amino acid residues have been mutated:
Ala14Pro, Lys83Arg, Gln108Leu;
Ala14Pro, Lys83Arg, Gln108Leu, Asp16Gly;
Ala14Pro, Lys83Arg, Gln108Leu, Asp16Gly, Asp54Glu;
Ala14Pro, Lys83Arg, Gln108Leu, Asp16Gly, Gly55Ala;
Glu1Asp;
Glu1Asp, Ala14Pro, Lys83Arg, Gln108Leu;
Glu1Asp, Ala14Pro, Lys83Arg, Gln108Leu, Asp16Gly;
Glu1Asp, Ala14Pro, Lys83Arg, Gln108Leu, Asp16Gly, Asp54Glu; or
Glu1Asp, Ala14Pro, Lys83Arg, Gln108Leu, Asp16Gly, Gly55Ala.

Aspect E-154: Trivalent polypeptide comprising or essentially consist of SEQ ID NO: 41.
Aspect E-155: Trivalent polypeptide comprising or essentially consist of SEQ ID NO: 42.
Aspect E-156: Trivalent polypeptide comprising or essentially consist of SEQ ID NO: 43.
Aspect E-157: Trivalent polypeptide comprising or essentially consist of one of SEQ ID NO: 44.
Aspect E-158: Polypeptide according to any of aspects E-1 to E-157, that can specifically bind to protein F of hRSV with a dissociation constant (K©) of 100 nM to 0.1 nM or less, preferably 10 nM to 0.1 nM or less, more preferably 1 nM to 0.1 nM or less.

Aspect E-159: Polypeptide according to any of aspects E-1 to E-158, that can specifically bind to protein F of hRSV with a $k_{on}$-rate of between $10^4$ $M^{-1}s^{-1}$ to about $10^7$ $M^{-1}s^{-1}$, preferably between $10^5$ $M^{-1}s^{-1}$ and $10^7$ $M^{-1}s^{-1}$, more preferably about $10^6$ $M^{-1}s^{-1}$ or more.

Aspect E-160: Polypeptide according to any of aspects E-1 to E-159, that can specifically bind to protein F of hRSV with a $k_{off}$ rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, more preferably between $5 \times 10^{-3}s^{-1}$ and $10^{-4}$ $s^{-1}$, or lower.

Aspect E-161: Polypeptide y according to any of aspects E-1 to E-160, that can neutralize hRSV (for example, as measured in a microneutralization assay on hRSV Long (such as e.g. described in Example 6) with an IC50 value between 10 pM and 1000 pM, preferably between 10 pM and 250 pM, more preferably between 50 pM and 200 pM or less.

Aspect E-162: Polypeptide according to any of aspects E-1 to E-161, that can neutralize hRSV (for example, as measured in a microneutralization assay on hRSV Long (such as e.g. described in Example 6) with an $IC_{50}$ value that is at least the same and preferably better, at least ten times better, preferably twenty times better, more preferably fifty times better, even more preferably sixty, seventy, eighty or more times better compared to the IC50 value obtained with Synagis®.

Aspect E-163: Polypeptide according to any of aspects E-1 to E-162, which is a multispecific construct.

Aspect F-1: Monovalent construct, comprising or essentially consisting of one amino acid sequence and/or one Nanobody® according to any of aspects A-1 to A-19.

Aspect F-2: Monovalent construct, comprising or essentially consisting of one amino acid sequence and/or one Nanobody® according to any of aspects B-1 to B-20.

Aspect F-3: Monovalent construct according to any of aspects F-1 or F-2, in which said amino acid sequence is chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies®.

Aspect F-4: Monovalent construct, that is chosen from the group consisting of SEQ ID NO's: 33-40 and 51.

Aspect F-5: Use of a monovalent construct according to any of aspects F-1 to F-4, in preparing a multivalent polypeptide according to any of aspects E-7 to E-156.

Aspect F-6: Use of a monovalent construct according to aspect F-5, wherein the monovalent construct is used as a binding domain or binding unit in preparing a multivalent construct comprising two or more binding units.

Aspect F-7: Use of a monovalent construct according to any of aspects F-5 or F-6, in preparing a multivalent construct that preferably exhibits intramolecular binding compared to intermolecular binding.

Aspect F-8: Use of a monovalent construct according to any of aspects F-5 to F-7, as a binding domain or binding unit in preparing a multivalent construct, wherein the binding domains or binding units are linked via a linker such that the multivalent polypeptide preferably exhibits intramolecular binding compared to intermolecular binding and/or the multivalent polypeptide can simultaneously bind all binding site on protein F of hRSV.

Aspect F-9: Use of a monovalent construct according to any of aspects F-1 to F-4 in preparing a bivalent polypeptide.

Aspect F-10: Use of two monovalent constructs according to any of aspects F-1 to F-4 in preparing a bivalent polypeptide.

Aspect F-11: Use of two monovalent constructs according to aspect F-10, in preparing a bivalent construct that preferably exhibits intramolecular binding compared to intermolecular binding.

Aspect F-12: Use of two monovalent constructs according to any of aspects F-10 or F-11, as a binding domain or binding unit in preparing a bivalent polypeptide, wherein the binding domains or binding units are linked via a linker such that the bivalent polypeptide preferably exhibits intramolecular binding compared to intermolecular binding and/or the bivalent polypeptide can simultaneously bind both binding site on protein F of hRSV.

Aspect F-13: Use of two monovalent constructs according to any of aspects F-10 to F-12, wherein the two monovalent constructs are identical.

Aspect F-14: Use of a monovalent construct according to any of aspects F-1 to F-4 in preparing a trivalent polypeptide.

Aspect F-15: Use of three monovalent constructs according to any of aspects F-1 to F-4 in preparing a trivalent polypeptide.

Aspect F-16: Use of three monovalent constructs according to aspect β-15, in preparing a trivalent construct that preferably exhibits intramolecular binding compared to intermolecular binding.

Aspect F-17: Use of three monovalent construct according to any of aspects F-15 or F-16, as a binding domain or binding unit in preparing a trivalent polypeptide, wherein the binding domains or binding units are linked via a linker such that the trivalent polypeptide preferably exhibits intramolecular binding compared to intermolecular binding and/or the trivalent polypeptide can simultaneously bind all three binding site on protein F of hRSV.

Aspect F-18: Use of three monovalent constructs according to any of aspects F-15 to F-17, wherein the three monovalent constructs are identical.

Aspect F-19: Use of two amino acid sequences with SEQ ID NO: 33 and an amino acid sequence with SEQ ID NO: 34 in preparing a trivalent polypeptide with SEQ ID NO: 41, wherein the amino acid sequence with SEQ ID NO: 34 is linked to at least two further amino acid sequences with SEQ ID NO: 33, via a 15GS linker.

Aspect F-20: Use of two amino acid sequences with SEQ ID NO: 35 and an amino acid sequence with SEQ ID NO: 36 in preparing a trivalent polypeptide with SEQ ID NO: 42, wherein the amino acid sequence with SEQ ID NO: 36 is linked to at least two further amino acid sequences with SEQ ID NO: 35, via a 15GS linker.

Aspect F-21: Use of two amino acid sequences with SEQ ID NO: 37 and an amino acid sequence with SEQ ID NO: 38 in preparing a trivalent polypeptide with SEQ ID NO: 43, wherein the amino acid sequence with SEQ ID NO: 38 is linked to at least two further amino acid sequences with SEQ ID NO: 37, via a 15GS linker.

Aspect F-22: Use of two amino acid sequences with SEQ ID NO: 39 and an amino acid sequence with SEQ ID NO: 40 in preparing a trivalent polypeptide with SEQ ID NO: 44, wherein the amino acid sequence with SEQ ID NO: 40 is linked to at least two further amino acid sequences with SEQ ID NO: 39, via a 15GS linker.

Aspect F-23: Use of two amino acid sequences with SEQ ID NO: 16 and an amino acid sequence with SEQ ID NO: 51 in preparing a trivalent polypeptide with SEQ ID NO: 50, wherein the amino acid sequence with SEQ ID NO: 51 is linked to at least two further amino acid sequences with SEQ ID NO: 16, via a 15GS linker.

Aspect E-163: Polypeptide according to any of aspects E-1 to E-162, which has an increased half-life, compared to the corresponding amino acid sequence and/or Nanobody® according to any of aspects A-1 to A-19 and B-1 to B-20 per se.

Aspect E-164: Polypeptide according to aspects E-163, in which one or more other binding units provide the polypeptide with increased half-life, compared to the corresponding amino acid sequence and/or Nanobody® according to any of aspects A-1 to A-19 and B-1 to 8-20 per se.

Aspect E-165: Polypeptide according to any of aspects E-163 or E-164, in which said one or more other binding units that provide the polypeptide with increased half-life is chosen from the group consisting of serum proteins or fragments thereof, binding units that can bind to serum proteins, an Fc portion, and small proteins or peptides that can bind to serum proteins.

Aspect E-166: Polypeptide according to any of aspects E-163 to E-165, in which said one or more other binding units that provide the polypeptide with increased half-life is chosen from the group consisting of human serum albumin or fragments thereof.

Aspect E-167: Polypeptide according to any of aspects E-163 to E-166, in which said one or more other binding units that provides the polypeptide with increased half-life are chosen from the group consisting of binding units that can bind to serum albumin (such as human serum albumin) or a serum immunoglobulin (such as IgG).

Aspect E-168: Polypeptide according to any of aspects E-163 to E-167, in which said one or more other binding units that provides the polypeptide with increased half-life are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies® that can bind to serum albumin (such as human serum albumin) or a serum immunoglobulin (such as IgG).

Aspect E-169: Polypeptide according to any of aspects E-163 to E-168, in which said one or more other binding units that provides the polypeptide with increased half-life is a Nanobody® that can bind to serum albumin (such as human serum albumin) or a serum immunoglobulin (such as IgG).

Aspect E-170: Polypeptide according to any of aspects E-163 to E-169, that has a serum half-life that is at least 1.5 times, preferably at least 2 times, such as at least 5 times, for example at least 10 times or more than 20 times, greater than the half-life of the corresponding amino acid sequence and/or Nanobody® according to any of aspects A-1 to A-19 and B-1 to B-20 per se.

Aspect E-171: Polypeptide according to any of aspects E-163 to E-170, that has a serum half-life that is increased with more than 1 hours, preferably more than 2 hours, more preferably more than 6 hours, such as more than 12 hours, or even more than 24, 48 or 72 hours, compared to the corresponding amino acid sequence and/or Nanobody® according to any of aspects A-1 to A-19 and B-1 to B-20 per se.

Aspect E-172: Polypeptide according to any of aspects E-163 to E-171, that has a serum half-life in human of at least about 12 hours, preferably at least 24 hours, more preferably at least 48 hours, even more preferably at least 72 hours or more; for example, of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Aspect G-1: Compound or construct, that comprises or essentially consists of one or more amino acid sequences and/or Nanobodies® according to any of aspects A-1 to A-19 and B-1 to B-20 and/or one or more polypeptides according to any of aspects E-1 to E-172, and optionally further comprises one or more other groups, residues, moieties or binding units, optionally linked via one or more linkers.

Aspect G-2: Compound or construct according to aspect G-1, in which said one or more other groups, residues, moieties or binding units are amino acid sequences.

Aspect G-3: Compound or construct according to any of aspects G-1 or G-2, in which said one or more linkers, if present, are one or more amino acid sequences.

Aspect G-4: Compound or construct according to any of aspects G-1 to G-3, in which said one or more other groups, residues, moieties or binding units are immunoglobulin sequences.

Aspect G-5: Compound or construct according to any of aspects G-1 to G-4, in which said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies®.

Aspect G-6: Compound or construct according to any of aspects G-1 to G-5, in which said one or more amino acid sequences of the invention are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies®.

Aspect G-7: Compound or construct according to any of aspects G-1 to G-6, that comprises or essentially consists of one or more Nanobodies® according to any of aspects A-1 to A-19 and B-1 to B-20, and in which said one or more other groups, residues, moieties or binding units are Nanobodies®.

Aspect G-8: Compound or construct according to any of aspects G-1 to G-7, which is a multivalent construct.

Aspect G-9: Compound or construct according to any of aspects G-1 to G-8, which is a multispecific construct.

Aspect G-10: Compound or construct according to any of aspects G-1 to G-9, which has an increased half-life, compared to the corresponding amino acid sequence and/or Nanobody® according to any of aspects A-1 to A-19 and B-1 to B-20 per se, or polypeptide according to any of aspects E-1 to E-162 per se.

Aspect G-11: Compound or construct according to any of aspects G-1 to G-10, in which said one or more other groups, residues, moieties or binding units provide the compound or construct with increased half-life, compared to the corresponding amino acid sequence and/or Nanobody® according to any of aspects A-1 to A-19 and B-1 to B-20 per se, or polypeptide according to any of aspects E-1 to E-162 per se.

Aspect G-12: Compound or construct according to aspect G-11, in which said one or more other groups, residues, moieties or binding units that provide the compound or construct with increased half-life is chosen from the group consisting of serum proteins or fragments thereof, binding units that can bind to serum proteins, an Fc portion, and small proteins or peptides that can bind to serum proteins.

Aspect G-13: Compound or construct according to any of aspects G-11 or G-12, in which said one or more other groups, residues, moieties or binding units that provide the compound or construct with increased half-life is chosen from the group consisting of human serum albumin or fragments thereof.

Aspect G-14: Compound or construct according to any of aspects G-11 to G-13, in which said one or more other groups, residues, moieties or binding units that provide the compound or construct with increased half-life are chosen from the group consisting of binding units that can bind to serum albumin (such as human serum albumin) or a serum immunoglobulin (such as IgG).

Aspect G-15: Compound or construct according to any of aspects G-11 to G-14, in which said one or more other groups, residues, moieties or binding units that provides the compound or construct with increased half-life are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies® that can bind to serum albumin (such as human serum albumin) or a serum immunoglobulin (such as IgG).

Aspect G-16: Compound or construct according to any of aspects G-11 to G-15, in which said one or more other groups, residues, moieties or binding units that provides the compound or construct with increased half-life is a Nanobody® that can bind to serum albumin (such as human serum albumin) or a serum immunoglobulin (such as IgG).

Aspect G-17: Compound or construct according to any of aspects G-10 to G-16, that has a serum half-life that is at least 1.5 times, preferably at least 2 times, such as at least 5 times, for example at least 10 times or more than 20 times, greater than the half-life of the compared to the corresponding amino acid sequence and/or Nanobody® according to any of aspects A-1 to A-19 and B-1 to B-20 per se, or polypeptide according to any of aspects E-1 to E-162 per se.

Aspect G-18: Compound or construct according to any of aspects G-10 to G-17, that has a serum half-life that is increased with more than 1 hours, preferably more than 2 hours, more preferably more than 6 hours, such as more than 12 hours, or even more than 24, 48 or 72 hours, compared to the corresponding amino acid sequence and/or Nanobody® according to any of aspects A-1 to A-19 and B-1 to B-20 per se, or polypeptide according to any of aspects E-1 to E-172 per se.

Aspect G-19: Compound or construct according to any of aspects G-10 to G-18, that has a serum half-life in human of at least about 12 hours, preferably at least 24 hours, more preferably at least 48 hours, even more preferably at least 72 hours or more; for example, of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Aspect M-1: Nucleic acid or nucleotide sequence, that encodes an amino acid sequence and/or Nanobody® according to any of aspects A-1 to A-19 and B-1 to B-20, a polypeptide according to any of aspects E-1 to E-172, a compound or construct according to any of aspects G-1 to G-19, that is such that it can be obtained by expression of a nucleic acid or nucleotide sequence encoding the same, or a monovalent construct according to any of aspects F-1 to F-4.

Aspect M-2: Nucleic acid or nucleotide sequence according to aspect M-1, that is in the form of a genetic construct.

Aspect M-3: Use of a nucleic acid or nucleotide sequence according to aspect M-1, that encodes a monovalent construct according to any of aspects F-1 to F-4, for the preparation of a genetic construct that encodes a multivalent polypeptide according to any of aspects E-7 to E-162.

Aspect M-4: Use of a nucleic acid or nucleotide sequence according to aspect M-2, wherein the genetic construct encodes a multivalent (such as a bivalent or trivalent) construct.

Aspect N-1: Host or host cell that expresses, or that under suitable circumstances is capable of expressing, an amino acid sequence and/or Nanobody® according to any of aspects A-1 to A-19 and B-1 to B-20, a polypeptide according to any of aspects E-1 to E-172, a compound or construct according to any of aspects G-1 to G-19, that is such that it can be obtained by expression of a nucleic acid or nucleotide sequence encoding the same, or a monovalent construct according to any of aspects F-1 to F-4; and/or that comprises a nucleic acid or nucleotide sequence according to aspects M-1 or M-2.

Aspect O-1: Composition, comprising at least one amino acid sequence and/or Nanobody® according to any of aspects A-1 to A-19 and B-1 to B-20, polypeptide according to any of aspects E-1 to E-172, compound or construct according to any of aspects G-1 to G-19, monovalent construct according to any of aspects F-1 to F-4, or nucleic acid or nucleotide sequence according to aspects M-1 or M-2.

Aspect O-2: Composition according to aspect O-1, which is a pharmaceutical composition.

Aspect O-3: Composition according to aspects O-1 or O-2, which is a pharmaceutical composition, that further comprises at least one pharmaceutically acceptable carrier, diluent or excipient and/or adjuvant, and that optionally comprises one or more further pharmaceutically active polypeptides and/or compounds.

Aspect P-1: Method for producing an amino acid sequence and/or Nanobody® according to any of aspects A-1 to A-19 and B-1 to B-20, a polypeptide according to any of aspects E-1 to E-172, a compound or construct according to any of aspects G-1 to G-19, that is such that it can be obtained by expression of a nucleic acid or nucleotide sequence encoding the same, or a monovalent construct according to any of aspects F-1 to F-4, or a composition according to any of aspects O-1 to O-3, said method at least comprising the steps of:
a) expressing, in a suitable host cell or host organism or in another suitable expression system, a nucleic acid or nucleotide sequence according to aspects M-1 or M-2, optionally followed by:
b) isolating and/or purifying the amino acid sequence and/or Nanobody® according to any of aspects A-1 to A-19 and B-1 to 8-20, the polypeptide according to any of aspects E-1 to E-172, the compound or construct according to any of aspects G-1 to G-19, that is such that it can be obtained by expression of a nucleic acid or nucleotide sequence encoding the same, or the monovalent construct according to any of aspects β-1 to F-4, thus obtained.

Aspect P-2: Method for producing an amino acid sequence and/or Nanobody® according to any of aspects A-1 to A-19 and B-1 to 8-20, a polypeptide according to any of aspects E-1 to E-172, a compound or construct according to any of aspects G-1 to G-19, that is such that it can be obtained by expression of a nucleic acid or nucleotide sequence encoding the same, or a monovalent construct according to any of aspects F-1 to F-4, or a composition according to any of aspects O-1 to O-3, said method at least comprising the steps of:
  a) cultivating and/or maintaining a host or host cell according to aspect N-1 under conditions that are such that said host or host cell expresses and/or produces at least one amino acid sequence and/or Nanobody® according to any of aspects A-1 to A-19 and B-1 to B-20, a polypeptide according to any of aspects E-1 to E-172, compound or construct according to any of aspects G-1 to G-19, that is such that it can be obtained by expression of a nucleic acid or nucleotide sequence encoding the same, or monovalent construct according to any of aspects F-1 to F-4, or composition according to any of aspects O-1 to O-3,
  optionally followed by:
  b) isolating and/or purifying the amino acid sequence and/or Nanobody® according to any of aspects A-1 to A-19 and B-1 to 8-20, the polypeptide according to any of aspects E-1 to E-172, the compound or construct according to any of aspects G-1 to O-19, that is such that it can be obtained by expression of a nucleic acid or nucleotide sequence encoding the same, or the monovalent construct according to any of aspects F-1 to F-4, or the composition according to aspects O-1 to O-3, thus obtained.

Aspect P-3: Method for preparing a bivalent or trivalent polypeptide according to any of aspects E-7 to E-156, said method comprising at least the steps of linking two or more monovalent amino acid sequences or monovalent construct according to any of aspects F-1 to F-4 and for example one or more linkers Aspect P-4: Method according to aspect P-3, comprising the steps of:
  a) linking two or more nucleic acid sequences according to aspect M-1, encoding a monovalent construct according to any of aspects F-1 to F-4 (and also for example nucleic acids encoding one or more linkers and further one or more further elements of genetic constructs known per se) to obtain a genetic construct according to aspect M-2;
  b) expressing, in a suitable host cell or host organism or in another suitable expression system, the genetic construct obtained in a)
  optionally followed by:
  c) isolating and/or purifying the bivalent or trivalent polypeptide according to any of aspects E-7 to E-156, thus obtained.

Aspect Q-1: Method for screening amino acid sequences directed against protein F of hRSV, said method comprising at least the steps of:
  a. providing a set, collection or library of nucleic acid sequences encoding amino acid sequences;
  b. screening said set, collection or library of nucleic acid sequences for nucleic acid sequences that encode an amino acid sequence that can bind to and/or has affinity for an envelope protein of a virus and that is cross-blocked or is cross blocking a Nanobody® of the invention, e.g. one of SEQ ID NO's: 5-24 (Table A-1) or one of SEQ ID NO's: 33-40 and 51 (Table A-4), or a polypeptide or construct comprising at least one Nanobody® of the invention, e.g. a polypeptide or construct comprising at least one of SEQ ID NO: 41-50 (see Table A-5); and
  c. isolating said nucleic acid sequence, followed by expressing said amino acid sequence.

Aspect R-1: Method for the prevention and/or treatment of hRSV infection, said method comprising administering, to a subject in need thereof, a pharmaceutically active amount of at least one amino acid sequence and/or Nanobody® according to any of aspects A-1 to A-19 and B-1 to B-20, polypeptide according to any of aspects E-1 to E-172, compound or construct according to any of aspects G-1 to G-19, monovalent construct according to any of aspects F-1 to F-4 and/or composition according to aspects O-1 to O-3.

Aspect R-2: Method for the prevention and/or treatment of at least one of respiratory illness, upper respiratory tract infection, lower respiratory tract infection, bronchiolitis (inflammation of the small airways in the lung), pneumonia, dyspnea, cough, (recurrent) wheezing and asthma, said method comprising administering, to a subject in need thereof, a pharmaceutically active amount of at least one amino acid sequence and/or Nanobody® according to any of aspects A-1 to A-19 and B-1 to B-20, polypeptide according to any of aspects E-1 to E-172, compound or construct according to any of aspects G-1 to G-19, monovalent construct according to any of aspects F-1 to F-4 and/or composition according to aspects O-1 to O-3.

Aspect R-3: Method for the prevention and/or treatment of at least one disease or disorder that can be prevented and/or treated by administering, to a subject in need thereof, an amino acid sequence and/or Nanobody® according to any of aspects A-1 to A-19 and B-1 to B-20, a polypeptide according to any of aspects E-1 to E-172, a compound or construct according to any of aspects G-1 to G-19, a monovalent construct according to any of aspects F-1 to F-4 and/or a composition according to aspects O-1 to O-3, said method comprising administering, to a subject in need thereof, a pharmaceutically active amount of at least one amino acid sequence and/or Nanobody® according to any of aspects A-1 to A-19 and B-1 to B-20, polypeptide according to any of aspects E-1 to E-172, compound or construct according to any of aspects G-1 to G-19, monovalent construct according to any of aspects F-1 to F-4 and/or composition according to aspects O-1 to O-3.

Aspect R-4: Method for immunotherapy, said method comprising administering, to a subject in need thereof, a pharmaceutically active amount of at least one amino acid sequence and/or Nanobody® according to any of aspects A-1 to A-19 and B-1 to B-20, polypeptide according to any of aspects E-1 to E-172, compound or construct according to any of aspects G-1 to G-19, monovalent construct according to any of aspects F-1 to F-4 and/or composition according to aspects O-1 to O-3.

Aspect R-5: Use of an amino acid sequence and/or Nanobody® according to any of aspects A-1 to A-19 and B-1 to B-20, a polypeptide according to any of aspects E-1 to E-172, a compound or construct according to any of aspects G-1 to G-19, a monovalent construct according to any of aspects F-1 to F-4 and/or composition according to aspects O-1 to O-3 in the preparation of a pharmaceutical composition for prevention and/or treatment of hRSV infection; and/or for use in one or more of the methods according to aspects R-1 to R-4.

Aspect R-6: Amino acid sequence and/or Nanobody® according to any of aspects A-1 to A-19 and B-1 to B-20, polypeptide according to any of aspects E-1 to E-172, compound or construct according to any of aspects G-1 to G-19, monovalent construct according to any of aspects F-1 to F-4 and/or composition according to aspects O-1 to O-3 for prevention and/or treatment of at least one of respiratory illness, upper respiratory tract infection, lower respiratory tract infection, bronchiolitis (inflammation of the small airways in the lung), pneumonia, dyspnea, cough, (recurrent) wheezing and asthma.

Aspect S-1: Part or fragment of an amino acid sequence and/or Nanobody® according to any of aspects A-1 to A-19 and B-1 to B-20, and/or a polypeptide according to any of aspects E-1 to E-172.

Aspect S-2: Part or fragment according to aspect S-1, that can specifically bind to antigenic II on protein F of hRSV and/or competes with Synagis® for binding protein F of hRSV.

Aspect S-3: Part of fragment according to any of aspects S-1 to S-2, that can specifically bind to protein F of hRSV with a dissociation constant ($K_D$) of 1000 nM to 1 nM or less, preferably 100 nM to 1 nM or less, more preferably 10 nM to 1 nM or less.

Aspect S-4: Part or fragment according to any of aspects S-2 to S-3, that can specifically bind to protein F of hRSV with a $k_{on}$-rate of between $10^4$ $M^{-1}s^{-1}$ to about $10^7$ $M^{-1}s^{-1}$, preferably between $10^5$ $M^{-1}s^{-1}$ and $10^7$ $M^{-1}s^{-1}$, more preferably about $10^6$ $M^{-1}s^{-1}$ or more.

Aspect S-5: Part or fragment according to any of aspects S-2 to S-4, that can specifically bind to protein F of hRSV with a $k_{off}$ rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, or lower.

Aspect S-6: Compound or construct, that comprises or essentially consists of one or more parts or fragments according to any of aspects S-1 to S-5, and optionally further comprises one or more other groups, residues, moieties or binding units, optionally linked via one or more linkers.

Aspect S-7: Compound or construct according to aspect S-6, in which said one or more other groups, residues, moieties or binding units are amino acid sequences.

Aspect S-8: Compound or construct according to aspects S-6 or S-7, in which said one or more linkers, if present, are one or more amino acid sequences.

Aspect S-9: Nucleic acid or nucleotide sequence, that encodes a part or fragment according to any of aspects S-1 to S-5 or a compound or construct according to any of aspects S-6 to S-8.

Aspect S-10: Composition, comprising at least one part or fragment according to any of aspects S-1 to S-5, compound or construct according to any of aspects S-6 to S-8, or nucleic acid or nucleotide sequence according to aspect S-9.

Aspect T-1: Derivative of an amino acid sequence and/or Nanobody® according to any of aspects A-1 to A-19 and B-1 to B-20.

Aspect T-2: Derivative according to aspect T-1, that can specifically bind to antigenic site II on protein F of hRSV and/or compete with Synagis® for binding protein F of hRSV.

Aspect T-3: Derivative according to any of aspects T-1 to T-2, that can specifically bind to protein F of hRSV with a $k_{on}$-rate of between $10^4$ $M^{-1}s^{-1}$ to about $10^7$ $M^{-1}s^{-1}$, preferably between $10^5$ $M^{-1}s^{-1}$ and $10^7$ $M^{-1}s^{-1}$, more preferably about $10^6 M^{-1}s^{-1}$ or more.

Aspect T-4: Derivative according to any of aspects T-2 to T-3, that can specifically bind to protein F of hRSV with a $k_{on}$-rate of between $10^4$ $M^{-1}s^{-1}$ to about $10^7$ $M^{-1}s^{-1}$, preferably between $10^5$ $M^{-1}s^{-1}$ and $10^7$ $M^{-1}s^{-1}$, more preferably about $10^6 M^{-1}s^{-1}$ or more.

Aspect T-5: Derivative according to any of aspects T-2 to T-4, that can specifically bind to protein F of hRSV with a $k_{off}$ rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}s^{-1}$ and $10^{-4}$ $s^{-1}$, or lower.

Aspect T-6: Derivative of a compound or construct according to any of aspects G-1 to G-19 or a polypeptide according to any of aspects E-1 to E-172.

Aspect T-7: Derivative according to aspect T-6, that can specifically bind to antigenic site II on protein F of hRSV and/or compete with Synagis® for binding protein F of hRSV.

Aspect T-8: Derivative according to any of aspects T-6 to 1-7, that can specifically bind to protein F of hRSV with a dissociation constant ($K_D$) of 100 nM to 0.1 nM or less, preferably 10 nM to 0.1 nM or less, more preferably 1 nM to 0.1 nM or less.

Aspect T-9: Derivative according to any of aspects T-6 to T-8, that can specifically bind to protein F of hRSV with a $k_{on}$-rate of between $10^4$ $M^{-1}s^{-1}$ to about $10^7$ $M^{-1}s^{-1}$, preferably between $10^5$ $M^{-1}s^{-1}$ and $10^7 M^{-1}s^{-1}$, more preferably about $10^6$ $M^{-1}s^{-1}$ or more.

Aspect T-10: Derivative according to any of aspects 1-6 to T-9, that can specifically bind to protein F of hRSV with a $k_{off}$ rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4} s^{-1}$, more preferably between $5 \times 10^{-3}s^{-1}$ and $10^{-4}$ $s^{-1}$, or lower.

Aspect T-11: Derivative according to any of aspects 1-6 to T-10, that can neutralize hRSV, e.g. in a microneutralization assay of RSV strain Long (such as e.g. described in Example 6), with an IC50 value between 10 pM and 1000 pM, preferably between 10 pM and 250 pM, more preferably between 50 pM and 200 pM or less.

Aspect T-12: Derivative according to any of aspects T-6 to T-11, that can neutralize hRSV, e.g. in a microneutralization assay of RSV strain Long (such as e.g. described in Example 6), with an IC50 value that is at least the same and preferably better, at least ten times better, preferably twenty times better, more preferably fifty times better, even more preferably sixty, seventy, eighty or more times better compared to the IC50 value obtained with Synagis®.

Aspect T-13: Derivative according to any of aspects T-1 to T-12, that has a serum half-life that is at least 1.5 times, preferably at least 2 times, such as at least 5 times, for example at least 10 times or more than 20 times, greater than the half-life of the corresponding amino acid sequence and/or Nanobody® according to any of aspects A-1 to A-19 and B-1 to 13-20 per se, polypeptide according to any of aspects E-1 to E-162 per se, compound or construct according to any of aspects G-1 to G-19 per se, or monovalent construct according to any of aspects F-1 to F-4 per se, respectively.

Aspect T-14: Derivative according to any of aspects T-1 to T-13, that has a serum half-life that is increased with more than 1 hours, preferably more than 2 hours, more preferably more than 6 hours, such as more than 12 hours, or even more than 24, 48 or 72 hours, compared to the corresponding amino acid sequence and/or Nanobody® according to any of aspects A-1 to A-19 and B-1 to B-20 per se, polypeptide according to any of aspects E-1 to E-162 per se, compound or construct according to any of aspects G-1 to G-19 per se, or monovalent construct according to any of aspects F-1 to F-4 per se, respectively.

Aspect T-15: Derivative according to any of aspects T-1 to T-14, that has a serum half-life in human of at least about 12 hours, preferably at least 24 hours, more preferably at least 48 hours, even more preferably at least 72 hours or more; for example, at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Aspect T-16: Derivative according to any of aspects T-1 to T-15, that is a pegylated derivative.

Aspect T-17: Compound or construct, that comprises or essentially consists of one or more derivatives according to any of aspects T-1 to T-16, and optionally further comprises one or more other groups, residues, moieties or binding units, optionally linked via one or more linkers.

Aspect T-18: Compound or construct according to aspect T-17, in which said one or more other groups, residues, moieties or binding units are amino acid sequences.

Aspect T-19: Compound or construct according to aspects T-17 or T-18, in which said one or more linkers, if present, are one or more amino acid sequences.

Aspect T-20: Nucleic acid or nucleotide sequence, that encodes a derivative according to any of aspects T-1 to T-16 or a compound or construct according to any of aspects T-17 to T-19.

Aspect T-21: Composition, comprising at least one derivative according to any of aspects T-1 to T-16, compound or construct according to any of aspects T-17 to T-19, or nucleic acid or nucleotide sequence according to aspect T-20.

Aspect U-1: A method for administering an effective amount of an amino acid sequence and/or Nanobody® according to any of aspects A-1 to A-19 and B-1 to B-20, a polypeptide according to any of claims E-1 to E-172, a compound or construct according to any of claims G-1 to G-19 and/or a monovalent construct according to any of claims F-1 to F-4, and/or a composition comprising the same, wherein said method comprises the step of administering the amino acid sequence and/or Nanobody® according to any of aspects A-1 to A-19 and B-1 to B-20, the polypeptide according to any of claims E-1 to E-172, the compound or construct according to any of claims G-1 to G-19 and/or the monovalent construct according to any of claims F-1 to F-4, and/or a composition comprising the same to the pulmonary tissue.

Aspect U-2: The method according to aspect U-1, wherein the amino acid sequence and/or Nanobody® according to any of aspects A-1 to A-19 and B-1 to B-20, the polypeptide according to any of claims E-1 to E-172, the compound or construct according to any of claims G-1 to G-19 and/or the monovalent construct according to any of claims F-1 to F-4, and/or a composition comprising the same is administered by use of an inhaler, intranasal delivery device or a device capable of generating an aerosol cloud.

Aspect U-3: Method according to any of aspects U-1 or U-2, wherein at least 5%, preferably at least 10%, 20%, 30%, 40%, more preferably at least 50%, 60%, 70%, and even more preferably at least 80% or more of the amino acid sequence and/or Nanobody® according to any of aspects A-1 to A-19 and B-1 to B-20, the polypeptide according to any of claims E-1 to E-172, the compound or construct according to any of claims G-1 to G-19 and/or the monovalent construct according to any of claims F-1 to F-4, and/or a composition comprising the same is stable in the pulmonary tissue for at least 24 hours, preferably at least 48 hours more preferably at least 72 hours.

Aspect U-4: Method according to any of aspects U-1 to U-3, wherein the amino acid sequence and/or Nanobody® according to any of aspects A-1 to A-19 and B-1 to B-20, the polypeptide according to any of claims E-1 to E-172, the compound or construct according to any of claims G-1 to G-19 and/or the monovalent construct according to any of claims F-1 to F-4, and/or a composition comprising the same are applied in pure form, i.e., when they are liquids or a dry powder.

Aspect U-5: Method according to any of aspects U-1 to U-3, wherein the amino acid sequence and/or Nanobody® according to any of aspects A-1 to A-19 and B-1 to B-20, the polypeptide according to any of claims E-1 to E-172, the compound or construct according to any of claims G-1 to G-19 and/or the monovalent construct according to any of claims F-1 to F-4, and/or a composition comprising the same are administered to the pulmonary tissue as composition or formulation comprising an amino acid sequence and/or Nanobody® according to any of aspects A-1 to A-19 and B-1 to B-20, a polypeptide according to any of claims E-1 to E-172, a compound or construct according to any of claims G-1 to G-19 and/or a monovalent construct according to any of claims F-1 to F-4, and a carrier suitable for pulmonary delivery.

Aspect U-6: Pharmaceutical composition comprising an amino acid sequence and/or Nanobody® according to any of aspects A-1 to A-19 and B-1 to B-20, a polypeptide according to any of claims E-1 to E-172, a compound or construct according to any of claims G-1 to G-19 and/or a monovalent construct according to any of claims F-1 to F-4, and a carrier suitable for pulmonary delivery.

Aspect U-7: Pharmaceutical device suitable for the pulmonary delivery of an amino acid sequence and/or Nanobody® according to any of aspects A-1 to A-19 and B-1 to B-20, a polypeptide according to any of claims E-1 to E-172, a compound or construct according to any of claims G-1 to G-19 and/or a monovalent construct according to any of claims F-1 to F-4 and/or suitable in the use of a composition comprising the same.

Aspect U-8: Pharmaceutical device according to aspect U-7 that is an inhaler for liquids (e.g. a suspension of fine solid particles or droplets) comprising an amino acid sequence and/or Nanobody® according to any of aspects A-1 to A-19 and B-1 to B-20, a polypeptide according to any of claims E-1 to E-172, a compound or construct according to any of claims G-1 to G-19 and/or a monovalent construct according to any of claims F-1 to F-4.

Aspect U-9: Pharmaceutical device according to aspect U-7 that is a device capable of generating an aerosol cloud comprising an amino acid sequence and/or Nanobody® according to any of aspects A-1 to A-19 and B-1 to B-20, a polypeptide according to any of claims E-1 to E-172, a compound or construct according to any of claims G-1 to G-19 and/or a monovalent construct according to any of claims F-1 to F-4.

Aspect U-10: Pharmaceutical device according to aspect U-7 that is a dry powder inhaler comprising an amino acid sequence and/or Nanobody® according to any of aspects A-1 to A-19 and B-1 to B-20, a polypeptide according to any of claims E-1 to E-172, a compound or construct according to any of claims G-1 to G-19 and/or a monovalent construct according to any of claims F-1 to F-4 in the form of a dry powder.

Aspect U-11: Method for the prevention and/or treatment of hRSV infection, said method comprising administering to the pulmonary tissue of a subject in need thereof, a pharmaceutically active amount of an amino acid sequence and/or Nanobody® according to any of aspects A-1 to A-19 and B-1 to B-20, a polypeptide according to any of claims E-1 to E-172, a compound or construct according to any of claims G-1 to G-19 and/or a monovalent construct according to any of claims F-1 to F-4 and/or of a pharmaceutical composition comprising the same.

Aspect U-12: Method for the prevention and/or treatment of respiratory illness, upper respiratory tract infection, lower respiratory tract infection, bronchiolitis (inflammation of the small airways in the lung), pneumonia, dyspnea, cough, (recurrent) wheezing and asthma, said method comprising administering to the pulmonary tissue of a subject in need thereof, a pharmaceutically active amount of an amino acid sequence and/or Nanobody® according to any of aspects A-1 to A-19 and B-1 to B-20, a polypeptide according to any of claims E-1 to E-172, a compound or construct according to any of claims G-1 to G-19 and/or a monovalent construct according to any of claims F-1 to F-4, and/or of a pharmaceutical composition comprising the same.

Aspect V-1: Method for the prevention and/or treatment of hRSV infection, said method comprising administering, to a subject in need thereof, a pharmaceutically active amount of a multivalent polypeptide according to any of aspects E-7 to E-162, and/or of a pharmaceutical composition comprising the same.

Aspect V-2: Use of a multivalent polypeptide according to any of aspects E-7 to E-162, and/or of a pharmaceutical composition comprising the same for binding and/or neutralization of hRSV.

Aspect V-3: Use of a multivalent polypeptide according to any of aspects E-7 to E-162, and/or of a pharmaceutical composition comprising the same for binding and/or neutralization of different strains of hRSV.

Aspect V-4: Use of a multivalent polypeptide according to any of aspects E-7 to E-162, and/or of a pharmaceutical composition comprising the same for binding and/or neutralization of one or more escape mutants of a virus.

Aspect V-5: Method or use according to any of aspects V-1 to V-4, wherein the multivalent polypeptide is bivalent.

Aspect V-6: Method or use according to any of aspects V-1 to V-4, wherein the multivalent polypeptide is trivalent.

Aspect V-7: Method or use according to any of aspects V-1 to V-6, wherein said multivalent polypeptide is administered according to any of the methods of claims U-1 to U-5 and/or U-11 to U-12.

Aspect V-8: Method for the prevention and/or treatment of infection by hRSV virus, said method comprising administering, to a subject in need thereof, a pharmaceutically active amount of a multivalent polypeptide according to any of aspects E-7 to E-162 and/or of a pharmaceutical composition comprising the same.

Aspect V-9: Method according to aspect V-8 wherein the multivalent compound or construct is selected from Table A-5 (SEQ ID NO's: 41-55).

Aspect V-10: Method according to any of aspects V-8 or V-9, wherein infection by one or more RSV escape mutants is treated.

Aspect V-11: Method according to aspect V-10, wherein the escape mutant is an escape mutant specific for antigenic site IL.

Aspect V-12: Use of a multivalent compound or construct according to any of aspects E-7 to E-162, and/or of a pharmaceutical composition comprising the same for binding and/or neutralization one or more different escape mutants of RSV.

Aspect V-13: Use according to claim V-12 wherein the escape mutant is an escape mutant specific for antigenic site II.

Aspect V-14: Method according to any of aspects V-8 or V-9, wherein infection by one or more strains of hRSV is treated.

Aspect V-15: Method according to aspect V-14, wherein the RSV strain is Long. Aspect V-16: Method according to aspect V-14, wherein the RSV strain is A-2.

Aspect V-17: Method according to aspect V-14, wherein the RSV strain is B-1.

Aspect V-18: Method according to aspect V-14, wherein the multivalent polypeptide binds and/or neutralizes RSV strain Long and A-2.

Aspect V-19: Method according to aspect V-14, wherein the multivalent polypeptide binds and/or neutralizes RSV strain Long and B-1.

Aspect V-20: Method according to aspect V-14, wherein the multivalent polypeptide binds and/or neutralizes RSV strain B-1 and A-2.

Aspect V-21: Method according to aspect V-14, wherein the multivalent polypeptide binds and/or neutralizes RSV strain Long, A-2 and B-1.

Aspect V-22: Use of a multivalent compound or construct according to any of aspects E-7 to E-162, and/or of a pharmaceutical composition comprising the same for binding and/or neutralization different strains of hRSV.

Aspect V-23: Use according to aspect V-22, wherein the strains of RSV are Long and A-2.

Aspect V-24: Use according to aspect V-22, wherein the strains of RSV are Long and B-1.

Aspect V-25: Use according to aspect V-22, wherein the strains of RSV are A-1 and B-1.

Aspect V-26: Use according to aspect V-22, wherein the strains of RSV are Long, A-2 and B-1.

EXAMPLES

Example 1: Immunizations

Two llamas (156 and 157) were immunized according to standard protocols with 6 boosts of hRSV $F_{TM}$-NN (membrane anchorless form of the fusion protein, 70 kDa; Corrall T. et al. 2007, BMC Biotechnol. 7: 17). Blood was collected from these animals 7 days after boost 6 and 10 days after boost 6. Two llamas (212 and 213) were immunized intramuscularly in the neck with 1 mg of RNA-inactivated RSV strain long A (Hytest, Turku Finland; #8RSV79), followed by 4 boosts of 0.5 mg RSV in a biweekly regimen. Two llamas (206 and 207) were immunized intramuscularly with 1 mg of RNA-inactivated RSV strain long A, boosted with 0.25 mg of RSV after 2 weeks, followed by 3 boosts with 50 µg of recombinant hRSV $F_{TM}$-NN (membrane anchorless form of the fusion protein, 70 kDa: Corral et al. 2007; BMC Biotechnol. 7: 17) in a biweekly regimen. For all immunizations the antigens were prepared as oil-PBS emulsions with Stimune as adjuvant. Blood was collected from these animals 4 days and 10 days after the fourth immunization, while also a Lymph node biopsy was taken 4 days after the fourth immunization.

Example 2: Library Construction

Peripheral blood mononuclear cells were prepared from blood samples using Ficoll-Hypaque according to the manufacturer's instructions. Next, total RNA was extracted from these cells as well as from the lymph node bow cells and used as starting material for RT-PCR to amplify Nanobody® encoding gene fragments. These fragments were cloned into phagemid vector derived from pUC119 which contains the LacZ promoter, a coliphage pIII protein coding sequence, a resistance gene for ampicillin or carbenicillin, a multicloning site and the gen3 leader sequence. In frame with the Nanobody® coding sequence, the vector codes for a C-terminal c-myc tag and a (His)6 tag. Phage was prepared according to standard methods and stored at 4° C. for further use, making phage libraries 156, 157, 206, 207, 212 and 213.

Example 3: Nanobody® Selection with the F-Protein of hRSV

To identify Nanobodies® recognizing the fusion protein of RSV, libraries 156, 157, 206, 207, 212 and 213 were used for selection on $F_{TM}$-NN (membrane anchorless form of the Long fusion protein, 70 kDa; Corral T. et al. 2007, BMC Biotechnol. 7: 17). In addition, selections were done using inactivated hRSV strain Long (Hytest #8RSV79). The $F_{TM}$-NN protein (25 ng/well) or RSV 5-0.5 µg/well) was immobilized on Nunc Maxisorp ELISA plates, next to a control with 0 µg/ml antigen. Bound phages were eluted using trypsin or 101F Fab (WO 06/050280, humanized monoclonal antibody, in-house produced) in 100 molar excess in consecutive first and second round of selections. As control for 101F Fab served Omnitarg Fab (anti-Her2; in-house produced). In order to identify Nanobodies® binding specifically to antigenic sites IV-VI epitopes on the RSV F-protein, outputs from the first round selections on $F_{TM}$-NN eluted with 101F Fab were used for second round selections using two biotinylated peptides: at first, a peptide comprising residues 422-436 of the F-protein (Long) (Abgent, San Diego, Calif.) encompassing the 101F binding epitope (Wu et al. 2007, J, Gen. Virol. 88: 2719-2723), secondly, a peptide mimic of the epitope of Mab19 (HWSISKPQ-PEG4-K-biotin)(Chargelegue et al. 1998, J. Virol. 72: 2040-2056).

Outputs of both rounds of selections were analyzed for enrichment factor (phage present in eluate relative to controls). Based on these parameters the best selections were chosen for further analysis. Individual colonies were picked and grown in 96 deep well plates (1 mL volume) and induced by adding IPTG for Nanobody® expression. Periplasmic extracts (volume: ~80 µl) were prepared according to standard methods.

Example 4: Screening for Nanobodies® that Bind to Antigenic Site II or IV-VI

Periplasmic extracts containing single Nanobodies® were analyzed for binding to the RSV F-protein (Long). In short, 1 µg/ml of $F_{TM}$-NN (Long) was immobilized directly on Maxisorp microtiter plates (Nunc). Free binding sites were blocked using 4% Marvel in PBS. Next, 10 µl of periplasmic extract containing Nanobody® of the different clones in 100 µl 2% Marvel PBST were allowed to bind to the immobilized antigen. After incubation and a wash step, binding of Nanobody® in the periplasmatic extracts at 1/10 dilution was revealed using rabbit-anti-VHH polyclonal antibodies. After a wash step the Nanobodies® in the periplasmic fractions were detected with a HRP-conjugated goat-anti-rabbit antibody. Binding specificity was determined based on OD values compared to controls having received no Nanobody®. In total 436 binders to RSV Long F-proteins were identified, showing a hit-rate of approximately 44%.

In a next step all binders were analysed for their ability to bind to antigenic site II by means of a competition ELISA with Synagis® Mab (Palivizumab, humanized monoclonal antibody, described in Zhao and Sullender 2005, J. Viral. 79: 396). In here 10 µg/ml hRSV Long (Hytest #8RSV79) was immobilized on Maxisorp microtiter plates (Nunc) and free binding sites were blocked using Superblock T (Pierce, 15120T). Periplasmatic extracts were diluted 1/10 and mixed with Synagis Mab (66 pM) prior to binding to the immobilized hRSV. Control periplasmic fractions selected against irrelevant proteins were included as background control, while previously identified Nanobodies® NC41 (class II epitope) and NC39 (class IV-VI epitope) served as positive and negative controls. The competitors were allowed to bind to the immobilized antigen with or without Nanobody®. For detection of Synagis Mab goat Anti-Human IgG, Fcγ fragment specific-HRP (Jackson ImmunoResearch, West Grove, Pa.) was used, after which the ELISA was developed according to standard procedures. Binding specificity was determined based on OD values compared to controls having received no Nanobody®. This assay resulted in 9 hits (Table B-1).

In a similar manner, periplasmatic extracts were analysed in a competition ELISA with 101F Fab (WO 06/050280, humanized monoclonal antibody, in-house produced) to identify clones of epitope class IV-VI. In this assay periplasmic extracts were diluted 1/100 and mixed with 101F Fab (2 nM) prior to binding to hRSV. Bound 101F Fab was detected using mouse anti-HA directed against the HA-tag (Zymed, 32-6700), followed by anti-mouse IgG-HRP conjugated secondary antibodies (Dako, Cat. No. P0260). Of the around 90 competitors identified that showed more than 50% inhibition, the best 101F Fab competitors were further tested at dilutions ranging from 1/300-1/1000 to allow differentiation between clones (Table B-1).

As third step, the Class II and IV-VI epitope clones were analyzed for binding to Hep2 cells infected with RSV B-1 strains. Binding to F-protein of RSV B-1 was assessed in a cell-based ELISA using Hep2 cells infected with RSV B-1 virus. In here Hep2 cells were seeded at a density of 1.5×10⁴ cells/well into 96-well plates in DMEM medium containing 10% fetal calf serum (FCS) supplemented with Penicillin and Streptomycin (100 U/ml and 100 µg/ml, respectively) and incubated for 24 hours at 37° C. in a 5% $CO_2$ atmosphere. The medium of the Hep2 cells was replaced with the virus dilution to allow infection in 0.1 ml of assay medium (DMEM medium supplemented with 2.5% fetal calf serum and Penicillin and Streptomycin). Cells were incubated for an additional 72 hours at 37° C. in a 5% CO2 atmosphere, after which cells were washed twice with 0.05% Tween-20 in PBS and once with PBS alone, after which the cells were fixed with 80° A, cold acetone (Sigma-Aldrich, St. Louis, Mo.) in PBS (100 µl/well) for 20 minutes at 4° C. and left to dry completely. Fixed Hep2 cells were blocked with 2% Bovine Serum Albumin (BSA) solution in PBS for 1 hour at room temperature. The ELISA follows essentially the same procedure as described above for the $F_{TM}$-NN protein, except that periplasmatic extracts were tested at 1/50 and 1/200 dilutions. As positive control periplasmatic extract of the RSV NC39 was used. In general the Class II epitope clones proved much weaker binders to Hep2-B1 cells than clones of the epitope Class IV-VI.

Sequence analysis reduced the total number of competing Nanobodies. Clones 8A1, 8B10 and 1B2 were found as multiple copies which were all ranked amongst the strongest binders to Hep2 B-1-infected cells. Multiple members of the large family 4 were also good binders to RSV B-1, including 13O1 and 19E2. From the group of Synagis® competitors, clones 19C4 and 1G8 were the best RSV B-1 binders. Based on the binding to both RSV long and B-1, on sequence, and on 101F competition, a selection was made from 101F competitors for further analysis as purified proteins (Table B-1). All Synagis competitors except clone 1E5 were also selected for further characterization.

Example 5: Production of hRSV Nanobodies®

Eight Nanobodies® recognising antigen site II (1G3, 1E4, 1A6, 1G8, 7B2, 19O4, 20C1, 20B2) and 11 antigenic site IV-VI Nanobodies® (1B2, 1A2, 8A1, 8B10, 13A1, 13B4, 13C1, 13D1, 19E2, 13E12, 23E5) were expressed and purified for further characterisation. Thereto the encoding sequences were recloned in an expression vector derived from pUC119 which contained the LacZ promoter, a resistance gene for kanamycin, a multicloning site and the OmpA signal peptide sequence. In frame with the Nanobody® coding sequence, the vector coded for a C-terminal c-myc tag and a (His)6 tag (SEQ ID NO: 25).

Expression occurred in *E. coli* TG-1 cells as c-myc, His6-tagged proteins in a culture volume of 1 L. Expression was induced by addition of 1 mM IPTG and allowed to continue for 3 hours at 37° C. After spinning the cell cultures, periplasmic extracts were prepared by freeze-thawing the pellets and resuspension in dPBS. These extracts were used as starting material for immobilized metal affinity chromatography (IMAC) using Histrap FF crude columns (GE healthcare, Uppsala, Sweden). Nanobodies® were eluted from the column with 250 mM imidazole and subsequently desalted towards dPBS.

Example 6: Identification of RSV Long Neutralizing Nanobodies®

All purified Nanobodies were analysed as purified proteins for neutralization of two different RSV A (Long and A-2) and one type B strain (B-1) in a micro-neutralization assay. Hep2 cells were seeded at a concentration of $1.5 \times 10^4$ cells/well into 96-well plates in DMEM medium containing 10% fetal calf serum (FCS) supplemented with Penicillin and Streptomycin (100 U/ml and 100 µg/ml, respectively) and incubated for 24 hours at 37° C. in a 5 $CO_2$ atmosphere. Viral stocks of RSV Long LM-2 (Accession No. P12568; ATCC VR-26), RSV A-2 (ATCC VR-1540; lot nr. 3199840), and RSV B-1 (ATCC VR-1580; lot nr. 5271356) were prepared into Hep2 cells and subsequently titrated to determine the optimal infectious dose for use in the micro neutralization assay. The virus stocks have been passaged several times from the ATCC stock. A standard quantity of hRSV strain Long LM-2, A-2 or B-1 was pre-incubated with serial dilutions of purified Nanobodies® (20 µl) in a total volume of 50 µl for 30 minutes at 37° C. The medium of the Hep2 cells was replaced with the premix to allow infection for 2 hours, after which 0.1 ml of assay medium was added. The assay was performed in DMEM medium supplemented with 2.5% fetal calf serum and Penicillin and Streptomycin (100 U/ml and 100 µg/ml, respectively). Cells were incubated for an additional 72 hours at 37° C. in a 5% CO2 atmosphere, after which cells were washed twice with 0.05 Tween-20 in PBS and once with PBS alone, after which the cells were fixed with 80% cold acetone (Sigma-Aldrich, St. Louis, Mo.) in PBS (100 µl/well) for 20 minutes at 4° C. and left to dry completely. Next the presence of the F-protein on the cell surface was detected in an ELISA type assay. Thereto, fixed Hep2 cells were blocked with 2 Bovine Serum Albumin (BSA) solution in PBS for 1 hour at room temperature, than incubated for 1 hour with Synagis® (2 µg/ml). For detection goat Anti-Human IgG, Fcγ fragment specific-HRP (Jackson ImmunoResearch, West Grove, Pa.) was used, after which the ELISA was developed according to standard procedures. Next to Synagis Mab a Nanobody directed against an irrelevant viral protein and the previously identified NC41 were included as controls.

The sequences of the respective F-proteins of the different RSV strains were verified by means of reverse-transcriptase PCR and subsequent sequence analysis. Briefly, total RNA was isolated from RSV-infected Hep2 cells using RNeasy mini kit (Qiagen, Venlo, Netherlands), after which complementary DNA was prepared using Superscript III reverse transcriptase kit (Invitrogen, Carlsbad, Calif.). The F-protein of RSV A strains was amplified and sequenced using the primers described in Kimura et al. 2004 (Antiviral Research 61: 165-171). For amplification of the RSV B-1 strain F-protein the following primers were used: FB1_outer_for: cttagcagaaaaccgtga (SEQ ID NO: 1); FB1_outer_rev: tgggt-tgatttgggattg (SEQ ID NO: 2); FB1_seq_1123-for: ggactga-tagaggatggta (SEQ ID NO: 3); FB1_seq_1526-rev: gctgact-tcacttggtaa (SEQ ID NO: 4). The sequence of RSV B-1 strain corresponded to Accession nr P13843, with an additional point mutation Ser540Leu. The sequence for the RSV Long M2 strain corresponded completely to the reported sequence (Accession nr M22643). The sequence for the strain RSV A-2 corresponded to Accession M11486. See also Table A-2.

Figure 1B:
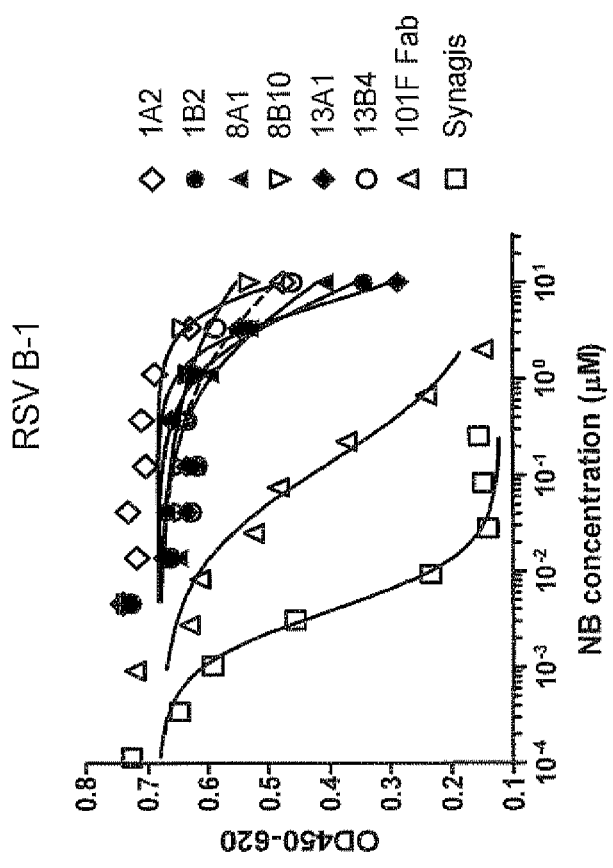
Figure 1C:
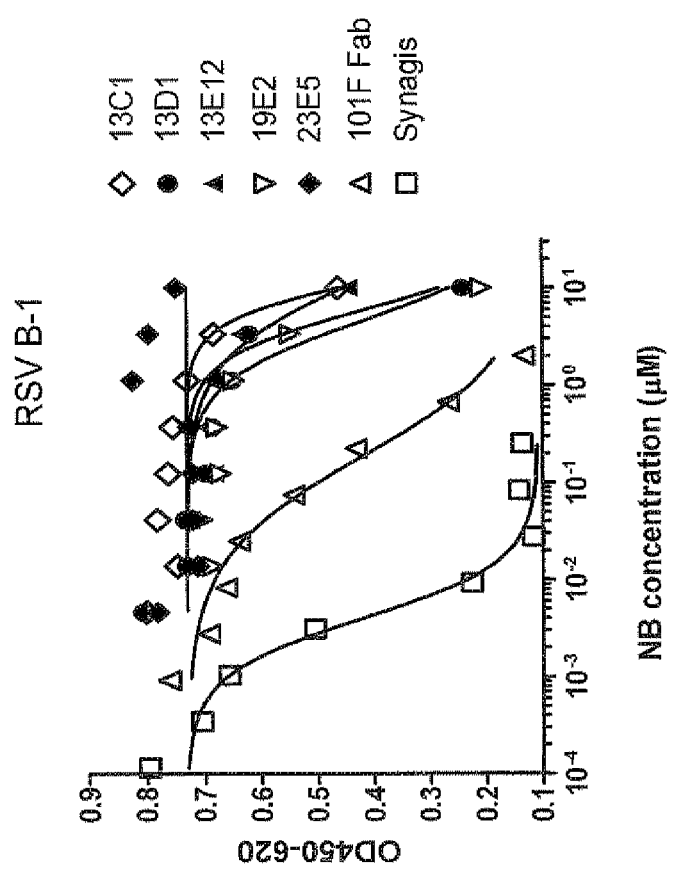

Nanobodies® from antigenic site II were good neutralizers of RSV Long in the following order: 7B2 (SEQ ID NO: 16), NC41 (SEQ ID NO: 24), 19C4 (SEQ ID NO: 21), 1G3 (SEQ ID NO: 20) and 1E4 (SEQ ID NO: 19), 20B2 (SEQ ID NO: 22), 1A6 (SEQ ID NO: 17) and 20C1 (SEQ ID NO: 23) (FIG. 1 and Table A-1). Only Nanobody 1G8 (SEQ ID NO: 18) had no neutralizing activity on Long M2 strain. The ranking of the Nanobody potencies was similar on the A-2 strain as on Long M2 strain (data not shown). No neutralization of RSV B-1 by any of the antigenic II Nanobodies in the tested range (10 µM) was observed.

Despite the screening for RSV B-1 binding, the antigenic site IV-VI specific Nanobodies® showed only weak neutralizing activity for hRSV B-1, and no neutralization of Long LM-2. Of these, the best neutralizers were 19E2, 13M and 13D1, all members of family 4, and 1B2 (Table A-1).

Example 7: Characterization of hRSV Nanobodies®

Competition with Synagis® and 101F Fab

The ability of purified Nanobodies® to compete with Synagis® Mab or 101F Fab for binding to $F_{TM}$-NN was determined in competition ELISA following the procedure as essentially described in Example 4. EC50 values are summarized in Table B-2.

Binding to F-Protein in Biacore

To determine the precise binding affinities of the purified Nanobodies®, a kinetic analysis was performed using Surface Plasmon resonance analysis on the $F_{TM}$-NN protein. For preincubation of the Sensorchip CM5, 10 μg/ml hRSV $F_{TM}$-protein was left on for 120 seconds. For immobilization by amine coupling, EDC/NHS was used for activation and ethanolamine HCl for deactivation (Biacore, amine coupling kit). 100 nM Synagis® was added and then 100 nM of the Nanobodies®. Evaluation of the off-rates was performed by fitting a 1:1 interaction model (Langmuir binding model) by Biacore T100 software v1.1. The off-rates and affinity constants are shown in Table B-2.

Determination of the Melting Temperature

As a measure for Nanobody® stability, the melting temperature (Tm) of purified Nanobodies in dPBS was determined by a fluorescence-based thermal shift assay. In here the Nanobodies dissolved in PBS or buffers with a different pH were mixed with a Sypro-orange dye (Invitrogen, #S6551) that binds to hydrophobic core residues that become exposed while the protein undergoes thermal unfolding. Nanobodies were stepwise heated from 37 to 90° C. with a ramp-rate of 4.4° C./s in a Roche Lightcycler 480 PCR machine (Roche). The Tm values are shown in Table B-2.

Example 8: Construction, Production and Characterization of Multivalent hRSV Nanobodies®

Multivalent Nanobody® constructs connected by Gly-Ser linkers of different lengths and composition were generated by means of separate PCR reactions (1 for the N-terminal, 1 for the middle (in case of trivalent) and 1 for the C-terminal Nanobody® subunit) using different sets of primers encompassing specific restriction sites. Similarly, multivalent constructs connected by Ala-Ala-Ala linker were generated. Both monospecific multivalents, using a single Nanobody as building block, or bispecific constructs using two different Nanobodies were generated. All constructs were cloned into an expression vector derived from pUC119 which contained the LacZ promoter, a resistance gene for kanamycin, a multicloning site and the OmpA signal peptide sequence. In frame with the Nanobody® coding sequence, the vector coded for a C-terminal c-myc tag and a (His)6 tag. In case a 35 Gly-Ser-linker was present in the multivalent construct, an expression vector was used derived from pUC119 which contained the LacZ promoter, a resistance gene for kanamycin and the OmpA signal peptide sequence. Directly downstream of the signal peptide a multiple cloning site was present for Nanobody® insertion, followed by a 35Gly-Ser linker encoding DNA sequence and a second multiple cloning site for cloning of a second Nanobody® sequence. In frame with the resulting Nanobody®-35Gly-Ser-Nanobody® coding sequence, the vector coded for a C-terminal c-myc tag and a (His)6 tag. Table B-3 lists the multivalent constructs generated with RSV-specific Nanobodies®. The sequences of the multivalent constructs are shown in Table A-3.

Multivalent RSV Nanobody® constructs were expressed, purified and further characterized. Production was done in *E. coli* TG1 cells, followed by purification from the periplasmic fraction via the His-tag by IMAC and desalting, essentially as described in Example 5. For some constructs also an affinity chromatography step using protein-A sepharose was applied. All trivalent Nanobodies® were subjected to gel filtration as a final step to remove possible bivalent and monovalent degradation products.

Example 9: Potency of Multivalent Constructs to Neutralize hRSV

Figure 2:
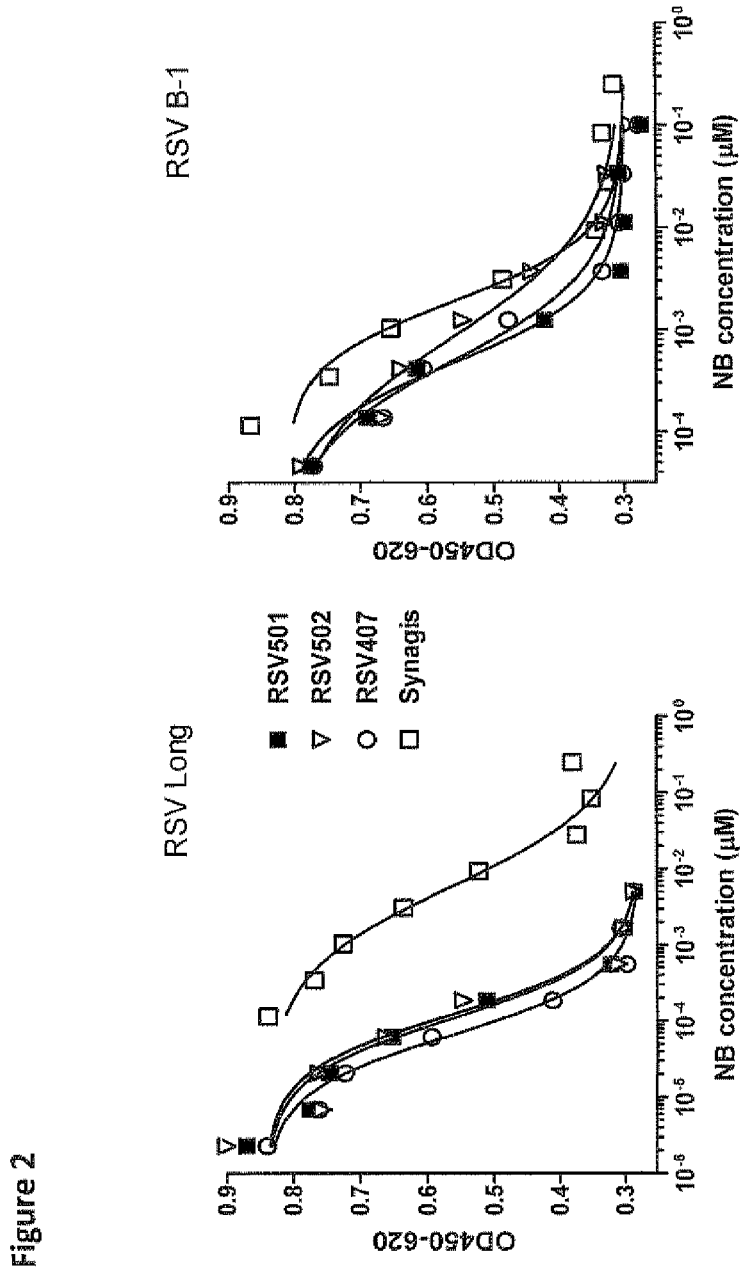
FIG. 2: depicts the neutralization of RSV Long and B-1 strains by trivalent Nanobodies.

The potency of the trivalent Nanobody® constructs of 7B2 (RSV501) and 1E4 (RSV502) were evaluated in the RSV neutralization assay on different RSV strains. As references both Synagis® Mab and the trivalent version of NC41 with the same 15GS linker (RSV407) were included. As shown in FIG. 2, trivalents RSV501 and RSV502 were very similar in neutralization of RSV Long (IC50 values of 110 pM and 124 pM respectively) and more than 40-fold more potent than Synagis®. On the B-1 strain, RSV501 behaved similar to RSV407, being around 4-8 fold more potent than Synagis®. Trivalent constructs with three Nanobodies® binding antigenic site II were at least 1000-fold more potent neutralizers on RSV B-1 strains than their monovalent counterparts.

Since Nanobodies of epitope class IV-VI were shown to be slightly better neutralizers of RSV B-1 than 7B2, different biparatopic trivalents comprising two 7B2 Nanobodies in combination with two distinct class IV-VI Nanobodies were also tested for neutralization. Nanobodies RSV513 (7B2-15GS-19E2-15GS-7B2) and RSV515 (7B2-15GS-8A1-15GS-7B2) showed approximately 12 times better neutralization than Synagis on B-1, with IC50 values around 150 pM. On RSV Long both constructs were 22-25 fold better than Synagis. For each of these constructs reduction of the linker length to 9GS resulted in slightly enhanced potencies on both viral strains (data not shown).

Example 10: Sequence Optimization of Nanobody® 7B2

The sequence of Nanobody® 7B2 was blasted to different human VH3 germline sequences and was found most similar to VH3-48, with 85% sequence identity in the framework regions. Since this Nanobody® has already high similarity to human VH-3 sequences, the sequence optimization mainly focused on the identification of residues that might improve stability. Three positions were modified for humanization purposes, Ala14Pro, Lys83Arg and Gln108Leu (numbering according to Kabat), resulting in a basic variant 7B2v22. Within this basic variant the additional mutation of Glu1Asp, Asp16Gly, Asp54Glu or Gly55Ala were investigated (7B2 variants 23-29), to modify residues that are potentially prone to post-translational modification such as Asp isomerisation and pyroglutamate formation (Table A-4).

All 7B2 variants were produced and purified as described in Example 5. Some variants were also expressed in *Pichia pastoris* allowing verification of the expression levels. In that case the purification of Nanobodies from the medium was done using protein A affinity chromatography, followed by a gel filtration step.

The thermal stability of 7B2 variants was determined by measurement of the melting temperature (Tm), as described in Example 7. For instance, variants 22 and 23 have Tm values of 86.0° C. and 85.6° C. in dPBS, respectively, which is slightly higher than observed for wildtype 7B2 (84.3° C.). Since these variants differ only on position 1, the Glu1Asp mutation did not negatively affect the Tm of the 7B2 basic variant.

To verify if the introduced mutations affected the heat-induced refolding of the protein, variants were stepwise heated to 5° C. above their respective Tm values, and subsequently cooled down to RT. The resulting fraction of refolded protein was analyzed for the presence of potential aggregates by means of spectrophotometry at 320 nm, while the functionality of the refolded Nanobodies was verified in a binding ELISA to hRSV long (as described in Example 4). In this refolding assay no difference between variant 22 and variant 23 was detected, both variants showing between 90-98% of functionality after heat-induced refolding in comparison to the non-heated reference samples.

The functionality of the 7B2 variants was also assessed by measurement of the potency in the RSV micro-neutralization assay on A Long and B-1 strains (see Example 4). On Long 7B2 variants 22 and 23 had IC50 values of 109 and 113 nM, in a similar range as wild type 7B2 (88 nM). On B-1 both 7B2 variants were equally potent as wildtype 7B2, arguing that the Glu1Asp mutation was permitted within 7B2.

Example 11: Preparation of Multivalent Constructs of Humanized 7B2 Nanobody®

Four of the 7B2 variants were formatted as trivalent constructs using 15GS linkers, 7B2 variant 22 (RSV525), variant 24 (RSV526), variant 26 (RSV527) and variant 28 (RSV528). In all trivalents the Asp1 was mutated to Glu in the first building block. Sequences are shown in Table A-5. Formatted constructs were cloned into the *Pichia* vector pAX98, transformed, after which the number of genomic incorporations was determined. Test expressions in *Pichia pastoris* were typically done with a low and high copy number clone to verify expression levels.

TABLES

TABLE A-1

| Sequences of monovalent Nanobodies ® that bind RSV F protein | | |
|---|---|---|
| Nanobody ® | SEQ ID NO: | Sequence |
| 8A1 | 5 | EVQLVESGGGLVQPGGSLRVSCAASGFTFNDYIMGWFRQAPGKERMFIAAISG TGTIKYYGDLVRGRFTISRDNAKNTVYLRIDSLNPEDTAVYYCAARQDYGLGY RESHEYDYWGQGTQVTVSS |
| 8B10 | 6 | EVQLVESGGGLVQAGASLRLSCAASGLAFSRYAMGWFRQAPGKERESVAAISS SGDNIYYADSVEGQFTMSRDNAKSSVYLQMINLKPEDTAVYYCAATSPLFVAS DYFEASRYGYWGQGTQVTVSS |
| 13A1 | 7 | EVQLVESGGGLVQPGGSLRLSCAASGLTLDYYALGWFRQAPGKEREGVSCISS ADHSTTYADSVKGRFTISWDNAKNTVYLQMNSLKPEDTAVYYCAADPALGCYS GNYYPRYDYWGQGTQVTVSS |
| 13B4 | 8 | EVQLVESGGGLVQAGGSLRLSCAASGFTFDDYAIGWFRQAPGKEREAVSCISS SDGSTYYADSVKGRFTISSDNAKNMVYLQMNSLKPEDTAVYYCAADLLRTAVG CLDYRGTYYPRTTMDYRGKGTLVTVSS |
| 13C1 | 9 | EVQLVESGGGLVQPGGSLRLSCEASGFTWDYYVIGWFRQAPGKEREGLSCISS DGSTTYADSVKGRFTISRDNAKNTVYLQMNSLEPEDTAVYYCATDPALGCYSG SYYPRYDYWGQGTQVTVSS |
| 19E2 | 10 | EVQLVESGGGLVQPGGSLRLSCAASGLTLDYYALGWFRQAPGKEREGVSCISS SDHTTTYTDSVKGRFTISWDNAKNTLYLQMNSLKPEDTAVYYCAADPALGCYS GSYYPRYDFWGQCTQVTVSS |
| 13D1 | 11 | EVQLVESGGGLVQPGGSLRLSCATSGFTEDYYVIGWFRQAPGKEREGVSCMSS SGDSTTYADSVKGRFTISRDNAKNMVYLQMTSLKPEDTAVYYCAADFALGCYS GSYYPRYDYWGQGTQVTVSS |
| 13E12 | 12 | EVQLVESGGGLVQAGGSLRLSCAASGRTFSRYIMGWFRQAPGKEREFVGAISR SGDITSFADFVKGRFTMSRDNAKNTLYLQMNSLEPEDTAVYSCAANSDTYYIY SDIVVPERYDYWGQGTQVTVSS |
| 23E5 | 13 | EVQLMESGGGLVQAGGSLRLSCAASGGTFSSYAMGWFRQAPGEERDEVAAIGW SGNSPYYAQFVKGRFTISRDNAKNTVHLQMNSLKPEDTAVYYCAAAHNTMGSD YEGYDYWGQGTQVTVSS |
| 1B2 | 14 | EVQLVESGGGLVQAGGSLRLSCAASGPTFSADTMGNFRQAPGKEREFVATIPW SGGIAYYSDSVKGRFTMSRDNAKNTVDLQMNSLKPEDTALYYCAGSSRIYIYS DSLSERSYDYWGQGTQVTVSS |
| 1A2 | 15 | EVQLVESGGGLVQAGGSLRLSCAASERTFSYYAMGWFRQAPGKEREFVATISR SGEWIYYKDAMKGRFTISRDNANNAVYLQMNSLQPEDTAIYYCAADSLGGFRS ASDYYNTNTYAYWGQGTQVTVSS |
| 7B2 | 16 | EVQLVESGGGLVQAGDSLRLSCAASGRTFSSYAMGWFRQAPGKEREFVAAISW SDGSTYYADSVKGRFTISRDNAKNTVYLQMNSLKPEDTAVYYCAADLTSTNPG SYIYIWAYDYWGQGTQVTVSS |

TABLE A-1-continued

Sequences of monovalent Nanobodies ® that bind RSV F protein

| Nanobody ® | SEQ ID NO: | Sequence |
|---|---|---|
| 1A6 | 17 | EVQLVESGGGLVQAGGSLRLSCAASGRTFSSYAMGWFRQAPGKEREFVAAIWW<br>SGGSTYYADSVKGRFTMSRDNAKNTVYLEMNNLKPEDTAVYYCAADTDSSNSG<br>SYLYTWAYDYWGQGTQVTVSS |
| 1G8 | 18 | EVQLVESGGGSVQAGGSLRLSCAASGGSFNRFGMGWFRRAPGKERDFVAAINL<br>SGDTTYYVDSVQGRFTISRDNANNIMYLQMNLLKPEDTADYYCAADPDPITAW<br>KQSGAGMDYWGRGTQVTVSS |
| 1E4 | 19 | EVQLVESGGGLVQAGGSLRLSCEASGRTFSSYGMGWFRQAPGKEREFVAAVSR<br>LSGPRTVYADSVKGRFTISRDNAENTVYLQMNSLKPEDTAVYTCAAELTNRNP<br>GAYYYTWAYDYWGQGTQVTVSS |
| 1G3 | 20 | EVQLVESGGGLVQAGGSLRLSCEASGRTYSRYGMGWFRQAPGKEREFVAAVSR<br>LSGPRTVYADSVKGRFTISRDNAENTVYLQMNSLKPEDTAVYTCAAELTNRNS<br>GAYYYAWAYDYWGQGTQVTVSS |
| 19C4 | 21 | EVQLVESGGGLVQAGGSLRLSCAASGRSFSNYVLGWFRQAPGKEREFVAAISF<br>RGDSAIGAPSVEGRFTISRDNAKNTGYLQMNSLVPDDTAVYYCGAGTPLNPGA<br>YIYEWSYDYWGRGTQVTVSS |
| 20B2 | 22 | EVQLVESGGGLVQAGGSLRLSCEASGRTFSSYDMGWFRQAPGKEREFVAAVTR<br>WSGARGVYADSVKGRFTISRDNAENTVHLQMNSLKPEDTAVYTCAADSINRNS<br>GAVYYTWAYDYWGQGTQVTVSS |
| 20C1 | 23 | EVQLVESGGGLVQAGGSLRLSCAASGRTFSSFAMGWFRQAPGKEREFVAAISW<br>SGGSTYYADSVKGRFTISGDNAKNTMYLQMNSLKPEDTAVYYCAADSEILNSG<br>AYYYSWAYVYWGQGTQVTVSS |
| NC41 | 24 | EVQLVESGGGLVQAGGSLSISCAASGGSLSNYVLGWFRQAPGKEREFVAAINW<br>RGDITIGPPNVEGRFTISRDNAKNTGYLQMNSLAPDDTAVYYCGAGTPLNPGA<br>YIYDWSYDYWGRGTQVTVSS |

TABLE A-2

F-protein sequences

| F-protein | SEQ ID NO: | Sequence |
|---|---|---|
| RSV LONG M-2 | 66 | MELPILKANAITTILAAVTFCFASSQNITEEFYQSTCSAYSKG<br>YLSALRTGWYTSVITIELSNIKENKCNGTDAKVKLIKQELDKY<br>KNAVTELQLLMQSTPAANNRARRELPRFMNYTLNNTKKTNVTL<br>SKKRKRRFLGFLLGVGSAIASGTAVSKVLHLEGEVNKIKSALL<br>STNKAVVSLSNGVSVLTSKVLDLKNYIDKQLLPIVNKQSCRIS<br>NTETVIEFQQKNNRLLEITREFSVNAGVTTPVSTYMLTNSELL<br>SLINDMPITNDQKKLMSNNVQIVRQQSYSIMSIIKEEVLAYVV<br>QLPLYGVIDTPCWKLHTSPLCTTNTKEGSNICLTRTDRGWYCD<br>NAGSVSFFPQAETCKVQSNRVFCDTMNSLTLPSEVNLCNVDIF<br>NPKYDCKIMTSKTDVSSSVITSLGAIVSCYGKTKCTASNKNRG<br>IIKTFSNGCDYVSNKGVDTVSVGNTLYYVNKQEGKSLYVKGEP<br>IINFYDPLVFPSDEFDASISQVNEKINQSLAFIRKSDELLHHV<br>NAGKSTTNIMITTIIIVIIVILLSLIAVGLLLYCKARSTPVTL<br>SKDQLSGINNIAFSN |
| RSV A-2 | 67 | MELLILKANAITTILTAVTFCFASGQNITEEFYQSTCSAVSKG<br>YLSALRTGWYTSVITIELSNIKKNKCNGTDAKVKLIKQELDKY<br>KNAVTELQLLMQSTQATNNRARRELPRFMNYTLNNAKKTNVTL<br>SKKRKRRFLGFLLGVGSAIASGVAVSKVLKLEGEVNKIKSALL<br>STNKAVVSLSNGVSVLTSKVLDLKNYIDKQLLPIVNKQSCSIS<br>NIETVIEFQQKNNRLLEITREFSVNAGVTTPVSTYMLTNSELL<br>SLINDMPITNDQKKLMSNNVQIVRQQSYSIMSIIKEEVLAYVV<br>QLPLYGVIDTPCWKLHTSPLCTTNTKEGSNICLTRTDRGWYCD<br>NAGSVSFFPQAETCKVQSNRVFCDTMNSLTLPSEVNLCNVDIF<br>NPKYDCKIMTSKTDVSSSVITSLGAIVSCYGKTKCTASNKNRG<br>IIKTFSNGCDYVSNKGVDTVSVGNTLYYVNKQEGKSLYVKGEP<br>IINFYDPLVFPSDEFDASISQVNEKINQSLAFIRKSDELLHNV<br>NAGKSTTNIMITTIIIVIIVILLSLIAVGLLLYCKARSTPVTL<br>SKDQLSGINNIAFSN |
| RSV B-1 | 68 | MELLIHRSSAIFLTLAVNALYLTSSQNITEEFYQSTCSAVSRG<br>YFSALRTGWYTSVITIELSNIKETKCNGTDTKVKLIKQELDKY<br>KNAVTELQLLMQNTPAANNRARREAPQYMNYTINTTKNLNVSI<br>SKKRKRRFLGFLLGVGSAIASGIAVSKVLHLEGEVNKIKNALL<br>STNKAVVSLSNGVSVLTSKVLDLKNYINNRLLPIVNQQSCRIS |

TABLE A-2-continued

F-protein sequences

| F-protein | SEQ ID NO: | Sequence |
|---|---|---|
| | | NIETVIEFQQMNSRLLEITREFSVNAGVTTPLSTYMLTNSELL SLINDMPITNDQKKLMSSNVQIVRQQSYSIMSIIKEEVLAYVV QLPTYGVIDTPCWKLHTSPLCTTNIKEGSNICLTRTDRGWYCD NAGSVSFFPQADTCKVQSNRVFCDTMNSLTLPSEVSLCNTDIF NSKYDCKIMTSKTDISSSVITSLGAIVSCYGKTKCTASNKNRG IIKTFSNGCDYVSNKGVDTVSVGNTLYYVNKLEGKNLYVKGEP IINYYDPLVFPSDEFDASISQVNEKINQSLAFIRRSDELLHNV NTGKSTTNIMITTIIIVIIVVLLLLIAIGLLLYCKAKNTPVTL SKDQLSGINNIAFSK |

TABLE A-3

Amino acid sequences of multivalent constructs that bind hRSV

| Construct | SEQ ID NO: | Sequence |
|---|---|---|
| R2V501 | 26 | EVQLVESGGGLVQAGDSLRLSCAASGRTFSSYAMGWFRQAPGKEREFVAAISW SDGSTYYADSVKGRFTISRDNAKNTVYLQMNSLKPEDTAVYYCAADLTSTNPG SYIYIWAYDYWGQGTQVTVSSGGGGSGGGGSGGGGSEVQLVESGGGLVQAGDS LRLSCAASGRTFSSYAMGWFRQAPGKEREFVAAISWSDGSTYYADSVKGRFTI SRDNAKNTVYLQMNSLKPEDTAVYYCAADLTSTNPGSYIYIWAYDYWGQGTQV TVSSGGGGSGGGGSGGGGSEVQLVESGGGLVQAGDSLRLSCAASGRTFSSYAM GWFRQAPGKEREFVAAISWSDGSTYYADSVKGRFTISRDNAKNTVYLQMKSLK PEDTAVYYCAADLTSTNPGSYIYIWAYDYWGQGTQVTVSS |
| RSV502 | 27 | EVQLVESGGGLVQAGGSLRLSCEASGRTFSSYGMGWFRQAPGKEREFVAAVSR LSGPRTVYADSVKGRFTISRDNAENTVYLQMNSLKPEDTAVYTCAAELTNRNR GAYYYTWAYDYWGQGTQVTVSSGGGGSGGGGSGGGGSEVQLVESGGGLVQAGG SLRLSCEASGRTFSSYGMGWFRQAPGKEREFVAAVSRLSGPRTVYADSVKGRF TISRDNAENTVYLQMNSLKPEDTAVYTCAAELTNRNPGAYYYTWAYDYWGQGT QVTVSSGGGGSGGGGSGGGGSEVQLVESGGGLVQAGGSLRLSCEASGRTFSSY GMGWFRQAPGKEREFVAAVSRLSGPRTVYADSVKGRFTISRDNAENTVYLQMN SLKPEDTAVYTCAAELTNRNPGAYYYTWAYDYWGQGTQVTVSS |
| RSV513 | 28 | EVQLVESGGGLVQAGDSLRLSCAASGRTFSSYAMGWFRQAPGKEREFVAAISW SDGSTYYADSVKGRFTISRDNAKNTVYLQMNSLKPEDTAVYYCAADLTSTNPG SYIYIWAYDYWGQGTQVTVSSGGGGSGGGGSGGGGSEVQLVESGGGLVQPGGS LRLSCAASGLTLDYYALGWFRQAPGKEREGVSCISSSDHTTTYTDSVKGRFTI SWDNAKNTLYLQMNSLKPEDTAVYYCAADPALGCYSGSYYPRYDFWGQGTQVT VSSGGGGSGGGGSGGGGSEVQLVESGGGLVQAGDSLRLSCAASGRTFSSYAMG WFRQAPGKEREFVAAISWSDGSTYYADSVKGRFTISRDNAKNTVYLQMNSLKP EDTAVYYCAADLTSTNPGSYIYIWAYDYWGQGTQVTVSS |
| RSV514 | 29 | EVQLVESGGGLVQAGDSLRLSCAASGRTFSSYAMGWFRQAPGKEREFVAAISW SDGSTYYADSVKGRFTISRDNAKNTVYLQMNSLKPEDTAVYYCAADLTSTNPG SYIYIWAYDYWGQGTQVTVSSGGGGSGGGSEVQLVESGGGLVQPGGSLRLSCA ASGLTLDYYALGWFRQAPGKEREGVSCISSSDHTTTYTDSVKGRFTISWDNAK NTLYLQMNSLKPEDTAVYYCAADPALGCYSGSYYPRYDFWGQGTQVTVSSGGG GSGGGSEVQLVESGGGLVQAGDSLRLSCAASGRTFSSYAMGWFRQAPGKEREF VAAISWSDGSTYYADSVKGRFTISRDNAKNTVYLQMNSLKPEDTAVYYCAADL TSTNPGSYIYIWAYDYWGQGTQVTVSS |
| RSV515 | 30 | EVQLVESGGGLVQAGDSLRLSCAASGRTFSSYAMGWFRQAPGKEREFVAAISW SDGSTYYADSVKGRFTISRDNAKNTVYLQMNSLKPEDTAVYYCAADLTSTNPG SYIYIWAYDYWGQGTQVTVSSGGGGSGGGGSGGGGSEVQLVESGGGLVQPGGS LRVSCAASGFTFNDYIMGWFRQAPGKERMFIAAISGTGTIKYYGDLVRGRFTI SRDNAKNTVYLRIDSLNPEDTAVYYCAARQDYGLGYRESHEYDYWGQGTQVTV SSGGGGSGGGGSGGGGSEVQLVESGGGLVQAGDSLRLSCAASGRTFSSYAMGW FRQAEGKEREFVAAISWSDGSTYYADSVKGRFTISRDNAKNTVYLQMNSLKPE DTAVYYCAADLTSTNPGSYIYIWAYDYWGQGTQVTVSS |
| RSV516 | 31 | EVQLVESGGGLVQAGDSLRLSCAASGRTFSSYAMGWFRQAPGKEREFVAAISW SDGSTYYADSVKGRFTISRDNAKNTVYLQMNSLKPEDTAVYYCAADLTSTNPG SYIYIWAYDYWGQGTQVTVSSGGGGSGGGSEVQLVESGGGLVQPGGSLRVSCA ASGFTFKDYIMGWFRQAPGKERMFIAAISGTGTIKYYGDLVRGRFTISRDNAK NTVYLRIDSLNPEDTAVYYCAARQDYGLGYRESHEYDYWGQGTQVTVSSGGGG SGGGSEVQLVESGGGLVQAGDSLRLSCAASGRTFSSYAMGWFRQAPGKEREFV AAISWSDGSTYYADSVKGRFTISRDNAKNTVYLQMNSLKPEDTAVYYCAADLT STNPGSYIYIWAYDYWGQGTQVTVSS |
| RSV407 | 32 | EVQLVESGGGLVQAGGSLSISCAASGGSLSNYVLGWFRQAPGKEREFVAAINW RGDITIGPPNVEGRFTISRDNAKNTGYLQMNSLAPDDTAVYYCGAGTPLNPGA YIYDWSYDYWGRGTQVTVSSGGGGSGGGGSGGGGSEVQLVESGGGLVQAGGSL |

TABLE A-3-continued

Amino acid sequences of multivalent constructs that bind hRSV

| Construct | SEQ ID NO: | Sequence |
|---|---|---|
| | | SISCAASGGSLSNYVLGWFRQAPGKEREFVAAINWRGDITIGPPNVEGRFTIS RDNAKNTGYLQMNSLAPDDTAVYYCGAGTPLNPGAYIYDWSYDYWGRGTQVTV SSGGGGSGGGGSGGGGSEVQLVESGGGLVQAGGSLSISCAASGGSLSNYVLGW FRQAPGKEREFVAAINWRGDITIGPPNVEGRFTISRDNAKNTGYLQMNSLAPD DTAVYYCGAGTPLNPGAYIYDWSYDYWGRGTQVTVSS |

TABLE A-4

Sequences of humanized and/or sequence optimized 7B2 variants

| Nanobody | SEQ ID | Sequence |
|---|---|---|
| 7B2v22 | 33 | EVQLVESGGGLVQPGDSLRLSCAASGRTFSSYAMGWFRQAPGKEREFVAAISWSDG STYYADSVKGRFTISRDNAKNTVYLQMNSLRPEDTAVYYCAADLTSTNPGSYIYIW AYDYWGQGTLVTVSS |
| 7B2v23 | 34 | DVQLVESGGGLVQPGDSLRLSCAASGRTFSSYAMGWFRQAPGKEREFVAAISWSDG STYYRDSVKGRFTISRDNAKNTVYLQMNSLRPEDTAVYYCAADLTSTNPGSYIYIW AYDYWGQGILVTVSS |
| 7B2v24 | 35 | EVQLVESGGGLVQPGGSLRLSCAASGRTFSSYAMGWFRQAPGKEREFVAAISWSDG STYYADSVKGRFTISRDNAKNTVYLQMNSLRPEDTAVYYCAADLTSTNPGSYIYIW AYDYWGQGTLVTVSS |
| 7B2v25 | 36 | DVQLVESGGGLVQPGGSLRLSCAASGRTFSSYAMGWFRQAPGKEREFVAAISWSDG STYYADSVKGRFTISRDNAKNTVYLQMNSLRPEDTAVYYCAADLTSTNPGSYIYIW AYDYWGQGTLVTVSS |
| 7B2v26 | 37 | EVQLVESGGGLVQPGGSLRLSCAASGRTFSSYAMGWFRQAPGKEREFVAATSWSEG STYYADSVKGRFTISRDNAKNTVYLQMNSLRPEDTAVYYCAADLTSTNPGSYIYIW AYDYWGQGTLVTVSS |
| 7B2v27 | 38 | DVQLVESGGGLVQPGGSLRLSCAASGRTFSSYAMGWFRQAPGKEREFVAAISWSEG STYYADSVKGRFTISRDNAKNTVYLQMNSLRPEDTAVYYCAADLTSTNPGSYIYIW AYDYWGQGTLVTVSS |
| 7B2v28 | 39 | EVQLVESGGGLVQPGGSLRLSCAASGRTFSSYAMGWFRQAPGKEREFVAAISWSDA STYYADSVKGRFTISRDNAKNTVYLQMNSLRPEDTAVYYCAADLTSTNPGSYIYIW AYDYWGQGTLVTVSS |
| 7B2v29 | 40 | DVQLVESGGGLVQPGGSLRLSCAASGRTFSSYAMGWFRQAPGKEREFVAAISWSDA STYYADSVKGRFTISRDNAKNTVYLQMNSLRPEDTAVYYCAADLTSTNPGSYIYIW AYDYWGQGTLVTVSS |
| RSV536 | 51 | DVQLVESGGGLVQAGDSLRLSCAASGRTFSSYAMGWFRQAPGKEREFVAAISWSDG STYYADSVKGRFTISRDNAKNTVYLQMNSLKPEDTAVYYCAADLTSTNPGSYIYIW AYDYWGQGTQVTVSS |

TABLE A-5

Amino acid sequence of multivalent humanized and/or sequence optimized constructs that bind hRSV

| Nanobody ® | SEQ ID NO | Sequence |
|---|---|---|
| RSV525 | 41 | DVQLVESGGGLVQPGDSLRLSCAASGRTFSSYAMGWFRQAPGKEREFVAAISWSDGSTYYA DSVKGRFTISRDNAKNTVYLQMNSLRPEDTAVYYCAADLTSTNPGSYIYIWAYDYWGQGTL VTVSSGGGGSGGGGSGGGGSEVQLVESGGGLVQPGDSLRLSCAASGRTFSSYAMGWFRQAP GKEREFVAAISWSDGSTYYADSVKGRFTISRDNAKNTVYLQMNSLRPEDTAVYYCAADLTS TNPGSYIYIWAYDYWGQGTLVTVSSGGGGSGGGGSGGGGSEVQLVESGGGLVQPGDSLRLS CAASGRTFSSYAMGWFRQAPGKEREFVAAISWSDGSTYYADSVKGRFTISRDNAKNTVYLQ MNSLRPEDTAVYYCAADLTSTNPGSYIYIWAYDYWGQGTLVTVSS |

TABLE A-5-continued

Amino acid sequence of multivalent humanized and/or sequence optimized constructs that bind hRSV

| Nanobody ® | SEQ ID NO | Sequence |
|---|---|---|
| RSV526 | 42 | DVQLVESGGGLVQPGGSLRLSCAASGRTFSSYAMGWFRQAPGKEREFVAAISWSDGSTYYA<br>DSVKGRFTISRDNAKNTVYLQMNSLRPEDTAVYYCAADLTSTNPGSYIYIWAYDYWGQGTL<br>VTVSSGGGGSGGGGSGGGGSEVQLVESGGGLVQPGGSLRLSCAASGRTFSSYAMGWFRQAP<br>GKEREFVAAISWSDGSTYYADSVKGRFTISRDNAKNTVYLQMNSLRPEDTAVYYCAADLTS<br>TNPGSYIYIWAYDYWGQGTLVTVSSGGGGSGGGGSGGGGSEVQLVESGGGLVQPGGSLRLS<br>CAASGRTFSSYAMGWFRQAPGKEREFVAAISWSDGSTYYADSVKGRFTISRDNAKNTVYLQ<br>MNSLRPEDTAVYYCAADLTSTNPGSYIYIWAYDYWGQGTLVTVSS |
| RSV527 | 43 | DVQLVESGGGLVQPGGSLRLSCAASGRTFSSYAMGWFRQAPGKEREFVAAISWSEGSTYYA<br>DSVKGRFTISRDNAKNTVYLQMNSLRPEDTAVYYCAADLTSTNPGSYIYIWAYDYWGQGTL<br>VTVESGGGGSGGGGSGGGGSEVQLVESGGGLVQPGGSLRLSCAASGRTFSSYAMGWFRQAP<br>GKEREFVAAISWSEGSTYYADSVKGRFTISRDNAKNTVYLQMNSLRPEDTAVYYCAADLTS<br>TNPGSYIYIWAYDYWGQGTLVTVSSGGGGSGGGGSGGGGSEVQLVESGGGLVQPGGSLRLS<br>CAASGRTFSSYAMGWFRQAPGKEREFVAAISWSEGSTYYADSVKGRFTISRDNAKNTVYLQ<br>MNSLRPEDTAVYYCAADLTSTNPGSYIYIWAYDYWGQGTLVTVSS |
| RSV528 | 44 | DVQLVESGGGLVQPGGSLRLSCAASGRTFSSYAMGWFRQAPGKEREFVAAISWSDASTYYA<br>DSVKGRFTISRDNAKNTVYLQMNSLRPEDTAVYYCAADLTSTNPGSYIYIWAYDYWGQGTL<br>VTVGSGGGGSGGGGSGGGGSEVQLVESGGGLVQPGGSLRLSCAASGRTFSSYAMGWFRQAP<br>GKEREFVAAISWSDASTYYADSVKGRFTISRDNAKNTVYLQMNSLRPEDTAVYYCAADLTS<br>TNPGSYIYIWAYDYWGQGTLVTVSSGGGGSGGGGSGGGGSEVQLVESGGGLVQPGGSLRLS<br>CAASGRTFSSYAMGWFRQAPGKEREFVAAISWSDASTYYADSVKGRFTISRDNAKNTVYLQ<br>MNSLRPEDTAVYYCAADLTSTNPGSYIYIWAYDYWGQGTLVTVSS |
| RSV531 | 45 | EVQLVESGGGLVQPGDSLRLSCAASGRTFSSYAMGWFRQAPGKEREFVAAISWSDGSTYYA<br>DSVKGRFTISRDNAKNTVYLQMNSLRPEDTAVYYCAADLTSTNPGSYIYIWAYDYWGQGTL<br>VTVSSGGGGSGGGGSGGGGSEVQLVESGGGLVQPGDSLRLSCAASGRTFSSYAMGWFRQAP<br>GKEREFVAAISWSDGSTYYADSVKGRFTISRDNAKNTVYLQMNSLRPEDTAVYYCAADLTS<br>TNPGSYIYIWAYDYWGQGTLVTVSSGGGGSGGGGSGGGGSEVQLVESGGGLVQPGDSLRLS<br>CAASGRTFSSYAMGWFRQAPGKEREFVAAISWSDGSTYYADSVKGRFTISRDNAKNTVYLQ<br>MNSLRPEDTAVYYCAADLTSTNPGSYIYIWAYDYWGQGTLVTVSS |
| RSV531' | 46 | VQLVESGGGLVQPGDSLRLSCAASGRTFSSYAMGWFRQAPGKEREFVAAISWSDGSTYYAD<br>SVKGRFTISRDNAKNTVYLQMNSLRPEDTAVYYCAADLTSTNPGSYIYIWAYDYWGQGTLV<br>TVSSGGGGSGGGGSGGGGSEVQLVESGGGLVQPGDSLRLSCAASGRTFSSYAMGWFRQAPG<br>KEREFVAAISWSDGSTYYADSVKGRFTISRDNAKNTVYLQMNSLRPEDTAVYYCAADLTST<br>NPGSYIYIWAYDYWGQGTLVTVSSGGGGSGGGGSGGGGSEVQLVESGGGLVQPGDSLRLSC<br>AASGRTFSSYAMGWFRQAPGKEREFVAAISWSDGSTYYADSVKGRFTISRDNAKNTVYLQM<br>NSLRPEDTAVYYCAADLTSTNPGSYIYIWAYDYWGQGTLVTVSS |
| RSV532 | 47 | EVQLVESGGGLVQPGGSLRLSCAASGRTFSSYAMGWFRQAPGKEREFVAAISWSDGSTYYA<br>DSVKGRFTISRDNAKNTVYLQMNSLRPEDTAVYYCAADLTSTNPGSYIYIWAYDYWGQGTL<br>VTVSSGGGGSGGGGSGGGGSEVQLVESGGGLVQPGGSLRLSCAASGRTFSSYAMGWFRQAP<br>GKEREFVAAISWSDGSTYYADSVKGRFTISRDNAKNTVYLQMNSLRPEDTAVYYCAADLTS<br>TNPGSYIYIWAYDYWGQGTLVTVSSGGGGSGGGGSGGGGSEVQLVESGGGLVQPGGSLRLS<br>CAASGRTFSSYAMGWFRQAPGKEREFVAAISWSDGSTYYADSVKGRFTISRDNAKNTVYLQ<br>MNSLRPEDTAVYYCAADLTSTNPGSYIYIWAYDYWGQGTLVTVSS |
| RSV533 | 48 | EVQLVESGGGLVQPGGSLRLSCAASGRTFSSYAMGWFRQAPGKEREFVAAISWSEGSTYYA<br>DSVKGRFTISRDNAKNTVYLQMNSLRPEDTAVYYCAADLTSTNPGSYIYIWAYDYWGQGTL<br>VTVSSGGGGSGGGGSGGGGSEVQLVESGGGLVQPGGSLRLSCAASGRTFSSYAMGQFRQAP<br>GKEREFVAAISWSEGSTYYADSVKGRFTISRDNAKNTVYLQMNSLRPEDTAVYYCAADLTS<br>TNPGSYIYIWAYDYWGQGTLVTVSSGGGGSGGGGSGGSGSEVQLVESGGGLVQPGGSLRLS<br>CAASGRTFSSYAMGWFRQAPGKEREFVAAISWSEGSTYYADSVKGRFTISRDNAKNTVYLQ<br>MNSLRPEDTAVYYCAADLTSTNPGSYIYIWAYDYWGQGTLVTVSS |
| RSV534 | 49 | EVQLVESGGGLVQPGGSLRLSCAASGRTFSSYAMGWFRQAPGKEREFVAAISWSDASTYYA<br>DSVKGRFTISRDNAKNTVYLQMNSLRPEDTAVYYCAADLTSTNPGSYIYIWAYDYWGQGTL<br>VTVSSGGGGSGGGGSGGGGSEVQLVESGGGLVQPGGSLRLSCAASGRTFSSYAMGWFRQAP<br>GKEREFVAAISWSDASTYYADSVKGRFTISRDNAKNTVYLQMNSLRPEDTAVYYCAADLTS<br>TNPGSYIYIWAYDYWGQGTLVTVSSGGGGSGGGGSGGGGSEVQLVESGGGLVQPGGSLRLS<br>CAASGRTFSSYAMGWFRQAPGKEREFVAAISWSDASTYYADSVKGRFTISRDNAKNTVYLQ<br>MNSLRPEDTAVYYCAADLTSTNPGSYIYIWAYDYWGQGTLVTVSS |
| RSV535 | 50 | DVQLVESGGGLVQAGDSLRLSCAASGRTFSSYAMGWFRQAPGKEREFVAAISWSDGSTYYA<br>DSVKGRFTISRDNAKNTVYLQMNSLKPEDTAVYYCAADLTSTNPGSYIYIWAYDYWGQGTQ<br>VTVSSGGGGSGGGGSGGGGSEVQLVESGGGLVQAGDSLRLSCAASGRTFSSYAMGWFRQAP<br>GKEREFVAAISWSDGSTYYADSVKGRFTISRDNAKNTVYLQMNSLKPEDTAVYYCAADLTS<br>TNPGSYIYIWAYDYWGQGTQVTVSSGGGGSGGGGSGSGGSEVQLVESGGGLVQAGDSLRDS<br>CAASGRTFSSYAMGWFRQAPGKEREFVAAISWSDGSTYYADSVKGRFTISRDNAKNTVYLQ<br>MNSLKPEDTAVYYCAADLTSTNPGSYIYIWAYDYWGQGTQVTVSS |

TABLE A-6

| Linker | SEQ ID NO: | Sequences |
|---|---|---|
| 5GS | 52 | GGGGS |
| 7GS | 53 | SGGSGGS |
| 9GS | 54 | GGGGSGGGS |
| 10GS | 55 | GGGGSGGGGS |
| 15GS | 56 | GGGGSGGGGSGGGGS |
| 18GS | 57 | GGGGSGGGGSGGGGGGS |
| 20GS | 58 | GGGGSGGGGSGGGGSGGGGS |
| 25GS | 59 | GGGGSGGGGSGGGGSGGGGSGGGGS |
| 30GS | 60 | GGGGSGGGGSGGGGSGGGGSGGGGSGGGGS |
| 35GS | 61 | GGGGSGGGGSGGGGSGGGGSGGGGSGGGGSGGGGS |
| G1 hinge | 62 | EPKSCDKTHTCPPCP |
| 9GS-G1 hinge | 63 | GGGGSGGGSEPKSCDKTHTCPPCP |
| G3 hinge | 64 | ELKTPLGDTTHTCPRCPEPKSCDTPPPCPRCPEPKSCDTPPPCPRCPEPKSCDTPPPCPRCP |
| 3Ala | 65 | AAA |

TABLE B-1

Screening for Nanobodies that bind epitope class II and IV-VI on the F-protein of RSV Long and B-1

| Clone | Llama | Selection | Family | Epitope class | Binding Long 1:10 PE (Fold blanc) | Hep2-B-1 (% control) | | % inhibition 101F Fab | | | % inhibition Synagis |
|---|---|---|---|---|---|---|---|---|---|---|---|
| | | | | | | 1:50 PE | 1:200 PE | 1:100 PE | 1:300 PE | 1:1000 PE | 1:10 PE |
| PMP8A1 | 206 | R1 trypsin | 1 | IV-VI | 3.7 | 98 | 92 | 82 | 55 | 20 | |
| PMP13A1 | 206 | R1 + 2 101F | 4sub1 | IV-VI | 2.9 | 84 | 65 | 74 | 46 | 13 | |
| PMP13C1 | 206 | R1 + 2 101F | 4sub1 | IV-VI | 3.0 | 104 | 86 | 57 | 37 | 9 | |
| PMP19E2 | 206 | R1 101F; R2 peptide | 4sub2 | IV-VI | 3.5 | 87 | 58 | 74 | 27 | 5 | |
| PMP13D1 | 206 | R1 + 2 101F | 4sub3 | IV-VI | 3.1 | 93 | 75 | 77 | 52 | 16 | |
| PMP13B4 | 206 | R1 + 2 101F | 5 | IV-VI | 2.7 | 75 | 56 | 82 | 47 | 20 | |
| PMP8B10 | 207 | R1 trypsin | 11 | IV-VI | 3.5 | 94 | 84 | 56 | 31 | 6 | |
| PMP13E12 | 207 | R1 + 2 101F | 14 | IV-VI | 3.7 | 97 | 75 | 74 | 28 | 8 | |
| PMP23E5 | 212 | R1 + 2 RSV-101F | 23 | IV-VI | 3.4 | 103 | 82 | 37 | 16 | — | |
| PMP1B2 | 156 | R1 RSV trypsin | LG21 | IV-VI | 3.8 | 88 | 85 | 82 | 58 | 25 | |
| PMP1A2 | 156 | R1 RSV trypsin | LG34 | IV-VI | 4.0 | 86 | 66 | 83 | 27 | 5 | |
| PMP7B2 | 212 | R1 trypsin | 16 | II | 4.7 | 61 | 41 | | | | 70 |
| PMP19C4 | 207 | R1 101F; R2 peptide | 29 | II | 2.5 | 72 | 50 | | | | 39 |
| PMP1A6 | 156 | R1 RSV trypsin | LG3-3 | II | 4.2 | 57 | 39 | | | | 67 |
| PMP1E4 | 156 | R1 RSV trypsin | LG3-2 | II | 3.6 | 55 | 55 | | | | 55 |
| PMP1G3 | 156 | R1 RSV trypsin | LG3-2 | II | 3.4 | 52 | 45 | | | | 52 |
| PMP1E5 | 156 | R1 RSV trypsin | LG3-1 | II | 3.4 | 54 | 37 | | | | 41 |
| PMP20B2 | 156 | R1 101F | LG3-1 | II | 3.0 | 32 | 32 | | | | 33 |
| PMP20C1 | 156 | R1 101F | LG40 | II | 2.7 | 37 | 35 | | | | 33 |
| PMP1G8 | 156 | R1 RSV trypsin | LG47 | II | 3.7 | 73 | 43 | | | | 57 |

TABLE B-2

Characteristics of hRSV Nanobodies

| Clone | Family | Epitope class | Neutralization Long IC50 (nM) | Neutralization B-1 IC50 (nM) | Competition 101F Fab IC50 (M) | Competition Synagis IC50 (M) | Kinetic analysis (Biacore) ka (1/Ms) | Kinetic analysis (Biacore) kd (1/s) | Kinetic analysis (Biacore) KD (nM) | Tm (° C.) |
|---|---|---|---|---|---|---|---|---|---|---|
| PRSV8A1 | 1 | IV-VI | — | 12230 | 2.81E−09 | | | | | 70.5 |
| PRSV8B10 | 11 | IV-VI | — | >15000 | 4.66E−09 | | 1.8E+05 | 3.4E−04 | 1.9 | 63.8 |
| PRSV13B4 | 5 | IV-VI | — | >15000 | 3.69E−09 | | | | | 69.5 |
| PRSV13A1 | 4sub1 | IV-VI | — | 6158 | 4.23E−09 | | 5.7E+05 | 3.5E−04 | 0.61 | 69.7 |
| PRSV13C1 | 4sub1 | IV-VI | — | 11400 | 3.83E−09 | | | | | 71.4 |
| PRSV19E2 | 4sub2 | IV-VI | — | 4554 | 2.93E−09 | | 4.6E+05 | 2.4E−04 | 0.52 | 69.4 |
| PRSV13D1 | 4sub3 | IV-VI | — | 5850 | 3.37E−09 | | | | | 69.6 |
| PRSV13E12 | 14 | IV-VI | — | 12320 | 3.52E−09 | | 1.1E+05 | 1.6E−04 | 1.5 | 69.8 |
| PRSV23E5 | 23 | IV-VI | — | >15000 | 1.73E−09 | | 1.6E+05 | 1.3E−03 | 7.9 | 65.6 |
| PRSV1B2 | LG21 | IV-VI | — | 7382 | 2.91E−09 | | 3.8E+05 | 1.7E−04 | 0.44 | 62.6 |
| PRSV1A2 | LG34 | IV-VI | — | 13690 | 2.90E−09 | | | | | 74.7 |
| PRSV7B2 | 16 | II | 108 | >10000 | | 1.93E−09 | 3.4E+05 | 4.9E−04 | 1.5 | 84.2 |
| PRSV19C4 | 29 | II | 332 | >10000 | | 2.09E−07 | | | | 70.8 |
| PR5V20B2 | LG3-1 | II | 1758 | >10000 | | ND | | | | ND |
| PRSV1E4 | LG3-2 | II | 463 | >10000 | | 4.37E−08 | | | | 64.5 |
| PRSV1G3 | LG3-2 | II | 413 | >10000 | | 7.25E−08 | | | | 62.8 |
| PRSV1A6 | LG3-3 | II | 4500 | >10000 | | ND | | | | ND |
| PRSV20C1 | LG40 | II | 5286 | >10000 | | ND | | | | ND |
| PRSV1G8 | LG | II | 10000 | >10000 | | ND | | | | ND |
| Synagis | | | 5.96 | 3.9 | | | 2.8E+05 | 1.8E−04 | 0.64 | |
| 101F fab | | | nd | 180 | | | | | | |
| NC41 | | | 221 | | | 4.16E−07 | 8.2E+05 | 6.7E−03 | 8.1 | 69.9 |

TABLE B-3

Nomenclature for multivalent Nanobody ® constructs directed against hRSV F-protein

| Name | Tag | Construct | SEQ ID NO |
|---|---|---|---|
| RSV501 | Myc-His6 | 7B2-15GS-7B2-15GS-7B2 | 26 |
| RSV502 | Myc-His6 | 1E4-15GS-1E4-15GS-1E4 | 27 |
| RSV513 | Myc-His6 | 7B2-15GS-19E2-15GS-7B2 | 28 |
| RSV514 | Myc-His6 | 7B2-9GS-19E2-9GS-7B2 | 29 |
| RSV515 | Myc-His6 | 7B2-15GS-8A1-15GS-7B2 | 30 |
| RSV516 | Myc-His6 | 7B2-9GS-8A1-9GS-7B2 | 31 |
| RSV407 | Myc-His6 | NC41-15GS-NC41-15GS-NC41 | 32 |

The invention claimed is:

1. A monovalent polypeptide that specifically binds protein F of hRSV comprising SEQ ID NO: 16 wherein one or more amino acid residues have been mutated selected from the group consisting of:
   (a) Glu1Asp;
   (b) Ala14Pro Lys83Arg and Gln108Leu;
   (c) Asp16Gly;
   (d) Asp54Glu; and
   (e) Gly55Ala,
   wherein said positions are determined according to Kabat numbering.

2. A polypeptide that specifically binds protein F of hRSV comprising a VHH, a humanized VHH, a camelized VH or a domain antibody with:
   a) the amino acid sequence of any one of SEQ ID NO: 33, 34, 35, 36, 37, 38, 39 or 40; or
   b) an amino acid sequence having no more than 3, preferably no more than 2, more preferably no more than 1 amino acid difference with the amino acid sequence of any one of SEQ ID NO: 33, 34, 35, 36 37, 38, 39, or 40, provided that:
      i) the amino acid sequence of the VHH, humanized VHH, camelized VH or the domain antibody has Proline (Pro, P) at position 14, Arginine (Arg, R) at position 83 and Leucine (Leu, L) at position 108, wherein said positions are determined according to Kabat numbering;
      ii) the VHH, humanized VHH, camelized VH or the domain antibody comprises the following CDR sequences:
         CDR1 is SYAMG (amino acids 31-35 of SEQ ID NO:33);
         CDR2 is AISWSDGSTYYADSVKG (amino acids 50-66 of SEQ ID NO:33), AISWSEGSTYYADSVKG (amino acids 50-66 of SEQ ID NO:37), or AISWSDASTYYADSVKG (amino acids 50-66 of SEQ ID NO:39); and
         CDR3 is DLTSTNPGSYIYIWAYDY (amino acids 99-116 of SEQ ID NO:33); and
      iii) the polypeptide binds protein F of hRSV with the same, about the same, or a higher affinity, and/or the polypeptide has the same, about the same, or a higher potency compared to the polypeptide without the 3, 2 or 1 amino acid difference.

3. The polypeptide according to claim 2, comprising
   a) the amino acid sequence of any one of SEQ ID NO: 35, 36, 37, 38, 39 or 40; or
   b) an amino acid sequence having no more than 3, preferably no more than 2, more preferably no more than 1 amino acid difference with the amino acid sequence of any one of SEQ ID NO: 35, 36, 37, 38, 39, or 40, provided that:
      i) the amino acid sequence of the VHH, humanized VHH, camelized VH or the domain antibody has
         Proline (Pro, P) at position 14, Arginine (Arg, R) at position 83, and Leucine (Leu, L) at position 108; and
         Glycine (Gly, G) at position 16, Glutamic acid (Glu, E) at position 54 and/or Alanine (Ala, A) at position 55,
         wherein said positions are determined according to Kabat numbering; and
      ii) the polypeptide binds protein F of hRSV with the same, about the same, or a higher affinity and/or polypeptide has the same, about the same, or a higher potency compared to the polypeptide without the 3, 2 or 1 amino acid difference.

4. A polypeptide that specifically binds protein F of hRSV, comprising a VHH, a humanized VHH, a camelized VH or a domain antibody with:
   a) the amino acid sequence of any one of SEQ ID NO: 34, 36, 38, 40, or 51; or
   b) an amino acid sequence having no more than 3, preferably no more than 2, more preferably no more than 1 amino acid difference with the amino acid sequence of any one of SEQ ID NO: 34, 36, 38, or 40, provided that:
      i) the amino acid sequence of the VHH, humanized VHH, camelized VH or the domain antibody has Aspartic acid (Asp, D) at position 1, wherein said position is determined according to Kabat numbering;
      ii) the VHH, humanized VHH, camelized VH or the domain antibody comprises the following CDR sequences:
         CDR1 is SYAMG (amino acids 31-35 of SEQ ID NO:33);
         CDR2 is AISWSDGSTYYADSVKG (amino acids 50-66 of SEQ ID NO:33), AISWSEGSTYYADSVKG (amino acids 50-66 of SEQ ID NO:37), or AISWSDASTYYADSVKG (amino acids 50-66 of SEQ ID NO:39); and
         CDR3 is DLTSTNPGSYIYIWAYDY (amino acids 99-116 of SEQ ID NO:33); and
      iii) the polypeptide binds protein F of hRSV with the same, about the same, or a higher affinity and/or the polypeptide has the same, about the same, or a higher potency compared to the polypeptide without the 3, 2 or 1 amino acid difference.

5. The monovalent polypeptide according to claim 1, that comprises or consists of the amino acid sequence of any one of SEQ ID NO: 33, 34, 35, 36, 37, 38, 39, 40, or 51.

6. A polypeptide that comprises one or more monovalent polypeptides according to claim 1, and optionally further comprises one or more other polypeptides, optionally linked via one or more peptidic linkers.

7. The polypeptide according to claim 6, wherein the polypeptide is a multivalent polypeptide that comprises at least two monovalent polypeptides.

8. The multivalent polypeptide according to claim 7, wherein the multivalent polypeptide comprises at least three monovalent polypeptides.

9. The multivalent polypeptide according to claim 7, wherein the multivalent polypeptide has aspartic acid (Asp, D) at position 1.

10. The multivalent polypeptide according to claim 7, wherein the multivalent polypeptide comprises or consists of two monovalent polypeptides.

11. The multivalent polypeptide according to claim 10, wherein the multivalent polypeptide has aspartic acid (Asp, D) at position 1.

12. The multivalent polypeptide according to claim 7, wherein the multivalent polypeptide comprises or consists of three polypeptides.

13. The polypeptide according to claim 12, wherein the multivalent polypeptide has aspartic acid (Asp, D) at position 1.

14. The multivalent polypeptide according to claim 12 wherein the multivalent polypeptide that specifically binds protein F of hRSV, comprises three VHHs, humanized VHHs, camelized VHs or single domain antibodies with:

a) the amino acid sequence of any one of SEQ ID NO: 41, 42, 43, 44, 45, 46, 47, 48, or 49; or
b) an amino acid sequence having no more than 3, preferably no more than 2, more preferably no more than 1 amino acid difference with the amino acid sequence of any one of SEQ ID NO: 41, 42, 43, 44, 45, 46, 47, 48, or 49, provided that:
  i) the VHHs, humanized VHHs, camelized VHs or domain antibodies have Proline (Pro, P) at position 14, Arginine (Arg, R) at position 83 and Leucine (Leu, L) at position 108, wherein said positions are determined according to Kabat numbering; and
  ii) the VHHs, humanized VHHs, camelized VHs or domain antibodies comprise the following CDR sequences:
    CDR1 is SYAMG (amino acids 31-35 of SEQ ID NO:33);
    CDR2 is AISWSDGSTYYADSVKG (amino acids 50-66 of SEQ ID NO:33), AISWSEGSTYYADSVKG (amino acids 50-66 of SEQ ID NO:37), or AISWSDASTYYADSVKG (amino acids 50-66 of SEQ ID NO:39); and
    CDR3 is DLTSTNPGSYIYIWAYDY (amino acids 99-116 of SEQ ID NO:33); and
  iii) the multivalent polypeptide binds protein F of hRSV with the same, about the same, or a higher affinity and/or the multivalent polypeptide has the same, about the same, or a higher potency compared to the polypeptide without the 3, 2 or 1 amino acid difference.

15. The multivalent polypeptide according to claim 14, wherein the multivalent polypeptide that specifically binds protein F of hRSV comprises,
a) the amino acid sequence of any one of SEQ ID NO: 42, 43, 44, 47, 48, or 49;
b) an amino acid sequence having no more than 3, preferably no more than 2, more preferably no more than 1 amino acid difference with the amino acid sequence of any one of SEQ ID NO: 42, 43, 44, 47, 48, or 49, provided that:
  i) the VHHs, humanized VHHs, camelized VHs or domain antibodies have
    Proline (Pro, P) at position 14, Arginine (Arg, R) at position 83 and Leucine (Leu, L) at position 108; and
    Glycine (Gly, G) at position 16, Glutamic acid (Glu, E) at position 54 and/or Alanine (Ala, A) at position 55,
    wherein said positions are determined according to Kabat numbering; and
  ii) the multivalent polypeptide binds protein F of hRSV with the same, about the same, or a higher affinity and/or the polypeptide has the same, about the same, or a higher potency compared to the polypeptide without the 3, 2 or 1 amino acid difference.

16. The polypeptide according to claim 12, wherein the multivalent polypeptide comprises or consists of the amino acid sequence of any one of SEQ ID NO: 41, 42, 43, 44, 45, 46, 47, 48, 49, or 50.

17. A construct, comprising or consisting of a monovalent polypeptide according to claim 1.

18. An isolated host or host cell that comprises a nucleic acid encoding the polypeptide according to claim 1.

19. A composition comprising at least one monovalent polypeptide according to claim 1.

20. The composition according to claim 19, which is a pharmaceutical composition.

21. A method for producing a monovalent polypeptide according to claim 1, comprising the steps of: a) expressing, in a suitable host cell or host organism or in another suitable expression system, a nucleic acid or nucleotide sequence that encodes the monovalent polypeptide, and b) isolating and/or purifying the monovalent polypeptide thus obtained.

22. A method for preparing a multivalent polypeptide according to claim 7, said method comprising linking two or more monovalent polypeptides or monovalent constructs using one or more linkers.

23. A method for treatment of hRSV infection comprising administering, to a subject in need thereof, a pharmaceutically active amount of at least one monovalent polypeptide according to claim 1.

24. A monovalent polypeptide according to claim 1 for neutralization of RSV.

25. A method for treating a subject comprising administering to the subject an effective amount of the monovalent polypeptide according to claim 1 or a composition comprising the monovalent polypeptide according to claim 1 to a pulmonary tissue of the subject.

26. A pharmaceutical composition comprising a monovalent polypeptide according to claim 1 and a carrier suitable for pulmonary delivery.

27. A pharmaceutical device suitable for pulmonary delivery comprising a monovalent polypeptide according to claim 1 and/or a composition comprising the monovalent polypeptide according to claim 1.

28. The pharmaceutical device according to claim 27, which is selected from the group consisting of an inhaler for liquids or a suspension of fine solid particles or droplets, a device capable of generating an aerosol cloud and a dry powder inhaler.

29. A method for treatment of hRSV infection, comprising administering to a pulmonary tissue of a subject in need thereof, a pharmaceutically active amount of a monovalent polypeptide according to claim 1 and/or of a pharmaceutical composition comprising the monovalent polypeptide according to claim 1.

30. A host or host cell that expresses, or that under suitable circumstances is capable of expressing, a polypeptide according to claim 6.

31. A composition comprising at least one polypeptide according to claim 6.

32. The composition according to claim 31, which is a pharmaceutical composition.

33. A polypeptide according to claim 6, for neutralization of RSV.

34. A pharmaceutical composition comprising the polypeptide according to claim 6, and a carrier suitable for pulmonary delivery.

35. A pharmaceutical device suitable for the pulmonary delivery of a monovalent polypeptide according to claim 6 a composition comprising the monovalent polypeptide according to claim 6.

36. A pharmaceutical device according to claim 35, which is selected from the group consisting of an inhaler for liquids or a suspension of fine solid particles or droplets, a device capable of generating an aerosol cloud and a dry powder inhaler.

37. The monovalent polypeptide according to claim 2, 3, 4, 14, or 15, wherein potency is determined by a microneutralization assay on hRSV Long.

38. The monovalent polypeptide according to claim 2, 3, 4, 14, or 15, wherein affinity is determined by surface plasmon resonance.

39. The monovalent polypeptide according to claim 2, 3, 4, 14, or 15, wherein potency is determined by a microneutralization assay on hRSV Long and wherein affinity is determined by surface plasmon resonance.

* * * * *